(12) United States Patent
Loosmore et al.

(10) Patent No.: US 6,849,447 B2
(45) Date of Patent: Feb. 1, 2005

(54) **PROTECTIVE RECOMBINANT *HAEMOPHILUS INFLUENZAE* HIGH MOLECULAR WEIGHT PROTEINS**

(75) Inventors: Sheena M. Loosmore, Aurora (CA); Yan-Ping Yang, Willowdale (CA); Michel H. Klein, Willowdale (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 10/193,764

(22) Filed: Dec. 11, 2002

(65) Prior Publication Data

US 2003/0133943 A1 Jul. 17, 2003

Related U.S. Application Data

(63) Continuation of application No. 09/167,568, filed on Oct. 7, 1998, now abandoned.

(51) Int. Cl.[7] .............................................. C12N 15/00
(52) U.S. Cl. .................. 435/320.1; 536/23.7; 536/24.1; 536/24.2
(58) Field of Search ...................... 435/320.1; 536/23.7, 536/24.1, 24.2; 424/256.1

(56) References Cited

U.S. PATENT DOCUMENTS

| | | | |
|---|---|---|---|
| 4,496,538 A | 1/1985 | Gordon | 424/92 |
| 5,194,254 A | 3/1993 | Barber et al. | 424/85.8 |
| 5,603,938 A | 2/1997 | Barenkamp | 424/256.1 |
| 5,869,065 A | * 2/1999 | Barenkamp | |

FOREIGN PATENT DOCUMENTS

| WO | WO 92/17167 | 10/1992 |
|---|---|---|
| WO | WO 97/36914 | 10/1997 |

OTHER PUBLICATIONS

Berkowitz et al. 1987. J. Pediatr. 110:509.
Claesson et al. 1989. J. Pediatr. 114:97.
Black, S.B., H.R. Shinefield, B. Fireman, R. Hiatt, M. Polen, E. Vittinghoff, The Northern California Kaiser Permanent Vaccine Study Center Pediatrics Group. Efficacy in infancy of oligosaccharide conjugate *Haemophilus influenzae* type b (HbOC) vaccine in a United States population of 61,080 children. 1991. Pediatr. Infect. Dis. J. 10:97–104.
Madore, D.V. 1996. Impact of immunization on *Haemophilus influenzae* type b disease. Infectious Agents and Disease 5:8–20.
Bluestone, C.D. 1982. Current concepts in otolaryngology. Otitis media in children: to treat or not to treat? N. Engl. J. Med. 306:1399–1404.
Barenkamp, S.J., and F.F. Bodor. 1990. Development of serum bactericidal activity following nontypable *Haemophilus influenzae* acute otitis media. Pediatr. Infect. Dis. 9:333–339.

Barenkamp, S.J., and E. Leininger. 1992. Cloning, expression, and DNA sequence analysis of genes encoding non-typeable *Haemophilus influenzae* high–molecular–weight surface–exposed proteins related to filamentous hemagglutinin of *Bordetella pertussis*. Infect. Immun. 60:1302–1313.
Barenkamp, S.J., and J.W. St. Geme III. 1994. Genes encoding high–molecular–weight adhesion proteins of nontypeable *Haemophilus influenzae* are part of gene clusters. Infect. Immun. 62:3320–3328.
St. Geme III, J.W. and S. Grass. 1998. Secretion of the *Haemophilus influenzae* HMW1 and HMW2 adhesins involves a periplasmic intermediate and requires the HMWB and HMWC proteins. Molec. Microbiol. 27:617–630.
St. Geme III, J.W., S. Falkow, and S.J. Barenkamp. 1993. High–molecular–weight proteins of nontypeable *Haemophilus influenzae* mediate attachment to human epithelial cells. Proc. Natl. Acad. Sci. USA 90:2875–2879.
Barenkamp, S.J. 1996. Immunization with high–molecular–weight adhesion proteins of nontypeable *Haemophilus influenzae* modifies experimental otitis media in chinchillas. Infect. Immun. 64:1246–1251.
Tabor, S., and C.C. Richardson. 1985. A bacteriophage T7 RNA polymerase/promoter system for controlled exclusive expression of specific genes. Proc. Natl. Acad. Sci. USA 82:1074–1078.
Patient, M.E., and D.K. Summers. 1993. ColE1 multimer formation triggers inhibition of *Escherichia coli* cell division. Molec. Microbiol. 9:1089–1095.
Barenkamp, S. 1986. Protection by serum antibodies in experimental nontypeable *Haemophilus influenzae* otitis media. Infect. Immun. 52:572–578.
Yang, Y.–P., S.M. Loosmore, B. Underdown, and M.H. Klein. 1998. Nasopharyngeal colonization with nontypeable *H. Influenzae* in chinchillas. Infect. Immun. 66:1973–1980.
Fleischmann et al. 1995. Whole–genome random sequencing and assembly of *Haemophilus influenzae* Rd. Science 269:496–512.
O'Hagan, DT. 1992. Oral delivery of vaccines. Formulation and clinical pharmaco kinetic considerations. Clin. Pharmacokinet 22(t): 1–10.

(List continued on next page.)

*Primary Examiner*—Jennifer E. Graser
(74) *Attorney, Agent, or Firm*—Sim & McBurney

(57) ABSTRACT

Protective high molecular weight (HMW) proteins are produced recombinantly by expression from *E. coli* by using a promoter effective in *E. coli* and a nucleic acid molecule which contains a modified operon of a non-typeable strain of Haemophilus. The modified operon contains the portion only of the A region which encodes the mature HMW protein and the complete B and C regions of the operon. Enhanced levels of expression of the HMW proteins can be achieved by including the *E. coli* cer gene, a further copy of the portion of the A region of the operon encoding the mature protein or both in the expression vector. Nucleotide and deduced amino acid sequences of the hmw1 and hmw2 genes and HMW1 and HMW2 proteins, respectively of several non-typeable *Haemophilus influenzae* strain have been identified.

3 Claims, 219 Drawing Sheets

OTHER PUBLICATIONS

Ulmer et al. 1993. Curr. Opinion Invest. Drugs 2:983–989.

Lockhoff, O., 1991. Glycolipids as immunomodulators: Synthesis and properties.

Nixon–George A., et al., 1990. The adjuvant effect of stearyl tyrosine on a recombinant subunit hepatitis B surface antigen. J. Immunol 144 (12) :4798–4802.

* cited by examiner

FIG. 1B

Oligonucleotides to re-create the N-terminus of the full-length HMW1A protein in plasmid DS-1091-2 or the N-terminus of the full-length HMW2A protein in plasmid DS-1094-2.

| | SEQ ID NO |
|---|---|
| | 1 |
| | 2 |
| | 3 |

```
                    M  N  K  I  Y  R  L  K  F  S  K  R  L  N  A  Bsm I
                    ↑                                              →
Xba I
→
CTAGAAATAATTTTGTTAACTTTAAGAAGGAGATATACATATGAACAAGATATATCGTCTCAAATTCAGCAAACGCCTGAATGCT
    TTTATTAAAACAATTGAAATTCTTCCTCTATATGTATACTTGTTCTATATAGCAGAGTTTAAGTCGTTTGCGGACTTAC
```

FIG.3B

Oligonucleotides to re-create the N-terminus of the mature HMW1A protein in plasmid DS-1046-1-1.

| | SEQ ID NO |
|---|---|
| M P D N V ... | |
| ↑ | |
| Xba I | |
| CTAGAAATAATTTGTTAACTTTAAGAAGGAGATATACATATGCCGGATAATGTAT... | 4 |
| TTTATTAAACAATTGAAATTCTTCCTCTATATGTATACGGCCTATTACATA... | |
| ...S I N A E T A G R S N T S E D D E Y T    BamH I | |
| | ↓ |
| ...CTATTAATGCAGAAACAGCAGGACGCAGCAATACTTCAGAAGACGATGAATACACG | 5 |
| ...GATAATTACGTCTTTGTCGTCCTGCGTCGTTATGAAGTCTTCTGCTACTTATGTGCCCTAG | 6 |

FIG.4B

Oligonucleotides used to re-create the N-terminus of the HMW2A protein in plasmid DS-1200-3.

SEQ ID NO

Xba I

M P D D ...

CTAGAAATAATTTTGTTTAACTTTAAGAAGGAGATATACATATGCCTGATGATG...
TTTATTAAAACAAATTGAAATTCTTCCTCTATATGTATACGGACTACTAC...

...V T I E A E D P L R N N T G I N D EcoR I 7

...TAACAATTGAAGCCGAAGACCCCCTTCGCAATAATACCGGTATAAATGATG 8
...ATTGTTAACTTCGGCTTCTGGGGGAAGCGTTATTATGGCCATATTTACTACTTAA 9

Construction of JB-*2330-7*, a T7 *hmw1A (125)* plasmid.

Oligonucleotides used to PCR amplify the 3'-end of hmw1A.

FIG. 8B oligonucleotides used to PCR amplify the 3'-end of *hmw2A*.

sense

|  | EcoR I | | SEQ ID NO |
|---|---|---|---|
| | ↓ | K R V L E K V K | 15 |
| 5' | CCGGAATTCCGAAACGGTCCTTGAAAAGTAAAAG | 3' | 5360.DC | 16 | antisense

| | T N V A D D D G Q P * | | 17 |
|---|---|---|---|
| | TACCAATGTTGCTGACGATGACGACCCGTAG | | 18 |
| 3' | ATGGTTACAAGACTGCTACTGCTGCTGGCATCCTAGGCGC | 5' | 5361.DC | 19 |
| | ↑ BamH I | | |

Extraction of rHMW1 from *E. coli*

FIG. 15.

The Stability of rHMW1 (abc/cer)

-20C (+ 20% glycerol)

Kinetics of Antibody Response to rHMW1 in Mice

FIG.17

Oligonucleotides used to PCR amplify hmwA genes from NTHi strains.

|  | SEQ ID NO |
|---|---| sense

```
        EcoR I
         ↓      K  E  W  L  L  D  P
5'  GGGAATTCCAAAGAGTGGTTGTTAGACCCGGA  3'    5522.SL      20
                                                         21
``` antisense

```
    M  K  N  I  K  S  R  L  K  L
    ATGAAAAATATAAAAAGCAGATTAAAACTC                               22
                                                                 23
3'  TACTTTTTATATTTTCGTCTAATTTTGAGGCTTAAGG  5'    5523.SL         24
                                         ↑
                                       EcoR I
```

FIG. 18A  Joyc hmw1A sequence

```
LYS GLU TRP LEU LEU ASP PRO ASP ASN VAL ...
A A A G A A T G G T T G T T A G A C C C G G A C A A T G T A T...
                    10                  20              30     ...

...SER ILE ASN ALA GLY THR SER GLU ARG ASN
          ...C C A T T A A C G C A G G C A C A T C A G A A C G T A A C
                      40                  50                  60

ASP ALA SER PRO THR GLU ASP PHE PRO THR ...
G A C G C T T C A C C A A C A G A A G A T T T C C C T A C C G...
             70                  80              90        ...

...GLY ALA GLY GLY LYS ASP ASN PRO LYS LYS
          ...G A G C A G G A G G A A A A G G A T A A C C C C A A A A A A
                      100                 110                 120

ASN ALA HIS ASN LYS PRO THR LEU ILE ASN ...
A A C G C T C A C A A C A A A C C G A C A T T A A T A A A C A...
             130                 140                150     ...

...THR THR LEU GLU ARG ILE LEU SER GLY ASN
          ...C A A C T C T T G A G C G T A T A T T A A G T G G C A A C
                      160                 170                 180

THR PHE VAL ASN ILE THR ALA ARG LYS ARG ...
A C C T T T G T T A A T A T C A C T G C C A G A A A A G A A...
             190                 200                210
```

FIG.18B

```
            ...ILE THR VAL ASN SER ASP ILE ASN ILE LYS
            ...T C A C A G T T A A T A G T G A T A T C A A C A T C A A A
               220                 230                 240

ASP SER HIS LEU ILE LEU TRP SER GLU ...
G A C A G C T C C C A T C T A A T A C T C T G G A G C G A A A...
               250                 260                 270
                                                       ...

...ASN ASP ASN SER SER GLY VAL ASP ILE LYS
                                ...A T G A T A A C A G C A G C G G C G T T G A T A T T A A A
                                    280                 290                 300
                                                                            ...

GLY ASN ILE THR SER THR GLY GLY SER ...
G G C A A T A T C A C T T C T A C T G G C G G A A G C T...
               310                 320                 330
                                                       ...

...LEU THR ILE TYR SER SER GLY TRP ILE ASP
                                ...T A A C T A T T T A C T C C A G C G G G C T G G A T T G A T
                                    340                 350                 360
                                                                            ...

ILE HIS LYS ASN ILE THR LEU ASN SER GLY ...
A T T C A T A A A A A C A T T A C G C T T A A T T C A G G G C...
               370                 380                 390
                                                        ...

...LEU LEU ASN ILE THR THR LYS GLN GLY ASP
                                ...T C T T A A A C A T T A C A A C T A A A A C A A G G A G A T
                                    400                 410                 420
                                                                            ...
```

FIG. 18C

```
ILE ALA PHE GLU LYS GLY ASN ASN PRO THR               ...
ATCGCCTTCGAAAAAGGGAATAACCCAACCA...
            430              440              450     ...

...ILE THR GLY GLN GLY THR ILE THR ALA GLY
                    ...TTACAGGTCAAGGGACTATTACCGCAGGC
                         460              470              480

ASN GLY LYS GLY PHE ARG PHE GLU ASN ALA               ...
AATGGTAAAGGTTTTAGGTTTGAAAACGCCT...
            490              500              510     ...

...SER LEU ASN GLY ILE GLY THR GLY LEU LEU
                    ...CCCTAAACGGTATTGGAACAGGGTTACTT
                         520              530              540

PHE ASN ILE LYS ARG ASP LEU GLY ASN ASN               ...
TTTAACATCAAAAGGGATTTAGGAAATAATT...
            550              560              570     ...

...PHE GLN ILE ILE ASN PHE PHE ASN GLY THR
                    ...TCCAAATCATAAACTTTTTTAACGGAACT
                         580              590              600

LEU ASN ILE SER GLY LYS VAL ASN ILE SER               ...
TTAAATATTTCAGGGAAAGTAAACATCTCAA...
            610              620              630     ...
```

FIG.18D

...MET VAL ILE PRO LYS LYS TRP ASP TYR SER
...T G G T C A T A C C T A A A A A A T G G A T T A T A G T
            640                          650                      660

LYS PHE ARG GLY ARG THR TYR TRP ASN VAL ...
A A A T T C A G G G G G C G A A C C T A T T G G A A C G T A A...
              670                        680                  690

...THR HIS LEU ASN VAL SER GLU GLY SER LYS
...C C C A T T T A A A T G T T T C C G A A G G C A G T A A G
                700                       710                      720

PHE ASN LEU THR ILE ASP SER ARG GLY ASP ...
T T T A A C C T C A C T A T C G A C T C C A G G A G A T G...
              730                        740                  750

...ASP THR ALA GLY THR LEU ASN THR PRO TYR
...A C A C T G C A G G C A C C C T T A A C A C C C C T T A T
                760                       770                      780

ASN LEU ASN GLY ILE SER PHE ASN LYS ASP ...
A A T T T A A A C G G T A T A T C A T T C A A C A A A G A C A...
              790                        800                  810

...THR ILE PHE ASP VAL LYS GLN ASN GLY ALA
...C T A T C T T T G A T G T T A A A C A A A C G G G G C A
                820                       830                      840

FIG. 18E

```
VAL  THR  PHE  ASP  ILE  LYS  ALA  PRO  ILE  GLY  ...
GTCACCTTTGACATCAAGGCGCCAATAGGGG...
              850                860         870      ...

SER  PHE  ASN  GLY  ASN  ILE  SER  VAL  SER  GLY  ...  VAL  ASN  ASN  ARG  ASN  LEU  ASN  TYR  ALA
TCATTCAATGGAAATATTTCAGTTTCAGGAG... ...TAAATAATAATCGTAATTTGAATTACGCA
              910                920         930      ...             880                890                900

SER  SER  THR  ALA  GLN  THR  PRO  GLY  VAL  ...  GLY  GLY  ASN  VAL  THR  PHE  LYS  LEU  LEU  ALA
TCATCCTCTACCGCTCAAACTCCCGGTGTAT... ...GAGGGAATGTCACTTTCAAACTTCTCGCC
              970                980         990      ...             940                950                960

GLY  GLY  SER  SER  LEU  GLU  PHE  ARG  THR  GLU  ...  PHE  ILE  ASN  SER  LYS  HIS  PHE  ASN  ALA  SER
GGAGGGTCGAGTTTAGAAACTGAAG...       ...TTATAAATTCTAAACACTTTAATGCTTCA
              1030               1040        1050     ...             1000               1010               1020
```

FIG. 18F

```
                                            ...GLY SER THR LYS VAL GLY PHE LEU ILE ASN
                                            ...G C T C A A C A A A A G T C G G G C T T C T T G A T A A A T
                                               ...                          1060                        1070                        1080

ASN ASP LEU THR LEU ASN ALA THR GLY GLY ...                    ...ASN ILE SER LEU LEU GLN VAL GLU GLY ILE
A A T G A T T T A A C C C T A A A T G C C A C C G G A G G T A...    ...A C A T A T C G C T C T T G C A A G T T G A A G G C A T T
                  1090                        1100         ...                       1120                        1130                        1140
                                                              ...

ASP GLY MET ILE GLY LYS GLY VAL VAL ALA ...                    ...LYS LYS ASN ILE THR PHE ALA GLY GLY ASN
G A C G G G A T G A T T G G T A A A G G C G T T G T A G C T A...    ...A A A A A A C A T A A C C T T T G C T G G A G G C A A T
                  1150                        1160         ...                       1180                        1190                        1200
                                                              ...

ILE THR PHE GLY SER LYS LYS ALA ILE THR ...                    ...GLU ILE GLU GLY ASN ALA THR ILE ASN ASN
A T C A C C T T T G G C T C C A A G A A A G C C A T A A C A G...    ...A A A T C G A A G G C A A T G C T A C T A T C A A T A A C
                  1210                        1220         ...                       1240                        1250                        1260
                                                              ...
```

FIG.18G

```
ASN ALA ASN VAL THR LEU ILE GLY SER ASP  ...
A A C G C T A A C G T C A C T C T T A T C G G T T C G G A T T ...
                        1270                              1280                    1290
                                                                    ...PHE ASP ASN HIS GLN LYS PRO LEU THR ILE
                                                                    ...T T G A C A A C C A T C A A A A A C C T T T A A C T A T T
                                                                                1300              1310              1320

LYS LYS ASP VAL ILE ILE ASN SER GLY ASN ...
A A A A A A G A T G T C A T C A T T A A T A G C G G C A A C C ...
                        1330                              1340                    1350
                                                                    ...LEU THR ALA GLY GLY ASN VAL ILE ASN ILE
                                                                    ...T T A C C G C T G G C G G C A A T G T T A T C A A T A T A
                                                                                1360              1370              1380

ASN GLY ASN LEU THR VAL ASN ASN GLY ALA ...
A A C G G A A A T C T T A C C G T T A A C A A T G G C G C C A ...
                        1390                              1400                    1410
                                                                    ...ASN LEU LYS ALA ILE THR ASN PHE THR PHE
                                                                    ...A T C T T A A A G C T A T C A C A A A T T T C A C T T T T
                                                                                1420              1430              1440

ASN VAL GLY GLY LEU PHE ASP ASN LYS GLY ...
A A T G T A G G C G G C T T G T T T G A C A A C A A A G G C A ...
                        1450                              1460                    1470
```

FIG.18H

```
                  ...ASN SER ASN ILE SER ILE ALA ARG GLY GLY
                  ...A T T C A A A T A T C T C C A T T G C T A G A G G A G G G
                                       1480              1490              1500

ALA LYS PHE LYS ASP ILE ASN ASN THR SER                 ...SER LEU ASN ILE THR THR ASN SER ASP THR
G C T A A A T T T A A A G A T A T C A A T A A C A C C A G T A...   ...G C T T A A A T A T T A C C A C C A A C T C C G A C A C C
                  1510              1520              1530                                1540              1550              1560

THR TYR ARG THR ILE ILE GLU GLY ASN ILE                 ...THR ASN LYS ALA GLY ASP LEU ASN ILE ILE
A C T T A C C G T A C C A T T A T A G A A G G T A A T A T A A...   ...C C A A C A A A G C A G G T G A T T T G A A T A T C A T T
                  1570              1580              1590                                1600              1610              1620

ASP ASN LYS GLY ASN ALA GLU ILE GLN ILE                 ...GLY GLY ASN ILE SER GLN LYS GLU GLY ASN
G A T A A T A A A G G T A A C G C T G A A A T C C A A A T T G...   ...G C G G C A A T A T C T C G C A A A A G A A G G T A A T
                  1630              1640              1650                                1660              1670              1680
```

FIG.18I

```
LEU THR ILE SER SER ASP LYS ILE ILE ASN ILE           ...
CTCACGATTTCTTCCGATAAAATTAATATCA...
          1690              1700             1710
                ...THR ASN GLN ILE THR ILE LYS LYS GLY VAL
                ...CTAACCAGATAACAATCAAGAAGGGTGTT
                         1720            1730            1740
                          ...

ASN LYS GLU ASP SER ASP SER SER THR ALA           ...
AATAAAGAGGATTCTGATTCAAGCACGGCAA...
         1750             1760             1770
                ...ASN ALA ASN LEU THR ILE LYS THR LYS
                ...ACAATGCTAATCTAACCATTAAAACCAAA
                         1780            1790            1800
                          ...

GLU LEU GLN LEU THR GLY ASP LEU ASN ILE           ...
GAATTGCAATTAACGGGAGACCTAAATATTT...
         1810             1820             1830
                ...SER GLY PHE ASP LYS ALA GLU ILE THR ALA
                ...CAGGCTTCGATAAAGCAGAAATCACAGCC
                         1840            1850            1860
                          ...

LYS GLU GLY ALA ASP LEU ILE ILE GLY ASN           ...
AAAGAGGGTGCCGATTTAATCATCGGTAATA...
         1870             1880             1890
                          ...
```

FIG. 18J

```
...SER ASP ASN ASN ASN ALA ASN ALA LYS
...G T G A T A A C A A C A A T G C T A A T G C T A A A
           1900            1910            1920

LYS VAL THR PHE ASN GLN VAL LYS ASP SER...
A A A G T A A C C T T T A A C C A G G T T A A A G A T T C G A...
           1930            1940            1950

...LYS ILE SER ALA GLY SER HIS ASN VAL THR
...A A A T C T C T G C T G G C A G T C A C A A T G T A A C A
           1960            1970            1980

LEU ASN SER LYS VAL GLU THR SER ASN GLY...
C T A A A C A G T A A A G T A G A A A C C T C T A A T G G C A...
           1990            2000            2010

...ASN ASN ASP ALA GLU SER ASN ASN GLY ASP
...A T A A T G A C G C T G A A A G C A A T A A T G G C G A T
           2020            2030            2040

SER THR SER LEU THR ILE ASN ALA LYS ASN...
A G C A C C A G C T T A A C T A T T A A T G C A A A A A A T G...
           2050            2060            2070

...VAL THR VAL ASN ASN ASN ILE THR SER HIS
...T A A C A G T A A A C A A C A A T A T T A C T T C T C A C
           2080            2090            2100
```

FIG. 18K

```
LYS THR VAL ASN ILE THR ALA SER GLU ASN ...
A A A C A G T A A A T A T C A C T G C G T C A G A A A A T G...
                    2110                    2120                    2130

...VAL THR THR LYS ALA GLY THR THR ILE ASN
                                  ...T T A C C A C C A A A G C G G G C A C A A C C A T T A A T
                                              2140                    2150                    2160

ALA THR ILE GLY SER VAL GLU VAL THR ALA ...
G C A A C C A T A G G T A G C G T A G A A G T A A C A G C C A...
                    2170                    2180                    2190

...LYS THR GLY ASP ILE LYS GLY GLY ILE GLU
                                  ...A A A C A G G T G A T A T T A A A G G T G G A A T T G A A
                                              2200                    2210                    2220

SER ASN SER GLY ASN VAL ASN ILE THR ALA ...
T C C A A T T C C G G T A A T G T A A A T A T T A C A G C G A...
                    2230                    2240                    2250

...SER GLY ASP THR LEU ASN VAL SER ASN ILE
                                  ...G C G G C G A C A C G C T T A A T G T A A G T A A C A T C
                                              2260                    2270                    2280

THR GLY GLN ASN VAL THR VAL ALA ALA ALA ...
A C A G G T C A A A A T G T G A C A G T G G C A G C A G C C T...
                    2290                    2300                    2310
```

FIG. 18L

```
THR ILE ASN ALA THR GLY THR GLY ASN ALA ASN ...        ...SER GLY ALA VAL THR THR LYS GLY SER
ACTATTAATGCAACAACTGGTAACTGCAAATA...        ...CAGGTGCCGTAACAACCACAAAAGGATCA
            2350              2360              2370             ...             2320                 2330                2340

GLU VAL LYS SER ALA SER GLY ASN VAL ASN ...        ...ILE THR THR LYS THR GLY GLU ILE ASN GLY
GAAGTTAAATCAGCTTCCGGTAATGTAAATA...        ...TTACAACCAAAAACAGGTGAAATTAATGGC
            2410              2420              2430             ...             2380                 2390                2400

SER ASN ILE THR GLY GLN ASN VAL THR VAL ...        ...ILE THR ALA SER GLY ASN THR LEU ASN VAL
AGTAACATCACTGGTCAAAATGTAACAGTAA...        ...TTACAGCGAGCGGCAATACACTTAATGTA
            2470              2480              2490             ...             2440                 2450                2460

...THR ALA ASN SER GLY ALA ILE THR THR THR
                                        ...CAGCAAACTCAGGTGCCATAACAACCACA
                                                 2500                 2510                2520
```

FIG.18M

```
GLU GLY SER THR ILE ASN ALA THR THR GLY ...
GAAGGCTCAACTATTAACGCGACAACAGGTG...
         2530              2540              2550
                                           ...ASP ALA ASN ILE THR THR GLN THR GLY ASN
                                           ...ATGCAAATATTACAACCCAAACAGGTAAT
                                                      2560              2570              2580

ILE ASN GLY LYS VAL GLU SER SER GLY ...
ATTAATGGTAAAGTTGAATCCAGTTCTGGTT...
         2590              2600              2610
                                           ...SER VAL THR LEU ILE ALA THR GLY GLN THR
                                           ...CTGTGACGCTTATTGCAACTGGACAAACT
                                                      2620              2630              2640

LEU ALA VAL GLY ASN ILE SER GLY ASP THR ...
CTTGCTGTAGGTAATATTTCAGGTGACACTG...
         2650              2660              2670
                                           ...VAL THR ILE THR ALA ASP LYS GLY LYS LEU
                                           ...TTACCATTACTGCGGATAAAGGTAAATTA
                                                      2680              2690              2700

THR THR GLN THR SER SER LYS ILE ASN GLY ...
ACCACACAAACAAGCTCTAAGATTAACGGAA...
         2710              2720              2730
```

FIG. 18N

```
                    ...THR LYS SER VAL THR THR SER SER GLN SER
                    ...C T A A G A G T G T A A C C A C C T C A A G C C A A T C A
                                               2740           2750            2760

GLY ASP ILE SER GLY THR ILE SER GLY ASN ...         ...THR VAL SER VAL SER ALA THR GLY SER LEU
G G T G A T A T T A G T G G C A C A A T T T C T G G T A A T A...    ...C G G T A A G C G T T A G T G C G A C C G G T A G C T T G
                    2770           2780          2790 ...                      2800          2810            2820

THR THR GLN ALA GLY SER LYS ILE GLU ALA ...         ...LYS THR GLY GLU ALA ALA ASN VAL THR SER ALA
A C C A C T C A A G C A G G C T C A A A A A T T G A A G C A A...    ...A A A C A G G T G A G G C T A A T G T A A C A A G C G C A
                    2830           2840 ...                          2850                      2860            2870            2880

THR GLY THR ILE GLY GLY THR ILE SER GLY ...         ...ASN THR VAL ASN VAL THR ALA ASN THR ASP
A C A G G T A C A A T T G G C G G T A C A A T C T C T G G C A...    ...A T A C A G T A A A T G T T A C A G C A A A T A C T G A T
                    2890           2900 ...                          2910                      2920            2930            2940
```

FIG.180

```
ASN LEU THR ILE LYS ASP GLY ALA ARG ILE  ...
AATTTAACTATTAAAGATGGCGCAAGAATTA...
                2950           2960          2970
                                                      ...LYS ALA THR GLY GLY ALA VAL THR LEU THR
                                                      ...AAGCAACGGGCGGAGCTGTGACTTTAACC
                                                                    2980          2990          3000

ALA GLY GLY THR LEU THR THR GLU THR  ...
GCAACAGGAGGTACTTTAACCACCGAAACAA...
            3010          3020          3030
                                                  ...SER SER ASP ILE THR SER SER ASN GLY GLN
                                                  ...GTTCTGATATTACCTCAAGCAATGGTCAG
                                                                 3040          3050          3060

THR THR LEU THR ALA LYS ASP SER SER ILE  ...
ACAACTCTCACGGCCAAGGATAGCAGTATCG...
             3070          3080          3090
                                                 ...ALA GLY SER ILE ASN ALA ALA ASN VAL THR
                                                 ...CAGGAAGCATCAATGCCGCCAATGTGACA
                                                              3100          3110          3120

LEU ASN THR THR GLY THR LEU THR THR VAL  ...
TTAAATACCACAGGCACTTTAACTACTGTGG...
              3130          3140          3150
```

FIG.18P

```
                                              ...ALA GLY SER LYS ILE GLU ALA ALA SER GLY
                                              ...CAGGTTCAAAAATCGAGGCAGCCAGTGGC
                                                                 3160          3170         3180

THR LEU VAL ILE ASN ALA LYS ASP ALA GLN                      ...LEU ASP GLY ALA ALA LEU GLY ASP ARG THR
ACCCTGGTTATTAATGCAAAAGATGCTCAGT...           ...TGGACGGCGGCATTAGGTGACCGTACA
          3190              3200         3210                     3220          3230         3240

GLU VAL ASN VAL THR ASN ALA ASN GLY SER                      ...GLY SER VAL ILE ALA THR THR SER SER ARG
GAAGTAAATGTAACTAACGCAAATGGCTCCG...           ...GCAGCGTAATCGCGACAACCTCAAGCAGA
          3250              3260         3270                     3280          3290         3300

VAL ASN ILE THR GLY ASP LEU ILE THR ILE                      ...ASN GLY LEU ASN ILE ILE SER LYS ASN GLY
GTGAACATCACTGGGGATTTAATCACAATAA...           ...ATGGATTAAATATCATTTCAAAAACGGT
          3310              3320         3330                     3340          3350         3360
```

FIG.18Q

```
LYS ASN THR VAL LEU LEU LYS GLY VAL GLU ...
A A A A A C A C C G T G C T G T T A A A A G G T G T T G A A A ...
                3370                3380                3390
                                                              ...ILE ASP VAL LYS TYR ILE GLN PRO GLY ILE
                                                              ...T T G A T G T G A A A T A C A T T C A A C C G G G C A T A
                                                                  3400                3410                3420

ALA SER VAL TYR GLU VAL ILE GLU VAL LYS ...
G C G A G C G T A T A T G A A G T A A T T G A A A G C A A A A C ...
                3430                3440                3450
                                                              ...ARG ALA LEU GLU LYS VAL LYS ASP LEU SER
                                                              ...G C G C T C T T G A G A A A G T G A A A G A T T T A T C T
                                                                  3460                3470                3480

ASP GLU ARG GLU ARG GLU ALA LEU ALA LYS LEU ...
G A T G A A G A A A G A G A A G C A T T A G C T A A G C T T G ...
                3490                3500                3510
                                                              ...GLY VAL SER ALA VAL ARG PHE ILE GLU PRO
                                                              ...G T G T G A G C G C T G T A C G T T T T A T T G A G C C A
                                                                  3520                3530                3540

ASN ASN THR ILE THR VAL ASP THR GLN ASN ...
A A T A A T A C A A T T A C A G T C G A T A C A C A A A A T G ...
                3550                3560                3570
```

FIG.18R

```
                              ...GLU PHE ALA THR ARG PRO LEU SER ARG ILE
                              ...A A T T T G C A A C C A G A C C A T T A A G T C G A A T A
                              ...                                      3590              3600
                                            3580

VAL ILE SER GLU GLY ARG ALA CYS PHE SER        ...ASN SER ASP GLY ALA THR VAL CYS VAL ASN
G T G A T T T C T G A A G G C A G G G C G T G T T T C T C A A ...  ...A C A G T G A T G G C G A C G G T G T G C G T T A A T
                    3610                3620          ...          3640                3650              3660
                                                      ...

ILE ALA ASP ASN GLY ARG ***
A T C G C T G A T A A C G G G C G G T A G
              3670              3680
```

FIG. 19A

Joyc hmm2A sequence

```
      LYS GLU TRP LEU LEU ASP PRO ASP ASN VAL ...
      AAA GAG TGG TTG TTA GAC CCG GAT AAT GTA...
                          10                  20                  30....
                                                          SER ILE GLU ASN PRO SER THR GLU ARG ASN
                                                      ...TCC ATT GAA AAT CCT TCA ACT GAA CGC AAT
                                                                  40                  50                  60

ASP SER ASN GLU ASP LEU GLU TYR THR GLY ....
      GAT TCC AAT GAA GAC CTA GAG TAT ACA GGA....
                          70                  80                  90....
                                                          THR GLY GLU ASN ILE ASN ASN PRO LYS VAL
                                                      ...ACA GGG GAA AAT ATA AAC AAC CCT AAG GTA
                                                                  100                 110                 120

ASN ASN GLN SER LYS LYS THR LEU THR SER ....
      AAT AAT CAG TCT AAA AAA ACA CTA ACA AGC....
                          130                 140                 150....
                                                          SER ILE LEU GLU ASN ILE LEU LYS LYS GLY
                                                      ...TCA ATC CCT TGA GAA CAT CCT GAA AAA GGC
                                                                  160                 170                 180
```

FIG. 19B

```
SER PHE VAL ASN ILE THR ALA THR ASP ASN ...               ILE TYR VAL ASN SER SER ILE ASN ILE GLY
TCTTTTGTTAACATTACTGCCACTGATAAC.... ...ATCTACGTTAATAGCTCTATCAACATCGGA
              190              200         210....                   220              230              240

ASP SER GLY HIS LEU ILE LEU SER GLY GLY ...           GLY ARG ASN GLY GLY VAL LYS ILE ASN
GACAGTGGTCACTTAATTCTCTCAGGTGGA.... ...GGCAGGAACGGCGGTGTTAAGATTAAT
              250              260         270....                   280              290              300

LYS ASN ILE THR SER THR GLY GLY SER LEU ...           THR ILE ASN SER LYS GLY TRP VAL ASP ILE
AAAAATATTACTTCCACGGGCGGAAGTTTA.... ...ACCATTAATTCCAAAGGATGGGTTGATATT
              310              320         330....                   340              350              360

HIS SER ASN ILE SER LEU GLY THR GLY PHE ...
CACTCCAATATTTCACTTGGTACGGGTTTT....
              370              380         390....
```

FIG.19C

```
                              ... LEU ASN ILE THR SER ASN GLY SER VAL ALA
                              ... T T G A A C A T T A C C T C T A A T G G T T C C G T G G C T
                              ...                           400                       410                       420

PHE GLU LYS ALA ASP LYS ASP LYS ALA ARG ...                     ... SER ALA ALA ASP ALA GLN ILE VAL ALA GLN
T T T G A G A A G G C A G A C A A A G A T A A G G C A C G T ...   ... A G C G C G G C A G A T G C T C A A A T T G T C G C A C A A
                  430                       440                  450                       460                       470                       480

GLY ILE ILE ASN LEU THR GLY GLU ASN LYS ...                     ... THR PHE ARG LEU ASN ASN VAL SER LEU ASN
G G C A T C A T A A A C C T C A C A G G G G A A A A C A A A ...   ... A C C T T T A G G C T T A A C A A T G T G T C T T T A A A T
                  490                       500                  510                       520                       530                       540

GLY VAL GLY GLN GLY LEU SER ILE THR SER ...                     ... ASN VAL GLY ASN GLN THR HIS LYS PHE ASP
G G A G T G G G G T C A A G G T C T A T C C A T C A C G T C A ... ... A A T G T G G G C A A T C A A A C T C A T A A A T T C G A T
                  550                       560                  570                       580                       590                       600
```

FIG.19D

```
GLY GLU ILE ASN ILE THR GLY ASN VAL THR ....
GGTGAAATTAACATAACTGGAAATGTAACA...
        610              620         630....

ILE ASN GLN THR ALA PRO ALA THR THR ALA
                              ...ATTAAATCAAACTGCACCTGCGACAACCGCA
                                 640              650              660

TYR TRP ASN PHE SER TYR ASP SER TYR TRP ....
TATTGGAATTTTAGCTACGATTCATATTGG...
        670              680         690....

ASN VAL SER THR LEU ASN VAL GLN LYS ASN
                              ...AACGTCAGTACTCTTAACGTACAAAAAAAC
                                 700              710              720

SER SER PHE THR PHE ILE LYS ARG THR GLU ....
TCAAGCTTTACCTTTATTAAGCGCACTGAA...
        730              740         750....

SER ASN ARG PHE GLY PRO THR THR PRO LEU
                              ...AGTAATCGCTTTGGCCCAACAACACCACTT
                                 760              770              780

ARG SER SER GLY GLY VAL PHE PHE ASN GLY ....
CGAAGCTCCGGAGGGGTATTCTTTAACGGC...
        790              800         810....
```

FIG.19E

```
        THR ASN SER ARG VAL LEU PHE ASN LEU LYS ....     THR ASN GLY ASN MET VAL LEU ASN VAL GLY
     ...ACTAATTCGAGAGTTTTGTTTAATTTGAAG....            ...ACGAATGGCAACATGGTGCTTAACGTCGGA
                         850              860     870                820           830           840

LEU PRO LEU GLN PHE ASN ALA ASN ILE THR ....     PRO ASN GLU ASN THR ASN ASN SER LYS PRO
     ...TTACCGCTTCAATTTAACGCCAATATTACA....             ...CCAAATGAGAATACAAACAACAGCAAGCCT
                         910              920     930                880           890           900

ILE HIS ALA ASN HIS SER GLY ARG GLY ALA ....     ALA ILE GLY GLY SER VAL SER PHE ASP
     ...ATACACGCCAATCATTCCGGCAGAGGGGCT....              ...GCCATTGGTGGAGGCTCTGTGTCTTTTGAT
                         970              980     990                940           950           960

GLU LEU LYS MET ASN THR ILE ASN ILE SER
                                                        ...GAATTAAAAATGAACACAATTAATATCTCT
                                                                      1000          1010          1020
```

FIG. 19F

```
ASP GLY THR SER LEU THR LEU GLN SER HIS ....        VAL ARG LYS ASP SER ALA PHE ILE ILE SER
G A C G G C A C C A G C C C T C A C C C T A C A A T C C C A T ... ... G T T C G C A A A G A T A G T G C T T T T A T A A T C A G T
            1030              1040           1050...            1060              1070              1080

LYS ASP LEU THR ILE ASN ALA THR GLY SER ....        ASN PHE THR LEU GLU GLN SER PRO ASP SER
A A A G A T T T A A C A A T A A A C G C A A C C G G T T C A ... ... A A T T T T A C T C T T G A G C A A T C A C C A G A C A G T
            1090              1100           1110...            1120              1130              1140

PHE THR ASP LYS TYR PRO GLY ARG ALA ILE ....        SER SER THR LYS ASN ILE THR ILE SER GLY
T T T A C T G A C A A A T A C C C C G G A A G A G C T A T T ... ... A G T T C A A C T A A A A A T A T A A C C A T C T C A G G T
            1150              1160           1170...            1180              1190              1200

GLY ASN VAL SER LEU GLY GLY GLN ASN SER ....
G G C A A C G T C T C T C T T G G T G G G C A A A A T T C A
            1210              1220           1230...
```

FIG.19G

```
              ...  SER SER ASP ILE LYS GLY ASN ILE THR ILE
              ...A G C A G T G A C A T C A A G G G A A A T A T T A C C A T C
                                   1240              1250              1260

LYS SER SER THR ASN VAL THR LEU LYS ALA ...         HIS ASN SER PRO ARG ASP PHE ALA SER ARG
A A A A G C T C A A C A A A T G T T A C A C T G A A A G C C ...C A T A A C A G C C C T C G G C G A C T T T G C T T C C A G A
         1270              1280         1290...             1300              1310              1320

THR LEU THR LEU GLY ASN LEU ASN VAL GLU ...         GLY ASN ILE THR LEU THR GLY SER VAL ALA
A C C T T A A C C C T T G G C A A C T T G A A T G T T G A A ...G G A A A T T T A A C C C T A A C C G G C T C A G T T G C G
         1330              1340         1350...             1360              1370              1380

ASP ILE LYS GLY ASN LEU SER ILE LEU ASN ...         ASP ALA THR PHE LYS GLY GLU THR SER GLU
G A T A T T A A A G G T A A C C T T T C C A T T C T T A A C ...G A T G C T A C T T T T A A G G A G A G A C C A G T G A A
         1390              1400         1410...             1420              1430              1440
```

FIG. 19H

```
ASN LEU ASN ILE THR GLY ASN PHE THR ASN ....
A A C C T A A A C A T C A C C G G C A A C T T C A C C A A T ...
              1450                    1460               1470....
        ... ASN GLY THR ALA ASP ILE ASN ILE LYS GLN
        ... A A T G G C A C C G C C G A C A T T A A T A T A A A A C A A
                     1480                    1490               1500

GLY VAL VAL ASN ILE GLN GLY ASN ILE THR ....
G G G G T G G T A A A C A T C C A A G G T A A T A T T A C C ...
              1510                    1520               1530....
        ... ASN LYS GLY LEU ASN ILE THR THR ASN
        ... A A T A A A G G T G G T T T A A A C A T T A C C A C T A A T
                     1540                    1550               1560

ALA GLN ASN ASN GLN LYS THR ILE ILE ASN ....
G C C C A A A A C A A T C A A A A A A C C A T T A T T A A C ...
              1570                    1580               1590....
        ... GLY ASN ILE THR ASN GLU GLY GLY ASP LEU
        ... G G A A A T A T A A C T A A C G A A G G C G G A G A T T T A
                     1600                    1610               1620

ASN ILE LYS ASP SER ASN ASN ALA GLU ....
A A C A T C A A G G A T A G T A A C A A T A A T G C T G A A
              1630                    1640               1650
```

FIG. 19I

```
                               ILE GLN ILE GLY GLY ASN ILE SER GLN LYS ....
                            ...A T C C A A A T T G G C G G C A A T A T C T C G C A A A A A
                                              1660                1670                1680

LYS GLY ASN LEU THR ILE SER SER ASP LYS ....
A A A G G C A A T C T C A C A A T T T C T T C T G A T A A A...
              1690                1700                1710....

ILE ASN ILE THR LYS LYS ILE THR ILE LYS
                            ...A T C A A T A T T A C C A A G A A G A T A A C A A T C A A A
                                              1720                1730                1740

ALA GLY VAL ASP GLU GLY GLY SER ASP SER ....
G C A G G C G T T G A T G A A G G T G G T T C T G A C T C A...
              1750                1760                1770....

SER PRO ALA SER ASN ALA ASN LEU THR ILE
                            ...A G C C C A G T A A T G C T A A T C T A A C C A T T
                                              1780                1790                1800

LYS THR LYS THR LEU GLU LEU THR GLY ASP ....
A A A A C C A A A A C G C T A G A A T T A A C A G G A G A C...
              1810                1820                1830....

LEU ASN ILE SER GLY PHE ASN LYS ALA GLU
                            ...C T A A A T A T T T C A G G C T T T A A T A A A G C A G A A
                                              1840                1850                1860
```

FIG.19J

ILE THR ALA LYS ASN GLY ASN ASP LEU THR ... ... ... ILE GLY LYS ALA SER ASP GLY ASN ALA ASN
ATTACAGCTAAAAATGGCAACGATTTAACT.... ...ATTGGCAAGGCTAGTGATGGTAATGCTAAT
  1870  1880  1890....  1900  1910  1920

ALA LYS LYS VAL THR PHE ASP LYS VAL LYS ... ... ... ASP SER LYS ILE SER ALA ASN GLY HIS ASN
GCTAAAAAAGTGACTTTTGACAAGGTTAAA.... ...GATTCAAAAATCTCAGCTAACGGTCACAAT
  1930  1940  1950....  1960  1970  1980

VAL THR LEU ASN SER LYS VAL GLU THR SER ... ... ... ASN SER ASP SER ALA SER ALA ASP ASP SER ASN
GTAACACTAAATAGCAAAGTGGAAACGTCT.... ...AATAGTGATAGTAGTGCTGATGATAGTAAT
  1990  2000  2010....  2020  2030  2040

ASP ASN ASN THR GLY LEU THR ILE SER ALA ...
GATAACAACACTGGTTTAACCATTTCCGCA....
  2050  2060  2070....

FIG. 19K

```
                                    ... LYS ASP VAL THR VAL ASN ASN ASP VAL THR
                                    ... A A A G A T G T A A C A G T A A A C A A T G A C G T C A C C
                                                                                              2100
                                                                                 2090

SER HIS LYS THR ILE ASN ILE SER ALA THR ....        ... THR GLY ASN VAL THR THR LYS GLU SER THR
T C C C A C A A G A C A A T A A A T A T C T C T G C C A C A ....   ... A C A G G A A A T G T A A C C A A A G A A A G C A C A
                              2110                         2130....                              2150                              2160
                                                                 ...

THR ILE ASN ALA ALA THR GLY SER VAL GLU ....        ... VAL THR ALA LYS THR GLY ASP ILE SER GLY
A C C A T T A A T G C G G C C A C A G G T A G C G T G G A A ....   ... G T A A C T G C T A A A A C A G G C G A T A T T A G T G G C
                              2170                         2190....                              2200                              2220
                                                                 ...                                                                 2210

THR ILE SER GLY ASN THR VAL ASN VAL THR ....        ... ALA THR ASP SER LEU THR THR GLN ALA SER
A C A A T T T C T G G T A A T A C A G T A A A T G T T A C A ....   ... G C A A C T G A T A G C T T A A C C A C C C A A G C A A G C
                              2230                         2250....                              2260                              2280
                                                                 ...                                                                 2270
```

FIG. 19L

SER SER ILE THR SER SER ASN GLY GLN THR ...
TCTAGCATTACCCTCAAGTAATGGTCAGACA...
       2290                2300              2310....
             ...    THR  LEU  THR  ALA  LYS  ASN  GLY  SER  ILE  ALA
             ...  ACTCTTACAGCCAAGAATGGCAGTATCGCA
                        2320              2330              2340

GLY SER ILE ASP ALA ALA ALA ASN VAL THR LEU ....
GGAAGTATTGATGCCGCTAATGTGACATTA...
       2350                2360              2370....
             ...  ASN  THR  THR  GLY  THR  LEU  THR  THR  VAL  ALA
             ...  AATACCACAGGCACCTTAACTACTGTAGCG
                        2380              2390              2400

GLY SER ASN ILE LYS ALA THR SER GLY THR ....
GGTTCAAACATTAAGGCAACCAGTGGCACT...
       2410                2420              2430....
             ...  LEU  ALA  ILE  ASN  ALA  LYS  ASP  ALA  LYS  LEU
             ...  TTAGCTATTAACGCAAAAGATGCTAAGTTA
                        2440              2450              2460

ASP GLY THR ALA SER GLY ASP ARG THR VAL ....
GATGGTACTGCATCAGGTGACCGCACAGTA...
       2470                2480              2490....

FIG.19M

```
                                          ...  VAL ASN ALA THR ASN ALA SER GLY SER GLY
                                          ...  GTAAATGCAACTAACGCAAGTGGCTCTGGT
                                                                              2510         2520

SER VAL THR ALA ALA THR SER SER ASN VAL ...       ... ASN ILE THR GLY ASP LEU SER THR ILE ASN
AGTGTGACTGCGGCAACCTCAAGTAACGTG...                 ...AATATCACTGGAGATTTAAGCACAAATAAAT
           2530                  2540                        2560                   2570             2580

GLY LEU ASN ILE ILE SER LYS ASN GLY LYS ...       ... ASN THR VAL VAL LEU LYS GLY ALA GLU ILE
GGATTAAATATCATTTCGAAAAATGGTAAA...                 ...AACACCGTAGTGTTAAAAGGTGCTGAAATT
           2590                  2600                        2620                   2630             2640

ASP VAL LYS TYR ILE GLN PRO GLY VAL ALA ...       ... SER ALA ASN GLU VAL ILE GLU ALA LYS ARG
GATGTGAAATATATTCAACCAGGTGTAGCA...                 ...AGTGCGAATGAGGTTATTGAAGCGAAGCGT
           2650                  2660                        2680                   2690             2700
```

FIG.19N

```
ALA LEU GLU LYS VAL LYS ASP LEU SER ASP ....
GCCCTTGAAAAAGTAAAAGATTTATCTGAT....
         2710              2720         2730....
                          ... GAA GAA AAA GAG AAA CAT TAG CTA AAA CTT GGT
                          ...GAAGAAAGAGAAACATTAGCTAAAACTTGGT
                                  2740         2750         2760

VAL SER ALA VAL ARG PHE VAL GLU PRO ASN ....
GTAAGTGCTGTACGTTTTGTTGAGCCAAAT....
         2770              2780         2790....
                          ... AAT ACA ATT ACA GTC AAT ACA CAA AAT GAA
                          ...AATACAATTACAGTCAATACACAAAATGAA
                                  2800         2810         2820

PHE THR ARG PRO SER SER GLN VAL THR ....
TTTACAACCAGACCGTCAAGTCAAGTGACA....
         2830              2840         2850....
                          ... ATT TCT GAA GAC AAG GCG TGT TTC TCA AGT
                          ...ATTTCTGAAGACAAGGCGTGTTTCTCAAGT
                                  2860         2870         2880
```

FIG. 190

```
GLY ASN GLY ALA ALA VAL CYS THR ASN VAL ...      THR ASP ASP ARG GLN ***
GGTAATGGTGCAGCAGTATGTACTAATGTT...     ...ACTGACGATAGACAGTAA
         2890              2900         2910...           2920
                                           :
                                           :
```

FIG. 20A

K1 hmw1A sequence

```
LYS GLU TRP LEU LEU ASP PRO ASP ASN VAL...
AAAGAGTGGTTGTTAGACCCGGATAATGTA...
         10          20          30...
                                        ...SER ILE ASN ALA PRO ALA LEU GLY ARG THR
                                        ...TCTATTAATGCACCCGCACTTGGACGTACT
                                              40          50          60

GLU SER THR PRO ASN ASN ASN GLU TYR ASP...
GAGAGTACCCCAAATAACAATGAGTACGAC...
         70          80          90...
                                        ...SER PRO ASN GLN ILE ASN TYR LYS ASN LYS
                                        ...TCGCCAAATCAAATTAACTATAAAAACAAA
                                             100         110         120

PRO SER LEU SER THR LEU THR ASN THR THR...
CCATCCCTAAGTACACTAACAAACACAACA...
        130         140         150...
                                        ...LEU GLU ILE LEU LYS ARG ASN THR SER
                                        ...CTTGAGAGAATATTAAAAAGAAACACCCTCT
                                             160         170         180
```

FIG. 20B

```
VAL ASN ILE THR ALA THR LYS THR ILE THR ...
GTTAATATCACTGCCACCAAAACAATCACA...
             190              200           210....

... VAL ASN SER ASP ILE ASN ILE GLY ASP SER
        ...GTTAATAGTGATATCAATATTGGAGACAGC
                  220              230              240

SER HIS LEU THR LEU TRP SER GLU GLY GLN ...
TCCCACTTAACCCTTTGGAGTGAGGGTCAG...
             250              260           270....

... GLY ARG GLY ASN VAL THR GLY ASN
        ...GGGAGAGGCGGCGTTAATGTTACAGGCAAT
                  280              290              300

ILE THR SER THR THR ASN GLY ASN LEU THR ...
ATTACTTCTACTACCAACGGAAACTTAACC...
             310              320           330....

... ILE TYR SER GLY TRP VAL ASP VAL HIS
        ...ATTTACTCTGGCGGATGGGTTGATGTTCAT
                  340              350              360

LYS ASN ILE THR LEU LYS SER GLY TYR LEU ...
AAAAACATTACACTTAAATCAGGGTACTTA....
             370              380           390....
```

FIG. 20C

```
                      ... ASN ILE THR THR LYS GLN GLY ASP ILE ALA
                      ... A A C A T T A C A A C T A A A C A A G G A G A C A T C G C C
                      ...                      400                      410                      420

PHE GLU ASP LYS PRO GLY LEU SER ASN LEU ...
T T C G A A G A C A A A C C A G G G C T G A G C A A C C T A ...
                    430                      440                      450 ...

... THR ILE THR ALA LYS GLY THR ILE ALA VAL
                      ... A C C A T T A C A G C T A A A G G G A C C A T T G C C G T G
                      ...                      460                      470                      480

ASN ASN LYS LYS GLY PHE ARG PHE ASP ASN ...
A A C A A C A A G A A A G G C T T T A G G T T T G A T A A T ...
                    490                      500                      510 ...

... VAL THR LEU ASN GLY THR GLY GLY LEU
                      ... G T C A C T C T A A A T G G A A C G G G A G G A G G G C T C
                      ...                      520                      530                      540

SER PHE LYS TYR ILE GLU THR GLY ASN ARG ...
T C T T T T A A A T A C A T C G A A A C C G G A A A T A G A ...
                    550                      560                      570 ...

... ASP SER ASN PHE GLU THR HIS PHE ARG GLY
                      ... G A T A G C A A T T T C G A A A C C C A T T T T A G A G G A
                      ...                      580                      590                      600
```

FIG.20D

ARG LEU ASN ILE SER GLY LYS VAL ASP ILE ....
AGATTAAATATTTCAGGGAAAAGTAGATATC....
         610                     620                    630....

... LEU MET GLN ALA ARG GLN GLU ASN TRP ASN
          ... TTAATGCAAGCAAGGCAGGAGAACTGGAAC
                         640                    650                     660

ARG ARG HIS TRP GLY ARG SER HIS TRP ASN ....
CGCAGACACTGGGGACGCTCCCACTGGAAT....
         670                     680                    690....

... VAL THR ARG LEU ASN VAL SER GLU ASN SER
          ... GTAACCCGATTGAACGTTTCTGAAAACAGT
                         700                    710                     720

TYR PHE ASN VAL THR ILE ASP SER SER GLY ....
TATTTTAACGTCACTATTGATAGCAGTGGC....
         730                     740                    750....

... SER ALA SER PRO GLY ALA GLY PRO LEU
          ... AGTGCCTCTTCCCCTGGCGCTGGCCCTCTG
                         760                    770                     780

ASN ALA GLN SER GLY LEU ASN GLY ILE SER ....
AATGCCCAATCGGGTTTAAATGGCATATCG....
         790                     800                    810....

FIG.20E

```
              ...  PHE ASN ASN ASP THR VAL PHE ASN ILE ALA
              ...  T T T A A T A A T G A C A C T G T T T T A A T A T T G C A
                                       820              830             840

ALA SER SER ALA VAL ASN PHE ASN ILE LYS  ...       ...  PRO PRO ILE VAL ASP LYS VAL THR ASN GLY
G C A A G T T C G G C G G T T A A C T T T A A C A T C A A A  ...       ...  C C A C C A A T A G T A G A C A A A G T A A C C A A C G G G
            850              860             870                              880             890             900

ASN HIS THR LEU PHE LYS GLY ASN ILE SER  ...       ...  VAL LEU GLY GLY GLY MET SER THR PHE ILE
A A T C A C A C A T T A T T C A A A G G G A A T A T T T C A  ...       ...  GLY GLY ASP VAL ASN PHE HIS P
                                                                         G T T T T A G G G G G G G G A T G T C A A C T T T C A T T
            910              920             930                              940             950             960

HE ASN ALA SER SER SER ASN TYR GLN THR  ...
T T A A C G C C T C C T C C A G C A A C T A C C A G A C T T  ...
            970              980             990
```

FIG. 20F

```
                                         ...TYR GLY VAL ILE ILE GLU SER GLN ASN PHE S
                                         ...ATGGCGTGATTATAGAGTCACAAAACTTTA
                                                1000           1010          1020

ER ALA SER GLY GLY SER SER LEU LYS PHE ...           ...LYS SER GLU GLY SER THR HIS ALA ALA PHE T
GTGCCTCAGGAGGGTCAAGCTTAAAATTCA...                    ...AAAGCGAAGGTTCGACACACGCCCGCTTTA
       1030              1040         1050...                  1060          1070          1080

HR ILE LYS ASN ASP LEU ILE LEU ASN ALA ...           ...THR GLY GLY ASN ILE SER LEU ASN GLN VAL A
CAATAAAAAATGATTTAATTTTAAATGCCA...                    ...CTGGGGGGCAATATCATTGAACCAAGTTG
       1090              1100         1110...                  1120          1130          1140

LA GLY ILE ASP SER ASN LEU LYS LYS SER ...           ...LEU ILE ALA ASN LYS ASN ILE THR PHE GLU G
CAGGTATTGATAGTAATCTCAAAAAAAGCC...                    ...TTATAGCCAATAAAACATAACCTTTGAAG
       1150              1160         1170...                  1180          1190          1200
```

FIG. 20G

```
LY  GLY ASN ILE THR LEU ALA ALA ASP LYS ....
G G G G C A A T A T C A C C C T T G C A G C C G A T A A A A . . .
         1210                    1220                   1230....
                    ...LYS PRO ILE GLU ILE LYS GLY ASN ILE THR V
                    ...A A C C A A T A G A A A T C A A A G G T A A T A T T A C T G
                            1240                    1250                    1260

AL  LYS GLU GLY ALA ASN VAL THR LEU ARG ....
T T A A A G A A G G A G C C A A T G T C A C C C T T C G T A . . .
         1270                    1280                    1290....
                    ...SER ALA ASN TYR GLY ASN ASP LYS SER ALA L
                    ...G C G C G A A T T A T G G T A A T G A C A A A T C A G C T T
                            1300                    1310                    1320

EU  SER ILE ARG GLY ASN VAL THR ASN LYS ....
T A A G T A T A A G A G G A A A T G T C A C T A A T A A A G . . .
         1330                    1340                    1350....
                    ...GLY ASN LEU THR VAL THR GLY SER ALA ILE A
                    ...G C A A T C T C A C C G T T A C C G G C T C C G C T A T C A
                            1360                    1370                    1380

SN  ILE GLU LYS ASN LEU THR VAL GLU GLY ....
A T A T A G A A A A A A T C T T A C C G T T G A A G G T A . . .
         1390                    1400                    1410....
```

FIG.20H

```
ER  PHE ASN VAL SER GLY LEU PHE ASP ASN ...SER ALA LYS PHE LEU ALA ASN PRO ASN TYR S
GCTTTAACGTATCCGGCCTATTTGACAACC.......GTGCTAAGTTTTTAGCTAAATCCAAATTACA
         1450                1460          1470...                 1420                1430                1440

...GLN GLY LYS SER ASN ILE SER ILE ALA LYS G
...AAGGCAAGTCAAACATTTCCATCGCTAAGG
                    1480                1490                1500

LY GLY ALA ILE PHE LYS ASP ILE GLU ASN ...THR GLY SER LEU ASN ILE THR THR LYS SER A
GAGGAGCTATTTTTAAAGATATCGAGAATA.......CTGGCAGTCTGAATATTACCACTAAATCCG
         1510                1520          1530...                 1540                1550                1560

SP SER ASN HIS HIS THR ILE ILE LYS GLY ...ASN ILE THR ASN ARG LYS GLY ASP LEU ASN I
ACTCCAACCACCACTATTATAAAGGGTA.......ATATAACTAACAGAAAAGGTGATTTAAATA
         1570                1580          1590...                 1600                1610                1620
```

FIG. 20I

```
ILE  THR  ASN  ASN  GLY  ASP  ASN  THR  GLU  ILE                                      ...
TCACGAATAATGGTGATAATACTGAAATCC...
                  1630              1640            1650...

...GLN  ILE  GLY  GLY  ASN  ILE  SER  GLN  LYS  GLU  G
     ...AAAATTGGCGGCAATATCTCGCAAAAGAAG
              1660              1670              1680

LY   ASN  LEU  THR  ILE  SER  SER  ASP  LYS  VAL                                      ...
GCAATCTCACAATTTCTTCTGATAAAGTCA...
                  1690              1700            1710...

...ASN  ILE  THR  GLU  ARG  ILE  THR  ILE  LYS  ALA  G
     ...ATATTACCGAGCGGATAACAATCAAAGCAG
              1720              1730              1740

LY   VAL  ASN  GLY  ASP  ASN  SER  ASP  SER  ASN                                      ...
GCGTTAATGGGGATAACTCTGATTCAAATG...
                  1750              1760            1770...

...GLU  ALA  THR  SER  ALA  ASN  LEU  THR  ILE  LYS  T
     ...AGGCAAACAAGTGCTAACCATTAAAA
              1780              1790              1800

HR   LYS  GLU  LEU  LYS  LEU  THR  ASN  ASP  LEU                                      ...
CCAAAGAGTTAAAATTAACAAACGACCTAA...
                  1810              1820            1830...
```

FIG. 20J

```
HR  ALA  LYS  ASP  ASN  SER  ASN  LEU  THR  ILE  ...ASN  ILE  SER  GLY  PHE  ASN  LYS  ALA  GLU  ILE  T
CAGCTAAAAGATAACAGTAATTAACTATTG....     ....ATATTTCAGGTTTTAATAAAGCAGAAATTA
         1870           1880   1890....                1840           1850           1860

...GLY  ASP  ASN  SER  ASP  ALA  GLY  ASN  THR  ASP  A
                                        ...GCGATAACAGTGACGCTGGCAATACTGACG
                                                1900           1910           1920

LA  LYS  LYS  VAL  THR  PHE  SER  ASN  VAL  LYS  ...ASP  SER  LYS  ILE  SER  ALA  SER  ASP  HIS  ASN  V
CTAAAAAAGTAACCTTTAGCAATGTTAAAG....      ...ATTCAAAAATCTCTGCTAGCGACCATAATG
         1930           1940   1950....                1960           1970           1980

AL  THR  LEU  ASN  SER  LYS  VAL  GLU  THR  SER  ...GLY  ASP  THR  ASP  SER  THR  GLU  ASP  GLY  GLY  A
TAACGCTAAACAGCAAAGTGGAAACATCTG....      ...GCGATACTGACAGCACTGAAGATGGCGGCA
         1990           2000   2010....                2020           2030           2040
```

FIG. 20K

```
SN  ASN  ASN  THR  GLY  LEU  THR  ILE  THR  ALA                   ...
A C A A T A A C A C C G G C T T A A C T A T T A C T G C A A...
                    2050                    2060                    2070

...LYS  ASN  VAL  THR  VAL  ASN  ASN  ILE  THR  S
                                   ...A A A A T G T A A C A G T A A A C A A C A A T A T T A C T T
                                                   2080                    2090                    2100

ER  HIS  LYS  THR  VAL  ASN  ILE  THR  ALA  SER                   ...
C T C A C A A A A C A G T A A A T A T C A C T G C G T C A G...
                    2110                    2120                    2130

...GLU  ASN  VAL  THR  THR  LYS  ALA  GLY  THR  THR  I
                                   ...A A A A T G T T A C C A C C A A A A G C G G G C A C A A C C A
                                                   2140                    2150                    2160

LE  ASN  ALA  THR  GLY  SER  VAL  GLU  VAL                   ...
T T A A T G C A A C C A C A G G T A G C G T A G A A G T A A...
                    2170                    2180                    2190

...THR  ALA  LYS  THR  GLY  ASP  ILE  LYS  GLY  GLY  I
                                   ...C A G C C A A A A C A G G T G A T A T T A A A G G T G G A A
                                                   2200                    2210                    2220

LE  GLU  SER  ASN  SER  GLY  ASN  VAL  ASN  ILE                   ...
T T G A A T C C A A T T C C G G T A A T G T A A A T A T T A...
                    2230                    2240                    2250
```

FIG.20L

```
                        ...THR ALA SER GLY ASP THR LEU ASN VAL SER A
                        ...CAGCGAGCGGCGACACGCTTAATGTAAGTA
                                         2260                    2270                   2280
SN ILE THR GLY GLN ASN VAL THR VAL ALA ...
ACATCACAGGTCAAAAATGTGACAGTGGCAG...
           2290                    2300                 2310....
                        ...ALA ALA SER GLY ALA VAL THR THR LYS G
                        ...CAGCCTCAGGTGCCGTAACAACCACAAAAG
                                         2320                     2330                  2340
LY SER THR ILE ASN ALA THR THR GLY ASN ...
GATCAAACTATTAATGCAACAACTGGTAATG...
           2350                   2360                  2370....
                        ...ALA ASN ILE THR THR LYS THR GLY GLU ILE A
                        ...CAAATATTACAACCAAAAACAGGTGAAATTA
                                         2380                    2390                   2400
SN GLY GLU VAL LYS SER ALA SER GLY ASN ...
ATGGCGAAGTTAAATCAGCTTCCGGTAATG...
           2410                   2420                  2430....
                        ...VAL ASN ILE THR ALA SER GLY ASN THR LEU A
                        ...TAAATATTACAGCGAGCGGCAATACACTTA
                                         2440                    2450                   2460
```

FIG.20M

SN  VAL  SER  ASN  ILE  THR  GLY  GLN  ASN  VAL  ...
A T G T A A G T A A C A T C A C T G G T C A A A A T G T A A ...
                    2470                      2490
                                        2480

...THR  VAL  THR  ALA  ASN  SER  GLY  ALA  ILE  THR  T
        ....C A G T A A C A G C A A A C T C A G G T G C C A T A A C A A
                          2500                      2520
                                        2510

HR  THR  GLU  GLY  SER  THR  ILE  ASN  ALA  THR  ...
C C A C A G A A G G C T C A A C T A T T A A C G C G A C A A ...
                    2530                      2550
                                        2540

...THR  GLY  ASP  ALA  ASN  ILE  THR  THR  GLN  THR  G
        ....C A G G T G A T G C A A A T A T T A C A A C C C A A A C A G
                          2560                      2580
                                        2570

LY  ASN  ILE  ASN  GLY  LYS  VAL  GLU  SER  SER  ...
G T A A T A T T A A T G G T A A A G T T G A A T C C A G T T ...
                    2590                      2610
                                        2600

...SER  GLY  SER  VAL  THR  LEU  ILE  ALA  THR  GLY  G
        ....C T G G T T C T G T G A C G C T T A T T G C A A C T G G A C
                          2620                      2640
                                        2630

LN  THR  LEU  ALA  VAL  GLY  ASN  ILE  SER  GLY  ...
A A A C T C T T G C T G T A G G T A A T A T T T C A G G T G ...
                    2650                      2670
                                        2660

FIG.20N

```
...ASP THR VAL THR ILE THR ALA ASP LYS GLY L
....A C A C T G T T A C C A T T A C T G C G G A T A A A G G T A
                                                          2700
            2680                      2690
...

YS LEU THR THR GLN THR SER SER LYS ILE                    ...
A A T T A A C C A C A C A A A C A A G C T C T A A G A T T A
            2710                      2720        2730
...

...ASN GLY THR LYS SER VAL THR THR SER SER G
                ....A C G G A A C T A A G A G T G T A A C C A C C T C A A G C C
                                                          2760
                            2740                      2750
...

LN SER GLY ASP ILE SER GLY THR ILE SER                    ...
A A T C A G G T G A T A T T A G T G G C A C A A T T T C T G
            2770                      2780        2790
...

...GLY ASN THR VAL SER VAL SER ALA THR GLY S
                ....G T A A T A C G G T A A G C G T T A G T G C G A C C G G T A
                                                          2820
                            2800                      2810
...

ER LEU THR THR GLN ALA GLY SER LYS ILE                    ...
G C T T G A C C A C T C A A G C A G G C T C A A A A A T T G
            2830                      2840        2850
...

...GLU ALA LYS THR GLY GLU ALA ASN VAL THR S
                ....A A G C A A A A A C A G G T G A G G C T A A T G T A A C A A
                                                          2880
                            2860                      2870
...
```

FIG.20O

```
ER  ALA THR GLY THR ILE ILE GLY GLY THR ILE ...
GCGCAACAGGTACAATTGGCGGTACAATCT...
         2890              2900              2910
                                   ...SER GLY ASN THR VAL ASN VAL THR ALA ASN T
                                   ...CTGGCAATACAGTAAATGTTACAGCAAATA
                                              2920              2930              2940

HR  ASP ASN LEU THR ILE LYS ASP GLY ALA ...
CTGATAATTTAACTATTAAAGATGGCGCAA...
         2950              2960              2970
                                   ...ARG ILE LYS ALA THR GLY GLY ALA VAL THR L
                                   ...GAATTAAAGCAACGGGCGGAGCTGTGACTT
                                              2980              2990              3000

EU  THR ALA THR GLY GLY THR LEU THR THR ...
TAACCGCAACAGGAGGTACTTTAACCACCG...
         3010              3020              3030
                                   ...GLU THR SER SER ASP ILE THR ACC TCA AGC AAT G
                                   ...AAACAAGTTCTGATATTACCTCAAGCAATG
                                              3040              3050              3060

LY  GLN THR THR LEU THR ALA LYS ASP SER ...
GTCAGACAACTTCTCACGGCCAAGGATAGCA...
         3070              3080              3090
```

FIG.20P

```
                    ...SER ILE ALA GLY SER ILE ASN ALA ALA ASN  V
                    ....GTATCGCAGGAAGCATCAATGCCGCCAATG
                                  3100              3110         3120

AL  THR LEU ASN THR THR GLY THR LEU THR ....
TGACATTAAATACCACAGGCACTTTAACTA...
       3130              3140       3150....

...THR VAL ALA GLY SER LYS ILE GLU ALA ALA  S
                    ...CTGTGGCAGGTTCAAAAATCGAGGCAGCCA
                              3160              3170         3180

ER  GLY THR LEU VAL ILE ASN ALA LYS ASP ....
GTGGCACCCTGGTTATTAATGCAAAAGATG...
       3190              3200       3210....

...ALA GLN LEU ASP GLY ALA ALA SER GLY ASP  H
                    ....CTCAGTTGGACGGGGCGGCATCAGGTGACC
                              3220              3230         3240

IS  THR VAL VAL ASN ALA THR ASN ALA ASN ....
ACACAGTAGTAAATGCAACCAACGCAAACG...
       3250              3260       3270....

...GLY SER GLY SER VAL ILE ALA THR THR SER  S
                    ...GCTCCGGCAGCCGTAATCGCGACAACCTCAA
                              3280              3290         3300
```

FIG.20Q

```
ER  ARG VAL ASN ILE THR GLY ASP LEU ILE ...
GCAGAGTGAACATCACTGGGGATTTAATCA...
    3310                        3320            3330....
            ...THR ILE ASN GLY LEU ASN ILE ILE SER LYS  A
            ...CAATAAATGGATTAAATATCATTTCAAAAA
                    3340                        3350                3360
SN  GLY LYS ASN THR VAL LEU LEU LYS GLY ...
ACGGTAAAAACACCGTGCTGTTAAAAGGTG...
    3370                        3380            3390....
            ...VAL GLU ILE ASP VAL LYS TYR ILE GLN PRO  G
            ...TTGAAATTGATGTGAAATACATTCAACCGG
                    3400                        3410                3420
LY  ILE ALA SER VAL ASN GLU ILE GLU VAL ILE GLU ...
GCATAGCGAGCGTAAATGAAATTGAAG...
    3430                        3440            3450....
            ...ALA LYS ARG ALA LEU GLU LYS VAL LYS ASP  L
            ...CGAAAACGCGCCCTTGAGAAAGTAAAAGATT
                    3460                        3470                3480
EU  SER ASP GLU GLU ARG GLU THR LEU ALA ...
TATCTGACGAAGAAAGAGAAACATTAGCTA...
    3490                        3500            3510....
```

FIG. 20R

```
                              ...LYS LEU GLY VAL SER ALA VAL ARG PHE ALA G
                              ...A A C T T G G C G T G A G C G C T G T A C G T T T T G C T G
                              ...                                 3520                    3530                    3540

LU  PRO ASN ASN ALA ILE THR ILE ASN THR ...            ...GLN ASN GLU PHE THR THR ARG PRO LEU SER G
A G C C A A A T A A T G C C A T T A C G A T T A A T A C A C...  ...A A A A T G A G T T T A C A A C C A G A C C A T T A A G T C
                3550                          3560                   3570...              ...                                 3580                    3590                    3600

IN  VAL THR ILE SER GLU GLY LYS VAL CYS ...            ...PHE LEU ILE GLY ASN GLY ALA THR ILE CYS T
A A G T G A C A A T T T C T G A A G G T A A G G T A T G T T...  ...T C T T A A T C G G C A A T G G C G C A A C A A T A T G C A
                3610                          3620                   3630...              ...                                 3640                    3650                    3660

HR  ASN ILE ALA ASP ILE GLU ARG ***
C C A A T A T T G C T G A T A T T G A G C G G G T A G
                3670                          3680
```

FIG. 21A

K21 hmw1A sequence

```
    LYS GLU TRP LEU LEU ASP PRO ASP ASP ILE ....
    AAAGAGTGGTTGTTAGACCCGGATGATATA...
                    10              20              30....

ASN ILE VAL SER ASN GLY SER ASN ILE ASP ALA
    ...AATATTGTCAACGGAAGTAATATTGATGCT
                    40              50              60

GLN LEU GLN PRO GLY ARG GLY ASP THR PRO ....
    CAATTACAGCCAGGTAGAGGCGATACACCC...
                    70              80              90....

ASN LYS VAL SER ALA GLU GLY LEU THR SER
    ...AACAAGGTTTCAGCAGAAGGCTTAACATCC
                    100             110             120

ILE ASN ASN ALA THR LEU SER THR ALA LEU ....
    ATTAACAATGCCACATTATCCACCGCTTTA...
                    130             140             150....

GLN LYS GLY ILE GLU VAL ASN ILE SER ALA
    ...CAAAAGGGTATTGAGGTCAACATTTCTGCC
                    160             170             180
```

FIG.21B

```
THR LYS ASN VAL THR VAL ASN ALA ASP VAL ...
A C A A A A A T G T A A C C G T C A A C G C G G A T G T T ...
                                                  210....
                                                        ...ASP VAL LYS ASN GLY THR LEU VAL LEU HIS
                                                        ...G A T G T T A A A A C G G A A C A T T A G T A T T A C A T
                                                             220                    230                    240

SER GLN ARG ASN GLY VAL LYS ILE ASN GLY ...
T C A C A A A G G A A T G G A G T T A A A A T T A A C G G T ...
                    250                    260         270....
                                                            ... ASN ILE THR SER THR GLN ASN GLY ASN LEU
                                                            ... A A T A T T A C C T C A A C A C A A A A T G G T A A T T T A
                                                                 280                    290                    300

THR ILE LYS THR GLY GLY LYS VAL ASP VAL ...
A C C A T T A A A A C A G G T G G C A A G G T T G A T G T T ...
              310                    320         330....
                                                       ... HIS LYS ASN ILE THR LEU GLY MET GLY PHE
                                                       ... C A T A A A A A T C A C A C T T G G T A T G G G T T T T
                                                            340                    350                    360

LEU ASN ILE THR SER ASP ASN ASN ILE THR ...
T T G A A T A T T A C T T C C G A T A A T A A C A T C A C C ...
                    370                    380         390....
```

FIG. 21C

```
         PHE GLU LYS GLY ASP ASN LEU THR ILE THR
     ... TTT GAA AAA GGT GAT AAT CTA ACC ATT ACC
                      400               410               420

ALA GLN GLY ASN ILE ILE SER ASN GLN GLU ...
GCC CAA GGA AAT ATA ATC TCT AAT CAA GAG ...
             430               440               450 ...

ASN LYS GLN LEU ARG PHE SER ASN VAL SER
     ... AAT AAA CAA CTT AGA TTT AGT AAT GTA TCT
                      460               470               480

LEU ASN GLY MET GLY ALA GLY LEU THR PHE ...
TTA AAT GGG ATG GGT GCG GGT TTA ACT TTT ...
             490               500               510 ...

THR ALA ASN LYS GLY ASN HIS THR HIS LYS
     ... ACT GCA AAA TAA AGG TAA TCA TAC CCA TAA G
                      520               530               540

PHE ASP GLY THR LEU ASN ILE SER GLY LYS ...
TTT GAT GGC ACG CTT AAC ATT TCC GGA AAG ...
             550               560               570 ...

VAL VAL ILE ASN GLN THR THR PRO HIS ASN
     ... GTA GTA ATT AAT CAA ACC ACC TCA CAA C
                      580               590               600
```

FIG.21D

ILE ALA PRO TRP ASN ALA SER ALA ASP SER....
ATTGCTCCATGGAATGCAAGTGCAGACTCT....
610          620          630....

TYR TRP ASN VAL THR THR LEU THR LEU GLY
                     ...TACTGGAATGTAACTACTCTTACTTTAGGT
                        640          650          660

ASN ASN ALA GLN PHE THR PHE ILE LYS PHE ....
AATAATGCGCAATTTACCTTTATTAAATTT....
670          680          ...

VAL ASP SER ASN ARG SER VAL ALA LEU ASN
                     ...GTCGATAGCAACCGCTCGGTAGCTCTTAAT
                        690          700          710          720

SER GLY SER ARG SER PHE ALA GLY VAL LYS ....
AGCGGTTCAAGAAGTTTTGCGGGGGTAAAG....
730          740          750....

PHE TYR GLY LYS ASN ASN GLU MET LYS PHE
                     ...TTCTACGGCAAGAATAATGAAATGAAATTT
                        760          770          780

ASN ILE GLY ASP ASN ALA ASN VAL GLU PHE ....
AATATTGGTGATAATGCTAATGTTGAATTC....
790          800          810....

FIG. 21E

```
                          ... LYS LEU LYS SER ASN ASP ASN THR SER ASN
                          ... AAGTTAAAATCAAAATGATAATACAAGCAAC
                              820                830              840
                          ...

ASN LYS PRO LEU PRO ILE GLN PHE LEU SER ...
AACAAACCACTACCAATTCAGTTTTTATCT...
        850                 860         870...
                                                ...

... ASN ILE SER ALA THR GLY ASN GLY THR VAL
                          ... AATATCTCAGCCACTGGTAATGGCACTGTA
                              880                890              900
                          ...

SER PHE ASP ILE HIS ALA ASN LEU SER ALA ...
TCTTTTGATATACATGCCAACTTGTCAGCA...
        910                 920         930...
                                                ...

... ARG SER THR GLU LEU ASN MET SER LEU ILE
                          ... AGGTCAACTGAGTTAAATATGAGTTTAATT
                              940                950              960
                          ...

ASN ILE SER ASN GLY VAL ASN PHE SER ILE ...
AACATTTCTAATGGGGTTAATTTTTCCATA...
        970                 980         990...
                                                ...

... ASN SER HIS VAL ARG GLY ASN ASN ALA PHE
                          ... AACTCCCATGTTCGCGGTAATAATGCTTTT
                              1000              1010              1020
                          ...
```

FIG. 21F

```
GLU ILE LYS LYS ASP LEU ILE ILE ASN ALA....
GAAATCAAAAAAGATTTAATTATAAATGCA...
         1030              1040          1050...

...THR GLY SER ASN PHE ASN LEU LYS GLN THR
              ...ACTGGCTCGAATTTTAATCTTAAGCAAACG
                  1060              1070              1080

LYS ASP LYS PHE ASP ASN SER TYR GLU LYS....
AAAGATAAATTTGACAATAGTTACGAAAAA...
         1090              1100

...ASN ALA ILE PHE SER THR HIS ASN LEU THR
              ...AACGCCATTTCTCAACTCATAACCTAACC
                  1120              1130              1140

ILE LEU GLY GLY ASN VAL THR LEU GLY GLY....
ATTCTTGGGGGCAATGTTACTCTAGGTGGG...
         1150              1160              1170

...GLU ASN SER SER ASN ILE LYS GLY ASN
              ...GAAAATTCAAGTAGTAATATTAAAGGAAAT
                  1180              1190              1200

ILE ASN ILE ASN SER LYS ALA ASN VAL THR....
ATCAACATCAATAGCAAGGCAAATGTTACA...
         1210              1220              1230
```

FIG. 21G

```
              ...  LEU GLN ALA HIS ALA GLY THR SER HIS LEU
              ...  TTA CAA GCT CAT GCC GGC ACG AGT CAC CTT
                                1240          1250          1260

ASP LYS LYS GLU ARG THR LEU GLY ...
GAT AAA AAA GAA AGA ACC CTT GGC ...
        1270          1280          1290

...  ASN VAL SER VAL GLY GLY ASN LEU ASN ILE
              ...  AAT GTA TCT GTT GGG GGA AAT TTA AAC ATA
                                1300          1310          1320

ILE GLY SER ASN ALA HIS ILE ASP GLY ASN ...
ATT GGC TCA AAT GCA CAC ATA TTG ACG GCA AT ...
        1330          1340          1350

...  LEU SER ILE ALA GLU SER ALA LYS PHE GLN
              ...  CTT TCT ATT GCA GAA AGT GCT AAA TTT CAA
                                1360          1370          1380

GLY LYS THR ASN ASN ASN LEU ASN ILE THR ...
GGA AAA ACC AAT AAC AAC CTA AAT ATT ACC ...
        1390          1400          1410

...  GLY THR PHE ASN ASN GLY THR ALA ASP
              ...  GGC ACC TTT ACC AAC AAC GGC ACC GCC GAC
                                1420          1430          1440
```

FIG.21H

```
ILE ASN ILE LYS GLN GLY VAL VAL LYS LEU ...                                                                    ...
ATTAATATAAAACAAGGAGTGGTAAAACTC...                                                                              ...
        1450              1460              1470...
                                        ... GLN GLY ASP ILE THR ASN ASN GLY ASN LEU
                                        ...CAAGGTGATATTACCAATAACGGTAATTTA
                                              1480              1490              1500

ASN ILE THR THR ASN ALA SER VAL ASN GLN ....                                                                   ...
AATATCACTACTAACGCCTCAGTCAATCAA...                                                                              ...
        1510              1520              1530...
                                        ... LYS THR ILE ILE ASN GLY ASN ILE THR ASN
                                        ...AAAACCATTATTAACGGAAATATAACTAAC
                                              1540              1550              1560

LYS GLY ASP LEU ASN ILE LYS ASP ILE ....                                                                       ...
AAAAAGGCGACTTAAACATCAAGGATATT...                                                                               ...
        1570              1580              1590...
                                        ... LYS ALA ASN ALA GLU ILE GLN ILE GLY GLY
                                        ...AAAGCCAACGCCGAAATCCAAATTGGCGGC
                                              1600              1610              1620

ASN ILE SER GLN LYS GLU GLY ASN LEU THR ....
AATATCTCGCAAAAAGAAGGTAATCTCACG...
        1630              1640              1650
```

FIG. 21I

```
                              ILE SER SER ASP LYS ILE ASN ILE THR LYS
                           ...ATTTCTTCTGACAAAATTAATATCACCAAA
                           ...       1660           1670          1680

ARG ILE GLU ILE LYS ALA ASP THR ASP GLN...
CGGATAGAAATTAAGGCAGATACTGATCAA...
         1690           1700         1710...
                               ...GLY ASN SER ASP SER GLY VAL ALA SER ASN
                               ...GGGAATTCTGATTCAGGCGTAGCAAGTAAT
                               ...         1720          1730         1740

ALA ASN LEU THR ILE LYS THR LYS GLU LEU...
GCTAATCTAACCATTAAACCAAAGAGTTA...
         1750          1760         1770...
                               ...THR LEU THR ASP ASN LEU ASN ILE SER GLY
                               ...ACATTAACAGACAATCTAAACATTTCAGGT
                               ...        1780          1790         1800

PHE ASN LYS ALA GLU ILE THR ALA LYS ASP...
TTTAATAAAGCAGAAATTACAGCTAAAGAT...
         1810          1820         1830...
                              ...ASN SER ASP LEU ILE ILE GLY LYS ALA SER
                              ...AACAGTGATTTAATTATTGGCAAGGCTAGC
                              ...       1840          1850         1860
```

FIG.21J

```
SER ASP ASN SER ASN ALA LYS GLN ILE THR ...                   ... PHE ASP LYS VAL LYS ASP SER LYS ILE SER
AGTGACAACAGTAATGCTAAACAAATAACC...                              ...TTTGACAAGGTTAAAGATTCAAAAATCTCA
            1870              1880                                           1890              1900              1910              1920

ALA GLY ASN HIS ASN VAL THR LEU ASN SER ...                   ... LYS VAL GLU THR SER ASN SER ASP GLY SER
GCTGGCAATCACAATGTAAACACTAAATAGC...                             ...AAAGTGGAAACGTCTAATAGCGATGGTAGC
            1930              1940                                           1950              1960              1970              1980

THR GLY ASN GLY SER ASP ASP ASN ASN ILE ...                   ... GLY LEU THR ILE SER ALA LYS ASP VAL THR
ACCGGAAACGGTAGCGATGACAACAATATC...                              ...GGCTTAACTATTTCCGCAAAGATGTAACG
            1990              2000                                           2010              2020              2030              2040

VAL ASN SER ASN ILE THR SER HIS LYS THR ...
GTAAATAGTAATATCACCTCTCACAAAACA...
            2050              2060              2070
```

FIG.21K

```
             ... VAL ASN ILE SER ALA SER GLU GLY GLY ILE
             ... G T A A A T A T C T C T G C A T C A G A A G G A G G T A T C
                                  2080                 2090                 2100
             ...

THR THR LYS ALA GLY THR THR ILE ASN ALA ...
A C T A C T A A A G C A G G C A C A A C C A T T A A T G C G ...
                  2110                 2120                 2130 ...
                                                               ...

... THR THR GLY SER VAL GLU VAL THR ALA LYS
             ... A C C A C A G G T A G C G T G G A A G T A A C T G C T A A A
                                  2140                 2150                 2160
             ...

THR GLY ASP ILE SER GLY THR ILE SER GLY ...
A C A G G C G A T A T T A G C G G T A C G A T T T C C G G T ...
                  2170                 2180                 2190 ...
                                                               ...

... LYS THR VAL SER VAL THR ALA THR THR ASP
             ... A A G A C A G T A A G T G T T A C A G C A A C C A C C G A C
                                  2200                 2210                 2220
             ...

SER LEU THR VAL LYS GLY ALA LYS ILE ...
A G T T T A A C T G T T A A A G G T G C G C A A A A T T ...
                  2230                 2240                 2250 ...
                                                             ...

... ASN ALA THR GLU GLY THR ALA THR LEU THR
             ... A A T G C G A C A G A A G G A A C T G C A A C C T T A A C T
                                  2260                 2270                 2280
             ...
```

FIG.21L

```
ALA  SER  GLY  LYS  LEU  THR  THR  GLU  ALA....
GCATCATCGGGCAAATTAACCACCGAGGCC....
            2290                   2300                2310...

ASN  SER  ALA  ILE  SER  GLY  ALA  ASN  GLY  VAL
                 ...AACTCTGCGATTAGCGGGGCTAACGGTGTA
                        2320                2330                2340

THR  ALA  SER  SER  GLN  SER  GLY  ASP  ILE  SER....
ACTGCCTCAAGTCAATCAGGCGATATTAGC....
            2350                  2360                 2370...

GLY  THR  ILE  SER  GLY  LYS  THR  VAL  SER  VAL
                 ...GGTACGATTTCCGGTAAGACAGTAAGTGTT
                        2380                2390                2400

THR  ALA  SER  SER  GLY  SER  LEU  THR  VAL  GLY....
ACAGCAAGCTCTGGCAGTTTAACTGTTGGA....
            2410                  2420                 2430...

GLY  ASP  ALA  LYS  ILE  ASN  ALA  THR  GLU  GLY
                 ...GGTGACGCAAAATTAATGCGACAGAAGGA
                        2440                2450                2460

ALA  ALA  THR  LEU  THR  ALA  THR  LYS  GLY  THR....
GCTGCGACTTTAACTGCAACAAAAGGCACT....
            2470                  2480                 2490...
```

FIG.21M

```
ALA ASN GLU GLY THR   LEU VAL ILE LEU ASN ALA ...   LEU THR THR VAL LYS GLY SER ASN ILE ASP
GCAAACGAAGGCACC   CTTAGTTATTAACGCA...   TTAACTACCGTGAAGGGTTCAAACATTGAC
        2530              2540  2550                 2500      2510       2520

... GLN ASP ALA THR   LEU ASN GLY ASP ALA SER
                      ... CAAGACGCCACT   AAATGGTGATGCATCA
                                2550    2560          2570   2580

GLY ASP ARG THR GLU   VAL ASN ALA VAL ASN ....   ALA SER GLY ASN VAL THR ALA LYS
GGCGACCGTACAGAAGT   GAATGCAGTCAAC....   GCAAGCGGCTCTGGTAACGTAACTGCGAAA
        2590              2600   2610                2620        2630       2640

... ALA SER GLY ASP ...   LEU SER THR ILE ASN GLY LEU ASN ILE ILE
                      ... GCAAGCGGCGAT...   TTAAGCACAATAAATGGATTAAATATCATT
                              2650    2660   2670         2680      2690      2700

THR SER SER VAL ASN
ACCTCAAGCAGTGTG
        2650
```

FIG.21N

| SER | LYS | ASN | GLY | LYS | ASN | THR | VAL | VAL | LEU | ... |
|---|---|---|---|---|---|---|---|---|---|---|
TCGAAAAATGGTAAAAACACCGTAGTGTTA...
2710            2720            2730...

| | LYS | GLY | ALA | GLU | ILE | ASP | VAL | LYS | TYR | ILE |
|---|---|---|---|---|---|---|---|---|---|---|
...AAAGGTGCTGAAATTGATGTGAAATATATT
        2740            2750            2760

| GLN | PRO | GLY | VAL | ALA | SER | ALA | ASN | GLU | VAL | ... |
|---|---|---|---|---|---|---|---|---|---|---|
CAACCAGGTGTAGCAAGTGCGAATGAGGTT...
2770            2780            2790...

| | ILE | GLU | ALA | LYS | ARG | ALA | LEU | GLU | LYS | VAL |
|---|---|---|---|---|---|---|---|---|---|---|
...ATTGAAGCGAAGCGTGCCCTTGAAAAAGTA
        2800            2810            2820

| LYS | ASP | LEU | SER | ASP | GLU | ARG | GLU | THR | ... |
|---|---|---|---|---|---|---|---|---|---|
AAAGATTTATCTGATGAAAGAGAAACA...
2830            2840            2850...

| | LEU | ALA | LYS | LEU | GLY | VAL | SER | ALA | VAL | ARG |
|---|---|---|---|---|---|---|---|---|---|---|
...TTAGCTAAACTTGGTGTAAGTGCTGTACGT
        2860            2870            2880

| PHE | ILE | GLU | PRO | ASN | ASN | THR | ILE | THR | VAL | ... |
|---|---|---|---|---|---|---|---|---|---|---|
TTTATTGAACCAAATAATACCATTACGGTT...
2890            2900            2910...

FIG.210

```
                    ... ASN THR GLN ASN GLU PHE THR THR ARG PRO
                    ... A A C A C A A A A T G A G T T T A C A A C C A G A C C A
                    ...                                                    2940
                         2920                    2930

SER SER GLN VAL THR ILE SER GLU GLY LYS ...
T C A A G T C A A G T G A C A A T T T C T G A A G G T A A G ...
                                                          2970 ...
       2950               2960

... ALA CYS PHE SER SER GLY ASN GLY ALA ALA
                    ... G C G T G T T T C T C A A G T G G T A A T G G C G C A G C A
                    ...                                                    3000
                         2980                    2990

VAL CYS THR ASN VAL ALA ASP ASP GLY GLN ...
G T A T G T A C C A A T G T T G C T G A C G A T G G A C A G ...
                                                         3030 ...
        3010              3020

... GLN ***
                    ... C A G T A G
```

FIG. 22A

LCDC2 hmw2A sequence

```
LYS GLU TRP LEU LEU ASP PRO ASP ASP ...
A A A G A G T G G T T G T T A G A C C C G G A T G A T G....
                    10                  20
```

```
                           ...VAL SER ILE ASP ALA PRO SER ALA GLU ARG THR
                           ....T A T C C A T T G A C G C A C C T T C G G C T G A A C G C A C T
                                           30             40             50             60
```

```
ASP THR GLY GLU GLU ASP VAL GLU TYR THR ...
G A C A C T G G C G A A G A G A C G T G G A A T A C A C C G....
                    70                  80
```

```
                           ...GLY THR GLY ALA ASP ILE ASN HIS GLN LYS GLN
                           ....G A A C A G G G G C T G A T A T T A A C C A T C A A A A A C A A
                                           90            100            110            120
```

```
ASN SER GLU THR LYS SER THR LEU THR ...
A A C A G C G A A A C C A A G T C A A C A T T A A C A A....
                   130                 140
```

```
                           ...ASN THR THR LEU GLU GLY MET LEU LYS ARG GLY
                           ....A C A C A A C T C T T G A G G G G A T G T T A A A A A G G G G G
                                          150            160            170            180
```

FIG.22B

```
LEU PHE VAL ASN ILE THR ALA ARG ASN                    ...ILE ARG VAL ASN SER THR ILE ASN ILE GLY
CTTTTGTTAATATCACCGCCAGAAATA...                         ...AAATCCGAGTTAATAGCACCATCAATATCGGG
            190              200                            210              220              230              240

ASP SER GLY HIS LEU THR LEU TYR LYS                    ...LYS ARG ASN ARG SER ASP GLY ILE GLN ILE
GATAGCGGCCATTTAACCCTTTACAAAA...                        ...AAAGAAAAATCGTAGCGATGGTATTCAAATT
            250              260                            270              280              290              300

ASN LYS ASP ILE THR SER THR GLY GLY                    ...SER LEU THR ILE ASN SER ASP ASP TRP VAL ASP
AACAAGGATATTACTTCTACAGGCGGAA...                        ...GTTTAACTATTAACTTCCGACGACTGGGTTGAT
            310              320                            330              340              350              360

ILE HIS GLY ASN ILE THR LEU GLY GLU
ATTCATGGAAATATCACGCTTGGTGAGG...
            370              380
```

FIG. 22C

```
                                    ...GLY PHE LEU ASN ILE THR SER SER ASP SER VAL
                                    ...GCT TTT TTA AAA TAT TAC CTC TAG TGA TTC CGT G
                                       ...390           400           410           420

ALA PHE GLU GLY GLY GLY ASN GLY ASN LYS ...    ...GLY ARG SER SER ALA SER ALA GLN ILE ILE ALA
GCT TTC GAG GGT GGA AAC GGC AAT AAA G...        ...GAC GTA GCT CAG CAA GTG CTC AAA TTA TCG CG
            430           440                         450           460           470           480

GLN GLY THR ILE THR LEU THR GLY GLU ...         ...ASN LYS THR PHE ARG LEU ASN ASN VAL SER LEU
CAG GGT ACT ATA ACT CTT ACT GGA GAA A...        ...ATA AAA CCT TTA GAC TCA ACA ATG TCT TTA
            490           500                         510           520           530           540

ASN GLY THR GLY ASN GLY LEU SER ILE ...         ...ILE SER THR ALA SER ASN LEU SER HIS ARG LEU
AAT GGG ACG GGT AAT GGT CTA AGT ATT A...        ...TTT CAA CAG CAA GCA ATT TAT CTC ATA GAC TT
            550                                       570           580           590           600
                                                    560
```

FIG.22D

```
ASP GLY GLU ILE ASN VAL SER GLY ASN       ...
GACGGTGAAATTAATGTATCTGGAAATG              ...
                610           620         ...

...VAL THR ILE ASN GLN THR THR GLN GLN ASN ILE
                              ...TAACAATTAATCAAACCACGCAGCAAACATT
                                     630           640           650          660

GLU TYR TRP LYS ALA SER SER ASP SER        ...
GAATACTGGAAAGGCTAGCAGCGATTCTT              ...
                670           680          ...

...TYR TRP ASN VAL THR SER PHE ASN LEU ARG GLU
                              ...ATTGGAATGTCACTTCTTTTAATTTGAGAGAA
                                     690           700           710          720

ASP SER LYS PHE THR PHE ILE LYS TYR        ...
GATTCAAAAGTTTACCTTTATCAAATACG              ...
                730           740          ...

...VAL ASN SER ALA ARG ASN GLY ASP VAL ARG GLY
                              ...TTAACTCTGCCAGAAATGGTGATGTAAGAGGA
                                     750           760           770          780

ARG SER PHE ALA GLY VAL ILE PHE ASN        ...
AGAAGTTTTGCAGGTGTGATATTTAATG               ...
                790           800          ...
```

FIG.22E

```
                        ...ALA LYS GLY LEU THR THR SER PHE ASN VAL LYS
                        ...C T A A A G G T C T C A C T A C A A G C T T T A A C G T C A A G
                               810             820             830             840

LYS GLY SER THR VAL ASP PHE LYS LEU...         ...LYS PRO ASN SER GLY TYR ASN SER GLN LYS ARG
A A A G G C T C G A C A G T T G A T T T T A A A T T A A...   ...A G C C A A A T T C A G G C T A T A A T T C A C A A A A A G G
              850             860                           870             880             890             900

ILE PRO ILE GLN PHE GLN SER ASN ILE...         ...SER VAL SER GLY GLY ARG VAL ASN ILE ASN
A T T C C A A T T C A A T T C C A A C A T C T...           ...C G G T C T C A G G A G G A A G G G T A A A C A T T A A C
              910             920                           930             940             950             960

THR LEU ALA ASN LEU THR GLY GLY GLY...         ...VAL GLU ILE ARG SER SER SER ILE ASN VAL SER
A C G C T C G C C A A T C T T A C A G G C G G A G G A G...   ...T T G A G A T A A G A T C G A G T T C A A T T A A T G T T T C T
              970             980                           990            1000            1010            1020
```

FIG.22F

```
ASP GLY SER THR LEU SER MET THR ALA ...
GATGGCTCAACCCTCTCTTATGACAGCTC...
         1030            1040
                              ...GLN ALA ARG ASP ARG ASN ALA PHE GLU ILE THR
                              ...AGGCTCGCGACAGGAATGCCTTTGAAATTACC
                                  1050            1060            1070            1080

LYS ASP LEU VAL ILE ASN ALA SER ASN ...
AAAGATTTAGTTATAAACGCAAGCAATT...
         1090            1100
                              ...SER ASN LEU SER ILE ILE GLN GLN ASN ASP GLY
                              ...CAAACCTATCTATTATACAGCAAAATGATGGA
                                  1110            1120            1130            1140

PHE ASP ASN ASN GLN LYS ALA ASN ALA ...
TTTGATAATAATCAAAAGGCAAATGCCA...
         1150            1160
                              ...ILE ASN SER LYS TYR ASN VAL THR ILE GLN GLY
                              ...TTAACTCAAAATATAACGTAACTATTCAAGGT
                                  1170            1180            1190            1200

GLY ASN VAL THR LEU GLY GLY GLN ASN ...
GGTAATGTTACCCTTGGCGGGCAAAATT...
         1210            1220
```

FIG.22G

```
                              ...SER SER SER THR ILE THR GLY SER VAL ASN ILE
                              ...C A A G C A G T A C A A T C A C A G G G A G T G T T A A T A T T
                                                         1240              1250              1260

GLY ALA ASN ALA ASN VAL THR LEU GLN ...           ...ALA HIS ASN GLY ASN ASP ARG ASN LYS LYS LEU
G G C G C T A A T G C A A A T G T T A C T T T G C A A G ... C C C A C A A T G G C A A T G A T A G A A A T A A A A A G C T A
            1270              1280                        1290              1300              1310              1320

THR PHE GLY ASN VAL SER VAL GLU GLY ...           ...GLU LEU ARG LEU VAL GLY ALA SER ALA ASN ILE
A C C T T C G G T A A T G T A T C T G T T G A A G G A G ... A A T T A A G G C T A G T T G G C G C A A G T G C A A A C A T T
            1330              1340                        1350              1360              1370              1380

ASN ASN ASN LEU SER VAL LYS SER GLY ...           ...ALA LYS PHE LYS ALA GLU THR ASN ASP ASN LEU
A A C A A C A A T C T T T A G T G T T A A G A G C G G T G ... C T A A A T T C A A A A G C A G A A A C A A A T G A C A A C C T A
            1390              1400                        1410              1420              1430              1440
```

FIG.22H

```
ASN ILE THR GLY THR PHE THR ASN ASN ...
AACATTACCGGCACCTTTACCAACAACG...
         1450            1460              ...
                                        ...GLY THR SER ILE ILE ASP VAL LYS LYS GLY ALA
                                        ...GCACCCTCCATAATTGATGTAAAAAAGGGGCG
                                           ...1470        1480         1490         1500

ALA LYS LEU GLY ASN ILE THR ASN ASP ...
GCAAAACTAGGCAATATTACCAATGATG...
         1510                 1520          ...
                                        ...GLY ASN LEU ASN ILE THR THR ASN ALA LYS ASN
                                        ...GTAATTTAAATATCACTACTAATGCTAAAAAC
                                           ...1530        1540         1550         1560

GLY GLN LYS SER VAL ILE ASN GLY ASN ...
GGTCAAAAAAGCGTTATCAACGGAAATA...
         1570                 1580           ...
                                        ...ILE THR ASN LYS ASN LYS GLY ALA LEU ASN ILE THR
                                        ...TAACTAACAATAAAGGTGCTTTAAATATTACG
                                           ...1590        1600         1610         1620

ASN ASN GLY ASN ASP THR GLU ILE GLN ...
AATAATGGTAATGACACTGAAATCCAAA...
         1630                 1640
```

FIG. 22I

```
        ...ILE GLY GLY ASN ILE SER GLN LYS GLU GLY ASN
        ...TTGGCGGCAATATCTCGCAAAAGAAGGTAAT
        ...1650                1660              1670              1680

LEU THR ILE SER SER ASP LYS ILE ASN
CTCACGATTTCTTCTGACAAAATTAATA...
        1690              1700              ...1710

...ILE THR LYS ARG ILE GLU ILE LYS ALA GLY THR
        ...TCACCAAAACGGATAGAAATTAAGGCAGGTACT
                         1720              1730              1740

ASP GLN GLY ASN SER ASP SER GLY VAL
GATCAAGGGAATTCTGATTCAGGCGTAG...
        1750              1760              ...1770

...ALA SER ASN ALA ASN LEU THR ILE LYS THR LYS
        ...CAAGTAATGCTAATCTAACCATTAAAACCAAA
                         1780              1790              1800

GLU LEU LYS LEU THR GLU ASN LEU ASN
GAATTGAAATTAACAGAAAACCTAAATA...
        1810              1820              ...1830

...ILE SER GLY PHE ASP LYS ALA GLU ILE VAL ALA
        ...TTTCAGGTTTTGATAAAGCAGAAATTGTAGCC
                         1840              1850              1860
```

FIG.22J

```
LYS GLU ASN ASN LEU ILE ILE GLY ...
AAAGAGAATAACAATTTAATTATTGGCA...
            1870         1880
                                    ...ASN ASN GLY ASP ASN ALA ASN ALA LYS THR
                                    ...ATAATAATGGCGACAATGCTAACGCCAAAACA
                                       ...1890         1900         1910         1920

VAL THR PHE ASN ASN VAL LYS ASP SER ...
GTAACTTTTAACAATGTTAAAGATTCAA...
            1930         1940
                                    ...LYS ILE SER ALA ASN GLY HIS ASN VAL THR LEU
                                    ...AAATCTCTGCTAACGGTCACAATGTGACACTA
                                       ...1950         1960         1970         1980

ASN SER LYS VAL GLU THR SER ASP GLY ...
AATAGCAAAGTGGAAACATCTGATGGAA...
            1990         2000
                                    ...ASN SER ASN THR GLU GLY ASN SER ASP ASN ASN
                                    ...ACAGTAACACTGAAGGTAATAGTGACAATAAC
                                       ...2010         2020         2030         2040

ALA GLY LEU THR ILE ASP ALA LYS ASN ...
GCCGGCTTAACTATCGATGCAAAAAATG...
            2050         2060
```

FIG.22K

```
                         ...VAL  THR  VAL  ASN  ASN  ASP  ILE  THR  SER  HIS  LYS
                         ...T A A C A G T A A A C A A C G A T A T C A C T T C T C A C A A A
                         ...2070                        2080                        2090                        2100

THR  VAL  ASN  ILE  THR  ALA  SER  GLU  ARG
A C A G T A A A T A T C A C T G C G T C A G A A A G G A...
                              2110                        2120

...ILE  ASP  THR  LYS  ALA  ASP  THR  THR  ILE  ASN  ALA
                         ...T T G A T A C T A A A G C T G A T A C A A C C A T T A A T G C A
                         ...2130                        2140                        2150                        2160

THR  THR  GLY  ASN  VAL  LYS  LEU  THR  ALA
A C C A C C G G C A A C G T G A A A C T A A C A G C T G...
                              2170                        2180

...VAL  THR  SER  ASP  ILE  GLN  GLY  ILE  LYS  SER
                         ...T A A C A A G T G A T A T C C A A G G T G G A A T T A A A T C T
                         ...2190                        2200                        2210                        2220

ASN  SER  GLY  ASP  VAL  ASN  ILE  THR  THR
A A T T C T G G T G A T G T A A A T A T C A C A A C C A...
                              2230                        2240

...SER  THR  GLY  SER  ILE  ASN  GLY  LYS  ILE  GLU  SER
                         ...G C A C A G G T A G C A T T A A C G G T A A A A T T G A A T C C
                         ...2250                        2260                        2270                        2280
```

FIG. 22L

```
LYS SER GLY SER VAL THR LEU THR ALA ...
AAGTCTGGCTCTGTAACACTTACCGCAA...
         2290                    ...2300
                    THR GLU LYS THR LEU THR VAL GLY ASN VAL SER
                    ...CCGAAAAAACTCTTACTGTAGGCAATGTTTCG
                       ...2310        2320        2330        2340

GLY ASN THR VAL THR VAL THR ALA ASN ...
GGCAACACCGTTACTGTTACTGCAAATA...
         2350                    ...2360
                    ARG GLY ALA LEU THR THR LEU ALA GLY SER THR
                    ...GAGGTGCATTAACCACTTTGGCAGGCTCTACG
                       ...2370        2380        2390        2400

ILE ASN GLY THR ASN GLY VAL THR THR ...
ATTAACGGGACTAACGGTGTAACTACCT...
         2410                    ...2420
                    SER SER GLN SER GLY GLU ILE GLY GLU VAL
                    ...CAAGTCAATCAGGCGAGATTGGCGGTGAGGTT
                       ...2430        2440        2450        2460

THR GLY LYS THR VAL SER VAL THR ALA ...
ACTGGTAAGACAGTAAGTGTTACAGCAA...
         2470                    ...2480
```

FIG.22M

```
           ...THR ALA GLY SER LEU THR VAL LYS GLY GLY ALA
           ...CTGCCGGGCAGCTTAACTGTTAAAGGTGGCGCA
              ..2490                                  2500                                  2510                              2520

LYS ILE ASN ALA THR GLU GLY THR ALA...
AAAATTAATGCGACAGAAGGAACTGCAA...
                    2530                                  2540                                  ...THR LEU THR ALA SER SER GLY LYS LEU THR THR
                                                                                            ...CCTTAACTGCATCATCGGGCAAATTAACCACC
                                                                                                ...2550                            2560                              2570                              2580

GLU ALA SER SER ASN ILE THR SER ALA...
GAGGCTAGCTCAAACATCACTTCAGCCA...
                    2590                                  2600                                  ...LYS GLY GLN VAL ASP LEU SER ALA GLN ASP GLY
                                                                                            ...AAGGTCAGGTAGACCTTTCAGCTCAGGATGGT
                                                                                                ...2610                            2620                              2630                              2640

SER ILE ALA GLY GLN ILE SER ALA ALA...
AGCATTGCAGGACAAATTAGTGCAGCTA...
                    2650                                  2660                                  ...ASN VAL THR LEU ASN THR THR GLY THR LEU THR
                                                                                            ...ATGTAACACTGAATACTACAGGCACTCTAACT
                                                                                                ...2670                            2680                              2690                              2700
```

FIG.22N

```
THR VAL GLU GLY SER SER ILE ASN ALA ...
ACCGTAGAGGGTTCAAGCATTAACGCAA...
                2710              2720
                                                    ...ASN GLU GLY THR LEU VAL ILE ASN ALA ASN ASP
                                                    ...ACGAAGGCACCTTGGTTATTAACGCAAACGAC
                                                    ...2730          2740              2750              2760

ALA LYS LEU ASP GLY LYS ALA SER GLY ...
GCCAAGTTAGATGGTAAGGCATCAGGTA...
            2770              2780
                                                    ...ASN ARG THR GLU VAL ASN ALA THR ASN ALA SER
                                                    ...ACCGTACAGAAGTAAATGCAACTAACGCAAGC
                                                    ...2790          2800              2810              2820

GLY SER GLY SER VAL THR ALA LYS THR ...
GGCTCTGGTAGCGTGACTGCGAAAACCT...
            2830              2840
                                                    ...SER SER SER VAL ASN ILE THR GLY ASP LEU ASN
                                                    ...CAAGCAGGCGTGAATATCACCGGGGATTTAAAC
                                                    ...2850          2860              2870              2880

THR ILE ASN GLY LEU ASN ILE ILE SER ...
ACAATAAATGGGTTAAATATCATTTCGG...
            2890              2900
```

FIG. 22O

```
          ...GLU ASN GLY ARG ASN THR VAL ARG LEU ARG GLY
          ...A A A A T G G T A G A A A C A C T G T G C G C T T A A G A G G C  2940
          ...2910                      2920              2930

LYS GLU ILE GLU VAL LYS TYR ILE GLN  ...PRO GLY VAL ALA SER VAL GLU GLU VAL ILE GLU
A A G G A A A T T G A G G T G A A A T A T A T C C A G C...C A G G T G T A G C A A G T G T A G A A G A A G T A A T T G A A  3000
                  2950                2960              ...2970          2980            2990

ALA LYS ARG VAL LEU GLU LYS VAL LYS  ...ASP LEU SER ASP GLU GLU ARG GLU THR LEU ALA
G C G A A A C G C G T C C T T G A G A A A G T G A A A G...A T T T A T C T G A T G A A G A A A G A G A A A C A T T A G C T  3060
                  3010                                ...3030          3040            3050

LYS LEU GLY VAL SER ALA VAL ARG PHE  ...ILE GLU PRO ASN ASN THR ILE THR VAL ASN THR
A A A C T T G G T G T A A G T G C T G T A C G T T T T A...T T G A A C C A A A A T A A T A C C A T T A C G G T T A A C A C A  3120
                  3070                3080            ...3090          3100            3110
```

FIG.22P

GLN ASN GLU PHE THR THR ARG PRO SER ...
CAAAATGAGTTTACAACCAGACCATCAA...
         3130                3140

...SER GLN VAL THR ILE SER GLU GLY LYS ALA CYS
...GTCAAGTGACAATTTCTGAAGGTAAGGCGTGT
   ...3150              3160              3170           3180

PHE SER SER GLY ASN GLY ALA ALA VAL ...
TTCTCAAGTGGTAATGGCGCAGCAGTAT...
         3190                3200         ...3210

...CYS THR ASN VAL ALA ASP ASP GLY GLN GLN ***
...GTACCAATGTTGCTGACGATGGACAGCAGTAG
                3220              3230              3240

FIG. 23A

PMH1 hmw1A sequence

→

LYS GLU TRP LEU LEU ASP PRO ASP ASN ...VAL ASN ILE VAL LYS GLY THR GLU LEU GLN ASN
A A A G A G T G G T T G T T A G A C C C G G A T A A T G ... T C A A T A T T G T T A A A G G A A C C G A A T T A C A G A A T
          10          20      ... 30         40        50       60

ASP LEU VAL VAL ARG GLY ASP SER ILE ...GLU LYS LYS ASN ALA PRO THR LYS THR THR ILE
G A T T T G G T T G T T A G G G G C G A T A G T A T T G ... A G A A A A A G A A T G C C C C T A C C A A G A C T A C A A T T
          70          80      ... 90     100      110     120

HIS ALA GLY SER ILE GLU GLN SER LEU ...MET LYS GLY GLY ALA VAL ASN ILE SER ALA THR
C A T G C A G G C T C T A T A G A A C A A T C T T T G A ... T G A A G G G T G G T G C A G T T A A T A T T T C T G C T A C A
         130        140     ... 150     160      170     180

FIG.23B

```
ASN LYS VAL ASN VAL THR THR ASP ILE    ...ASN VAL TYR ASN GLY ALA LEU THR LEU HIS SER
AATAAAGTAAATGTTACTACAGATATTA...        ...ATGTTTATAAATGGAGCATTAACGTTACACTCA
              190                             210              220              230              240

GLU ARG ASP GLY VAL GLU ILE ASN GLY     ...ASN ILE THR PRO SER GLU LYS ASN GLY ASN LEU THR
GAACGAGATGGAGTTGAAATTAACGGTA...         ...ATATTACCTCAGAAAAAAATGGTAATTTAACC
              250                             270              280              290              300

ILE LYS ALA GLY SER TRP VAL ASP VAL     ...HIS LYS ASN ILE THR LEU GLY GLU GLY PHE LEU
ATTAAAGCAGGTAGCTGGGTTGATGTTC...         ...ATAAAAAATATCACACTTGGCGAGGGTTTTTTG
              310                             330              340              350              360

ASN ILE THR SER GLY ASP ILE ALA PHE     ...
AATATTACTTCCGGTGATATCGCCTTCG...
              370                             380
```

FIG. 23C

```
                          ...GLU LYS GLY ASN ASN LEU THR ILE THR ALA GLN
                          ...A A A A A G G T A A T A A T C T A A C C A T T A C C G C T C A A
                          ...390              400              410              420

GLY ASN ILE THR SER ASN LYS ASP GLY  ...
G G A A A T A T A A C C C T C T A A T A A A G A C G G A A  ...
            430              440               ...

...LYS GLN LEU ARG LEU ASN ASN VAL SER LEU ASN
                          ...A A C A A C T T A G A C T T A A T A A T G T A T C T T T A A A T
                          ...450              460              470              480

GLY THR GLY ALA GLY LEU ASN PHE ILE  ...
G G A A C A G G T G C A G G T T T A A A C T T T A T T G  ...
            490              500               ...

...ALA ASN GLN ASN ASN PHE THR HIS ASN ILE SER
                          ...C A A A T C A A A A A T A A T T T T A C A C A A C A T T A G T
                          ...510              520              530              540

GLY ALA ILE ASN ILE SER GLY VAL VAL  ...
G G C G C G A T T A A C A T T T C C G G A G T A G T A A  ...
            550              560               ...

...THR ILE ASN GLN THR THR LYS LYS ASN ALA LYS
                          ...C G A T T A A T C A A A C T A C G A A A A A A A C G C T A A G
                          ...570              580              590              600
```

FIG.23D

ALA TRP ASN THR SER TYR ASP SER TYR ...
GCATGGAATACAAGCTATGACTCTTACT...
          610                  620

...TRP ASN VAL SER THR LEU SER ASN ASP
...GGAACGTATCTCTTACTTTAAGCAATGAT
     630              640              650         660

ALA LYS PHE THR PHE ILE LYS TYR VAL ...
GCGAAATTTACCTTTATTAAATATGTCG...
          670                  680              ...690

...ASP SER ASN HIS SER THR ASN SER SER ASP SER
...ACAGCAATCATTCGACAAACTCCAGTGATTCA
              700              710              720

ARG SER PHE ALA GLY VAL LYS PHE HIS ...
CGAAGTTTTGCGGGAGTAAAGTTCCACG...
          730                  740              ...750

...GLY LYS ASN ASN GLU MET LYS PHE ASN ILE GLY
...GCAAGAATAAATGAAATTTAATATTGGT
              760              770              780

ASN ASN ALA LYS ALA GLU PHE ARG LEU ...
AATAATGCCAAGGCTGAATTTAGGTTAA...
          790                  800

FIG.23E

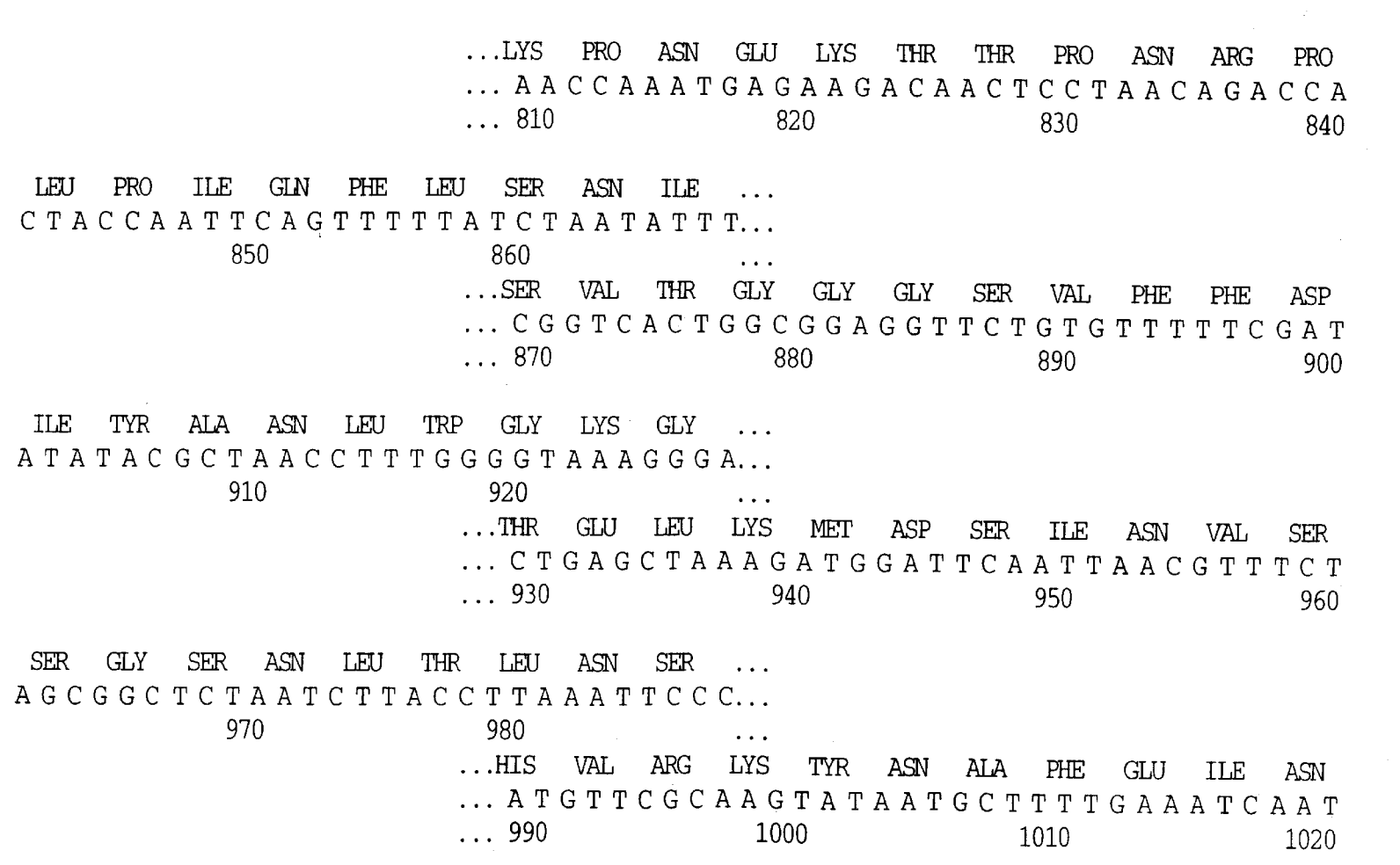

```
                        ...LYS PRO ASN GLU LYS THR THR PRO ASN ARG PRO
                        ...A A C C A A A T G A G A A G A C A A C T C C T A A C A G A C C A
                        ...810              820              830              840

LEU PRO ILE GLN PHE LEU SER ASN ILE...
C T A C C A A T T C A G T T T T T A T C T A A T A T T T...
            850              860

...SER VAL THR GLY GLY SER VAL PHE PHE ASP
                        ...C G G T C A C T G G C G G A G G T T C T G T G T T T T C G A T
                        ...870              880              890              900

ILE TYR ALA ASN LEU TRP GLY LYS GLY...
A T A T A C G C T A A C C T T T G G G G T A A A G G G A...
            910              920

...THR GLU LEU LYS MET ASP SER ILE ASN VAL SER
                        ...C T G A G C T A A A G A T G G A T T C A A T T A A C G T T T C T
                        ...930              940              950              960

SER GLY SER ASN LEU THR LEU ASN SER...
A G C G G C T C T A A T C T T A C C T T A A A T T C C C...
            970              980

...HIS VAL ARG LYS TYR ASN ALA PHE GLU ILE ASN
                        ...A T G T T C G C A A G T A T A A T G C T T T T G A A A T C A A T
                        ...990              1000             1010             1020
```

FIG.23F

```
LYS ASP LEU THR ILE ASN ALA THR ASN ...
AAAGACTTAACTATAAACGCAACTAATT...
          1030          1040
                                      ...SER ASN PHE ASN LEU ARG GLN THR SER ASP SER
                                      ....CAAATTTCAACCTCAGACAGACGTCAGATAGT
                                          ...1050          1060          1070          1080

PHE ARG ASN GLY TYR ARG ASN ALA ...
TTTCGTAACGGGTACCGCAATAATGCCA...
          1090          1100
                                      ...ILE ASN SER THR HIS ASN ILE SER ILE LEU GLY
                                      ....TCAATTCAACCCACACATATCCATCTTGGGC
                                          ...1110          1120          1130          1140

GLY ASN VAL THR LEU GLY GLY GLN ASN ...
GGCAACGTCACTCTCGGCGGACAAAACT...
          1150          1160
                                      ...SER SER SER ILE MET GLY ASN ILE ILE ILE
                                      ....CAAGCAGCAGCATTATGGGGAATATCATCATC
                                          ...1170          1180          1190          1200

LYS ARG ALA ALA ASN VAL THR LEU GLU ...
AAGCGAGCAGCAAATGTTACGCTAGAAG...
          1210          1220
```

FIG.23G

```
                      ...ALA ASP ASN SER HIS ASN SER ASP ASN VAL LYS
                      ... CCG ATA AAT AGT CAC AAT TCT GAC AAC GTA AAG
                         ...1230                1240                1250          1260

ASP ARG THR ILE ASN LEU GLY ASN LEU ...    ...THR VAL GLU GLY ASN LEU ILE GLY GLU
GAT AGA ACT ATA AAT CTT GGC AAC TTG A...   ...CCG TTG AGG GAA TTT AAG TTA ATT GGC GAA
               1270                  1280     ...1290               1300               1310               1320

ASN ALA ASN ILE ASN GLY ASN LEU SER ...    ...ILE GLU LYS GLU ALA ILE PHE LYS GLY LYS THR
AAT GCA AAT ATT AAC GGC AAT CTC TCC A...   ...TTG AAA AAG AAG CCA TCT TTA AAG GAA AAA CC
               1330                  1340    ...1350              1360              1370               1380

LYS ASP SER LEU ASN ILE THR GLY ASN ...    ...PHE THR ASN ASN GLY THR ALA GLU ILE ASN ILE
AAG GAC AGC CTA AAC ATC ACC GGC AAC T...   ...TT ACC AAT AAT GGC ACT GCC GAA TTA ATA TA
               1390                  1400    ...1410             1420               1430              1440
```

FIG.23H

```
SER  GLN  GLY  VAL  VAL  SER  LEU  GLY  ASP  ...
AGCCAAGGAGTGGTAAGTCTTGGCGATA...
              1450                1460
                                        ...ILE  THR  ASN  ASP  GLY  LYS  LEU  ASN  ILE  THR  THR
                                        ...TTACCAATGATGGCAAATTAAACATCACCACT
                                              1470          1480          1490          1500

HIS  ALA  LYS  SER  GLY  GLN  LYS  SER  ILE  ...
CACGCCAAGAGCGGTCAAAAAGCATTA...
              1510                1520
                                        ...ILE  ARG  GLY  ASP  ILE  ASN  LYS  GLN  GLY  ASN
                                        ...TCCGCGGAGATATAAACAAAGGGAAT
                                              1530          1540          1550          1560

LEU  ASN  ILE  THR  ASP  ASN  SER  ASN  ...
TTAAATATTACGGACAATAATAGTAATG...
              1570                1580
                                        ...ALA  GLU  ILE  GLU  ILE  GLY  GLY  ASN  ILE  SER  GLN
                                        ...CTGAAATTGAAATTGGCGGCAATATCTCGCAA
                                              1590          1600          1610          1620

LYS  GLU  GLY  ASN  LEU  THR  ILE  SER  SER  ...
AAAGAAGGTAATCTCACCATTTCTTCTG...
              1630                1640
```

FIG. 23I

```
                                 ...ASP LYS VAL ASN ILE THR LYS GLN ILE THR ILE
                                 ...ATAAAGTCAATATTACCAAACAGATAACAATC
                                 ...1650                 1660                 1670                 1680

LYS ALA GLY VAL ASP GLY GLU SER SER ...SER SER THR ALA SER ASP ALA ASN LEU THR
AAAGCAGGCGTTGATGGGGAGAGTTCTA... ...GTTCAAGCACAGCAAGTGATGCCAATCTAACC
         1690                 1700         ...1710                 1720                 1730                 1740

ILE LYS THR LYS GLU LEU THR LEU THR ...ASP ASN LEU ASN ILE SER GLY PHE ASN LYS ALA
ATTAAAACCAAAGAGTTAACATTAACAG... ...ACAATCTAAACATTTCAGGTTTTAATAAAGCA
         1750                 1760         ...1770                 1780                 1790                 1800

GLU ILE THR ALA LYS ASP ASN SER ASP ...LEU ILE ILE GLY LYS ALA SER SER ASP ASN SER
GAAATTACAGCTAAAGATAACAGTGATT... ...TAATTATTGGCAAGGCTAGCAGTGACAACAGT
         1810                 1820         ...1830                 1840                 1850                 1860
```

FIG.23J

```
ASN ALA LYS GLN VAL THR PHE ASP LYS                    ...
A A T G C T A A A C A A G T A A C C T T T G A C A A G G...
                    1870                         1880
                                                                ...VAL LYS ASP SER LYS ILE SER ALA GLY ASN HIS
                                                                ...T T A A A G A T T C A A A A A T C T C A G C T G G C A A T C A C
                                                                   ...1890              1900              1910              1920

ASN VAL THR LEU ASN SER LYS VAL GLU                    ...
A A T G T A A C A C T A A A T A G C A A A G T G G A A A...
                    1930                         1940
                                                                ...THR SER ASN SER ASP GLY SER THR GLY ASN GLY
                                                                ...C G T C T A A T A G C G A T G G T A G C A C C G G A A A C G G T
                                                                   ...1950              1960              1970              1980

SER ASP ASP ASN ASN ILE GLY LEU THR                    ...
A G C G A T G A C A A C A A T A T C G G C T T A A C T A...
                    1990                         2000
                                                                ...ILE SER ALA LYS ASP VAL THR VAL ASN SER ASN
                                                                ...T T T C C G C A A A A G A T G T A A C G G T A A A T A G T A A T
                                                                   ...2010              2020              2030              2040

ILE THR SER HIS LYS THR VAL ASN ILE                    ...
A T C A C C T C T C A C A A A A C A G T A A A T A T C T...
                    2050                         2060
```

FIG.23K

```
                    ...SER ALA SER GLU GLY GLY ILE THR THR LYS ALA
                    ...CTGCATCAGAAGGAGGTATCACTACTAAAGCA
                       2070                 2080                 2090            2100

GLY THR ILE ASN ALA THR THR GLY  ...SER VAL GLU VAL THR ALA LYS THR GLY ASP ILE
GGCACAACCATTAATGCGACCACCAGGTA... ...GCGTGGAAGTAACTGCTAAAACAGGCGATATT
         2110                    2120                      2130                  2140                 2150            2160

SER GLY THR ILE SER GLY LYS THR VAL  ...SER VAL THR ALA SER THR GLY ASP LEU THR VAL
AGCGGGTACGATTTCCGGTAAGACAGTAA...     ...GTGTTACAGCAAGCACTGGCGATTTAACTGTT
         2170                    2180                     2190                   2200                 2210            2220

ARG LYS ALA ALA ALA THR ILE SER ALA THR  ...GLU GLY ALA ALA THR LEU THR ALA THR GLY ASN
AGGAAAGCTGCAACCATTAGTGCGACAG...          ...AAGGAGCTGCAACCTTAACCGCAACAGGGAAT
         2230                    2240                    2250                    2260                 2270            2280
```

FIG.23L

THR LEU THR THR GLU ALA GLY SER SER ...
A C C T T G A C T A C T G A A G C C G G T T C T A G C A ...
                    2290                      2300
                                    ...ILE THR SER THR LYS GLY GLN VAL ASP LEU SER
                                    ...T C A C T T C A A C T A A G G G T C A G G T A G A C C T T T C A
                                       ...2310                  2320                  2330                  2340

ALA GLN ASP GLY SER ILE ALA GLY GLN ...
G C T C A G G A T G G T A G C A T T G C A G G A C A A A ...
                    2350                      2360
                                    ...ILE SER ALA ALA ASN VAL THR LEU ASN THR THR
                                    ...T T A G T G C A G C T A A T G T G A C A T T A A A T A C C A C A
                                       ...2370                  2380                  2390                  2400

GLY THR LEU THR THR VAL GLU GLY SER ...
G G C A C C T T A A C T A C T G T A G A A G G T T C A A ...
                    2410                      2420
                                    ...ASN ILE LYS ALA THR SER GLY THR LEU ALA ILE
                                    ...A C A T T A A A G G C A A C C A G T G G C A C C T T A G C T A T T
                                       ...2430                  2440                  2450                  2460

ASN ALA LYS ASP ALA LYS LEU ASP GLY ...
A A C G C A A A A G A C G C T A A G C T A G A T G G T A ...
                    2470                      2480

FIG.23M

```
              ...THR ALA SER GLY ASN ARG THR GLU VAL ASN ALA
              ...C G G C A T C A G G T A A C C G T A C A G A A G T A A A T G C A
              ...2490            2500            2510            2520

THR ASN ALA SER GLY SER GLY SER VAL ...
A C T A A C G C A A G T G G T T C T G G T A G C G T G A ...
              2530            2540

...THR ALA LYS THR SER SER ASN VAL ASN ILE THR
              ...C T G C G A A A A C C T C A A G T A A T G T G A A T A T C A C C
              ...2550            2560            2570            2580

GLY ASP LEU SER THR ILE ASN GLY LEU ...
G G G G A T T T A A G C A C A A T A A A T G G G T T A A ...
              2590            2600

...ASN ILE ILE SER GLU ASN GLY ARG ASN THR VAL
              ...A T A T C A T T T C G G A A A A T G G T A G A A A C A C T G T G
              ...2610            2620            2630            2640

ARG LEU ARG GLY LYS GLU ILE ASP VAL ...
C G C T T A A G A G G C A A G G A A A T T G A T G T G A ...
              2650            2660

...LYS TYR ILE GLN PRO GLY VAL ALA SER VAL GLU
              ...A A T A T A T C C A A C C A G G T G T A G C A A G C G T A G A A
              ...2670            2680            2690            2700
```

FIG.23N

```
GLU VAL ILE GLU ALA LYS ARG VAL LEU ...
G A G G T A A T T G A A G C G A A A C G C G T C C T T G ...
                2710                    2720
                        ...GLU LYS VAL LYS ASP LEU SER ASP GLU GLU ARG
                        ...A G A A A G T A A A A G A T T T A T C T G A C G A A G A A A G A
                             ...2730              2740              2750              2760

GLU THR LEU ALA LYS LEU GLY VAL SER ...
G A A A C A C T A G C C A A A C T T G G T G T A A G T G ...
                2770                    2780
                        ...ALA VAL ARG PHE VAL GLU PRO ASN ASN ALA ILE
                        ...C T G T A C G T T T C G T T G A G C C A A A T A A T G C C A T T
                             ...2790              2800              2810              2820

THR ILE ASN THR GLN ASN GLU PHE THR ...
A C G A T T A A T A C A C A A A A T G A A T T T A C A A ...
                2830                    2840
                        ...THR ARG PRO SER SER GLN VAL ILE ILE SER GLU
                        ...C C A G A C C G T C A A G T C A A A G T G A T A A T T T C T G A A
                             ...2850              2860              2870              2880

GLY LYS ALA CYS PHE SER GLY ASN ...
G G T A A G G C G T G T T T C T C A A G T G G T A A T G ...
                2890                    2900
```

```
...GLY  ALA  ALA  VAL  CYS  THR  ASN  VAL  ALA  ASP  ASP
...GCG  CAG  CAG  TAT  GTA  CCA  ATG  TTG  CTG  ACG  AT
...2910          2920          2930          2940

GLY  GLN  PRO  ***
GGA  CAG  CCC  GTA G
              2950
```

PMH1 *hmw2A* sequence

```
         →
LYS GLU TRP LEU LEU ASP PRO ASP ASP ...
A A A G A G T G G T T G T T A G A C C C G G A T G A T G...
                    10                    20
         ...VAL THR ILE ALA ALA GLY ALA PRO GLY ARG ASN
         ...T A A C T A T T G C C G C A G G C G C G C C A G G A C G T A A C
                        30                    40                    50                    60

ASP GLY SER VAL ASP ASP PHE PRO PHE PRO          ...
G A T G G T T C A G T A G A C G A C T T T T T C C C A... 
                    70                    80
         ...THR GLY ARG GLY ASP ASP ALA SER ASN ALA LYS
         ...C T G G A A G A G G G G A T G A T G C T A G T A A T G C A A A A
                        90                    100                   110                   120

THR ASN HIS PRO ASP LYS PRO THR LEU          ...
A C A A A C C A T C C A G A C A A G C C G A C A T T A A...
                    130                   140
         ...THR ASN THR THR VAL GLU ASN ALA LEU LYS ASN
         ...C A A A C A C A A C T G T T G A G A A C G C A T T A A A A A A C
                        150                   160                   170                   180
```

FIG.24B

```
ASN THR PHE VAL ASN ILE THR ALA LYS           ...
A A C A C C T T T G T T A A C A T A A C C G C C A A A A...
              190                        200
                                                              ...ASN LYS ILE THR VAL ASN SER ASP ILE ASN ILE
                                                              ...A T A A A A T C A C A G T T A A T A G C G A C A T C A A T A T C
                                                                        210              220              230              240

LYS GLY GLY ALA HIS LEU THR LEU TYR           ...
A A A G G T G G C G C G C C C A C C T A A C C C T C T A T A...
              250                        260              270
                                                              ...SER LYS ASN ASN LYS LYS SER SER VAL LYS ILE
                                                              ...G C A A A A C A A T A A A A A G T A G C G T T A A G A T T
                                                                        280              290              300

ASN GLY ASN ILE THR SER THR THR ASN           ...
A A T G G C A A T A T T A C T T C T A C C A C T A A C G...
              310                        320
                                                              ...GLY ASN LEU THR ILE TYR SER SER GLY TRP VAL
                                                              ...G A A A C T T A A C T A T T T A C T C C A G C G G C T G G G T T
                                                                        330              340              350              360

ASP ILE HIS LYS ASN ILE THR LEU ASN           ...
G A T A T C C A T A A A A A C A T T A C G C T T A A C A...
              370                        380
```

FIG.24C

```
           ...THR GLY TYR LEU ASN ILE THR ALA GLY GLY SER
           ...C A G G T T A C C T G A A T A T T A C C G C T G G G G T T C T  420
              ...390                      400                410

VAL ALA PHE GLU LYS ALA GLY ASN GLU ...
G T A G C C T T C G A G A A A G C C G G A A A T G A G A ...
              430                      440

...LYS GLY ARG GLN VAL SER GLU SER VAL ILE LYS
                                 ...A A G G G C G C C A A G T A T C A G A A T C T G T A A T C A A A  480
                                    ...450                      460                470

ALA GLN GLY VAL ILE THR SER GLY VAL ...
G C C C A G G G A G T T A T C A C C T C A G G T G T A G ...
              490                      500

...GLY GLU GLY PHE ARG PHE ASN ASN VAL SER LEU
                                 ...G G G A A G G C T T T A G G T T T A A T A A C G T C T C C C T A  540
                                    ...510                      520                530

ASN GLY VAL GLY ALA GLY LEU ARG PHE ...
A A T G G C G T T G G C G C A G G A C T G C G C T T C G ...
              550                      560

...VAL GLY GLN LYS ASN ILE SER SER ASN SER TRP
                                 ...T T G G T C A G A A A A A T A T C A G T A G C A A C T C T T G G  600
                                    ...570                      580                590
```

FIG.24D

```
ARG GLU ASN THR ILE LYS ASN ARG PHE
AGAGAAACACCATCAAAAACAGATTCG...
            610                    ...ASP GLY ASN LEU ASN ILE SER GLY LYS VAL ASN
                                   ...ATGGGAATTTAAATATCTCAGGAAAGGTAAAT
                                       620                                      660
                                          ...                             ...
                                             630                    650

VAL SER MET ASP VAL SER GLY THR LYS
GTTTCAAATGGATGTATCCGGGACAAAGT...
            670                   ...TRP HIS THR ARG ILE ASN GLY ARG THR TYR TRP
                                  ...GGCATACAAGAATTAACGGGCGCACCTACTGG
                                      680                                     720
                                         ...                            ...
                                            690                    710

ASN VAL THR THR LEU ASN VAL ALA SER
AATGTAACCACTCTAAACGTTGCCTCAG...
            730                   ...GLY SER SER PHE ASN LEU SER ILE ASP ALA SER
                                  ...GTAGTAGTTTCAATCTCAGTATCGACGCCAGT
                                      740                                     780
                                         ...                            ...
                                            750                    770

GLY ILE SER SER GLY ASN GLN ASP ASP
GGAATTTCTTCAGGTAACCAGGACGACA...
            790                 
                                   800
```

FIG.24E

```
            ...ILE THR ASN ARG GLY LEU ASN GLY ILE THR PHE
            ...T A A C A A A T A G G G T T T A A A T G G C A T A A C A T T T
            ...810                 820                 830                 840

ASN GLY GLU ASN THR PHE ASN ILE ALA...
A A T G G A G A A A A C A C T T T T A A T A T C G C A C...
        850                 860

...GLN GLY SER THR ALA ASN PHE HIS ILE LYS THR
            ...A G G G C T C A A C A G C T A A C T T T C A T A T C A A A A C G
            ...870                 880                 890                 900

SER VAL MET THR PRO LYS PRO ASN SER...
T C A G T A A T G A C C C C T A A A C C C A A C T C G A...
        910                 920

...ASN TYR ALA LEU PHE ASN GLY ASN ILE SER VAL
            ...A C T A C G C A T T A T T T A A T G G A A A T A T T T C A G T T
            ...930                 940                 950                 960

LEU GLY GLY THR VAL ASN PHE GLU...
T T A G G A G G A A C T G T C A A C T T T G A A C...
        970                 980

...LEU ASN ALA SER SER THR HIS THR SER
            ...T T A A T G C C T C A T C T A G C A C C C A C A A C T T C T
            ...990                 1000                1010                1020
```

FIG.24F

GLY ALA ILE ILE ASN SER GLN ASN PHE ...
G G C G C A A T T A T A A A T T C T C A A A A T T T T A...
                1030                    1040

...ASN VAL SER GLY GLY SER LYS ASN LEU LYS
...A T G T C T C A G G T G G G T C A A A A T T A A A T C T C A A G
    ...1050            1060                    1070            1080

ALA SER GLY SER THR ASN THR ALA PHE ...
G C T T C A G G C T C A A C A A A T A C C G C T T T T T...
                1090                    1100

...LEU ILE LYS ASN ASN LEU THR LEU ASN ALA THR
...T A A T A A A A A T A A T T T A A C T T T A A A C G C T A C T
    ...1110            1120                    1130            1140

GLY GLY ASN ILE GLU ILE LYS GLN VAL ...
G G A G G T A A T A T A G A A A T T A A A C A G G T T G...
                1150                    1160

...GLU GLY THR ASP SER ARG ILE GLN LYS GLY VAL
...A G G G T A C C G A T T C G C A T T C A A A A G G T G T T
    ...1170            1180                    1190            1200

VAL ALA GLU GLN ASN ILE ILE PHE GLU ...
G T A G C C G A A C A A A A C A T A A T T T T T G A A G...
                1210                    1220

FIG.24G

```
                          ...GLY GLY ASN ILE THR LEU GLY SER GLN LYS ALA
                          ...G G G G T A A C A T C A C C C T T G G C T C C C A A A A A G C C
                             ...1230                1240               1250              1260

PRO THR GLU ILE LYS GLY ASP VAL THR                  ...VAL LYS GLN GLY THR ASN ALA THR LEU ARG SER
C C A A C A G A A A T A A A A G G C G A T G T T A C C G...  ...T C A A A C A A G G A A C C A A C G C C A C T C T C A G A A G C
                1270                  1280                   ...1290               1300               1310              1320

ALA ASN PHE ASP ASN HIS LYS GLY ALA                  ...LEU ILE VAL ASN GLY ASN VAL THR ALA ASN GLY
G C G A A T T T T G A C A A C C A C A A A G G T G C C T... ...T A A T T G T G A A T G G A A A C G T T A C C G C C A A T G G C
                1330                  1340                   ...1350               1360               1370              1380

ASN LEU THR ALA ASP GLY ASP THR ILE                  ...LYS ILE LYS GLY ASN LEU ASP VAL ALA GLN GLY
A A C C T T A C T G C G G A C G G C G A C A C T A T T A... ...A A A T A A A A G G C A A T C T T G A T G T T G C A C A A G G C
                1390                  1400                   ...1410               1420               1430              1440
```

FIG.24H

ALA LYS PHE ASN GLY SER THR LYS ASN ...
GCTAAATTTAACGGCAGCACAAAAACA...
         1450          1460

...ASN LEU ASN ILE THR GLY THR PHE THR ASN ASN
...ACCTAAACATTACTGGCACCTTTACCAACAAC
     ...1470          1480          1490          1500

GLY THR SER ILE ILE ASP ILE THR GLN ...
GGCACTTCTATAATCGATATAACACAAG...
         1510          1520

...GLY VAL VAL ASN LEU GLY ASN VAL THR ASN ASP
...GGGTGGTAAACCCTTGGTAATGTTACCAATGAC
     ...1530          1540          1550          1560

GLY LYS LEU ASN ILE THR THR HIS ALA ...
GGCAAATTAAACATCACCACTCACGCCA...
         1570          1580

...LYS SER GLY GLN LYS SER ILE ILE ARG GLY ASP
...AGAGCGGTCAAAAAAGCATTATCCGCGGAGAT
     ...1590          1600          1610          1620

ILE ILE ASN LYS GLN GLY ASN LEU ASN ...
ATAATTAACAAACAAGGGAATTTAAATA...
         1630          1640

FIG. 24I

```
                             ...ILE THR ASP ASN ASN SER ASN ALA GLU ILE GLU
                             ...T T A C G G A C A A T A A T A G T A A T G C T G A A A T T G A A
                                ...1650         1660          1670           1680

ILE GLY GLY ASN ILE SER GLN LYS GLU ...
A T T G G C G G C A A T A T C T C G C A A A A G A A G...
                 1690                 1700

...GLY ASN LEU THR ILE SER SER ASP LYS VAL ASN
                             ...G T A A T C T C A C C A T T T C T T C T G A T A A A G T C A A T
                                ...1710         1720          1730           1740

ILE THR LYS GLN ILE THR ILE LYS ALA ...
A T T A C C A A A C A G A T A A C A A T C A A A G C A G...
                 1750                1760

..GLY VAL ASP GLY GLU SER SER SER SER SER THR
                             ...G C G T T G A T G G G G A G A G T T C T A G T T C A A G C A C A
                                ...1770          1780          1790          1800

ALA SER ASP ALA ASN LEU THR ILE LYS ...
G C A A G T G A T G C C A A T C T A A C C A T T A A A A...
                 1810                1820

...THR LYS GLU LEU THR PHE THR ASP ASN LEU ASN
                             ...C C A A A G A G T T A A C A T T C A C A G A C A A T C T A A A C
                                ...1830          1840          1850          1860
```

FIG. 24J

```
ILE SER GLY PHE ASN LYS ALA GLU ILE
ATTTCAGGTTTTAATAAAGCAGAAATTA...
            1870              1880
    ...THR ALA LYS ASP ASN SER ASP LEU ILE ILE GLY
    ...CAGCTAAAGATAACAGTGATTTAATTATTGGC
       ...1890          1900         1910        1920

LYS ALA SER SER ASP ASN SER ASN ALA
AAGGCTAGCAGTGACAACAGTAATGCTA...
            1930              1940
    ...LYS GLN VAL THR PHE ASP LYS VAL LYS ASP SER
    ...AACAAGTAACCTTTGACAAGGTTAAAGATTCA
       ...1950          1960         1970        1980

LYS ILE SER ALA GLY ASN HIS ASN VAL
AAAATCTCAGCTGGCAATCACAATGTAA...
            1990              2000
    ...THR LEU ASN SER LYS VAL GLU THR SER ASN SER
    ...CACTAAATAGCAAAGTGGAAACGTCTAATAGC
       ...2010          2020         2030        2040

ASP GLY SER THR GLY ASN GLY SER ASP
GATGGTAGCACCGGAAACGGTAGCGATG...
            2050              2060
```

FIG.24K

```
                    ...ASP ASN ASN ILE GLY LEU THR ILE SER ALA LYS
                    ...A C A A C A A T A T C G G C T T A A C T A T T C C G C A A A A
                       ...2070              2080              2090              2100

ASP VAL THR VAL ASN SER ASN ILE THR ...           ...SER HIS LYS THR VAL ASN ILE SER ALA SER GLU
G A T G T A A C G G T A A A T A G T A A T A T C A C C T...    ...C T C A C A A A A C A G T A A A T A T C T C T G C A T C A G A A
                  2110              2120                                 2130              2140              2150              2160

GLY GLY ILE THR THR LYS ALA GLY THR ...           ...THR ILE ASN ALA THR THR GLY SER VAL GLU VAL
G G A G G T A T C A C T A C T A A A G C A G G C A C A A... ...C C A T T A A T G C G A C C A C A G G T A G C G T G G A A G T A
                  2170              2180                                 2190              2200              2210              2220

THR ALA LYS THR GLY ASP ILE SER GLY ...           ...THR ILE SER GLY LYS THR VAL SER VAL THR ALA
A C T G C T A A A A C A G G C G A T A T T A G C G G T A... ...C G A T T T C C G G T A A G A C A G T A A G T G T T A C A G C A
                  2230              2240                                 2250              2260              2270              2280
```

FIG.24L

```
SER THR GLY ASP LEU THR VAL ARG LYS ...
A G C A C T G G C G A T T T A A C T G T T A G G A A A G...
                2290                           2300
                                                       ALA ALA THR ILE SER VAL THR GLU GLY ALA ALA
                                                    ...C T G C A A C C A T T A G T G T G A C A G A A G G A G C T G C A
                                                       ...2310                     2320                     2330                     2340

THR LEU THR ALA THR GLY ASN THR LEU ...
A C C T T A A C C G C A A C A G G G A A T A C C T T G A...
                2350                           2360
                                                       THR THR GLU ALA GLY SER SER ILE THR SER THR
                                                    ...C T A C T G A A G C C G G T T C T A G C A T C A C T T C A A C T
                                                       ...2370                     2380                     2390                     2400

LYS GLY GLN VAL ASP LEU SER ALA GLN ...
A A G G G T C A G G T A G A C C T T T C A G C T C A G G...
                2410                           2420
                                                       ASP GLY SER ILE ALA GLY GLN ILE SER ALA ALA
                                                    ...A T G G T A G C A T T G C A G G A C A A A T T A G T G C A G C T
                                                       ...2430                     2440                     2450                     2460

ASN VAL THR LEU ASN THR THR GLY THR ...
A A T G T G A C A T T A A A T A C C A C A G G C A C C T...
                2470                           2480
```

FIG.24M

```
            ...LEU THR THR VAL GLU GLY SER ASN ILE LYS ALA
            ...T A A C T A C T G T A G A A G G T T C A A A C A T T A A G G C A
               ...2490           2500          2510         2520

THR SER GLY THR LEU ALA ILE ASN ALA...
A C C A G T G G C A C C T T A G C T A T T A A C G C A A...
          2530                  2540        ...2550
                                            ...LYS ASP ALA LYS LEU ASP GLY THR ALA SER GLY
                                            ...A A G A C G C T A A G C T A G A T G G T A C G G C A T C A G G T
                                                         2560          2570         2580

ASN ARG THR GLU VAL ASN ALA THR ASN...
A A C C G T A C A G A A G T A A A T G C A A C T A A C G...
          2590                 2600         ...2610
                                             ...ALA SER GLY SER GLY SER VAL ALA LYS THR
                                             ...C A A G T G G T T C T G G T A G C G T G A C T G C G A A A A C C
                                                          2620          2630         2640

SER SER ASN VAL THR ILE THR GLY ASP...
T C A A G T A A T G T G A A T A T C A C C G G G G A T T...
          2650                 2660         ...2670
                                             ...LEU SER THR ILE ASN GLY LEU ASN ILE ILE SER
                                             ...T A A G C A C A A T A A A T G G G T T A A A T A T C A T T T C G
                                                          2680          2690         2700
```

FIG.24N

```
GLU ASN GLY ARG ASN THR VAL ARG LEU ...
GAAAATGGTAGAAAACACTGTGCGCTTAA...
         2710              2720
                                    ...ARG GLY LYS GLU ILE ASP VAL LYS TYR ILE GLN
                                    ....GAGGCAAGGAAATTGATGTGAAATATCCAA
                                       ...2730       2740         2750        2760

PRO GLY VAL ALA SER VAL GLU GLU VAL ...
CCAGGTGTAGCAAGCGTAGAAGAGGTAA...
         2770             2780
                                    ...ILE GLU ALA LYS ARG VAL LEU GLU LYS VAL LYS
                                    ....TTGAAGCGAAACGCGTCCTTGAGAAAGTAAAA
                                       ...2790       2800         2810        2820

ASP LEU SER ASP GLU GLU ARG GLU THR ...
GATTTATCTGACGAAGAAAGAGAAACAC...
         2830             2840
                                    ...LEU ALA LYS LEU GLY VAL SER ALA VAL ARG PHE
                                    ....TAGCCAAACTTGGTGTAAGTGCTGTACGTTTC
                                       ...2850       2860         2870        2880

VAL GLU PRO ASN ASN ALA ILE THR ILE ...
GTTGAGCCAAATAATGCCATTACGATTA...
         2890             2900
```

FIG. 240

```
                              ...ASN THR GLN ASN GLU PHE THR THR ARG PRO SER
                              ...A T A C A C A A A A A T G A A T T T A C A A C C A G A C C G T C A
                                 ..2910                    2920                    2930                    2940

SER GLN VAL ILE ILE SER GLU GLY LYS...          ...ALA CYS PHE SER SER GLY ASN GLY ALA ALA VAL
A G T C A A G T G A T A A T T T C T G A A G G T A A G G...          ...C G T G T T T C T C A A G T G G T A A T G G C G C A G C A G T A
                    2950                    2960                              ...2970                    2980                    2990                    3000

CYS THR ASN VAL ALA ASP ASP GLY GLN...          ...PRO ***
T G T A C C A A T G T T G C T G A C G A T G G A C A G C...          ...C G T A G
                    3010                    3020                              ...3030
```

FIG. 25A

Strain 15 *hmw1A* sequence

↓

LYS GLU TRP LEU LEU ASP PRO ASP ASN VAL ...
AAA GAG TGG TTG TTA GAC CCG GAT AAT GTA A...
           10              20            30

...THR ILE GLU ALA PRO SER TYR SER ARG GLY
...C A A T T G A A G C C C C T T C C T A T T C T C G C G G T
                   40             50            60

ASN ALA GLY ILE ASP SER GLU PHE PRO GLY ...
AAT GCC GGG TAT AGA TAG TGA ATT CCC GGG CG...
           70             80            90

...GLY SER GLY THR LYS GLU SER PRO LYS THR
...GTT CGG GCA CAA AGG AAA GCC CTA AAA CA
          100           110         120

ASN GLY GLU GLN PRO THR VAL LEU THR ASN ...
AAC GGC GAA CAG CCG ACA GTA TTA ACC AAT G...
          130           140         150

...GLU THR ILE SER ASN TYR LEU LYS SER GLY
...AAA CCA TTT CAA ATT ATC TGA AAA GCG GC
          160           170         180

FIG.25B

```
THR TRP VAL MET ASN ILE THR ALA LYS LYS ...
ACCTGGGTAATGAATATAAACAGCCAAGAAAA...
         190                 200                210

...ASN LEU THR VAL ASN SER SER ILE ASN ILE
                    ...ATCTTACCGTTAACAGCTCAATTAACATT
                             220              230           240

GLY ASP SER SER HIS LEU ILE LEU HIS SER ...
GGAGACAGCTCCCACTTAATCCTTCATAGTG...
         250                 260                270

...GLU GLY LYS ASN ASN GLY VAL LYS ILE
                    ...AAGGCAAGAATAACGGCGTGTTAAGATT
                             280              290           300

LYS GLU ASP ILE THR SER ASN GLY GLY ASN ...
AAAGAAGACATTACCTCTAATGGCGGAAACT...
         310                 320                330

...LEU THR ILE GLN SER GLY GLY TRP VAL ASP
                    ...TAACCATTCAATCCGGCGGATGGGTTGAT
                             340              350           360

VAL HIS LYS ASN ILE THR LEU GLY THR GLY ...
GTTCACAAAAATATTACGCTTGGCACAGGCA...
         370                 380                390
```

FIG.25C

```
          ...THR LEU ASN ILE THR ALA LYS GLY SER ILE
          ...C C T T G A A T A T T A C A G C T A A A G G A T C C A T A
             ...                          400                     410                     420

ALA PHE GLU GLY ASN GLY THR GLU LYS ALA          ...ARG ASN ALA SER SER ALA GLN ILE THR ALA
G C C T T T G A G G G A A A C G G T A C A G A A A A A G C C C...   ...G C A A C G C A T C A A G C G C T C A A A T C A C C G C G
                      430                     440            450                          460                     470                     480
                                                                                                                                          ...

GLN GLY THR ILE THR ASN THR GLY ASP GLN          ...LYS GLN LEU ARG LEU ASN ASN VAL SER ILE
C A G G G A A C T A T A A C C A A T A C T G G C G A T C A A A...   ...A A C A A C T C A G A C T T A A T A A T G T A T C T A T T
                      490                     500            510                          520                     530                     540
                                                                                                                                          ...

ASN GLY THR GLY ILE GLY LEU ASN PHE VAL          ...SER ILE GLN PRO ASN THR SER HIS ARG PHE
A A T G G G A C G G G T A T A G G T T T A A A T T T T G T T T...   ...C A A T T C A G C C T A A C A C T T C T C A C A G A T T T
                      550                     560            570                          580                     590                     600
                                                                                                                                          ...
```

FIG. 25D

```
ASP GLY GLU LEU ILE ILE SER GLY ARG VAL                                    ...HIS VAL ASN GLN THR  THR PRO LYS ASN LEU
GAT GGG GAG CTT ATT ATT TCA GGG AGA GTA C...                               ...ATG TTA ATC AAA CCA CAC CTA AAA ACC TG
              610                    620             630                                640                650              660

SER PHE TRP LYS VAL SER ASP GLU SER TYR                                    ...TRP ASN VAL SER HIS LEU THR VAL LYS GLU
TCT TTT TGG AAG GTA TCC GAT GAA TCT TAT T...                               ...GGA ATG TCA GCC ATC TTA CCG TAA AAG AG
              670                    680             690                                700                710              720

LYS SER ALA PHE SER PHE THR LYS PHE ALA                                    ...LEU ASN ASN ASN HIS GLY ARG GLU THR SER
AAG TCA GCA TTC TCA TTT ACC AAG TTT GCG T...                               ...TAA ATA ACA ATC ATG GCC GAG AGA CTT CC
              730                    740             750                                760                770              780

ARG TYR ARG LYS GLY GLY VAL ILE PHE
AGA TAC CGC AAA GGT GGA GGT GTA ATC TTT C...
              790                    800             810
```

FIG. 25E

```
            ...ARG SER PRO THR GLY HIS THR ASN PHE THR
            ...G C T C A C C T A C C G G T C A C A A A T T T C A C A
                                820                 830              840
            ...

VAL LYS GLN GLY SER VAL ALA ASN PHE SER            ...PHE LYS ALA ASN ASP THR ASN HIS ALA
G T T A A A C A A G G C T C A G T G G C T A A T T T T T C A T    ...T C A A G G C A A A A A T G A T A C A A A T C A T G C A
              850                 860                 870                  880                 890               900
                                                      ...                                                          ...

ASN GLN LEU PRO ILE GLN PHE ASN SER ASN            ...ILE SER VAL ASP GLY GLY LYS VAL LEU
A A T C A A C T C C C G A T T C A G T T T A A C T C T A A T A    ...T C T C A G T C G A T G G A G G A G G A A A G T C C T T
              910                  920                 930                 940                 950               960
                                                      ...                                                          ...

PHE CYS ILE THR SER ASN TYR SER GLY ARG            ...SER VAL GLY ILE GLY MET SER SER ILE ASN
T T T T G T A T A A C C T C C A A C T A C T C C G G C A G A T    ...C A G T G G G G A T A G G A A T G T C T A G C A T T A A T
              970                 980                 990                1000                1010              1020
                                                      ...                                                          ...
```

FIG. 25F

```
VAL  SER  ASP  GLY  SER  ASN  LEU  THR  PHE  ASN  ...
G T T T C T G A T G G C T C A A A C C T T A C T T T T A A T T...
                    1030                1040                1050      ...

...SER  SER  ILE  ARG  GLY  GIN  GLU  ALA  PHE  ASN
                                   ...C T T C C A T T C G C G G C C A G G A A G C C T T T A A T
                                                           1060                1070                1080

ILE  SER  LYS  ASP  LEU  THR  ILE  ASN  ALA  THR  ...
A T C A G T A A A G A T T T A A C C A T A A A T G C A A C C G...
                    1090                1100                1110      ...

...GLY  SER  PHE  PHE  GLU  LEU  GLY  GIN  TYR  SER
                                   ...G T T C A T T T T T T G A A C T T G G G C A A T A C T C G
                                                           1120                1130                1140

ASP  THR  PHE  ASN  GLY  ASN  GLY  PHE  ASN  HIS  ...
G A T A C C T T T A A T G G T A A T G G C T T T A A C C A C G...
                    1150                1160                1170      ...

...ASP  ALA  ILE  LYS  SER  THR  HIS  ASN  ILE  SER
                                   ...A C G C C A T T A A A T C A A C T C A C A A T A T C C
                                                           1180                1190                1200

ILE  LEU  GLY  GLY  ASN  VAL  THR  LEU  GLY  GLY  ...
A T C T T A G G T G G C A A T G T T A C C C T T G G C G G G C...
                    1210                1220                1230      ...
```

FIG.25G

```
                            ...GLN ASP SER SER THR ILE THR GLY ASN
                            ....A A G A T T C A A G C A G T A C C A T T A C A G G T A A T
                                   1240         1250             1260
                             ...

ILE ASN ILE SER GLN ALA ALA ASN VAL THR ...
A T C A A T A T C T C T C A G G C A G C A A A T G T T A C C T...
           1270              1280         1290
                                                  ...

...LEU ARG ALA TYR ASN GLY ASN GLY ARG ASN
                             ...T G C G A G C T T A T A A T G G T A A C G G T C G A A A C
                                    1300             1310             1320
                              ...

LYS GLN LEU THR LEU GLY ASN VAL SER ILE ...
A A A C A A C T A A C C C T T G G C A A T G T A T C T A T T G...
           1330              1340         1350
                                                  ...

...GLU GLY ASN LEU SER LEU ILE GLY ALA SER
                             ...A A G G G A A T T A A G T T T A A T C G G T G C A A G T
                                    1360             1370             1380
                              ...

ALA ASN ILE ASN GLY ASN LEU SER VAL LYS ...
G C A A A T A T T A A C G G C A A C C T T T C C G T T A A A G...
           1390              1400         1410
                                                  ...

...GLU ASN ALA LYS PHE LYS GLY GLU THR GLN
                             ...A A A A T G C T A A A T T T A A A G G G A A A C C C A A
                                    1420             1430             1440
                              ...
```

FIG. 25H

ASP ASN LEU ASN ILE THR GLY THR PHE ILE ...
GACAAACTTGAACATCACCGGCACCTTTATCA...
        1450              1460             1470

...ASN ASN GLY ASP SER LYS ILE ASN ILE SER
...ATAACGGCGACTCTAAAATCAATATATCT
          1480              1490              1500

GLN GLY VAL VAL LYS LEU GLY ASN VAL THR ...
CAAGGAGTGGTAAAACTTGGCAATGTTACCA...
        1510              1520             1530

...ASN ASP GLY ASN LEU ASN ILE THR THR HIS
...ATGATGGTGATTTAAACATTACCACTCAC
          1540              1550              1560

ALA LYS HIS ASN GLN ARG SER ILE ILE GLY ...
GCTAAACACAACCAAAGAAGCATCATCGGCG...
        1570              1580             1590

...GLY ASP ILE ILE ASN LYS LYS GLY SER LEU
...GAGATATAATCAACAAAAAGGAAGCTTA
          1600              1610              1620

ASN ILE THR ASP SER ASN LYS ASN ALA GLU ...
AATATTACAGACAGTAATAAGAATGCTGAAA...
        1630              1640             1650

FIG.25I

```
GLU GLY ASN LEU THR ILE     ...ILE GLN ILE GLY GLY ASN ILE SER GLN LYS
GAAGGCAAATCTCACGATTTCT      ...TCCAAATTGGCGGCAATATCTCGCAAAA
         1690                       1660           1670          1680
                            ...                                  ...

...ILE SER SER ASP LYS
                            ...TCACGATTTCTTCCGATAAAA
                                     1700        1710
                            ...                      ...

...ILE ASN ILE THR ASN GLN ILE THR ILE LYS
                            ...TCAATATTACCAATCAGATAACAATCAAA
                                     1720         1730         1740
                            ...                                  ...

ALA GLY VAL ASP GLY GLU ASN SER ASP SER
GCAGGTGTTGATGGGGAGAATTCCGATTCAG           ...
         1750                    1760
                                          ...

...ASP ALA THR ASN ASN ALA ASN LEU THR ILE
                            ...ACGCGACAAACAATGCCAATCTAACCATT
                                     1780         1790         1800
                            ...                                  ...

LYS THR LYS GLU LEU LYS LEU THR GLN ASP
AAAACCAAAGAATTGAAATTAACGCAAGACC           ...
         1810         1820        1830
                                          ...

...LEU ASN ILE SER GLY PHE ASN LYS ALA GLU
                            ...TAAATATTTCAGGTTTCAATAAAGCAGAG
                                     1840         1850        1860
                            ...
```

FIG.25J

```
ILE THR ALA LYS ASP GLY SER ASP LEU THR
ATTACAGCTAAAGATGGTAGTGATTTAACTA...
              1870           1880           1890
          ...ILE GLY ASN THR PHE ASN SER ALA ASP SER THR
          ...TTGGTAACACCAATAGTGCTGATAGTACT
                    1900           1910           1920

ASN ALA LYS LYS VAL THR PHE ASN GLN VAL
AATGCCAAAAAAGTAACCTTTAACCAGGTTA...
              1930           1940           1950
          ...LYS ASP SER LYS ILE SER ALA GLY ASP HIS
          ...AAGATTCAAAAATCTCTGCTGGCGACCAT
                    1960           1970           1980

ASN VAL THR LEU ASN SER LYS VAL GLU THR
AATGTGACACTAAATAGCAAAGTGGAAACAT...
              1990           2000           2010
          ...SER GLY ASN THR ASP ASN THR GLY ASP GLY
          ...CTGGTAATACTGACAACACTGGAGACGGC
                    2020           2030           2040

SER GLY ASN ASN ALA GLY LEU THR ILE ALA
AGTGGCAATAATGCCGGCTTAACTATTGCCG...
              2050           2060           2070
```

FIG. 25K

```
                    ...ALA LYS ASN VAL GLU VAL LYS ASN ASN ILE
                    ...C G A A A A A T G T A G A A G T A A A A A C A A C A T T
                    ...                                      2090              2100
                                    2080

THR SER ASN LYS THR VAL ASN ILE THR ALA ...
A C T T C T A A C A A A A C A G T A A A T A T C A C C G C G T...
                2110                    2120              2130    ...

...SER GLU LYS LEU THR THR LYS ALA ASP ALA
        ...C A G A A A A A C T T A C C A C C A A A G C G G A T G C A
                    2140                    2150                    2160
        ...

THR ILE ASN ALA THR GLY ASN VAL GLU ...
A C C A T T A A T G C A A C C A C T G G T A A C G T A G A A G...
                2170                    2180              2190    ...

...VAL THR ALA LYS THR GLY ASP ILE LYS GLY
        ...T G A C A G C C A A A A C A G G T G A T A T T A A A G G T
                    2200                    2210                    2220
        ...

GLU VAL LYS SER THR SER GLY ASN VAL ASN ...
G A A G T C A A A T C C A C T T C C G G T A A T G T A A A T A...
                2230                    2240              2250    ...

...ILE THR ALA ASN GLY ASP THR LEU ASN VAL
        ...T T A C A G C A A A C G G C G A C A C G C T T A A T G T A
                    2260                    2270                    2280
        ...
```

FIG. 25L

```
SER ASN VAL SER GLY ASN ALA VAL THR ILE
AGTAATGTTTCAGGCAATGCTGTTACCATCA...
         2290                   2300           2310
                        THR ALA ASP LYS GLY LYS LEU THR THR GLN
                     ...CTGCAGATAAGGGCAAATTAACCACCCAA
                            2320           2330           2340

ALA SER SER SER ILE THR SER ASN ASN GLY
GCAAGCTCTAGCATTACCCTCAAACAATGGCC...
         2350                   2360           2370
                        GLN THR THR LEU THR ALA LYS ASP GLY SER
                     ...AGACAACTCTTACAGCCAAGGATGGCAGT
                            2380           2390           2400

ILE ALA GLY SER ILE ASN ALA ALA ASN VAL
ATCGCAGGAAGCATCAATGCCGCCAATGTGA...
         2410                   2420           2430
                        THR LEU ASN THR THR GLY THR LEU THR THR
                     ...CATTAAATACCACAGGCACTTTAACTACT
                            2440           2450           2460

VAL GLU GLY SER ASN ILE ASN ALA ALA SER
GTAGAAGGTTCAAACATTAACGCCAGCCAGTG...
         2470                   2480           2490
```

FIG. 25M

```
         ...GLY THR LEU VAL ILE ASN ALA LYS ASP ALA
         ...GTACCTTGGTTATTAATGCAAAAGATGCT
            ...                    2510              2520
                 2500

LYS LEU ASN GLY ALA ALA SER GLY ASP HIS ...
AAGTTGAACGGCGCGGCATCAGGTGACCACA...
                 2530              2540    2550 ...

...THR VAL VAL ASN ALA THR ASN ALA SER GLY
         ...CAGTAGTAAATGCAACTAACGCAAGTGGC
                          2560              2570          2580

SER GLY SER VAL THR ALA VAL THR SER SER ...
TCTGGTAGTGTGACTGCGGTAACCTCAAGTA...
                 2590              2600    2610 ...

...ASN VAL ASN ILE THR GLY ASP LEU SER THR
         ...ATGTGAAATATCACCGGGGATTTAAGTACA
                          2620              2630          2640

VAL ASN GLY LEU ASN ILE ILE SER LYS ASN ...
GTAAATGGATTAAATATCATTTCGAAAAATG...
                 2650              2660    2670 ...

...GLY ARG ASN THR VAL VAL LEU LYS GLY THR
         ...GTAGAAACACCGTAGTGTTAAAAGGTACT
                          2680              2690          2700
```

FIG. 25N

```
GLU ILE GLU VAL LYS TYR ILE GLN PRO GLY
GAAATTGAGGTGAAATATATCCAGGTG...          ...VAL ALA SER VAL GLU VAL ILE GLU ALA
         2710          2720          2730          ...TAGCAAGTGTAGAAGAAGTAATTGAAGCG
                                                              2740          2750          2760

LYS ARG VAL LEU GLU LYS VAL LYS ASP LEU
AAACGCGTCCTTGAGAAAGTGAAAGATTTAT...      ...SER ASP GLU ARG GLU THR LEU ALA LYS
         2770          2780          2790          ...CTGATGAAGAAAGAGAAACATTAGCTAAA
                                                              2800          2810          2820

LEU GLY VAL SER ALA VAL ARG PHE ILE GLU
CTTGGTGTAAGTGCTGTACGTTTTATTGAAC...      ...PRO ASN ASN THR ILE THR VAL ASN THR GLN
         2830          2840          2850          ...CAAATAATACCATTACGGTTAACACACAA
                                                              2860          2870          2880
```

FIG.25O

ASN GLU PHE THR THR ARG PRO SER SER GLN ...
AATGAGTTTACAACCAGACCATCAAG...
         2890              2900        2910

...VAL THR ILE SER GLU GLY LYS ALA CYS PHE
...TGACAATTTCTGAAGGTAAGGCGTGTTTC
              2920              2930          2940

SER SER GLY ASN GLY ALA ALA VAL CYS THR ...
TCAAGTGGTAATGGCGCAGCAGTATGTTACCA...
         2950              2960        2970

...ASN VAL ALA ASP GLY GLN GLN ***
...ATGTTGCTGACGGATGGACAGCAGTAG
              2980              2990

FIG. 26A

NTHi strain 15 *lmm2A* sequence

```
ASN SER ALA SER GLY SER HIS MET PRO ...
GAATTCGGCTTCGGGATCCCATATGCCG...
        10              20
                                    ↓
                           ... GLU ASN VAL TYR ILE ASN ALA GLY ASP ALA GLY
                           ... GAGAATGTATATATTAATGCAGGAGACGCAGG
                                   30           40           50           60

ARG SER ASP THR ASN LEU GLU ASN GLU ...
GCGTAGTGACACTAATTTAGAAAACGAA...
        70              80
                                    ... GLU TYR THR GLY THR GLY GLU SER ALA ASP THR
                                    ... GAATACACAGGAACAGGAGAGAGTGCTGATAC
                                            90          100          110          120

PRO LYS ARG ASN ASN ASN THR LYS THR ...
TCCAAAACGAAACAATAACACAAAGACA...
        130             140
                                    ... THR LEU THR ASN SER THR LEU GLU LYS ILE LEU
                                    ... ACACTAACAAACTCAACGCTTGAGAAGATATT
                                            150          160          170          180
```

FIG. 26B

```
ALA ARG GLY SER PHE VAL ASN ILE THR...
AGCAAGAGGCTCTTTTGTTAATATCACT...
            190                 200
                                    ...ALA ASN ASN GLU ILE ARG VAL ASN SER ASP ILE
                                    ...GCCAACAATGAAATCAGAGTTAATAGTGATAT
                                       ...210           220           230           240

ASN ILE GLY GLY ASN SER HIS LEU THR...
CAATATCGGAGGCAAACTCCCACCTAACC...
            250                 260
                                    ...LEU TRP SER SER LYS ASN LYS ASN SER GLY VAL
                                    ...CTCTGGAGCAGCAAAAATAAAAACAGTGGCGT
                                       ...270           280           290           300

LEU ILE ASN GLY ASN ILE THR SER THR...
TCTGATTAATGGCAATATCACTTCTACT...
            310                 320
                                    ...ALA ASN GLY ASN LEU THR ILE TYR SER SER GLY
                                    ...GCTAACGGAAACTTAACCATTTACTTCTAGCGG
                                       ...330           340           350           360

TRP VAL ASP ILE HIS LYS ASN ILE THR...
ATGGGTTGATATTCATAAAAATATTACG...
            370                 380
```

FIG. 26C

```
          ...  LEU  GLU  SER  GLY  ARG  LEU  ASN  ILE  THR  THR  LYS
          ...  C T T G A A T C A G G A C G C T T A A A C A T T A C A A C T A A
          ...  390                 400                 410                 420

GLU  GLY  ASP  VAL  ALA  PHE  GLU  LYS  GLY  ...       ...  ASN  ASN  LEU  THR  ILE  THR  GLY  GLN  GLY  THR  ILE
 A G A A G G A G A T G T C G C C T T T G A A A A A G G G  ...       ...  A A T A A C C T A A C C A T T A C A G G T C A A G G A A C T A T
                         430                 440                           ...  450                 460                 470                 480

THR  ALA  GLY  ASN  ASN  LYS  GLY  PHE  ARG  ...       ...  PHE  GLU  ASN  VAL  SER  LEU  ASN  GLY  THR  GLY  THR
 T A C A G C A G G C A A T A A T A A A G G C T T T A G A  ...       ...  T T T G A A A A T G T C T C T C T A A A T G G C A C T G G G A C
                         490                 500                           ...  510                 520                 530                 540

GLY  LEU  LEU  PHE  ASN  LEU  SER  ARG  PRO  ...       ...  GLN  LYS  ASN  ASN  SER  LEU  VAL  THR  ASN  TYR  PHE
 T G G C T T G C T T T T T A A T C T C A G T A G A C C A  ...       ...  C A A A A A A C A A T A G T C T C G T C A C A A A C T A T T T
                         550                 560                           ...  570                 580                 590                 600
```

FIG.26D

```
ASN GLY THR LEU ASN ILE SER GLY SER ...
T A A T G G G A C T T T A A A T A T T T C A G G A A G C ...
                  610                           620
                                                    ...VAL ASN ILE SER MET ILE PRO PRO ASN ALA THR
                                                    ...G T A A A T A T C T C A A T G A T T C C A C C T A A T G C T A C
                                                            630              640              650              660

SER ASN TRP TYR SER ARG TYR LYS GLY ...
A A G C A A T T G G T A C A G C A G A T A C A A A G G G ...
                  670                           680
                                                    ...ARG THR TYR TRP ASN ILE THR HIS LEU ASN ALA
                                                    ...C G A A C C T A T T G G A A T A T A A C C C A C T T A A A T G C
                                                            690              700              710              720

SER GLU ASP SER ASN PHE ASN LEU THR ...
C T C C G A A G A T A G C A A C T T T A A C C T T A C T ...
                  730                           740
                                                    ...ILE ASP SER SER ALA GLU ASP GLY SER ALA PRO
                                                    ...A T T G A C T C C C G G C A G A G G A T G G C T C A G C C C C
                                                            750              760              770              780

LEU LEU SER SER TYR THR LEU ASN GLY ...
T C T T T T A T C C A G T T A T A C C T T A A A C G G C ...
                  790                           800
```

FIG.26E

```
              ...  ILE  SER  PHE  THR  THR  ASP  THR  THR  PHE  ASN  VAL
              ...  A T A T C A T T C A C C A C A G A T A C C A C C T T T A A T G T
              ...      810                 820                 830             840

ASN  LYS  ASN  ALA  LYS  VAL  ASN  PHE  ASN  ...       ILE  LYS  ALA  PRO  ILE  GLY  THR  ILE  ASN  GLN  TYR
T A A T A A A A T G C A A A A G T C A A C T T T A A C  ...  A T C A A A G C A C C A A T A G G G A C T A T A A A T C A A T A
              850                 860                         ...   870                 880                 890             900

ASN  ASN  LEU  ASN  TYR  ALA  LEU  PHE  ASN  ...       GLY  ASN  ILE  SER  VAL  SER  GLY  GLY  ASN  VAL
C A A T A A C C T G A A T T A C G C A T T A T T C A A T  ...  G G G A A C A T T T C A G T T T C A G G A G G G G A A T G T
              910                 920                         ...   930                 940                 950             960

THR  PHE  ARG  LEU  ASN  ALA  SER  SER  SER  ...       ASN  GLN  GLN  THR  PRO  GLY  VAL  ILE  ILE  ASN  SER
C A C C T T T C A G G C T T A A C G C T T C A T C C T C T  ...  A A C C A G C A A A C C C C T G G C G T A A T T A T A A A T T C
              970                 980                         ...   990                1000                1010             1020
```

FIG.26F

```
LYS HIS LEU ASN ALA SER LYS GLY SER....
T A A A C A C C T T A A T G C T T C A A A A G G G T C G....
                    1030                    1040
                                                            SER LEU ARG PHE GLU THR THR GLY SER THR LYS
                                                        ...A G C T T A A G A T T T G A A A C T A C A G G T T C A A C A A A
                                                        ...1050                   1060                    1070                    1080

VAL GLY PHE LEU ILE ASN ASN ASP LEU ...                     THR LEU ASN ALA THR GLY GLY ASN ILE SER LEU
A G T C G G T T T T T T A A T A A A T G A T T T A...    ...A C T T T A A A C G C C A C T G G A G G C A A T A T C G C T
                    1090                   1100            ...1110                   1120                    1130                    1140

LEU GLN VAL GLU GLY ILE ASP GLY MET ...                     ILE GLY GLU GLY VAL VAL ALA LYS LYS ASN ILE
C T T G C A G G T T G A A G G C A T T G A C G G G A T G... ...A T T G G T G A A G G C G T T G T A G C T A A A A A A A C A T
                    1150                    1160           ...1170                   1180                    1190                    1200

THR PHE THR GLY GLY ASN ILE THR PHE ...
A A C C T T T A C T G G A G G C A A T A T C A C C T T T...
                    1210                    1220
```

FIG. 26G

```
              ... GLY SER LYS LYS ALA ILE THR GLU ILE LYS GLY
              ... GGCTCCAAGAAAAGCCATAACAGAGAAATCAAAGG
              ...1230              1240              1250              1260

ASN VAL THR ILE ASN GLU ASN THR ASN ...
CAATGTTACTATCAATGAAAACACCAAC...
            1270              1280

... ALA THR LEU ILE GLY SER ASP PHE ASN ASP HIS
                        ... GCCACTCTTTATCGGTTCGGATTTTAACGATCA
                           ...1290              1300              1310              1320

LYS LYS PRO LEU ASN ILE LYS GLY ASP ...
TAAAAAACCTTTAAATATAAAAGGAGAT...
              1330              1340

... VAL VAL ASN ARG GLY ASN LEU THR ALA GLY GLY
                        ... GTCGTCAATAGAGGCAAACCTTACCGCTGGCGG
                           ...1350              1360              1370              1380

ASN VAL ILE ASN ILE GLY GLY ASN LEU ...
CAATGTTATCAATATAGGCGGAAATCTT...
              1390              1400

... THR VAL GLU ASN GLY ALA ASN LEU LYS ALA ILE
                        ... ACCGTTGAAAATGGCGCCAATCTTAAAGCTAT
                           ...1410              1420              1430              1440
```

FIG.26H

```
THR ASN PHE THR PHE ASN VAL GLY GLY ...
CACAAATTTCACTTTTAATGTAGGCGGC...
            1450            1460                            ...

... LEU PHE ASN ASN LYS GLY ASN SER ASN ILE SER
                ... TTGTTTAACAACAAAGGCAATTCAAATATCTC
                      ..1470             1480             1490             1500

ILE ALA ARG GLY GLY ALA LYS PHE LYS ...      ASP ILE ASN ASN THR SER SER LEU ASN ILE THR
CATTGCTAGAGGAGGGGCTAAATTTAAA...              ...GATATCAATAACACCAGTAGCTTAAATATTAC
              1510             1520                            ...1530             1540             1550             1560

THR ASN SER ASP THR THR TYR ARG THR ...       ILE ILE GLU GLY ASN ILE THR ASN LYS ALA GLY
CACCAACTCCGACACCACTTACCGTACC...               ...ATTATAGAAGGTAATATAACCAACAAAGCAGG
              1570             1580                            ...1590             1600             1610             1620

ASP LEU ASN ILE ILE ASP ASN LYS GLY ...
TGATTTGAATATCATTGATAATAAAGGT...
              1630             1640                            ...
```

FIG. 26I

```
                                    ASN ALA GLU ILE GLN ILE GLY GLY ASN ILE SER
                                ....A A C G C T G A A A T C C A A A T T G G C G G C A A C A T C T C
                                ...1650               1660              1670              1680

GLN LYS GLU GLY ASN LEU THR ILE SER....
G C A A A A A G A A G G T A A C C T C A C G A T T T C C....
              1690              1700

SER ASP LYS ILE ASN ILE THR LYS GLN ILE THR
                                ....T C C G A T A A A A T C A A T A T T A C C A A A C A G A T A A C
                                   ...1710              1720              1730              1740

ILE LYS LYS GLY VAL ASN GLY GLU ASN....
A A T C A A G A A A G G G T G T T A A C G G A G A G A A C....
              1750              1760

SER ASP SER SER THR LYS SER GLN ALA ASN LEU
                                ....T C T G A T T C A A G T A C G A A A A G T C A A G C C A A T C T
                                   ...1770              1780              1790              1800

THR ILE LYS THR LYS GLU LEU LYS LEU....
A A C C A T T A A A A C C A A A G A A T T G A A A T T A....
              1810              1820

THR GLN ASP LEU ASN ILE SER GLY PHE ASN LYS
                                ....A C A C A A G A C C T A A A T A T T T C A G G C T T C A A C A A
                                   ...1830              1840              1850              1860
```

FIG. 26J

```
ALA LYS ILE VAL ALA LYS ASP SER SER ....
AGCAAAAGATTGTAGCTAAAAGATAGTAGT....
            1870            1880
                    ... ASN LEU THR ILE GLY ASN SER ASP ASP SER GLY
                    ...AATTTAACTATTGGTAATAGTGATGATAGCGG
                           1890          1900          1910          1920

ASN THR SER ALA LYS THR VAL THR PHE ....
CAATACTAGCGCTAAAACAGTAACTTTT....
            1930            1940
                    ... ASN ASN VAL LYS ASP SER LYS ILE SER ALA ASP
                    ...AACAATGTTAAAGATTCAAAAATCTCTGCTGA
                           1950          1960          1970          1980

GLY HIS LYS VAL THR LEU ASN SER LYS ....
CGGTCACAAGGTGACACTAAAATAGCAAA....
            1990            2000
                    ... VAL LYS THR LEU SER ASP ASN ASN THR
                    ...GTGAAAACACTTAGTGATAATGATAACAACAC
                           2010          2020          2030          2040

GLU GLY GLY SER ASP ASN ASN THR GLY ....
TGAAGGTGGCAGTGACAACAATACCGGT....
            2050            2060
```

FIG.26K

```
                              ...  LEU  THR  ILE  THR  ALA  LYS  ASP  VAL  GLU  VAL  ASN
                              ...  T T A A C T A T T A C T G C A A A A G A T G T A G A A G T A A A
                              ...2070                        2080                        2090                        2100

ASN  ASN  ILE  THR  SER  HIS  LYS  THR  VAL  ...                      ...  ASN  VAL  SER  ALA  ALA  ASN  GLY  GLY  ILE  THR  THR
C A A C A A T A T T A C T T C T C A C A A A A C A G T G ...              ... A A C G T C T C T G C G G C A A A T G G A G G G A T T A C C A C
                      2110                        2120                                  2130                        2140                        2150                        2160

LYS  THR  GLY  THR  THR  ILE  ASN  ALA  THR  ...                       ...  ALA  GLY  ASN  VAL  GLU  ILE  THR  ALA  HIS  THR  GLY
T A A A A C A G G T A C A A C C A T T A A T G C A A C C ...              ... G C C G G G T A A C G T G G A G A T A A C C G C T C A T A C A G G
                      2170                        2180                                  2190                        2200                        2210                        2220

SER  ILE  GLN  GLY  GLY  ILE  GLU  SER  LYS  ...                       ...  PRO  GLY  SER  VAL  THR  ILE  VAL  ALA  GLY  GLY  ASP
C A G T A T C C A A G G C G G A A T T G A G T C C A A G ...              ... C C T G G C T C T G T G A C A A T T G T G G C A G G C G G C G A
                      2230                        2240                                  2250                        2260                        2270                        2280
```

FIG. 26L

```
THR LEU ALA VAL GLY ASN ILE SER GLY ...       ... ASN ALA VAL THR VAL THR ALA ASN SER GLY ALA
TACTCTTGCTGTAGGTAATATTTCAGGC...          ...AACGCCGTTACTGTTACTGCAAATAGCGGTGC
             2290           2300                  2310           2320           2330           2340

LEU THR THR LEU ALA GLY SER THR ILE ...       ... LYS GLY THR GLU SER ILE THR THR SER SER GLN
ATTAACCACTTTGGCAGGCTCTACAATT...          ...AAAGGAACCGAGAGTATAACCACTTCAAGTCA
             2350           2360                  2370           2380           2390           2400

SER GLY ASN ILE GLY GLY LYS ILE SER ...       ... GLY LYS THR VAL ASN VAL LYS ALA THR ASN SER
ATCAGGTAATATCGGCGGTAAATTTCC...           ...GGCAAGACAGTAAACGTTAAAGCAACTAATAG
             2410           2420                  2430           2440           2450           2460

LEU THR THR GLN ALA ASP SER LYS ILE ...
TTTAACCACCCAAGCAGAGACTCAAAATT...
             2470           2480
```

FIG.26M

```
                                    ... GLU ALA THR GLU GLY GLU ALA ASN VAL THR SER
                                    ... G A A G C G A C T G A A G G C G A G G C T A A T G T A A C A A G
                                       ...2490                    2500                    2510                    2520

LYS THR SER ILE ILE GLY GLY THR ILE ...
C A A A A C A A G C A T A A T T G G C G G T A C A A T T ...
                                    2530                    2540

... SER GLY GLY THR VAL GLU VAL THR ALA THR GLU
                                    ... T C T G G T G G C A C A G T A G A A G T T A C C G C G A C C G A
                                       ...2550                    2560                    2570                    2580

GLY LEU THR THR GLN ALA GLY SER THR ...
A G G T T T A A C C A C C C A A G C A G G C T C T A C G ...
                                    2590                    2600

... ILE THR GLY THR GLU SER VAL THR THR SER SER
                                    ... A T T A C T G G A A C C G A G A G C G T G A C C A C T T C A A G
                                       ...2610                    2620                    2630                    2640

GLN SER GLY ASN ILE GLY GLY MET ILE ...
C C A A T C A G G T A A T A T C G G C G G C A T G A T T ...
                                    2650                    2660

... SER GLY GLY LYS VAL GLU VAL SER ALA THR LYS
                                    ... T C T G G T G G C A A A G T A G A A G T T A G C G C A A C C A A
                                       ...2670                    2680                    2690                    2700
```

FIG.26N

```
ASP LEU ILE THR LYS SER GLY SER GLU ....
AGATTTAATTACTAAATCCGGTTCAGAG...
         2710                    2720
                                      .... ILE LYS ALA THR ALA GLY VAL GLU ASN VAL THR
                                      ....ATTAAAGCAACGGGCGAGGTGAATGTAAC
                                             ...2730            2740              2750            2760

SER ALA THR GLY THR ILE ASP GLY THR ....
AAGTGCAACAGGTACAATTGACGGTACG...
         2770                    2780
                                      .... ILE SER GLY ASN THR VAL ASN VAL THR ALA ASN
                                      ....ATTTCCGGTAATACGGTAAATGTTACAGCAAA
                                             ...2790            2800              2810            2820

THR GLY ASP LEU THR VAL GLU ASP ALA ....
TACTGGCGATTTAACTGTTGAAGATGCC...
         2830                    2840
                                      .... ALA LYS ILE ASP ALA THR GLY GLY ALA ALA THR
                                      ....GCAAAAATTGATGCGACAGGAGGAGCCGCGAC
                                             ...2850            2860              2870            2880

LEU THR ALA THR SER GLY LYS LEU THR ....
CCTAACTGCAACATCGGGCAAATTAACC...
         2890                    2900
```

FIG. 26O

```
                        ... THR LYS ALA SER SER SER ILE THR SER ALA ASN
                        ... A C T A A G G C T A G T T C A A G C A T T A C T T C A G C T A A
                              2910            2920            2930            2940

ASN GLN VAL ASN LEU SER ALA LYS ASP ...     GLY SER ILE GLY GLY ASN ILE ASN ALA ALA ASN
T A A C C A G G T A A A C C T T T C A G C T A A G G A T ...     G G T A G C A T T G G G G G A A A T C A A T G C T G C T A A
          2950            2960                      2970            2980            2990            3000

VAL THR LEU ASN THR THR GLY ALA LEU ...     THR THR VAL LYS GLY SER SER ILE ASN ALA ASN
T G T A A C A C T G A A T A C T A C A G G C G C T C T A ...     A C T A C C G T G A A G G G T T C A A G C A T T A A C G C A A A
          3010            3020                      3030            3040            3050            3060

SER GLY THR LEU VAL ILE ASN ALA LYS ...     ASP ALA GLU LEU ASN GLY GLU ALA SER GLY ASN
C A G C G G G C A C C C T T G G T T A T T A A C G C A A A A ...     G A C G C T G A G C T A A A T G G T G A G G C A T C A G G T A A
          3070            3080                      3090            3100            3110            3120
```

FIG.26P

```
HIS THR VAL VAL ASN ALA ALA THR ASN ALA ...
CCATACAGTAGTGAATGCAGCAACCAACGCA...
            3130                      3140

... ASN GLY SER GLY SER VAL ILE ALA THR THR SER
                ... AATGGCTTCCGGCAGCCGTAATCGCGACAACCTC
                   ...3150              3160              3170              3180

SER ARG VAL ASN ILE THR GLY ASP LEU ...
AAGCAGAGTGAACATCACTGGGGATTTA...
            3190                      3200

... ILE THR ILE ASN GLY LEU ASN ILE ILE SER LYS
                ... ATCACAATAAATGGATTAAATATCATTTCAAAA
                   ...3210              3220              3230              3240

ASN GLY ILE ASN THR VAL LEU LEU LYS ...
AAACGGTATAAACACCGTACTGTTAAAA...
            3250                      3260

... GLY VAL LYS ILE ASP VAL LYS TYR ILE GLN PRO
                ... GGCGTTAAAATTGATGTGAAATACATTCAACC
                   ...3270              3280              3290              3300

GLY ILE ALA SER VAL ASP GLU VAL ILE ...
GGGTATAGCAAGCGTAGATGAAGTAATT...
            3310                      3320
```

FIG.26Q

```
LEU SER ASP GLU ARG GLU ALA LEU ...      ... GLU ALA LYS ARG ILE LEU GLU LYS VAL LYS ASP
TTTATCTGATGAAGAAAGAGAAGCGTTA...           ...GAAGCGAAACGCATCCTTGAGAAGGTAAAAGA
      3370         3380                        3330         3340         3350         3360

... ALA LYS LEU GLY VAL SER ALA VAL ARG PHE ALA
                                          ...GCTAAACTTGGCGTAAGCGCTGTACGTTTTGC
                                                3390         3400         3410         3420

GLU PRO ASN ASN ALA ILE THR ILE ASN ...   ... THR GLN ASN GLU PHE THR THR ARG PRO SER SER
TGAGCCAAATAATGCCATTACGATTAAT...           ...ACACAAAAATGAGTTTACAACCAGACCATCAAG
      3430                                     ...3450         3460         3470         3480

GLN VAL THR ILE SER GLU GLY LYS VAL ...   ... CYS PHE LEU ILE GLY ASN GLY ALA THR ILE CYS
TCAAGTGACAATTTCTGAAGGTAAGGTA...           ...TGTTTCTTAATCGGCAATGGTGCAACAATATG
      3490         3500                         ...3510         3520         3530         3540
```

FIG.26R

```
THR ASN ILE ALA ASP ILE GLU ARG ***
CACCAATATTGCTGATATTGAGCGGGTAG
         3550        3560
```

FIG.27A

| | |
|---|---|
| ACACGGTTCT CTTAATACTA GTACAAACCC ACAATAAAAT ATGACAAACA ACAATTACAA | 60 |
| CACCTTTTTT GCAGTCTATA TGCAAATATT TTAAAAAATA GTATAAATCC GCCATATAAA | 120 |
| ATTGTATAAT CTTTCATCTT TCATCTTCA TCTTTCATCT TTCATCTTTC ATCTTTCATC | 180 |
| TTTCATCTCT CATCTCTTCA CTTTCATCTT CTTTTCATCT TCTTTCATCT TTCATCTTTC | 240 |
| ACATGCCCTG ATGAACCGAG GAAGGGAG GAGGGCAAG AATGAAGAGG GAGCTGAACG | 300 |
| AAGCAAATG ATAAAGTAAT TTAATTGTTC AACTAACCTT AGGAGAAAAT ATG AAC | 356 |
| | Met Asn |
| | 1 |

| AAG CTA TAT CGT CTC AAA TTC AGC AAA CGC CTG AAT GCT TTG GTT GCT | 404 |
|---|---|
| Lys Leu Tyr Arg Leu Lys Phe Ser Lys Arg Leu Asn Ala Leu Val Ala | |
| 5 10 15 | |

| GTG TCT GAA TTG GCA CGG GGT TGT GAC CAT TCC ACA GAA AAA GGC AGC | 452 |
|---|---|
| Val Ser Glu Leu Ala Arg Gly Cys Asp His Ser Thr Glu Lys Gly Ser | |
| 20 25 30 | |

FIG.27B

```
GAA AAA CCT GCT CGC ATG AAA GTG CGT CAC TTA GCG TTA AAG CCA CTT    500
Glu Lys Pro Ala Arg Met Lys Val Arg His Leu Ala Leu Lys Pro Leu
 35                  40                  45                  50

TCC GCT ATG TTA CTA TCT TTA GGT GTA ACA TCT ATT CCA CAA TCT GTT    548
Ser Ala Met Leu Leu Ser Leu Gly Val Thr Ser Ile Pro Gln Ser Val
         55                  60                  65

TTA GCA AGC GGC TTA CAA GGA ATG GAT GTA CAC GGC ACA GCC ACT        596
Leu Ala Ser Gly Leu Gln Gly Met Asp Val His Gly Thr Ala Thr
                 70                  75                  80

ATG CAA GTA GAT GGT AAT AAA ACC ATT ATC CGC AAC AGT GTT GAC GAT    644
Met Gln Val Asp Gly Asn Lys Thr Ile Ile Arg Asn Ser Val Asp Asp
         85                  90                  95

ATC ATT AAT TGG AAA CAA TTT AAC ATC GAC CAA AAT GAA ATG GTG CAG    692
Ile Ile Asn Trp Lys Gln Phe Asn Ile Asp Gln Asn Glu Met Val Gln
        100                 105                 110

TTT TTA CAA GAA AAC AAC TCC GCC GTA TTC AAC CGT GTT ACA TCT        740
Phe Leu Gln Glu Asn Asn Ser Ala Val Phe Asn Arg Val Thr Ser
115                 120                 125                 130
```

FIG.27C

```
AAC CAA ATC TCC CAA TTA AAA GCG ATT TTA GAT TCT AAC GGA CAA GTC      788
Asn Gln Ile Ser Gln Leu Lys Gly Ile Leu Asp Ser Asn Gly Gln Val
                135                     140                 145

TTT TTA ATC AAC CCA AAT GGT ATC ACA ATA GGT AAA GAC GCA ATT ATT      836
Phe Leu Ile Asn Pro Asn Gly Ile Thr Ile Gly Lys Asp Ala Ile Ile
                150                     155                 160

AAC ACT AAT GGC TTT ACG GCT TCT ACG CTA GAC ATT TCT AAC GAA AAC      884
Asn Thr Asn Gly Phe Thr Ala Ser Thr Leu Asp Ile Ser Asn Glu Asn
                165                     170                 175

ATC AAG GCG CGT AAT TTC ACC TTC GAG CAA ACC AAA GAT AAA GCG CTC      932
Ile Lys Ala Arg Asn Phe Thr Phe Glu Gln Thr Lys Asp Lys Ala Leu
        180                     185                     190

GCT GAA ATT GTG AAT CAC GGT TTA ATT ACT GTC GGT AAA GAC GGC AGT      980
Ala Glu Ile Val Asn His Gly Leu Ile Thr Val Gly Lys Asp Gly Ser
            195                     200                 205     210

GTA AAT CTT ATT GGT GGC AAA GTG AAA AAC GAG GGT GTG ATT AGC GTA     1028
Val Asn Leu Ile Gly Gly Lys Val Lys Asn Glu Gly Val Ile Ser Val
            215                     220                 225
```

FIG.27D

```
AAT GGT GGC AGC ATT TCT TTA CTC GCA GGG CAA AAA ATC ACC ATC AGC    1076
Asn Gly Gly Ser Ile Ser Leu Leu Ala Gly Gln Lys Ile Thr Ile Ser
            230                 235                 240

GAT ATA ATA AAC CCA ACC ATT ACT TAC AGC ATT GCC GCG CCT GAA AAT    1124
Asp Ile Ile Asn Pro Thr Ile Thr Tyr Ser Ile Ala Ala Pro Glu Asn
            245                 250                 255

GAA GCG GTC AAT CTG GCC GAT ATT TTT GCC AAA GGC GGT AAC ATT AAT    1172
Glu Ala Val Asn Leu Gly Asp Ile Phe Ala Lys Gly Gly Asn Ile Asn
            260                 265                 270

GTC CGT GCT GCC ACT ATT CGA AAC CAA GGT AAA CTT TCT GCT GAT TCT    1220
Val Arg Ala Ala Thr Ile Arg Asn Gln Gly Lys Leu Ser Ala Asp Ser
            275                 280                 285                 290

GTA AGC AAA GAT AAA AGC GGC AAT ATT GTT CTT TCC GCC AAA GAG GGT    1268
Val Ser Lys Asp Lys Ser Gly Asn Ile Val Leu Ser Ala Lys Glu Gly
            295                 300                 305

GAA GCG GAA ATT GCC GGT GTA ATT GGC GGT GTA ATT TCC GCT CAA AAT CAG CAA GCT AAA    1316
Glu Ala Glu Ile Gly Gly Val Ile Ser Ala Gln Asn Gln Gln Ala Lys
            310                 315                 320
```

FIG.27E

GGC GGC AAG CTG ATG ATT ACA GGC GAT AAA GTC ACA TTA AAA ACA GGT       1364
Gly Gly Lys Leu Met Ile Thr Gly Asp Lys Val Thr Leu Lys Thr Gly
                325                 330                 335

GCA GTT ATC GAC CTT TCA GGT AAA GAA GGG GGA GAA ACT TAC CTT GGC       1412
Ala Val Ile Asp Leu Ser Gly Lys Glu Gly Gly Glu Thr Tyr Leu Gly
            340                 345                 350

GGT GAC GAG CGC GGC GAA AAG GGC ATT CAA TTA GCA AAG AAA               1460
Gly Asp Glu Arg Gly Glu Lys Gly Ile Gln Leu Ala Lys Lys
355                 360                 365             370

ACC TCT TTA GAA AAA GGC TCA ACC ATC AAT GTA TCA GGC AAA GAA AAA       1508
Thr Ser Leu Glu Lys Gly Ser Thr Ile Asn Val Ser Gly Lys Glu Lys
        375                 380                 385

GGC GGA CGC GCT ATT GTG TGG GGC GAT ATT GCG TTA ATT GAC GGC AAT       1556
Gly Gly Arg Ala Ile Val Trp Gly Asp Ile Ala Leu Ile Asp Gly Asn
    390                 395                 400

ATT AAC GCT CAA GGT GAT AGT GGT GAT ATC GCT AAA ACC GGT GGT TTT GTG  1604
Ile Asn Ala Gln Gly Asp Ser Gly Asp Ile Ala Lys Thr Gly Gly Phe Val
405                 410                 415

FIG.27F

```
GAG ACG TCG GGG CAT GAT TTA TTC ATC AAA GAC AAT GCA ATT GTT GAC      1652
Glu Thr Ser Gly His Asp Leu Phe Ile Lys Asp Asn Ala Ile Val Asp
                420                         425                 430

GCC AAA GAG TGG TTG TTA GAC CCG GAT AAT GTA TCT ATT AAT GCA GAA      1700
Ala Lys Glu Trp Leu Leu Asp Pro Asp Asn Val Ser Ile Asn Ala Glu
        435                         440                 445         450

ACA GCA GGA CGC AGC AAT ACT TCA GAA GAC GAT GAA TAC ACG GGA TCC      1748
Thr Ala Gly Arg Ser Asn Thr Ser Glu Asp Asp Glu Tyr Thr Gly Ser
            455                         460                     465

GGG AAT AGT GCC AGC ACC CCA AAA CGA AAC AAA GAA AAG ACA ACA TTA      1796
Gly Asn Ser Ala Ser Thr Pro Lys Arg Asn Lys Glu Lys Thr Thr Leu
    470                         475                             480

ACA AAC ACA ACT CTT GAG AGT ATA CTA AAA AAA GGT ACC TTT GTT AAC      1844
Thr Asn Thr Thr Leu Glu Ser Ile Leu Lys Lys Gly Thr Phe Val Asn
        485                         490                 495

ATC ACT GCT AAT CAA CGC ATC TAT GTC AAT AGC TCC ATT AAT TTA TCC      1892
Ile Thr Ala Asn Gln Arg Ile Tyr Val Asn Ser Ser Ile Asn Leu Ser
            500                         505                     510
```

FIG. 27G

```
AAT GGC AGC TTA ACT CTT TGG AGT GAG GGT CCG AGC GGT GGC GGT    1940
Asn Gly Ser Leu Thr Leu Trp Ser Glu Gly Arg Ser Gly Gly Val
515                 520                 525                 530

GAG ATT AAC AAC GAT ATT ACC ACC GGT GAT GAT ACC AGA GGT GCA AAC 1988
Glu Ile Asn Asn Asp Ile Thr Thr Gly Asp Asp Thr Arg Gly Ala Asn
        535                 540                 545

TTA ACA ATT TAC TCA GGC GGC TGG GTT GAT GTT CAT AAA AAT ATC TCA 2036
Leu Thr Ile Tyr Ser Gly Gly Trp Val Asp Val His Lys Asn Ile Ser
550                 555                 560

CTC GGG GCG CAA AAC ATA AAC ATT ACA GCT AAA CAA GAT ATC GCC    2084
Leu Gly Ala Gln Asn Ile Asn Ile Thr Ala Lys Gln Asp Ile Ala
565                 570                 575

TTT GAG AAA GGA AGC AAC CAA GTC ATT ACA GGT CAA GGG ACT ATT ACC 2132
Phe Glu Lys Gly Ser Asn Gln Val Ile Thr Gly Gln Gly Thr Ile Thr
580                 585                 590

TCA GGC AAT CAA AAA GGT TTT AGA TTT AAT AAT GTC TCT CTA AAC GGC 2180
Ser Gly Asn Gln Lys Gly Phe Arg Phe Asn Asn Val Ser Leu Asn Gly
595                 600                 605                 610
```

FIG.27H

ACT GGC AGC GGA CTG CAA TTC ACC ACT AAA AGA ACC AAT AAA TAC GCT    2228
Thr Gly Ser Gly Leu Gln Phe Thr Thr Lys Arg Thr Asn Lys Tyr Ala
            615                 620                 625

ATC ACA AAT AAA TTT GAA GGG ACT TTA AAT ATT TCA GGG AAA GTG AAC    2276
Ile Thr Asn Lys Phe Glu Gly Thr Leu Asn Ile Ser Gly Lys Val Asn
            630                 635                 640

ATC TCA ATG GTT TTA CCT AAA AAT GAA AGT GGA TAT GAT AAA TTC AAA    2324
Ile Ser Met Val Leu Pro Lys Asn Glu Ser Gly Tyr Asp Lys Phe Lys
            645                 650                 655

GGA CGC ACT TAC TGG AAT TTA ACC TCC TTA AAT GTT TCC GAG AGT GGC    2372
Gly Arg Thr Tyr Trp Asn Leu Thr Ser Leu Asn Val Ser Glu Ser Gly
            660                 665                 670

GAG TTT AAC CTC ACT ATT GAC TCC AGA GGA AGC GAT AGT GCA GGC ACA    2420
Glu Phe Asn Leu Thr Ile Asp Ser Arg Gly Ser Asp Ser Ala Gly Thr
            675                 680                 685                 690

CTT ACC CAG CCT TAT AAT TTA AAC GGT ATA TCA TTC AAC AAA GAC ACT    2468
Leu Thr Gln Pro Tyr Asn Leu Asn Gly Ile Ser Phe Asn Lys Asp Thr
            695                 700                 705

FIG. 27I

```
ACC TTT AAT GTT GAA CGA AAT GCA AGA GTC AAC TTT GAC ATC AAG GCA    2516
Thr Phe Asn Val Glu Arg Asn Ala Arg Val Asn Phe Asp Ile Lys Ala
710                             715                             720

CCA ATA AAT AAG TAT TCT AGT TTG AAT TAC GCA TCA TTT AAT            2564
Pro Ile Gly Ile Asn Lys Tyr Ser Ser Leu Asn Tyr Ala Ser Phe Asn
725                             730                             735

GGA AAC ATT TCA GTT TCG GGA GGG GGG AGT GTT GAT TTC ACA CTT CTC    2612
Gly Asn Ile Ser Val Ser Gly Gly Gly Ser Val Asp Phe Thr Leu Leu
740                             745                             750

GCC TCA TCC TCT AAC GTC CAA ACC CCC GGT GTA GTT ATA AAT TCT AAA    2660
Ala Ser Ser Ser Asn Val Gln Thr Pro Gly Val Val Ile Asn Ser Lys
755                             760                             765                             770

TAC TTT AAT GTT TCA ACA GGG TCA AGT TTA AGA TTT AAA ACT TCA GGC    2708
Tyr Phe Asn Val Ser Thr Gly Ser Ser Leu Arg Phe Lys Thr Ser Gly
775                             780                             785

TCA ACA AAA ACT GGC TTC TCA ATA GAG AAA GAT TTA ACT TTA AAT GCC    2756
Ser Thr Lys Thr Gly Phe Ser Ile Glu Lys Asp Leu Thr Leu Asn Ala
790                             795                             800
```

FIG.27J

```
ACC GGA GGC AAC ATA ACA CTT TTG CAA GTT GAA GGC ACC GAT GGA ATG    2804
Thr Gly Gly Asn Ile Thr Leu Leu Gln Val Glu Gly Thr Asp Gly Met
805                             810                             815

ATT GGT AAA GGC ATT GTA GCC AAA AAA AAC ATA ACC TTT GAA GGA GGT    2852
Ile Gly Lys Gly Ile Val Ala Lys Lys Asn Ile Thr Phe Glu Gly Gly
        820                             825                     830

AAC ATC ACC TTT GGC TCC AGG AAA GCC GTA ACA GAA ATC GAA GGC AAT    2900
Asn Ile Thr Phe Gly Ser Arg Lys Ala Val Thr Glu Ile Glu Gly Asn
835                             840                             845                 850

GTT ACT ATC AAT AAC AAC GTC ACT CTT ATC GGT TCG GAT TTT            2948
Val Thr Ile Asn Asn Asn Val Thr Leu Ile Gly Ser Asp Phe
        855                             860                     865

GAC AAC CAT CAA AAA CCT TTA ACT ATT AAA AAA GAT GTC ATC ATT AAT    2996
Asp Asn His Gln Lys Pro Leu Thr Ile Lys Lys Asp Val Ile Ile Asn
870                             875                             880

AGC GGC AAC CTT ACC GCT GGA GGC AAT ATT GTC AAT ATA GCC GGA AAT    3044
Ser Gly Asn Leu Thr Ala Gly Gly Asn Ile Val Asn Ile Ala Gly Asn
        885                             890                     895
```

FIG.27K

```
CTT ACC GTT GAA AGT AAC GCT AAT TTC AAA GCT ATC ACA AAT TTC ACT    3092
Leu Thr Val Glu Ser Asn Ala Asn Phe Lys Ala Ile Thr Asn Phe Thr
900                             905                 910

TTT AAT GTA GGC GGC TTG TTT GAC AAC AAA GGC AAT TCA AAT ATT TCC    3140
Phe Asn Val Gly Gly Leu Phe Asp Asn Lys Gly Asn Ser Asn Ile Ser
915                             920                 925             930

ATT GCC AAA GGA GGG GCT CGC TTT AAA GAC ATT GAT AAT TCC AAG AAT    3188
Ile Ala Lys Gly Gly Ala Arg Phe Lys Asp Ile Asp Asn Ser Lys Asn
935                             940                 945

TTA AGC ATC ACC AAC ACC AAC TCC AGC TCC ACT TAC CGC ACT ATT ATA AGC 3236
Leu Ser Ile Thr Asn Thr Asn Ser Ser Ser Thr Tyr Arg Thr Ile Ile Ser
950                             955                 960

GGC AAT ATA ACC AAT AAA AAC GGT GAT TTA AAT ATT ACG AAC GAA GGT    3284
Gly Asn Ile Thr Asn Lys Asn Gly Asp Leu Asn Ile Thr Asn Glu Gly
965                             970                 975

AGT GAT ACT GAA ATG CAA ATT GGC GGC GAT GTC TCG CAA AAA GAA GGT    3332
Ser Asp Thr Glu Met Gln Ile Gly Gly Asp Val Ser Gln Lys Glu Gly
980                             985                 990
```

FIG.27L

```
AAT CTC ACG ATT TCT TCT GAC AAA ATC AAT ATT ACC AAA CAG ATA ACA    3380
Asn Leu Thr Ile Ser Ser Asp Lys Ile Asn Ile Thr Lys Gln Ile Thr
995                 1000                1005                1010

ATC AAG GCA GGT GTT GAT GGG GAG AAT TCC GAT TCA GAC GCG ACA AAC    3428
Ile Lys Ala Gly Val Asp Gly Glu Asn Ser Asp Ser Asp Ala Thr Asn
            1015                1020                1025

AAT GCC AAT CTA ACC ATT AAA ACC AAA GAA TTG AAA TTA ACG CAA GAC    3476
Asn Ala Asn Leu Thr Ile Lys Thr Lys Glu Leu Lys Leu Thr Gln Asp
        1030                1035                1040

CTA AAT ATT TCA GGT TTC AAT AAA GCA GAG ATT ACA GCT AAA GAT GGT    3524
Leu Asn Ile Ser Gly Phe Asn Lys Ala Glu Ile Thr Ala Lys Asp Gly
            1045                1050                1055

AGT GAT TTA ACT ATT GGT AAC ACC AAT AGT GCT GAT GGT ACT AAT GCC    3572
Ser Asp Leu Thr Ile Gly Asn Thr Asn Ser Ala Asp Gly Thr Asn Ala
        1060                1065                1070

AAA AAA GTA ACC TTT AAC CAG GTT AAA GAT TCA AAA ATC TCT GCT GAC    3620
Lys Lys Val Thr Phe Asn Gln Val Lys Asp Ser Lys Ile Ser Ala Asp
1075                1080                1085                1090
```

FIG.27M

```
GGT CAC AAG GTG ACA CTA CAC AGC AAA GTG GAA ACA TCC GGT AGT AAT       3668
Gly His Lys Val Thr Leu His Ser Lys Val Glu Thr Ser Gly Ser Asn
              1095                1100                1105

AAC ACT GAA GAT AGC AGT GAC AAT AAT GCC GGC TTA ACT ATC GAT           3716
Asn Thr Glu Asp Ser Ser Asp Asn Asn Ala Gly Leu Thr Ile Asp
          1110                1115                1120

GCA AAA AAT GTA ACA GTA AAC AAC AAT ATT ACT TCT CAC AAA GCA GTG       3764
Ala Lys Asn Val Thr Val Asn Asn Ile Thr Ser His Lys Ala Val
              1125                1130                1135

AGC ATC TCT GCG ACA AGT GGA GAA ATT ACC ACT AAA ACA GGT ACA ACC       3812
Ser Ile Ser Ala Thr Ser Gly Glu Ile Thr Thr Lys Thr Gly Thr Thr
              1140                1145                1150

ATT AAC GCA ACC ACT GGT AAC GTG GAG ATA ACC GCT CAA ACA GGT AGT       3860
Ile Asn Ala Thr Thr Gly Asn Val Glu Ile Thr Ala Gln Thr Gly Ser
              1155                1160                1165                1170

ATC CTA GGT GGA ATT GAG TCC AGC TCT GTA ACA CTT ACT GCA               3908
Ile Leu Gly Gly Ile Glu Ser Ser Ser Val Thr Leu Thr Ala
              1175                1180                1185
```

FIG.27N

ACC GAG GGC GCT CTT GCT GTA AGC AAT ATT TCG GGC AAC ACC GTT ACT   3956
Thr Glu Gly Ala Leu Ala Val Ser Asn Ile Ser Gly Asn Thr Val Thr
                1190                      1195                1200

GTT ACT GCA AAT AGC GGT GCA TTA ACC ACT TTG GCA TCT ACA ATT       4004
Val Thr Ala Asn Ser Gly Ala Leu Thr Thr Leu Ala Gly Ser Thr Ile
                1205                      1210                1215

AAA GGA ACC GAG AGT GTA ACC ACT TCA AGT CAA TCA GGC GAT ATC GGC   4052
Lys Gly Thr Glu Ser Val Thr Thr Ser Ser Gln Ser Gly Asp Ile Gly
                1220                      1225                1230

GGT ACG ATT TCT GGT GGC ACA GTA GAG GTT AAA GCA ACC GAA AGT TTA   4100
Gly Thr Ile Ser Gly Gly Thr Val Glu Val Lys Ala Thr Glu Ser Leu
                1235                      1240                      1250

ACC ACT CAA TCC AAT TCA AAA ATT AAA GCA ACA ACA GGC GAG GCT AAC   4148
Thr Thr Gln Ser Asn Ser Lys Ile Lys Ala Thr Thr Gly Glu Ala Asn
                1255                      1260                1265

GTA ACA AGT GCA ACA GGT ACA ATT GGT GGT ACG ATT TCC GGT AAT ACG   4196
Val Thr Ser Ala Thr Gly Thr Ile Gly Gly Thr Ile Ser Gly Asn Thr
                1270                      1275                1280

FIG.27O

```
GTA AAT GTT ACG GCA AAC GCT GGC GAT TTA ACA GTT GGG AAT GGC GCA    4244
Val Asn Val Thr Ala Asn Ala Gly Asp Leu Thr Val Gly Asn Gly Ala
                1285                    1290                1295

GAA ATT AAT GCG ACA GAA GGA GCT GCA ACC TTA ACT ACA TCA TCG GGC    4292
Glu Ile Asn Ala Thr Glu Gly Ala Ala Thr Leu Thr Thr Ser Ser Gly
                1300                    1305                1310

AAA TTA ACT ACC GAA GCT AGT TCA CAC ATT ACT TCA GCC AAG GGT CAG    4340
Lys Leu Thr Thr Glu Ala Ser Ser His Ile Thr Ser Ala Lys Gly Gln
                1315                    1320                1325                1330

GTA AAT CTT TCA GCT CAG GAT GGT AGC GTT GCA GGA AGT ATT AAT GCC    4388
Val Asn Leu Ser Ala Gln Asp Gly Ser Val Ala Gly Ser Ile Asn Ala
                1335                    1340                1345

GCC AAT GTG ACA CTA AAT ACT ACA GGC ACT TTA ACT ACC GTG AAG GGT    4436
Ala Asn Val Thr Leu Asn Thr Thr Gly Thr Leu Thr Thr Val Lys Gly
                1350                    1355                1360

TCA AAC ATT AAT GCA ACC AGC GGT ACC TTG GTT ATT AAC GCA AAA GAC    4484
Ser Asn Ile Asn Ala Thr Ser Gly Thr Leu Val Ile Asn Ala Lys Asp
                1365                    1370                1375
```

FIG.27P

```
GCT GAG CTA AAT GGC GCA TTG GGT AAC CAC ACA GTG GTA AAT GCA       4532
Ala Glu Leu Asn Gly Ala Ala Leu Gly Asn His Thr Val Val Asn Ala
                    1380                1385                1390

ACC AAC GCA AAT GGC TCC GGC AGC GTA ATC GCG ACA ACC TCA AGC AGA   4580
Thr Asn Ala Asn Gly Ser Gly Ser Val Ile Ala Thr Thr Ser Ser Arg
            1395                1400                1405      1410

GTG AAC ATC ACT GGG GAT TTA ATC ACA ATA AAT GGA TTA AAT ATC ATT   4628
Val Asn Ile Thr Gly Asp Leu Ile Thr Ile Asn Gly Leu Asn Ile Ile
    1415                1420                1425

TCA AAA AAC GGT ATA AAC ACC GTA CTG TTA AAA GGC GTT AAA ATT GAT   4676
Ser Lys Asn Gly Ile Asn Thr Val Leu Leu Lys Gly Val Lys Ile Asp
1430                1435                1440

GTG AAA TAC ATT CAA CCG GGT ATA GCA AGC GTA GAT GAA GTA ATT GAA   4724
Val Lys Tyr Ile Gln Pro Gly Ile Ala Ser Val Asp Glu Val Ile Glu
        1445                1450                1455

GCG AAA CGC ATC CTT GAG AAG GTA AAA GAT TTA TCT GAT GAA GAA AGA   4772
Ala Lys Arg Ile Leu Glu Lys Val Lys Asp Leu Ser Asp Glu Glu Arg
            1460                1465                1470
```

FIG.27Q

```
GAA GCG TTA GCT AAA CTT GGA GTA AGT GCT GTA CGT TTT ATT GAG CCA        4820
Glu Ala Leu Ala Lys Leu Gly Val Ser Ala Val Arg Phe Ile Glu Pro
1475                    1480                    1485            1490

AAT AAT ACA ATT ACA GTC GAT ACA CAA AAT GAA TTT GCA ACC AGA CCA        4868
Asn Asn Thr Ile Thr Val Asp Thr Gln Asn Glu Phe Ala Thr Arg Pro
            1495                    1500                    1505

TTA AGT CGA ATA GTG ATT TCT GAA GGC AGG GCG TGT TTC TCA AAC AGT        4916
Leu Ser Arg Ile Val Ile Ser Glu Gly Arg Ala Cys Phe Ser Asn Ser
        1510                    1515                    1520

GAT GGC GCG ACG GTG TGC GTT AAT ATC GCT GAT AAC GGG CGG                4958
Asp Gly Ala Thr Val Cys Val Asn Ile Ala Asp Asn Gly Arg
                1525                    1530            1535

TAGCGGTCAG TAATTGACAA GGTAGATTTC ATCCTGCAAT GAAGTCATTT TATTTTCGTA      5018

TTATTTACTG TGTGGGTTAA AGTTCAGTAC GGGCTTTACC CATCTGTAA AAAATTACGG      5078

AGAATACAAT AAAGTATTTT TAACAGGTTA TTATTATG                              5116
```

FIG.28A

```
TAAATATACA AGATAATAAA AATAAATCAA GATTTTGTG ATGACAAACA ACAATTACAA     60

CACCTTTTT GCAGTCTATA TGCAAATATT TTAAAAAAAT AGTATAAATC CCCCATATAA    120

AATGTATAA TCTTTCATCT TTCATCTTTA ATCTTTCATC TTTCATCTTT CATCTTTCAT    180

CTTTCATCTT TCATCTTTCA TCTTTCATCT TTCATCTTTC ATCTTTCATC TTTCATCTTT    240

CACATGAAAT GATGAACCGA GGGAAGGGAG GGAGGGGCAA GAATGAAGAG GGAGCTGAAC    300

GAACGCAAAT GATAAAGTAA TTTAATTGTT CAACTAACCT TAGGAGAAAA T ATG AAC    357
                                                        Met Asn
                                                          1

AAG ATA TAT CGT CTC AAA TTC AGC AAA CGC CTG AAT GCT TTG GTT GCT    405
Lys Ile Tyr Arg Leu Lys Phe Ser Lys Arg Leu Asn Ala Leu Val Ala
         5                  10                  15

GTG TCT GAA TTG GCA CGG GGT TGT GAC CAT TCC ACA GAA AAA GGC TTC    453
Val Ser Glu Leu Ala Arg Gly Cys Asp His Ser Thr Glu Lys Gly Phe
 20                  25                  30

CGC TAT GTT ACT ATC TTT AGG TGT AAC CAC TTA GCG TTA AAG CCA CTT    501
Arg Tyr Val Thr Ile Phe Arg Cys Asn His Leu Ala Leu Lys Pro Leu
 35                  40                  45                  50
```

FIG. 28B

| | | | | | | | | | | | | | | | | |
|---|---|---|---|---|---|---|---|---|---|---|---|---|---|---|---|---|
| TCC | GCT | ATG | TTA | CTA | TCT | TTA | GGT | GTA | ACA | TCT | ATT | CCA | CAA | TCT | GTT | 549 |
| Ser | Ala | Met | Leu | Leu | Ser | Leu | Gly | Val | Thr | Ser | Ile | Pro | Gln | Ser | Val | |
| | | | 55 | | | | | 60 | | | | | | 65 | | |

| | | | | | | | | | | | | | | | | |
|---|---|---|---|---|---|---|---|---|---|---|---|---|---|---|---|---|
| TTA | GCA | AGC | GGC | TTA | CAA | GGA | ATG | GAT | GTA | CAC | GGC | ACA | GCC | ACT | | 597 |
| Leu | Ala | Ser | Gly | Leu | Gln | Gly | Met | Asp | Val | His | Gly | Thr | Ala | Thr | | |
| | | | 70 | | | | | 75 | | | | | 80 | | | |

| | | | | | | | | | | | | | | | | |
|---|---|---|---|---|---|---|---|---|---|---|---|---|---|---|---|---|
| ATG | CAA | GTA | GAT | GGT | AAT | AAA | ACC | ATT | ATC | CGC | AAC | AGT | GTT | GAC | GCT | 645 |
| Met | Gln | Val | Asp | Gly | Asn | Lys | Thr | Ile | Ile | Arg | Asn | Ser | Val | Asp | Ala | |
| | | 85 | | | | | 90 | | | | | 95 | | | | |

| | | | | | | | | | | | | | | | | |
|---|---|---|---|---|---|---|---|---|---|---|---|---|---|---|---|---|
| ATC | ATT | AAT | TGG | AAA | CAA | TTT | AAC | ATC | GAC | CAA | AAT | GAA | ATG | GTG | CAG | 693 |
| Ile | Ile | Asn | Trp | Lys | Gln | Phe | Asn | Ile | Asp | Gln | Asn | Glu | Met | Val | Gln | |
| | 100 | | | | | 105 | | | | | 110 | | | | | |

| | | | | | | | | | | | | | | | | |
|---|---|---|---|---|---|---|---|---|---|---|---|---|---|---|---|---|
| TTT | TTA | CAA | GAA | AAC | AAC | TCC | GCC | GTA | TTC | AAC | CGT | GTT | ACA | TCT | | 741 |
| Phe | Leu | Gln | Glu | Asn | Asn | Ser | Ala | Val | Phe | Asn | Arg | Val | Thr | Ser | | |
| 115 | | | | | 120 | | | | | 125 | | | | 130 | | |

| | | | | | | | | | | | | | | | | |
|---|---|---|---|---|---|---|---|---|---|---|---|---|---|---|---|---|
| AAC | CAA | ATC | TCC | CAA | TTA | AAA | GGG | ATT | TTA | GAT | TCT | AAC | GGA | CAA | GTC | 789 |
| Asn | Gln | Ile | Ser | Gln | Leu | Lys | Gly | Ile | Leu | Asp | Ser | Asn | Gly | Gln | Val | |
| | | | | 135 | | | | | 140 | | | | | 145 | | |

| | | | | | | | | | | | | | | | | |
|---|---|---|---|---|---|---|---|---|---|---|---|---|---|---|---|---|
| TTT | TTA | ATC | AAC | CCA | AAT | GGT | ATC | ACA | ATA | GGT | AAA | GAC | GCA | ATT | ATT | 837 |
| Phe | Leu | Ile | Asn | Pro | Asn | Gly | Ile | Thr | Ile | Gly | Lys | Asp | Ala | Ile | Ile | |
| | 150 | | | | | 155 | | | | | 160 | | | | | |

FIG. 28C

```
AAC ACT AAT GGC TTT ACG GCT TCT ACG CTA GAC ATT TCT AAC GAA AAC    885
Asn Thr Asn Gly Phe Thr Ala Ser Thr Leu Asp Ile Ser Asn Glu Asn
165                     170                     175

ATC AAG GCG CGT AAT TTC ACC TTC GAG CAA ACC AAA GAT AAA GCG CTC    933
Ile Lys Ala Arg Asn Phe Thr Phe Glu Gln Thr Lys Asp Lys Ala Leu
        180                     185                     190

GCT GAA ATT GTG AAT CAC GGT TTA ATT ACT GTC GGT AAA GAC GGC AGT    981
Ala Glu Ile Val Asn His Gly Leu Ile Thr Val Gly Lys Asp Gly Ser
195                     200                     205             210

GTA AAT CTT ATT GGT GGC AAA GTG AAA AAC GAG GGT GTG ATT AGC GTA   1029
Val Asn Leu Ile Gly Gly Lys Val Lys Asn Glu Gly Val Ile Ser Val
        215                     220                     225

AAT GGT GCC AGC ATT TCT TTA CTC GCA GGG CAA AAA ATC ACC ATC AGC   1077
Asn Gly Gly Ser Ile Ser Leu Leu Ala Gly Gln Lys Ile Thr Ile Ser
230                     235                     240

GAT ATA ATA AAC CCA ACC ATT ACT TAC AGC ATT ACC GCC CCT GAA AAT   1125
Asp Ile Ile Asn Pro Thr Ile Thr Tyr Ser Ile Thr Ala Ala Pro Glu Asn
        245                     250                     255

GAA GCG GTC AAT CTG GGC GAT ATT TTT GCC AAA GGC GGT AAC ATT AAT   1173
Glu Ala Val Asn Leu Gly Asp Ile Phe Ala Lys Gly Gly Asn Ile Asn
260                     265                     270
```

FIG.28D

| | | | | | | | | |
|---|---|---|---|---|---|---|---|---|
| GTC | CGT | GCT | GCC | ACT | ATT | CGA | AAC | CAA | GGT | AAA | CTT | TCT | GCT | GAT | TCT | 1221 |
| Val | Arg | Ala | Ala | Thr | Ile | Arg | Asn | Gln | Gly | Lys | Leu | Ser | Ala | Asp | Ser |
| 275 | | | | 280 | | | | | 285 | | | | | 290 | |

GTC CGT GCT GCC ACT ATT CGA AAC CAA GGT AAA CTT TCT GCT GAT TCT    1221
Val Arg Ala Ala Thr Ile Arg Asn Gln Gly Lys Leu Ser Ala Asp Ser
275              280                 285                 290

GTA AGC AAA GAT AAA AGC GGC AAT ATT GTT CTT TCC GCC AAA GAG GGT    1269
Val Ser Lys Asp Lys Ser Gly Asn Ile Val Leu Ser Ala Lys Glu Gly
         295                 300                 305

GAA GCG GAA ATT GGC GGT GTA ATT TCC GCT CAA AAT CAG CAA GCT AAA    1317
Glu Ala Glu Ile Gly Gly Val Ile Ser Ala Gln Asn Gln Gln Ala Lys
    310                 315                 320

GGC AAG ATG ATT ACA GGC GAT AAA GTC ACA TTA AAA ACA GGT            1365
Gly Lys Met Ile Thr Gly Asp Lys Val Thr Leu Lys Thr Gly
325                 330                 335

GCA GTT ATC GAC CTT TCA GGT AAA GAA GGG GGA GAA ACT TAC CTT GGC    1413
Ala Val Ile Asp Leu Ser Gly Lys Glu Gly Gly Glu Thr Tyr Leu Gly
340                 345                 350

GGT GAC GAG GGC CGC GGT GAA AAA AAC GGC ATT CAA TTA GCA AAG AAA    1461
Gly Asp Glu Gly Arg Gly Glu Lys Asn Gly Ile Gln Leu Ala Lys Lys
355                 360                 365                 370

ACC TCT TTA GAA AAA GTA TCA ACC ATC AAT GTA TCA GGC AAA GAA AAA    1509
Thr Ser Leu Glu Lys Gly Ser Thr Ile Asn Val Ser Gly Lys Glu Lys
         375                 380                 385

FIG. 28E

```
GGC GGA CGC GCT ATT GTG TGG GGC GAT ATT GCG TTA ATT GAC GCC AAT      1557
Gly Gly Arg Ala Ile Val Trp Gly Asp Ile Ala Leu Ile Asp Gly Asn
            390                 395                 400

ATT AAC GCT CAA GGT AGT GAT ATC GCT AAA ACC GGT GGT TTT GTG          1605
Ile Asn Ala Gln Gly Ser Asp Ile Ala Lys Thr Gly Gly Phe Val
        405                 410                 415

GAG ACA TCG GGG CAT TAT TTA TCC ATT GAC AGC AAT GCA ATT GTT AAA      1653
Glu Thr Ser Gly His Tyr Leu Ser Ile Asp Ser Asn Ala Ile Val Lys
        420                 425                 430

ACA AAA GAG TGG CTA CTA GAC CCT GAT GAT GTA ACA ATT GAA GCC GAA      1701
Thr Lys Glu Trp Leu Leu Asp Pro Asp Asp Val Thr Ile Glu Ala Glu
        435                 440                 445                 450

GAC CCC CTT CGC AAT AAT ACC GGT ATA AAT GAT GAA TTC CCA ACA GGC      1749
Asp Pro Leu Arg Asn Asn Thr Gly Ile Asn Asp Glu Phe Pro Thr Gly
        455                 460                 465

ACC GGT GAA GCA AGC GAC CCT AAA AAA AGC GAA CTC AAA ACA ACG          1797
Thr Gly Glu Ala Ser Asp Pro Lys Lys Ser Glu Leu Lys Thr Thr
        470                 475                 480

CTA ACC AAT ACA ACT ATT TCA AAT TAT CTG AAA AAC GCC TGG ACA ATG      1845
Leu Thr Asn Thr Thr Ile Ser Asn Tyr Leu Lys Asn Ala Trp Thr Met
        485                 490                 495
```

FIG. 28F

```
AAT ATA ACG GCA TCA AGA AAA CTT ACC GTT AAT AGC TCA ATC AAC ATC           1893
Asn Ile Thr Ala Ser Arg Lys Leu Thr Val Asn Ser Ser Ile Asn Ile
        500                 505                 510

GGA AGC AAC TCC CAC TTA ATT CTC CAT AGT AAA GGT CAG CGT GGC GGA           1941
Gly Ser Asn Ser His Leu Ile Leu His Ser Lys Gly Gln Arg Gly Gly
    515                 520                 525                 530

GGC GTT CAG ATT GAT GGA GAT ATT ACT TCT AAA GGC GGA AAT TTA ACC           1989
Gly Val Gln Ile Asp Gly Asp Ile Thr Ser Lys Gly Gly Asn Leu Thr
        535                 540                 545

ATT TAT TCT GGC GGA TGG GTT GAT GTT CAT AAA AAT ATT ACG CTT GAT           2037
Ile Tyr Ser Gly Gly Trp Val Asp Val His Lys Asn Ile Thr Leu Asp
    550                 555                 560

CAG GGT TTT TTA AAT ATT ACC GCC TCC GTA GCT TTT GAA GGT GGA               2085
Gln Gly Phe Leu Asn Ile Thr Ala Ala Ser Val Ala Phe Glu Gly Gly
        565                 570                 575

AAT AAC AAA GCA CGC GAC GCG GCA AAT GCT AAA ATT GTC GCC CAG GGC           2133
Asn Asn Lys Ala Arg Asp Ala Ala Asn Ala Lys Ile Val Ala Gln Gly
    580                 585                 590

ACT GTA ACC ATT ACA GGA GAG GGA AAA GAT TTC AGG GCT AAC AAC GTA           2181
Thr Val Thr Ile Thr Gly Glu Gly Lys Asp Phe Arg Ala Asn Asn Val
        595                 600                 605                 610
```

FIG. 28G

```
TCT TTA AAC GGA ACG GGT AAA GGT CTG AAT ATC ATT TCA TCA GTG AAT    2229
Ser Leu Asn Gly Thr Gly Lys Gly Leu Asn Ile Ile Ser Ser Val Asn
                 615                 620                 625

AAT TTA ACC CAC AAT CTT AGT GGC ACA ATT AAC ATA TCT GGG AAT ATA    2277
Asn Leu Thr His Asn Leu Ser Gly Thr Ile Asn Ile Ser Gly Asn Ile
                 630                 635                 640

ACA ATT AAC CAA ACT ACG AGA AAG AAC ACC TCG TAT TGG CAA ACC AGC    2325
Thr Ile Asn Gln Thr Thr Arg Lys Asn Thr Ser Tyr Trp Gln Thr Ser
                 645                 650                 655

CAT GAT TCG CAC TGG AAC GTC AGT GCT CTT AAT CTA GAG ACA GGC GCA    2373
His Asp Ser His Trp Asn Val Ser Ala Leu Asn Leu Glu Thr Gly Ala
                 660                 665                 670

AAT TTT ACC TTT ATT AAA TAC TAT ATT TCA AGC AAT AGC AAA GGC TTA ACA    2421
Asn Phe Thr Phe Ile Lys Tyr Tyr Ile Ser Asn Ser Lys Gly Leu Thr
                 675                 680                 685                 690

ACA CAG TAT AGA AGC TCT GCA GGG GTG AAT TTT AAC GGC GTA AAT GGC    2469
Thr Gln Tyr Arg Ser Ser Ala Gly Val Asn Phe Asn Gly Val Asn Gly
                 695                 700                 705

AAC ATG TCA TTC AAT CTC AAA GAA GCG AAA GTT AAT TTC AAA TTA    2517
Asn Met Ser Phe Asn Leu Lys Glu Ala Lys Val Asn Phe Lys Leu
                 710                 715                 720
```

FIG.28H

```
AAA CCA AAC GAG AAC ATG AAC ACA AGC AAA CCT TTA CCA ATT CGG TTT    2565
Lys Pro Asn Glu Asn Met Asn Thr Ser Lys Pro Leu Pro Ile Arg Phe
            725                 730                 735

TTA GCC AAT ATC ACA GCC ACT GGT GGG GCC TCT GTT TTT GAT ATA        2613
Leu Ala Asn Ile Thr Ala Thr Gly Gly Gly Ser Val Phe Phe Asp Ile
        740                 745                 750

TAT GCC AAC CAT TCT GGC AGA GGG GCT GAG TTA AAA ATG AGT GAA ATT    2661
Tyr Ala Asn His Ser Gly Arg Gly Ala Glu Leu Lys Met Ser Glu Ile
    755                 760                 765                 770

AAT ATC TCT AAC GGC GCT AAT TTT ACC TTA AAT TCC CAT GTT CGC GGC    2709
Asn Ile Ser Asn Gly Ala Asn Phe Thr Leu Asn Ser His Val Arg Gly
        775                 780                 785

GAT GAC GCT TTT AAA ATC AAC GAC TTA ACC ATA AAT GCA ACC AAT        2757
Asp Asp Ala Phe Lys Ile Asn Asp Leu Thr Ile Asn Ala Thr Asn
        790                 795                 800

TCA AAT TTC AGC CTC AGA CAG ACG AAA GAT GAT TTT TAT GAC GGG TAC    2805
Ser Asn Phe Ser Leu Arg Gln Thr Lys Asp Asp Phe Tyr Asp Gly Tyr
        805                 810                 815

GCA CGC ATC AAT TCA AAT TCA ACC TAC AAC ATA TCC ATT CTG GGC GGT    2853
Ala Arg Ile Asn Ser Asn Ser Thr Tyr Asn Ile Ser Ile Leu Gly Gly
        820                 825                 830
```

FIG. 28I

```
AAT GTC ACC CTT GGT GGA CAA AAC TCA AGC AGC ATT ACG GGG AAT   2901
Asn Val Thr Leu Gly Gly Gln Asn Ser Ser Ser Ile Thr Gly Asn
835                 840                 845                 850

ATT ACT ATC GAG AAA GCA AAT GTT ACG CTA GAA GCC AAT AAC GCC   2949
Ile Thr Ile Glu Lys Ala Asn Val Thr Leu Glu Ala Asn Asn Ala
         855                 860                 865

CCT AAT CAG CAA AAC ATA AGG GAT AGA GTT ATA AAA CTT GGC AGC TTG   2997
Pro Asn Gln Gln Asn Ile Arg Asp Arg Val Ile Lys Leu Gly Ser Leu
     870                 875                 880

CTC GTT AAT GGG AGT TTA ACT GGC GAA AAT GCA GAT ATT AAA   3045
Leu Val Asn Gly Ser Leu Thr Gly Glu Asn Ala Asp Ile Lys
885                 890                 895

GGC AAT CTC ACT ATT TCA GAA AGC GCC ACT TTT AAA GGA AAG ACT AGA   3093
Gly Asn Leu Thr Ile Ser Glu Ser Ala Thr Phe Lys Gly Lys Thr Arg
         900                 905                 910

GAT ACC CTA AAT ATC ACC GGC AAT TTT ACC AAT AAT GGC ACT GCC GAA   3141
Asp Thr Leu Asn Ile Thr Gly Asn Phe Thr Asn Asn Gly Thr Ala Glu
915                 920                 925                 930

ATT AAT ATA ACA CAA GGA GTG GTA AAA CTT GGC AAT GTT ACC AAT GAT   3189
Ile Asn Ile Thr Gln Gly Val Val Lys Leu Gly Asn Val Thr Asn Asp
         935                 940                 945
```

FIG.28J

```
GGT GAT TTA AAC ATT ACC ACT CAC GCT AAA CGC AAC CAA AGA AGC ATC    3237
Gly Asp Leu Asn Ile Thr Thr His Ala Lys Arg Asn Gln Arg Ser Ile
950                 955                 960

ATC GGC GAT ATA ATC AAC AAA ATC AAC AAA GGA AGC TTA AAT ATT ACA GAC    3285
Ile Gly Asp Ile Ile Asn Lys Lys Gly Ser Leu Asn Ile Thr Asp
    965                 970                 975

AGT AAT GAT GCT GAA ATT CAA ATT GGC GGC AAT GCC ATC TCG CAA AAA    3333
Ser Asn Asp Ala Glu Ile Gln Ile Gly Gly Asn Ile Ser Gln Lys
980                 985                 990

GAA GGC AAC CTC ACG ATT TCT TCC GAT AAA ATT AAT ATC ACC AAA CAG    3381
Glu Gly Asn Leu Thr Ile Ser Ser Asp Lys Ile Asn Ile Thr Lys Gln
995                 1000                1005                1010

ATA ACA ATC AAA AAG GGT ATT GAT GGA GAG GAC TCT AGT TCA GAT GCG    3429
Ile Thr Ile Lys Lys Gly Ile Asp Gly Glu Asp Ser Ser Ser Asp Ala
        1015                1020                1025

ACA AGT AAT GCC AAC CTA ACT ATT AAA ACC AAA GAA TTG AAA TTG ACA    3477
Thr Ser Asn Ala Asn Leu Thr Ile Lys Thr Lys Glu Leu Lys Leu Thr
        1030                1035                1040

GAA GAC CTA AGT ATT TCA GGT TTC AAT AAA GCA GAG ATT ACA GCC AAA    3525
Glu Asp Leu Ser Ile Ser Gly Phe Asn Lys Ala Glu Ile Thr Ala Lys
        1045                1050                1055
```

FIG. 28K

```
GAT GGT AGA GAT TTA ACT ATT GGC AAC AGT AAT GAC GGT AAC AGC GGT    3573
Asp Gly Arg Asp Leu Thr Ile Gly Asn Ser Asn Asp Gly Asn Ser Gly
1060                              1065                    1070

GCC GAA GCC AAA ACA GTA ACT TTT AAC AAT GTT AAA GAT TCA AAA ATC    3621
Ala Glu Ala Lys Thr Val Thr Phe Asn Asn Val Lys Asp Ser Lys Ile
1075                              1080                    1085                1090

TCT GCT GAC GGT CAC AAT GTG ACA CTA AAT AGC AAA GTG AAA ACA TCT    3669
Ser Ala Asp Gly His Asn Val Thr Leu Asn Ser Lys Val Lys Thr Ser
             1095                              1100                    1105

AGC AGC AAT GGC GGA CGT GAA AGC AAT AGC GAC AAC GAT ACC GGC TTA    3717
Ser Ser Asn Gly Gly Arg Glu Ser Asn Ser Asp Asn Asp Thr Gly Leu
      1110                              1115                    1120

ACT ATT ACT GCA AAA AAT GTA GAA AAC AAA AAT GAT ATT ACT TCT CTC    3765
Thr Ile Thr Ala Lys Asn Val Glu Asn Lys Asn Asp Ile Thr Ser Leu
             1125                              1130                    1135

AAA ACA GTA AAT ATC ACC GCG TCG GAA AAG GTT ACC ACA ACA GCA GGC    3813
Lys Thr Val Asn Ile Thr Ala Ser Glu Lys Val Thr Thr Thr Ala Gly
      1140                              1145                    1150

TCG ACC ATT AAC GCA AAT GGC AAA GCA AGT ATT ACA ACC AAA ACA        3861
Ser Thr Ile Asn Ala Thr Asn Gly Lys Ala Ser Ile Thr Thr Lys Thr
1155                              1160                    1165                1170
```

FIG. 28L

GGT GAT ATC AGC GGT ACG ATT TCC GGT AAC ACG GTA AGT GTT AGC GCG    3909
Gly Asp Ile Ser Gly Thr Ile Ser Gly Asn Thr Val Ser Val Ser Ala
              1175                    1180                  1185

ACT GGT GAT TTA ACC ACT AAA TCC GGC TCA AAA ATT GAA GCG AAA TCG    3957
Thr Gly Asp Leu Thr Thr Lys Ser Gly Ser Lys Ile Glu Ala Lys Ser
              1190                    1195                  1200

GGT GAG GCT AAT GTA ACA AGT GCA ACA GTT GGT ACA ATT GGC GGT ACA ATT    4005
Gly Glu Ala Asn Val Thr Ser Ala Thr Val Gly Thr Ile Gly Gly Thr Ile
              1205                    1210                  1215

TCC GGT AAT ACG GTA AAT GTT ACG GCA AAC GCT GGC GAT TTA ACA GTT    4053
Ser Gly Asn Thr Val Asn Val Thr Ala Asn Ala Gly Asp Leu Thr Val
              1220                    1225                  1230

GGG AAT GGC GCA GAA ATT AAT GCG ACA GAA GGA GCT GCA ACC TTA ACC    4101
Gly Asn Gly Ala Glu Ile Asn Ala Thr Glu Gly Ala Ala Thr Leu Thr
              1235                    1240                  1245                  1250

GCA ACA GGG AAT ACC TTG ACT ACT GAA GCC TCT AGC ATC ACT TCA    4149
Ala Thr Gly Asn Thr Leu Thr Thr Glu Ala Gly Ser Ser Ile Thr Ser
              1255                    1260                  1265

ACT AAG GGT CAG GTA GAC CTC TTG GCT CAG AAT GGT AGC ATC GCA GGA    4197
Thr Lys Gly Gln Val Asp Leu Leu Ala Gln Asn Gly Ser Ile Ala Gly
              1270                    1275                  1280

FIG.28M

```
AGC ATT AAT GCT GCT AAT GTG ACA TTA AAT ACT ACA GGC ACC TTA ACC    4245
Ser Ile Asn Ala Ala Asn Val Thr Leu Asn Thr Thr Gly Thr Leu Thr
                1285                1290                1295

ACC GTG GCA GGC TCG GAT ATT AAA GCA ACC AGC GGC ACC TTG GTT ATT    4293
Thr Val Ala Gly Ser Asp Ile Lys Ala Thr Ser Gly Thr Leu Val Ile
                1300                1305                1310

AAC GCA AAA GAT GCT AAG CTA AAT GGT GAT GCA TCA GGT GAT AGT ACA    4341
Asn Ala Lys Asp Ala Lys Leu Asn Gly Asp Ala Ser Gly Asp Ser Thr
        1315                1320                1325        1330

GAA GTG AAT GCA GTC AAC AGC GGC TCT GGT AGT GTG ACT GCG GCA        4389
Glu Val Asn Ala Val Asn Ala Ser Gly Ser Val Thr Ala Ala
                1335                1340                1345

ACC TCA AGC AGT GTG AAT ATC ACT GGG GAT TTA AAC ACA GTA AAT GGG    4437
Thr Ser Ser Ser Val Asn Ile Thr Gly Asp Leu Asn Thr Val Asn Gly
                1350                1355                1360

TTA AAT ATC ATT TCG AAA GAT GGT AGA AAC ACT GTG CGC TTA AGA GGC    4485
Leu Asn Ile Ile Ser Lys Asp Gly Arg Asn Thr Val Arg Leu Arg Gly
                1365                1370                1375

AAG GAA ATT GAG GTG AAA TAT ATC CAG CCA GGT GTA GCA AGT GTA GAA    4533
Lys Glu Ile Glu Val Lys Tyr Ile Gln Pro Gly Val Ala Ser Val Glu
                1380                1385                1390
```

FIG.28N

```
GAA GTA ATT GAA GCG AAA CGC GTC CTT GAA AAA GTA AAA GAT TTA TCT     4581
Glu Val Ile Glu Ala Lys Arg Val Leu Glu Lys Val Lys Asp Leu Ser
1395                    1400                1405                1410

GAT GAA GAA AGA GAA ACA TTA GCT AAA CTT GGT GTA AGT GCT GTA CGT     4629
Asp Glu Glu Arg Glu Thr Leu Ala Lys Leu Gly Val Ser Ala Val Arg
        1415                1420                1425

TTT GTT GAG CCA AAT AAT ACA ATT ACA GTC AAT ACA CAA AAT GAA TTT     4677
Phe Val Glu Pro Asn Asn Thr Ile Thr Val Asn Thr Gln Asn Glu Phe
            1430                1435                    1440

ACA ACC AGA CCG TCA AGT CAA GTG ATA ATT TCT GAA GGT AAG GCG TGT     4725
Thr Thr Arg Pro Ser Ser Gln Val Ile Ile Ser Glu Gly Lys Ala Cys
                1445                1450                1455

TTC TCA AGT GGT AAT GGC GCA CGA GTA TGT ACC AAT GTT GCT GAC GAT     4773
Phe Ser Ser Gly Asn Gly Ala Arg Val Cys Thr Asn Val Ala Asp Asp
            1460                1465                1470

GGA CAG CCG TAGTCAGTAA TTGACAAGT AGATTTCATC CTTGCAATGAA            4822
Gly Gln Pro
1475

GTCATTTTAT TTTCGTATTA TTTACTGTGT GGGTAAAGT TCAGTACGG CTTTACCCAT     4882

CTTGTAAAAA ATTACGAGA ATACAATAAA GTATTTTAA CAGGTATTA TTATG          4937
```

FIG. 29A  Alignment of HMW proteins

```
         10        20        30        40        50
MNKIYRLKFSKRLNALVAVSELARGCDHSTEKGSEKPARMKVRHLALKPLSAMLLS
.......................................................

110       120       130       140       150
NWKQFNIDQNEMVQFLQENNNSAVFNRVTSNQISQLKGILDSNGQVFLINPNGITI
.......................................................

210       220       230       240       250
GLITVGKDGSVNLIGGKVKNEGVISVNGGSISLLAGQKITISDIINPTITYSIAAP
.......................................................

310       320       330       340       350
LSAKEGEAEIGGVISAQNQQAKGGKLMITGDKVTLKTGAVIDLSGKEGGETYLGGD
.......................................................

410       420       430       440↓      450
GNINAQGSGDIAKTGGFVETSGHDLFIKDNAIVDAKEWLLDPDNVSINAETAGRSN
........................Y.S.DS....KT........D.T.E..DPL.N.
                                           ...........T.E.PSYS.G.
                                           .........E..Y...GD....D
                                           ...............G.SE.ND
                                           ............ENPSTE.ND
                                           ........E.T.G.GDV...D
                                           ........D...D.PS.E.TD
                                           ..........N.VKG.ELQND
                                           ........D.T.A.GAP..ND
                                           ...............PAL..TE
                                           ........DIN.VNGSNIDAQ 510       520       530       540       550
ANQRIYVNSSINL-SNGSLTLWSEGRSGG-GVEINNDITTGDDTRGANLTIYSGGW
.SRKLT......IG..SH.I.H.QR..-..Q.DG...S----K.G........
.KKNLT......IGDSSH.I.H...KNN.-..K.KE...S----N.G....Q....
..NE.R...D..IGG.SH.....SKNKNS-..L..GN..S---.ANG......S..
.RK..T...D..IKDSSH.I....NDNSS-..D.KGN..S---.T.GS.....S..
.TDN........IGDS.H.I.SGG..N..-..K..KN..S----T.GS...N.K..
.KNK.L...D..IKE.SH.I.W..RDGNS-..Q.DGN..S---AT.GS..V..S..
```

FIG.29B

```
         60        70        80        90       100
LGVTSIPQSVLASGLQGMDVVHGTATMQVDGNKTIIRNSVDAII              12-1
...........................................              12-2

160       170       180       190       200
GKDAIININGFTASTLDISNENIKARNFTFEQTKDKALAEIVNH              12-1
...........................................              12-2

260       270       280       290       300
ENEAVNLGDIFAKGGNINVRAATIRNQGKLSADSVSKDKSGNIV              12-1
...........................................              12-2

360       370       380       390       400
ERGEGKNGIQLAKKTSLEKGSTINVSGKEKGGRAIVWGDIALID              12-1
...........................................              12-2

460       470       480       490       500
TS-EDDEY-TGSGNSASTPKRNKE--KTTLTNTTLESILKKGTFV-NIT         12-1
.G-IN..FP..TGE-..D..K.S.L-........ISNY..NAWIM-...        12-2
AG-I.S.FPG...TKE.-..T.G.Q-P.V...E.ISNY...S..W.M...       15-1
.NL.NE..-..T.E..D.....NNT-........S...K..AR.S..-...      15-2
A.-PTEDFP..A.GKDN-..K.AHN-.P..I.....R...SGN...-...       Joyc-1
SN-..L..-..T.ENINN..V.NQS-.K...SSI..N.....S..-...        Joyc-2
D.-S.TAFP..T.ERN.-..T.AQN-RP.I...S..Q...N....-...        LCDC2-1
.G-..V...-.T.ADINHQ.Q.S.T-.S........GM...R.L..-...       LCDC2-2
LV-V-------R.D--.IE.K.APT-...IHAGSI.QS.M..GA.-...S       PMH1-1
G.-V..FFP..R.DD..NA.T.HPD-.P......V.NA..NN...-...        PMH1-2
STPNNN..—D.P.QINY--K..PS-LS........R...RN.S.-...         K1-1
LQP-------.R.D---..NKVSAEGL.SIN.A...STA.Q..IE.-...S      K21-1

560       570       580       590
VDVHKNISLGAQGNININITAKQ-DIAFEKGS-N-------QVITGQ           12-1
.......T.D-..FL....AS--V...G.N-.KARDAANAK.VA.            12-2
.......T..T-.TL.....G-S.T..GNGTEKARNASSAQ..A.            15-1
..I....T.ES-.RL...T.EG.V.....N-.-------LT....            15-2
I.I....T.NS-.LL...T..G.......N-.-------PT....            Joyc-1
..I.S.....T-.FL...SNG-SV....ADKDKARSAADAQ.VA.            Joyc-2
```

FIG.29C

```
.RNK.R...T..IGDS.H...YKKRKNRSD.IQ..K...S----.G.S-...N.DD.
.TNKVN.TTD..V-Y..A...H..RD----.....GN..S---EKNG....KA.S.
.KNK.T...D..IKGGAH...Y.KNNKKS-S.K..GN..S---.TNG......S..
.TKT.T...D..IGDSSH.......QGR.-..NVTGN..S---.TNG.........
.TKNVT..ADVDV-K..T.V.H.QRN----..K..GN..S---.QNG....KT..K 600       610       620       630
G--TITSGNQ-KGFRFNNVSLNGTGSGLQFTTKRTN------KYAITNKFEGTLNI
.TV...GEG--.D..A........K..NIISSVN.---------L.HNLS..I..
.--...NTGDQ.QL.L....I....I..N.VSIQP.---------TSHR.D.E.I.
.--...A..N-.....E........T..L.NLS.PQ----KNNSLV..Y.N.....
.--...A..G-.....E.A....I.T..L.NI..DL----GNNFQ.I.F.N.....
.--I.NLTGEN.T..L.......V.Q..SI.SNVG.---------Q.H..D.EI..
.--...ASK--.....D..T.S.VKK.FL.KYSQ..---NNKDSNFE.H.R.....
.--...LTGEN.T..L.........N..SIISTAS.---------LSHRLD.EI.V
.--N...NKDG.QL.L.........A..N.IANQN.---------F.HNIS.AI..
.--V....VG-E...........V.A..R.VGQKNISSNSWRENT.K.R.D.N...
.--..AVN.K-.....D..T.....G...S.KYIE.G---NRDSNFE.H-.R.R...
.--N.I.NQEN.QL..S......M.A..T..ANKG.---------H.H..D.....

690       700       710       720       730
DSRGS-----DSAGTLTQPYNLNGISFNKDTTFNVERNARVNFDIKAPIG-INKYS
S.---NSKGLTTQYRSSA.V.F..VNG.M-S-..LKEG.K...KL.-.NE-NMNT.
LNNNH-GRETSR-YRKGGGVIFRSPTGHTN--.T.KQGSVA...SF..KND-T.HAN
..-----SAE.GSAP.LSS.T......TT......NK..K...N......T..Q.N
....D-----.T.....NT.............I.D.KQ.GA.T........-V.NNR
E.NRFGPTTPLRS---SGGVFF..TNG.MVL--..GT.S..L.NL.-.NE-NT.N.
.NS.SRP--SPG..P.YRRSG........N..V...ASGSA...S..P..V-S.VHD
N.ARNGDVR----GRSFAGVIF.AKGLTTS--...KKGST.D.KL.-.NSGYNSQK
..NHS---TNSSDSRSFAGVKFH.KNNEMK--..IGN...KAE.RL.-.NEKTTPNR
.AS.ISSGNQDDITNRG----....T..GEN...IAQGSTA..H..TSVMTP.PN.
..SGSAS--SPG..P.NAQSG........N..V..IAASSA...N..P..V-DKVTN

..NRSVA--LNSGSRSFAGVKFY.KNNEMK--..IGD..N.E.KL.SNDNTSNNKP 790       800       810       820       830
RFKTSGSTKTGFSIEKDLTLNATGGNITLLQVEGT--DGMIGK-GIVAKKNITFEG
TLNSHVRGDDA.K.N....I...NS.FS.R.TKDFY..YARN-A.NSTY..SIL.
```

FIG.29D

```
........T.NS-.YL...T.SG.V...Q.N--------DLT....           LCDC2-1
..I.G..T..E-.FL...SSD-SV...G.NG.KGRSSASAQ.IA.            LCDC2-2
........T..E-.FL...SG--........N-.--------LT..A.         PMH1-1
..I....T.NT-.YL....GG-SV....AGNEKGRQVSES...KA.           PMH1-2
........T.KS-.YL...T..G.....DKPGLS-----NLT..AK           K1-1
........T..M-.FL...SDN-N.T....D- -------LT..A.           K21-1

640       650       660       670       680
SGKVNISMVLPKNESG-YDKFKGRTYWNLTSLNVSESGEFNLT--I            12-1
..NIT.NQTTR..T.--.WQTSHDSH..VSA...LETGAN.TFIKY.          12-2
..R.HVNQTT...L.--FW.VSDES...VSH.T.K.KSA.SF.KFA           15-1
..S.....IP.NAT.NW.SRY.......I.H..A..DSN....--.           15-2
..........I..-KWD-.S..R......V.H.....GSK....--.          Joyc-1
T.N.T.NQTA.ATTA--.WN.SYDS...VST...QKNSS.TFIKRT           Joyc-2
....D.L.QARQENWN-RRHS-...SH..V.R....TNSYL.I.--.          LCDC2-1
..N.T.NQTTQQ.IE--.W.ASSDS...V..F.LR.DSK.TFIKYV           LCDC2-2
..V.T.NQTTK..AK--AWNTSYDS...VST.TL.NDAK.TFIKYV           PMH1-1
.....V..DVSGTKWH-TRIN-......V.T...ASGSS...S--.           PMH1-2
....D.L.QARQENWN-RRHW-...SH..V.R.....NSY..V.--.          K1-1
....V.NQTT.H.-IA-PWNASADS...V.T.TLGNNAQ.TFIKFV           K21-1

740       750       760       770       780
SLNYASFNGNISVSGGGSVDFTLLASSSNVQTPGVVINSKYFNVSTGSSL        12-1
KPLPIR.LA..TAT.....F.DIY.NH.---GR.AELKMSEI.I.N.ANF       12-2
-QLPIQ..S....D...K.L.CITSNY.---GRS.G.GMSSI...D..N.       15-1
N....L..........N.T.R.N.....Q.....I....HL.A.K....        15-2
N...............N.T.K......TA.....F....H..A.G....       Joyc-1
KP.PLQ..A..TAI.....S.DIH.NH.---GR.AELKMNTI.I.D.T..       Joyc-2
G-.HTL....V..L...D.N.HFN.....HW.H....K.QN..A.E....       LCDC2-1
RIPIQ.QS........R.NINT..NLT---GG..E.R.SSI...D..T.        LCDC2-2
PLPIQ.LS....T.....F.DIY.NLW---GK.TELKMDSI...S..N.        PMH1-1
-...L.......L...T.N.E.N....THT.S.AI...QN....G..K.        PMH1-2
G-.HTL.K.....L...                                        K1-1
          ..D.N.HFN.....Y..Y..I.E.QNFSA.G....             K1-1
-LPIQ.LS...AT.N.T.S.DIH.NL.---ARSTEL.MSLI.I.N.VNF        K21-1

840       850       860       870       880
GNITFGSRKAVTEIEGNVTINNNANVTLIGSDFDNHQ--KPLTIKK-DVI        12-1
```

FIG. 29E

```
T.NS.IRGQEA.N.S....I....SFFE.G.YSD.FNGNGFNHDA.KSTH..SIL.
..E.T....V..L.NN..........S......I--.....E-.V........T.
E.RAE....V..L.NN..........S......I--......-.V........A.
TLQSHVRKDSA.I.S....I....S.F..E.SPDSFT.KYP.R-A.SST....IS.
...SE...R.A.T..S...........S.N..A.I--..NLQ.-SL..N.......
SMTAQARDRNA.E.T...VI..SNS.LSII.QNDGFDNNQKAN-A.NS.Y.V.IQ.
TLNSHVRKYNA.E.N....I...NS.FN.R.TSDSFRN.YRNN-A.NSTH..SIL.
NL.A....N.A.L.KNN..........EIK.....--.SR.Q.-.V..EQ..I...
K..SE...HAA.T.KN..I........S.N..A.I--.SNLK.-SLI.N.......
SINSHVRGNNA.E.K...II....S.FN.K.TKDKFDNSYEKN-A.FSTH.L.IL.

890       900       910       920       930
INSGNLTAGGNIVNIAGNLTVESNANFKAITNFTFNVGGLFDNKGNSNISIAKGGA
LVN.S.SLT.ENAD.K....ISES.T..GK.RD.L.IT.N.T.N.TAE.N.TQ.VV
.E-....SLI.ASA..N...S.KE..K..GE.QDNL.IT.T.I.N.D.K.N.SQ.VV
NR-........VI..G......NG..L..............N..........R...
............VI..N.....NNG..L..........................R...
V-E....LT.SVAD.K...SILND.T..GE.SENL.IT.N.T.N.TAD.N.KQ.VV
-.K....VT.SAI..EK.....GS.K.L.NP.YS...S.....Q.K..........
VE-.E.RLV.ASA..NN..S.K.G.K...E..DNL.IT.T.T.N.T.I.DVK..A.
VE-...SLI.ENA..N...SI.KE.I..GK.KDSL.IT.N.T.N.TAE.N.SQ.VV
TAN.....D.DTIK.K...D.AQG.K.NGS.KNNL.IT.T.T.N.T.I.D.TQ.VV
NK-....VT.SAI..EK.....GS.K.L.NP.YS...S.....Q.K..........
SVG...NII.SNAH.D...SIAES.K.QGK..NNL.IT.T.T.N.TAD.N.KQ.VV 990      1000      1010      1020      1030
TEMQIGGDVSQKEGNLTISSDKINITKQITIKAGVDGENSDSDATNNANLTIKTKE
A.I....NI.....................K.I...D.S....S............
A.I....NI..................N.............................
A.I....NI.....................K..N......STKSQ............
A.I....NI..................N.....K..NK.D...STA............
A.I....NI...K..............K........EGG...SPAS........T
A.I....NI..................N.....K..NK.D...STA............
..I....NI..........................R.E....T.QG....GVAS............
A.IE...NI.................V................S.S.STASD............
A.IE...NI.................V................S.S.STASD............
..I....NI.................V..ER........N.D....NEATS............
A.I....NI..........................R.E...DT.QG....GVAS............
```

FIG. 29F

```
..V.L.GQNSSSS.T..I..EKA.....EANNAP.Q.NIRDRV..LG-SL    12-2
..V.L.GQDSSST.T..IN.SQA.....RAYNGNGRN--.Q..--LGN.S    15-1
.......K..I...K.....E.T.A.......ND.K--...N..G-..V    15-2
.......K..I......A.................--.........-...    Joyc-1
..VSL.GQNSSSD.K..I..KSST....KAHNSPRDFASRT..--LGNLN    Joyc-2
....LAAD.KPI..K..I.VKEG.....RSANYG.DK--SA.S.R-GN.T    LCDC2-1
..V.L.GQNSSST.T.S.N.GA......QAHNGNDRN--.K..--FGN.S    LCDC2-2
..V.L.GQNSSSS.M..II.KRA.....EADNSH.SDNV.DR..NLGNLT    PMH1-1
....L..Q..P...K.D..VKQGT.A..RSAN....---.GAL.VNGN.-    PMH1-2
....LAAD.KPI..K..I.VKEG.....RSANYG.DK--SA.S.-RGN.T    K1-1
..V.L.GENSSSN.K..IN..SK.....QAHAGTS.LDK.ER.LTLGN.-    K21-1

940       950       960       970       980
RFK-DIDNSKNLSITTNSSSTYRTIISGNITNKNGDLNITNEGSD        12-1
KLG-NVT.DGD.N...HAKRNQ.S..G.D.I..K.S....DSNN.        12-2
KLG-NVT.DGD.N...HAKHNQ.S..G.D.I..K.S....DSNKN       15-1
K..-..N.TSS.N.....DT......E......A.....IDNKGN       15-2
K..-..N.TSS.N.....DT......E......A.....IDNKGN       Joyc-1
NIQGN.T.KGG.N....AQNNQK...N......EG.....KDSNNN      Joyc-2
H..-..N.T.S.N.....D.A.....E......S.......DNKNN      LCDC2-1
KLG-N.T.DG..N....AKNGQKSV.N.....NK.A.....N.N.       LCDC2-2
SLG-..T.DGK.N...HAK.GQKS..R.D.I..Q.N....DNN.N       PMH1-1
NLG-NVT.DGK.N...HAK.GQKS..R.D.I..Q.N....DNN.N       PMH1-2
I..-..E.TGS.N...K.D.NHH...K.....RK........N.DN      K1-1
KLQG..T.NG..N....A.VNQK...N......K.....KDIKAN       K21-1

1040      1050      1060      1070      1080
LKLTQDLNISGFNKAEITAKDGSDLTIGNIN-SADGTNAKKVTFN        12-1
....E..S..............R......S.DGNS.AE..T....      12-2
....................................-...S........   15-1
................K.V...S.N.....SDD.GN-.S..T....      15-2
.Q..G.......D.......E.A..I...SDNNNNA-........      Joyc-1
.E..G...............N.N.....KASDGNA--.......D      Joyc-2
.Q..G.......D.......E.A..I...SDNNNNA-........      LCDC2-1
....EN......D....V..ENNN.I...N.--G.NA...T....      LCDC2-2
.T..DN..............N...I..KA--.S.NS...Q...D      PMH1-1
.TF.DN..............N...I..KA--.S.NS...Q...D      PMH1-2
```

FIG.29G

```
         1090      1100       1110      1120      1130
QVKDSKISADGHKVTLHSKVET-SGSNNNNTEDSSDNNA-GLTIDAKNVTVNNNITS
N............N...N...K.-.S..GGR.SN...DT-....T....E..KD...
.........GD.N...N.....-..NTD..G.G.G...-....A....E.K.....
N............N...K.L.DND....GG....T-....T..D.E.......
.........GS.N...N.....-.NG..DA.SNNGDST-S...N..........
K........N..N...N.....-.N.DSSAD..N...T-....S..D.....DV..
.........S.N...N.....-.NG..DA.SNNGDGT-S...N...I........
N........N..N...N.....-.DG.S...GN.....-.............D...
K........GN.N...N.....-.N.DGS.GNG..D.NI....S..D....S....
K........GN.N...N.....-.N.DGS.GNG..D.NI....S..D....S....
N........SD.N...N.....-.GDTDS...GGN..T-....T............
K........GN.N...N.....-.N.DGS.GNG..D.NI....S..D....S....

1190      1200      1210
SVTLTATEGALAVSNISGNIVTVTANSGALTTLAGSTI------------------
--------------------------------------------------------
--------------------------------------------------------
...IV.GGDT...G.....A.................------------------
N.NI..SGDT.N....T.QN...A.A...V..TK....NATTGSANITTKTGEING
.......GE............I...K.K...Q....V------------------
--------------------------------------------------------
--------------------------------------------------------
--------------------------------------------------------
N.NI..SGDT.N....T.QN...A.A...V..TK....NATTGNANITTKTGEING
...A.---------------------------------------------------

--------------------------------------------------------
--------------------------------------------------------
--------------------------------------------------------
--------------------------------------------------------
NATTGDANITTQTGNINGKVESSSGSVTLIATGQTLAVGNISGDTVTITADKGKLT
--------------------------------------------------------
--------------------------------------------------------
-----DVNITTSTGSINGKIESKSGSVTLTATEKTLTVGNVSGNIVTVTANRGALT
--------------------------------------------------------
```

FIG.29H

```
....N................N.N....DNSD-.GN.D......S         K1-1
.T..DN.................N...I..KA--.S.NS...QI..D       K21-1

1140       1150      1160      1170      1180
HKAVSISATSGEITTKTGTTINATTGNVEITAQTGSILGGIESSSG         12-1
L.T.N.T.SEK-V..TA.S.....N.KAS..TK..D.S.-------        12-2
N.T.N.T.SEK-L...ADA..........V..K..D.K.EVK.T--        15-1
..T.NV..AN.G.............A......H....Q.....KP.       15-2
..T.N.T.SEN-V...A........I.S..V..K..D.K.....N..       Joyc-1
..TIN....T.NV...ES.....A...S..V..K..D.S.-------       Joyc-2
..T.N.T.SEN-V...A.........S..V..K..D.K.KV..T..        LCDC2-1
..T.N.T.SER-.D..AD..........KL..V.SD.-...K.N..        LCDC2-2
..T.N...SE.G....A..........S...V..K.-----------       PMH1-1
..T.N...SE.G....A..........S...V..K.-----------       PMH1-2
..T.N.T.SEN-V...A.........S..V..K..D.K.....N..        K1-1
..T.N...SE.G....A..........S...V..K..D.S.T.SGKTV      K21-1

-----------------------------------------------       12-1
-----------------------------------------------       12-2
-----------------------------------------------       15-1
-----------------------------------------------       15-2
EVKSASGNVNITASGNTLNVSNITGQNVTVTANSGAITTTEGSTI          Joyc-1
-----------------------------------------------       Joyc-2
-----------------------------------------------       LCDC2-1
-----------------------------------------------       LCDC2-2
-----------------------------------------------       PMH1-1
-----------------------------------------------       PMH1-2
EVKSASGNVNITASGNTLNVSNITGQNVTVTANSGAITTTEGSTI          K1-1
-----------------------------------------------       K21-1

1220      1230      1240      1250
-------KGTESVTTSSQSGDIGGTISGGTVEVKAT-ESL               12-1
-----------------------.....N..S.S..-GD.               12-2
-----------------------------------------              15-1
-------.....I........N...K...K..N....-N..              15-2
TQTSSKIN..K............S.....N..S.S..-G..              Joyc-1
-----------------------.....N..N.T..D.--               Joyc-2
```

FIG.29I

```
------------------------------------------------------
NATTGDANITTQTGNINGKVESSSGSVTLIATGQTLAVGNISGDTVTITADKGKLT
-----------------------------TDLTTVKGGAKINATEGTATLTASSGKLT
------------------------------------------------------
------------------------------------------------------
------------------------------------------------------
TTQADSKIEATEGEANVTSKTSIIGGTISGGTVEVTATEGLTTQAGSTITGTESVT
------------------------------------------------------
------------------------------------------------------
------------------------------------------------------
------------------------------------------------------
------------------------------------------------------
------------------------------------------------------
------------------------------------------------------
------------------------------------------------------
------------------------------------------------------

1260      1270      1280      1290      1300
TTQSNSKIKATTGEANVTSATGTIGGTISGNTVNVTANAGDLTVGNGAEINATEGA
..K.G...E.KS..........................................
---------------------------------...-..I...-..TLNVS----.VSGN.
I.K.G.E....A..V........D...........T.....EDA.K.D..G..
...AG...E.K...........................TDN..IKD..R.K..G..
------------------------------------------------------
..K.G.E...K....................A......T.....EDA.K.D..G..
--------------------------------------------..KG..K......T
-------------------.D.S.....K..S...ST.....RKA.T.S.....
-------------------.D.S.....K..S...ST.....RKA.T.S.....
...AG...E.K............................TDN..IKD..R.K..G..
----------------------------------------...GD.K.......

1360      1370      1380      1390      1400
LNTTGTLTTVKGSNINATSGTLVINAKDAELNGAALGNHTVVNATNANGSGSVIAT
..........A..D.K..........K...D.S.DS.E...V..S.....T.A
..........E......A........K.....S.D.........S.....T.V
.....A......S...N.............E.S.....................
..........A..K.E.A........Q.D.....DR.E..V.............
..........A...K......A.....K.D.T.S.DR........S.....T.A
```

FIG. 29J

```
-------SAING..A.......S.....N..K.S.I-GD.              LCDC2-1
TLAGSTIN..NG........E...EVT.K...S.T..AG..             LCDC2-2
-----------------------------------------             PMH1-1
-----------------------------------------             PMH1-2
TQTSSKIN..K............S.....N..S.S..G-..             K1-1
TEANSAIS.ANG..A.......S.....K...S.T.SSG..             K21-1

-----------------------------------------             12-1
-----------------------------------------             12-2
-----------------------------------------             15-1
TSSQSGNIGGMISGGKVEVSATKDL                             15-2
-----------------------------------------             Joyc-1
-----------------------------------------             Joyc-2
-----------------------------------------             LCDC2-1
-----------------------------------------             LCDC2-2
-----------------------------------------             PMH1-1
-----------------------------------------             PMH1-2
-----------------------------------------             K1-1
-----------------------------------------             K21-1

1310      1320      1330      1340      1350
ATLTTSSGKLTTEASSHITSAKGQVNLSAQDGSVAGSINAANVT           12-1
....ATGNT.....G.S...T....D.L..N..I..........          12-2
V.I.ADK.....Q...S...NN..TT.T.K...I..........          15-1
....AT......K...S....NN......K...IG.N.......          15-2
V...ATG.T....T..D...SN..TT.T.K.S.I..........          Joyc-1
----------...Q...S...SN..TT.T.KN..I....D.....         Joyc-2
....AT......K...S....NN......K...IG.N.......          LCDC2-1
....A..........N........D.......I..Q.S.....           LCDC2-2
....ATGNT.....G.S...T....D.......I..Q.S.....          PMH1-1
....ATGNT.....G.S...T....D.......I..Q.S.....          PMH1-2
V...ATG.T....T..D...SN..TT.T.K.S.I..........          K1-1
....ATK.T...-------------------------------           K21-1

1410      1420      1430      1440      1450
TSSRVNITGDLITINGLNIISKNGINTVLLKGVKIDVKYIQPGI           12-1
...S........N.V........D.R...R.R.KE.E.......V         12-2
...N........S.V..........R...V...TE.E.......V         15-1
```

FIG.29K

```
.....A........S...N.................E.S.....................
..........E..S...NE.......N..K.D.K.S..R.E......S.....T.K
..........E....K......A.....K.D.T.S..R.E......S.....T.K
..........E....K......A.....K.D.T.S..R.E......S.....T.K
........A..K.E.A..........Q.D...S.D..................
---------.....D.NE.......Q..T...D.S.DR.E...V..S...N.T.K
          1460      1470      1480      1490      1500
ASVDEVIEAKRILEKVKDLSDEEREALAKLGVSAVRFIEPNNTITVDTQNEFATRP
...E.......V...........T.............V........N.....T...
...E.......V...........T......................N.....T...
............................................A....A..IN.....T...
...Y.......A.............................................
..AN.......A...........T.............V........N.....T...
............................................A....A..IN.....T...
..E.......V...........T.......................N.....T...
...E.......V...........T.............V....A..IN.....T...
...E.......V...........T.............V....A..IN.....T...
...N.......A...........T............A....A..IN.....T...
..AN.......A...........T......................N.....T...
```

FIG.29L

```
........................................         15-2
.....................K......E..........         Joyc-1
...N.......S............K...V...AE........V     Joyc-2
........................................         LCDC2-1
...S.......N.........E..R...R.R.KE.E.......V    LCDC2-2
...N.......S.........E..R...R.R.KE.........V    PMH1-1
...N.......S.........E..R...R.R.KE.........V    PMH1-2
.....................K......E..........         K1-1
...S.......S............K...V...AE........V     K21-1

1510      1520      1530
LSRIVISEGRACFSNSDGATVCVNIADNGR-*                 12-1
S.QVI....K....SGN..R..T.V..D.QP*                 12-2
S.QVT....K....SGN..A..T.V..D.QQ*                 15-1
S.QVT....KV..LIGN...I.T....IE.*                  15-2
...........................*                     Joyc-1
S.QVT...DK....SGN..A...T.VT.DRQ*                 Joyc-2
S.QVT....KV..LIGN...I.T....IE.*                  LCDC2-1
S.QVT....K....SGN..A..T.V..D.QQ*                 LCDC2-2
S.QVI....K....SGN..A..T.V..D.QP*                 PMH1-1
S.QVI....K....SGN..A..T.V..D.QP*                 PMH1-2
..QVT....KV..LIGN...I.T....IE.-*                 K1-1
S.QVT....K....SGN..A..T.V..D.QQ*                 K21-1
```

FIG. 30

Oligonucleotides used to determine whether PCR amplified hmwA genes were hmw1 or hmw2.

| | | | | | SEQ ID NO |
|---|---|---|---|---|---|
| 5' | TCTTTTGCTGTGGCTGATGCCCTA | 3' | | 5672.SL | 74 |
| 5' | CACTGATAGTTGCTCATATTCGCC | 3' | | 5676.SL | 75 |
| | V G V H K N | | | | 76 |
| | GGTTGATGTTCATAAAAATAT | | | | 77 |
| 3' | CCAACTACAAGTATTTTTATA | 5' | | 5742.SL | 78 |
| | G G S L T I N S | | | | 79 |
| | GCCGGAAGTTAACTATTAACTC | | | | 80 |
| 3' | CCGCCTTCAAATTGATAATTGAG | 5' | | 5743.SL | 81 |

FIG. 31B

Oligonucleotides used to PCR amplify the 3'-end of *hmw1A* and 5'-end of *hmw1B* to construct a generic expression vector.

3'-end of *hmw1A*

|  |  | SEQ ID NO |
|---|---|---|
|           EcoR I | | 82 |
|     G  V  D  G  E↓N  S  D  S  D | | |
| 5' GGTGTTGATGGGGAGAATTCCGATTCAGACG 3' | 5947.SL | 83 |

|  |  |  |
|---|---|---|
|     V  C  V  N  I  A  D  N  G  R  * | | 84 |
|     GTGTGGTTAATATCCTGATAACGGGCGGTAG | | 85 |
| 3' CACACGCAATTATAGGACTATTGCCCGCCATCAGATCTCCGG 5' | 5948.SL | 86 |
|                                                       ↑Xba I | | |

FIG. 31B'

5'-end of hmw1B

```
                    XbaI
                     ↓
5'  GGCCCTCTAGACGGTCAGTAATTGACAAGGTAGATTTCATCC                                3'   5949.SL   87

G  R  Q  W  F  D  L  R  E  F  N  M  A
    GGTCGTCAGTGGTTCGATTTGCGTGAATTCAATATGGCA
5'                                                                                             88
3'  CCAGCAGTCACCAAGCTAAACGCACTTAAGTTATACCGT                                   5'   5950.SL   89
                                       ↑                                                       90
                                     EcoRI
```

FIG. 32B

Oligonucleotides used to PCR amplify the LCDC2 *hmw2A* gene for expression sense

```
        BamH I  Nde I
              ↓  ↓     M  P  D  D  V  S  I  D  A  P  S  A  E
5'  CGGGATCCCATATGCCGGATGATGTTTCTATCGATGCACCTTCGGCTGAA  3'   5972.SL   91
                                                                       92
``` antisense

```
     A  A  V  C  T  N  V  A  D  D  G  Q  Q  *
5'  GCAGCAGTATGTACCAATGTTGCTGACGATGACAGCAGTAGT           3'            93
3'  CGTCGTCATACATGGTTACAACGACTGCTACCTGTCGTCATCAGATCTG   5'   5973.SL   94
                                                ↑                       95
                                              XBA I
```

Construction of DS-2400-13, a pBR T7 hmwA/T7 hmwABC/cer/KanRplasmid

SEQUENCE LISTING

<160> NUMBER OF SEQ ID NOS: 91
<210> SEQ ID NO 1
<211> LENGTH: 15
<212> TYPE: PRT
<213> ORGANISM: Haemophilus influenzae

<400> SEQUENCE: 1

Met Asn Lys Ile Thr Arg Leu Lys Phe Ser Lys Arg Leu Asn Ala
 1               5                   10                  15

<210> SEQ ID NO 2
<211> LENGTH: 86
<212> TYPE: DNA
<213> ORGANISM: Haemophilus influenzae

<400> SEQUENCE: 2
ctagaaataa ttttgtttaa ctttaagaag gagatataca tatgaacaag atatatcgtc      60
tcaaattcag caaacgcctg aatgct                                            86

<210> SEQ ID NO 3
<211> LENGTH: 80
<212> TYPE: DNA
<213> ORGANISM: Haemophilus influenzae

<400> SEQUENCE: 3
tttattaaaa caaattgaaa ttcttcctct atatgtatac ttgttctata tagcagagtt      60
taagtcgttt gcggacttac                                                   80

<210> SEQ ID NO 4
<211> LENGTH: 24
<212> TYPE: PRT
<213> ORGANISM: Haemophilus influenzae

<400> SEQUENCE: 4

Met Pro Asp Asn Val Ser Ile Asn Ala Glu Thr Ala Gly Arg Ser Asn
 1               5                  10                  15

Thr Ser Glu Asp Asp Glu Tyr Thr
            20

<210> SEQ ID NO 5
<211> LENGTH: 114
<212> TYPE: DNA
<213> ORGANISM: Haemophilus influenzae

<400> SEQUENCE: 5
ctagaaataa ttttgtttaa ctttaagaag gagatataca tatgccggat aatgtatcta      60
ttaatgcaga acagcagga cgcagcaata cttcagaaga cgatgaatac acgg            114

<210> SEQ ID NO 6
<211> LENGTH: 114
<212> TYPE: DNA
<213> ORGANISM: Haemophilus influenzae

<400> SEQUENCE: 6
tttattaaaa caaattgaaa ttcttcctct atatgtatac ggcctattac atagataatt      60
acgtctttgt cgtcctgcgt cgttatgaag tcttctgcta cttatgtgcc ctag           114

<210> SEQ ID NO 7
<211> LENGTH: 21
<212> TYPE: PRT
<213> ORGANISM: Haemophilus influenzae

<400> SEQUENCE: 7

Met Pro Asp Asp Val Thr Ile Glu Ala Glu Asp Pro Leu Arg Asn Asn
 1               5                  10                  15

Thr Gly Ile Asn Asp
            20

<210> SEQ ID NO 8
<211> LENGTH: 105
<212> TYPE: DNA
<213> ORGANISM: Haemophilus influenzae

<400> SEQUENCE: 8
ctagaaataa ttttgtttaa ctttaagaag gagatataca tatgcctgat gatgtaacaa      60
ttgaagccga agacccctt cgcaataata ccgtataaa tgatg          105

<210> SEQ ID NO 9
<211> LENGTH: 105
<212> TYPE: DNA
<213> ORGANISM: Haemophilus influenzae

<400> SEQUENCE: 9
tttattaaaa caaattgaaa ttcttcctct atatgtatac ggactactac attgttaact    60
tcggcttctg ggggaagcgt tattatggcc atatttacta cttaa                  105

<210> SEQ ID NO 10
<211> LENGTH: 13
<212> TYPE: PRT
<213> ORGANISM: Haemophilus influenzae

<400> SEQUENCE: 10

Thr Ser Gly Thr Leu Val Ile Asn Ala Lys Asp Ala Glu
 1               5                  10

<210> SEQ ID NO 11
<211> LENGTH: 41
<212> TYPE: DNA
<213> ORGANISM: Haemophilus influenzae

<400> SEQUENCE: 11
caaccagcgg taccttggtt attaacgcaa aagacgctga g             41

<210> SEQ ID NO 12
<211> LENGTH: 8
<212> TYPE: PRT
<213> ORGANISM: Haemophilus influenzae

<400> SEQUENCE: 12

Val Asn Ile Ala Asp Asn Gly Arg
 1               5

<210> SEQ ID NO 13
<211> LENGTH: 29
<212> TYPE: DNA
<213> ORGANISM: Haemophilus influenzae

<400> SEQUENCE: 13
gcgttaatat cgctgataac gggcggtag                          29

<210> SEQ ID NO 14
<211> LENGTH: 45
<212> TYPE: DNA
<213> ORGANISM: Haemophilus influenzae

<400> SEQUENCE: 14
ggccaagctt ctcgagctac cgcccgttat cagcgatatt aacgc         45

<210> SEQ ID NO 15
<211> LENGTH: 8
<212> TYPE: PRT
<213> ORGANISM: Haemophilus influenzae

<400> SEQUENCE: 15

Lys Arg Val Leu Glu Lys Val Lys
 1               5

```
<210> SEQ ID NO 16
<211> LENGTH: 36
<212> TYPE: DNA
<213> ORGANISM: Haemophilus influenzae

<400> SEQUENCE: 16
ccggaattcc gaaacgcgtc cttgaaaaag taaaag                            36

<210> SEQ ID NO 17
<211> LENGTH: 9
<212> TYPE: PRT
<213> ORGANISM: Haemophilus influenzae

<400> SEQUENCE: 17

Thr Asn Val Ala Asp Asp Gly Gln Pro
  1               5

<210> SEQ ID NO 18
<211> LENGTH: 31
<212> TYPE: DNA
<213> ORGANISM: Haemophilus influenzae

<400> SEQUENCE: 18
taccaatgtt gctgacgatg gacagccgta g                                 31

<210> SEQ ID NO 19
<211> LENGTH: 39
<212> TYPE: DNA
<213> ORGANISM: Haemophilus influenzae

<400> SEQUENCE: 19
cgcggatcct acggctgtcc atcgtcagca acattggta                         39

<210> SEQ ID NO 20
<211> LENGTH: 7
<212> TYPE: PRT
<213> ORGANISM: Haemophilus influenzae

<400> SEQUENCE: 20

Lys Glu Trp Leu Leu Asp Pro
  1               5

<210> SEQ ID NO 21
<211> LENGTH: 32
<212> TYPE: DNA
<213> ORGANISM: Haemophilus influenzae

<400> SEQUENCE: 21
gggaattcca aagagtggtt gttagacccg ga                                32

<210> SEQ ID NO 22
<211> LENGTH: 10
<212> TYPE: PRT
<213> ORGANISM: Haemophilus influenzae

<400> SEQUENCE: 22

Met Lys Asn Ile Lys Ser Arg Leu Lys Leu
  1               5                  10

<210> SEQ ID NO 23
<211> LENGTH: 30
<212> TYPE: DNA
<213> ORGANISM: Haemophilus influenzae

<400> SEQUENCE: 23
```

-continued

```
atgaaaaata taaaaagcag attaaaactc                              30

<210> SEQ ID NO 24
<211> LENGTH: 38
<212> TYPE: DNA
<213> ORGANISM: Haemophilus influenzae

<400> SEQUENCE: 24
ggaattcgga gttttaatct gcttttttata tttttcat                    38

<210> SEQ ID NO 25
<211> LENGTH: 3681
<212> TYPE: DNA
<213> ORGANISM: Haemophilus influenzae

<400> SEQUENCE: 25
aaagaatggt tgttagaccc ggacaatgta tccattaacg caggcacatc agaacgtaac    60
gacgcttcac caacagaaga tttccctacc ggagcaggag gaaaggataa ccccaaaaaa   120
aacgctcaca caaaccgac attaataaac acaactcttg agcgtatatt aagtggcaac    180
acctttgtta atatcactgc cagaaaaaga atcacagtta atagtgatat caacatcaaa   240
gacagctccc atctaatact ctggagcgaa atgataaca gcagcggcgt tgatattaaa    300
ggcaatatca cttctactac tggcggaagc ttaactattt actccagcgg ctggattgat   360
attcataaaa acattacgct taattcaggg ctcttaaaca ttacaactaa acaaggagat   420
atcgccttcg aaaagggaa taccccaacc attacaggtc aagggactat taccgcaggc   480
aatggtaaag gttttaggtt tgaaaacgcc tccctaaacg gtattggaac agggttactt   540
tttaacatca aagggattt aggaaataat ttccaaatca taacttttt taacggaact   600 ttaaatattt cagggaaagt aaacatctca atggtcatac ctaaaaaatg ggattatagt   660
aaattcaggg gcgaaccta ttggaacgta acccatttaa atgtttccga aggcagtaag   720
tttaacctca ctatcgactc cagaggagat gacactgcag gcaccttaa cacccttat   780 aatttaaacg gtatatcatt caacaaagac actatctttg atgttaaaca aaacggggca   840
gtcacctttg acatcaaggc gccaataggg gtaaataata tcgtaatttt gaattacgca   900
tcattcaatg gaaatatttc agtttcagga ggagggaatg tcacttcaa acttctcgcc   960 tcatcctcta ccgctcaaac tcccggtgta tttataaatt ctaaacactt taatgcttca  1020
ggagggtcga gttagaatt tagaactgaa ggctcaacaa aagtcggctt cttgataaat  1080
aatgatttaa ccctaaatgc caccggaggt aacatatcgc tcttgcaagt tgaaggcatt  1140
gacgggatga ttggtaaagg cgttgtagct aaaaaaaaca taccctttgc tggaggcaat  1200
atcacctttg gctccaagaa agccataaca gaaatcgaag gcaatgctac tatcaataac  1260
aacgctaacg tcactcttat cggttcggat tttgacaacc atcaaaaacc tttaactatt  1320
aaaaaagatg tcatcattaa tagcggcaac cttaccgctg gcggcaatgt tatcaatata  1380
aacgaaaatc ttaccgttaa caatggcgcc aatcttaaag ctatcacaaa tttcactttt  1440
aatgtaggcg gcttgtttga caacaaaggc aattcaaata tctccattgc tagaggaggg  1500
gctaaattta agatatcaa taacaccagt agcttaaata ttaccaccaa ctccgacacc  1560
acttaccgta ccattataga aggtaatata accaacaaag caggtgattt gaatatcatt  1620
gataataaag gtaacgctga aatccaaatt ggcggcaata tctcgcaaaa agaaggtaat  1680
ctcacgattt cttccgataa aattaatatc actaaccaga taacaatcaa gaagggtgtt  1740
```

| | | | |
|---|---|---|---|
| aataaagagg attctgattc aagcacggca aacaatgcta atctaaccat taaaaccaaa | 1800 |
| gaattgcaat taacgggaga cctaaatatt tcaggcttcg ataaagcaga aatcacagcc | 1860 |
| aaagagggtg ccgatttaat catcggtaat agtgataata acaacaatgc taatgctaaa | 1920 |
| aaagtaacct ttaaccaggt taaagattcg aaaatctctg ctggcagtca caatgtaaca | 1980 |
| ctaaacagta aagtagaaac ctctaatggc aataatgacg ctgaaagcaa taatggcgat | 2040 |
| agcaccagct taactattaa tgcaaaaaat gtaacagtaa caacaatat tacttctcac | 2100 |
| aaaacagtaa atatcactgc gtcagaaaat gttaccacca agcgggcac aaccattaat | 2160 |
| gcaaccatag gtagcgtaga agtaacagcc aaaacaggtg atattaaagg tggaattgaa | 2220 |
| tccaattccg gtaatgtaaa tattacagcg agcggcgaca cgcttaatgt aagtaacatc | 2280 |
| acaggtcaaa atgtgacagt ggcagcagcc tcaggtgccg taacaaccac aaaaggatca | 2340 |
| actattaatg caacaactgg taatgcaaat attacaacca aaacaggtga attaatggc | 2400 |
| gaagttaaat cagcttccgg taatgtaaat attacagcga gcggcaatac acttaatgta | 2460 |
| agtaacatca ctggtcaaaa tgtaacagta acagcaaact caggtgccat aacaaccaca | 2520 |
| gaaggctcaa ctattaacgc gacaacaggt gatgcaaata ttacaaccca aacaggtaat | 2580 |
| attaatggta aagttgaatc cagttctggt tctgtgacgc ttattgcaac tggacaaact | 2640 |
| cttgctgtag gtaatatttc aggtgacact gttaccatta ctgcggataa aggtaaatta | 2700 |
| accacacaaa caagctctaa gattaacgga actaagagtg taaccacctc aagccaatca | 2760 |
| ggtgatatta gtggcacaat ttctggtaat acggtaagcg ttagtgcgac cggtagcttg | 2820 |
| accactcaag caggctcaaa aattgaagca aaaacaggtg aggctaatgt aacaagcgca | 2880 |
| acaggtacaa ttggcggtac aatctctggc aatacagtaa atgttacagc aaatactgat | 2940 |
| aatttaacta ttaaagatgg cgcaagaatt aaagcaacgg gcggagctgt gactttaacc | 3000 |
| gcaacaggag gtactttaac caccgaaaca agttctgata ttacctcaag caatggtcag | 3060 |
| acaactctca cggccaagga tagcagtatc gcaggaagca tcaatgccgc caatgtgaca | 3120 |
| ttaaatacca caggcacttt aactactgtg gcaggttcaa aaatcgaggc agccagtggc | 3180 |
| accctggtta ttaatgcaaa agatgctcag ttggacggcg cggcattagg tgaccgtaca | 3240 |
| gaagtaaatg taactaacgc aaatggctcc ggcagcgtaa tcgcgacaac ctcaagcaga | 3300 |
| gtgaacatca ctggggattt aatcacaata aatggattaa atatcatttc aaaaaacggt | 3360 |
| aaaaacaccg tgctgttaaa aggtgttgaa attgatgtga aatacattca accgggcata | 3420 |
| gcgagcgtat atgaagtaat tgaagcaaaa cgcgctcttg agaaagtgaa agatttatct | 3480 |
| gatgaagaaa gagaagcatt agctaagctt ggtgtgagcg ctgtacgttt tattgagcca | 3540 |
| aataatacaa ttacagtcga tacacaaaat gaatttgcaa ccagaccatt aagtcgaata | 3600 |
| gtgatttctg aaggcagggc gtgtttctca acagtgatg cgcgacggt gtgcgttaat | 3660 |
| atcgctgata acgggcggta g | 3681 |

<210> SEQ ID NO 26
<211> LENGTH: 1226
<212> TYPE: PRT
<213> ORGANISM: Haemophilus influenzae

<400> SEQUENCE: 26

Lys Glu Trp Leu Leu Asp Pro Asp Asn Val Ser Ile Asn Ala Gly Thr
1               5                   10                  15

Ser Glu Arg Asn Asp Ala Ser Pro Thr Glu Asp Phe Pro Thr Gly Ala
            20                  25                  30

-continued

```
Gly Gly Lys Asp Asn Pro Lys Lys Asn Ala His Asn Lys Pro Thr Leu
         35                  40                  45
Ile Asn Thr Thr Leu Glu Arg Ile Leu Ser Gly Asn Thr Phe Val Asn
     50                  55                  60
Ile Thr Ala Arg Lys Arg Ile Thr Val Asn Ser Asp Ile Asn Ile Lys
 65                  70                  75                  80
Asp Ser Ser His Leu Ile Leu Trp Ser Glu Asn Asp Asn Ser Ser Gly
                 85                  90                  95
Val Asp Ile Lys Gly Asn Ile Thr Ser Thr Gly Gly Ser Leu Thr
                100                 105                 110
Ile Tyr Ser Ser Gly Trp Ile Asp Ile His Lys Asn Ile Thr Leu Asn
                115                 120                 125
Ser Gly Leu Leu Asn Ile Thr Thr Lys Gln Gly Asp Ile Ala Phe Glu
        130                 135                 140
Lys Gly Asn Asn Pro Thr Ile Thr Gly Gln Gly Thr Ile Thr Ala Gly
145                 150                 155                 160
Asn Gly Lys Gly Phe Arg Phe Glu Asn Ala Ser Leu Asn Gly Ile Gly
                165                 170                 175
Thr Gly Leu Leu Phe Asn Ile Lys Arg Asp Leu Gly Asn Asn Phe Gln
                180                 185                 190
Ile Ile Asn Phe Phe Asn Gly Thr Leu Asn Ile Ser Gly Lys Val Asn
        195                 200                 205
Ile Ser Met Val Ile Pro Lys Lys Trp Asp Tyr Ser Lys Phe Arg Gly
        210                 215                 220
Arg Thr Tyr Trp Asn Val Thr His Leu Asn Val Ser Glu Gly Ser Lys
225                 230                 235                 240
Phe Asn Leu Thr Ile Asp Ser Arg Gly Asp Thr Ala Gly Thr Leu
                245                 250                 255
Asn Thr Pro Tyr Asn Leu Asn Gly Ile Ser Phe Asn Lys Asp Thr Ile
                260                 265                 270
Phe Asp Val Lys Gln Asn Gly Ala Val Thr Phe Asp Ile Lys Ala Pro
        275                 280                 285
Ile Gly Val Asn Asn Asn Arg Asn Leu Asn Tyr Ala Ser Phe Asn Gly
290                 295                 300
Asn Ile Ser Val Ser Gly Gly Asn Val Thr Phe Lys Leu Leu Ala
305                 310                 315                 320
Ser Ser Ser Thr Ala Gln Thr Pro Gly Val Phe Ile Asn Ser Lys His
                325                 330                 335
Phe Asn Ala Ser Gly Gly Ser Ser Leu Glu Phe Arg Thr Glu Gly Ser
                340                 345                 350
Thr Lys Val Gly Phe Leu Ile Asn Asn Asp Leu Thr Leu Asn Ala Thr
        355                 360                 365
Gly Gly Asn Ile Ser Leu Leu Gln Val Glu Gly Ile Asp Gly Met Ile
        370                 375                 380
Gly Lys Gly Val Val Ala Lys Lys Asn Ile Thr Phe Ala Gly Gly Asn
385                 390                 395                 400
Ile Thr Phe Gly Ser Lys Lys Ala Ile Thr Glu Ile Glu Gly Asn Ala
                405                 410                 415
Thr Ile Asn Asn Asn Ala Asn Val Thr Leu Ile Gly Ser Asp Phe Asp
        420                 425                 430
Asn His Gln Lys Pro Leu Thr Ile Lys Lys Asp Val Ile Ile Asn Ser
        435                 440                 445
```

-continued

```
Gly Asn Leu Thr Ala Gly Gly Asn Val Ile Asn Ile Asn Gly Asn Leu
    450                 455                 460
Thr Val Asn Asn Gly Ala Asn Leu Lys Ala Ile Thr Asn Phe Thr Phe
465                 470                 475                 480
Asn Val Gly Gly Leu Phe Asp Asn Lys Gly Asn Ser Asn Ile Ser Ile
                485                 490                 495
Ala Arg Gly Gly Ala Lys Phe Lys Asp Ile Asn Asn Thr Ser Ser Leu
            500                 505                 510
Asn Ile Thr Thr Asn Ser Asp Thr Thr Tyr Arg Thr Ile Ile Glu Gly
        515                 520                 525
Asn Ile Thr Asn Lys Ala Gly Asp Leu Asn Ile Ile Asp Asn Lys Gly
    530                 535                 540
Asn Ala Glu Ile Gln Ile Gly Gly Asn Ile Ser Gln Lys Glu Gly Asn
545                 550                 555                 560
Leu Thr Ile Ser Ser Asp Lys Ile Asn Ile Thr Asn Gln Ile Thr Ile
                565                 570                 575
Lys Lys Gly Val Asn Lys Glu Asp Ser Asp Ser Ser Thr Ala Asn Asn
            580                 585                 590
Ala Asn Leu Thr Ile Lys Thr Lys Glu Leu Gln Leu Thr Gly Asp Leu
        595                 600                 605
Asn Ile Ser Gly Phe Asp Lys Ala Glu Ile Thr Ala Lys Glu Gly Ala
    610                 615                 620
Asp Leu Ile Ile Gly Asn Ser Asp Asn Asn Asn Ala Asn Ala Lys
625                 630                 635                 640
Lys Val Thr Phe Asn Gln Val Lys Asp Ser Lys Ile Ser Ala Gly Ser
                645                 650                 655
His Asn Val Thr Leu Asn Ser Lys Val Glu Thr Ser Asn Gly Asn Asn
            660                 665                 670
Asp Ala Glu Ser Asn Asn Gly Asp Ser Thr Ser Leu Thr Ile Asn Ala
        675                 680                 685
Lys Asn Val Thr Val Asn Asn Ile Thr Ser His Lys Thr Val Asn
    690                 695                 700
Ile Thr Ala Ser Glu Asn Val Thr Thr Lys Ala Gly Thr Thr Ile Asn
705                 710                 715                 720
Ala Thr Ile Gly Ser Val Glu Val Thr Ala Lys Thr Gly Asp Ile Lys
                725                 730                 735
Gly Gly Ile Glu Ser Asn Ser Gly Asn Val Asn Ile Thr Ala Ser Gly
            740                 745                 750
Asp Thr Leu Asn Val Ser Asn Ile Thr Gly Gln Asn Val Thr Val Ala
        755                 760                 765
Ala Ala Ser Gly Ala Val Thr Thr Lys Gly Ser Thr Ile Asn Ala
    770                 775                 780
Thr Thr Gly Asn Ala Asn Ile Thr Thr Lys Thr Gly Glu Ile Asn Gly
785                 790                 795                 800
Glu Val Lys Ser Ala Ser Gly Asn Val Asn Ile Thr Ala Ser Gly Asn
                805                 810                 815
Thr Leu Asn Val Ser Asn Ile Thr Gly Gln Asn Val Thr Val Thr Ala
            820                 825                 830
Asn Ser Gly Ala Ile Thr Thr Glu Gly Ser Thr Ile Asn Ala Thr
        835                 840                 845
Thr Gly Asp Ala Asn Ile Thr Thr Gln Thr Gly Asn Ile Asn Gly Lys
    850                 855                 860
Val Glu Ser Ser Ser Gly Ser Val Thr Leu Ile Ala Thr Gly Gln Thr
```

-continued

```
            865                 870                 875                 880
Leu Ala Val Gly Asn Ile Ser Gly Asp Thr Val Thr Ile Thr Ala Asp
                885                 890                 895
Lys Gly Lys Leu Thr Thr Gln Thr Ser Ser Lys Ile Asn Gly Thr Lys
            900                 905                 910
Ser Val Thr Thr Ser Ser Gln Ser Gly Asp Ile Ser Gly Thr Ile Ser
            915                 920                 925
Gly Asn Thr Val Ser Val Ser Ala Thr Gly Ser Leu Thr Thr Gln Ala
        930                 935                 940
Gly Ser Lys Ile Glu Ala Lys Thr Gly Glu Ala Asn Val Thr Ser Ala
945                 950                 955                 960
Thr Gly Thr Ile Gly Gly Thr Ile Ser Gly Asn Thr Val Asn Val Thr
                965                 970                 975
Ala Asn Thr Asp Asn Leu Thr Ile Lys Asp Gly Ala Arg Ile Lys Ala
            980                 985                 990
Thr Gly Gly Ala Val Thr Leu Thr Ala Thr Gly Gly Thr Leu Thr Thr
        995                 1000                1005
Glu Thr Ser Ser Asp Ile Thr Ser Ser Asn Gly Gln Thr Thr Leu Thr
    1010                1015                1020
Ala Lys Asp Ser Ser Ile Ala Gly Ser Ile Asn Ala Ala Asn Val Thr
1025                1030                1035                1040
Leu Asn Thr Thr Gly Thr Leu Thr Thr Val Ala Gly Ser Lys Ile Glu
                1045                1050                1055
Ala Ala Ser Gly Thr Leu Val Ile Asn Ala Lys Asp Ala Gln Leu Asp
            1060                1065                1070
Gly Ala Ala Leu Gly Asp Arg Thr Glu Val Asn Val Thr Asn Ala Asn
        1075                1080                1085
Gly Ser Gly Ser Val Ile Ala Thr Thr Ser Ser Arg Val Asn Ile Thr
    1090                1095                1100
Gly Asp Leu Ile Thr Ile Asn Gly Leu Asn Ile Ile Ser Lys Asn Gly
1105                1110                1115                1120
Lys Asn Thr Val Leu Leu Lys Gly Val Glu Ile Asp Val Lys Tyr Ile
                1125                1130                1135
Gln Pro Gly Ile Ala Ser Val Tyr Glu Val Ile Glu Ala Lys Arg Ala
            1140                1145                1150
Leu Glu Lys Val Lys Asp Leu Ser Asp Glu Glu Arg Glu Ala Leu Ala
        1155                1160                1165
Lys Leu Gly Val Ser Ala Val Arg Phe Ile Glu Pro Asn Asn Thr Ile
    1170                1175                1180
Thr Val Asp Thr Gln Asn Glu Phe Ala Thr Arg Pro Leu Ser Arg Ile
1185                1190                1195                1200
Val Ile Ser Glu Gly Arg Ala Cys Phe Ser Asn Ser Asp Gly Ala Thr
                1205                1210                1215
Val Cys Val Asn Ile Ala Asp Asn Gly Arg
            1220                1225
```

<210> SEQ ID NO 27
<211> LENGTH: 3663
<212> TYPE: DNA
<213> ORGANISM: Haemophilus influenzae

<400> SEQUENCE: 27

```
ccggacaatg tatccattaa cgcaggcaca tcagaacgta acgacgcttc accaacagaa      60
gatttcccta ccggagcagg aggaaaggat aaccccaaaa aaaacgctca caacaaaccg     120
```

```
acattaataa acacaactct tgagcgtata ttaagtggca acacctttgt taatatcact      180
gccagaaaaa gaatcacagt taatagtgat atcaacatca aagacagctc ccatctaata      240
ctctggagcg aaaatgataa cagcagcggc gttgatatta aaggcaatat cacttctact      300
actggcggaa gcttaactat ttactccagc ggctggattg atattcataa aaacattacg      360
cttaattcag ggctcttaaa cattacaact aaacaaggag atatcgcctt cgaaaaaggg      420
aataacccaa ccattacagg tcaagggact attaccgcag gcaatggtaa aggttttagg      480
tttgaaaacg cctccctaaa cggtattgga acagggttac ttttaacat caaaagggat       540 ttaggaaata atttccaaat cataaacttt tttaacgaa ctttaaatat ttcagggaaa       600
gtaaacatct caatggtcat acctaaaaaa tgggattata gtaaattcag ggggcgaacc      660
tattggaacg taacccattt aaatgttttcc gaaggcagta agtttaacct cactatcgac    720
tccagaggag atgacactgc aggcacccct aacacccctt ataatttaaa cggtatatca      780
ttcaacaaag acactatctt tgatgttaaa caaaacgggg cagtcacctt tgacatcaag      840
gcgccaatag gggtaaataa taatcgtaat ttgaattacg catcattcaa tggaaatatt      900
tcagtttcag gaggagggaa tgtcactttc aaacttctcg cctcatcctc taccgctcaa      960
actcccggtg tatttataaa ttctaaacac tttaatgctt caggagggtc gagtttagaa     1020
tttagaactg aaggctcaac aaaagtcggc ttcttgataa ataatgattt aaccctaaat     1080
gccaccggag gtaacatatc gctcttgcaa gttgaaggca ttgacgggat gattggtaaa     1140
ggcgttgtag ctaaaaaaaa cataaccttt gctggaggca atatcacctt tggctccaag     1200
aaagccataa cagaaatcga aggcaatgct actatcaata caacgctaa cgtcactctt     1260 atcggttcgg attttgacaa ccatcaaaaa cctttaacta ttaaaaaaga tgtcatcatt     1320
aatagcggca accttaccgc tggcggcaat gttatcaata taaacggaaa tcttaccgtt     1380
aacaatggcg ccaatcttaa agctatcaca aatttcactt ttaatgtagg cggcttgttt     1440
gacaacaaag gcaattcaaa tatctccatt gctagaggag gggctaaatt taaagatatc     1500
aataacacca gtagcttaaa tattaccacc aactccgaca ccacttaccg taccattata     1560
gaaggtaata taaccaacaa agcaggtgat ttgaatatca ttgataataa aggtaacgct     1620
gaaatccaaa ttggcggcaa tatctcgcaa aaagaaggta atctcacgat ttcttccgat    1680
aaaattaata tcactaacca gataacaatc aagaagggtg ttaataaaga ggattctgat     1740
tcaagcacgg caaacaatgc taatctaacc attaaaacca aagaattgca attaacggga     1800
gacctaaata tttcaggctt cgataaagca gaaatcacag ccaaagaggg tgccgattta     1860
atcatcggta atagtgataa taacaacaat gctaatgcta aaaaagtaac ctttaaccag     1920
gttaaagatt cgaaaatctc tgctggcagt cacaatgtaa cactaaacag taaagtagaa     1980
acctctaatg gcaataatga cgctgaaagc aataatggcg atagcaccag cttaactatt     2040
aatgcaaaaa atgtaacagt aaacaacaat attacttctc acaaaacagt aaatatcact     2100
gcgtcagaaa atgttaccac caaagcgggc acaaccatta atgcaaccat aggtagcgta     2160
gaagtaacag ccaaaacagg tgatattaaa ggtggaattg aatccaattc cggtaatgta     2220
aatattacag cgagcggcga cacgcttaat gtaagtaaca tcacaggtca aaatgtgaca     2280
gtggcagcag cctcaggtgc cgtaacaacc acaaaaggat caactattaa tgcaacaact     2340
ggtaatgcaa atattacaac caaaacaggt gaaattaatg gcgaagttaa atcagcttcc     2400
ggtaatgtaa atattacagc gagcggcaat acacttaatg taagtaacat cactggtcaa     2460
```

-continued

```
aatgtaacag taacagcaaa ctcaggtgcc ataacaacca cagaaggctc aactattaac    2520
gcgacaacag gtgatgcaaa tattacaacc caaacaggta atattaatgg taaagttgaa    2580
tccagttctg gttctgtgac gcttattgca actggacaaa ctcttgctgt aggtaatatt    2640
tcaggtgaca ctgttaccat tactgcggat aaggtaaat taaccacaca aacaagctct     2700
aagattaacg gaactaagag tgtaaccacc tcaagccaat caggtgatat tagtggcaca    2760
atttctggta atacggtaag cgttagtgcg accggtagct tgaccactca agcaggctca    2820
aaaattgaag caaaaacagg tgaggctaat gtaacaagcg caacaggtac aattggcggt    2880
acaatctctg gcaatacagt aaatgttaca gcaaatactg ataatttaac tattaaagat    2940
ggcgcaagaa ttaaagcaac gggcggagct gtgactttaa ccgcaacagg aggtacttta    3000
accaccgaaa caagttctga tattacctca agcaatggtc agacaactct cacgccaag    3060 gatagcagta tcgcaggaag catcaatgcc gccaatgtga cattaaatac cacaggcact    3120
ttaactactg tggcaggttc aaaaatcgag gcagccagtg gcaccctggt tattaatgca    3180
aaagatgctc agttggacgg cgcggcatta ggtgaccgta cagaagtaaa tgtaactaac    3240
gcaaatggct ccggcagcgt aatcgcgaca acctcaagca gagtgaacat cactggggat    3300
ttaatcacaa taaatggatt aaatatcatt tcaaaaaacg gtaaaaacac cgtgctgtta    3360
aaaggtgttg aaattgatgt gaaatacatt caaccgggca tagcgagcgt atatgaagta    3420
attgaagcaa aacgcgctct tgagaaagtg aaagatttat ctgatgaaga aagagaagca    3480
ttagctaagc ttggtgtgag cgctgtacgt tttattgagc caataatac aattacagtc     3540 gatacacaaa atgaatttgc aaccagacca ttaagtcgaa tagtgattc tgaaggcagg    3600 gcgtgtttct caaacagtga tggcgcgacg gtgtgcgtta atatcgctga taacgggcgg    3660
tag                                                                  3663
```

<210> SEQ ID NO 28
<211> LENGTH: 1220
<212> TYPE: PRT
<213> ORGANISM: Haemophilus influenzae

<400> SEQUENCE: 28

```
Pro Asp Asn Val Ser Ile Asn Ala Gly Thr Ser Glu Arg Asn Asp Ala
 1               5                  10                  15

Ser Pro Thr Glu Asp Phe Pro Thr Gly Ala Gly Gly Lys Asp Asn Pro
            20                  25                  30

Lys Lys Asn Ala His Asn Lys Pro Thr Leu Ile Asn Thr Thr Leu Glu
        35                  40                  45

Arg Ile Leu Ser Gly Asn Thr Phe Val Asn Ile Thr Ala Arg Lys Arg
    50                  55                  60

Ile Thr Val Asn Ser Asp Ile Asn Ile Lys Asp Ser Ser His Leu Ile
65                  70                  75                  80

Leu Trp Ser Glu Asn Asp Asn Ser Ser Gly Val Asp Ile Lys Gly Asn
                85                  90                  95

Ile Thr Ser Thr Thr Gly Gly Ser Leu Thr Ile Tyr Ser Ser Gly Trp
           100                 105                 110

Ile Asp Ile His Lys Asn Ile Thr Leu Asn Ser Gly Leu Leu Asn Ile
       115                 120                 125

Thr Thr Lys Gln Gly Asp Ile Ala Phe Glu Lys Gly Asn Asn Pro Thr
   130                 135                 140

Ile Thr Gly Gln Gly Thr Ile Thr Ala Gly Asn Gly Lys Gly Phe Arg
145                 150                 155                 160
```

-continued

```
Phe Glu Asn Ala Ser Leu Asn Gly Ile Gly Thr Gly Leu Leu Phe Asn
            165                 170                 175

Ile Lys Arg Asp Leu Gly Asn Phe Gln Ile Ile Asn Phe Phe Asn
        180                 185                 190

Gly Thr Leu Asn Ile Ser Gly Lys Val Asn Ile Ser Met Val Ile Pro
            195                 200                 205

Lys Lys Trp Asp Tyr Ser Lys Phe Arg Gly Arg Thr Tyr Trp Asn Val
    210                 215                 220

Thr His Leu Asn Val Ser Glu Gly Ser Lys Phe Asn Leu Thr Ile Asp
225                 230                 235                 240

Ser Arg Gly Asp Asp Thr Ala Gly Thr Leu Asn Thr Pro Tyr Asn Leu
                245                 250                 255

Asn Gly Ile Ser Phe Asn Lys Asp Thr Ile Phe Asp Val Lys Gln Asn
            260                 265                 270

Gly Ala Val Thr Phe Asp Ile Lys Ala Pro Ile Gly Val Asn Asn Asn
                275                 280                 285

Arg Asn Leu Asn Tyr Ala Ser Phe Asn Gly Asn Ile Ser Val Ser Gly
    290                 295                 300

Gly Gly Asn Val Thr Phe Lys Leu Leu Ala Ser Ser Thr Ala Gln
305                 310                 315                 320

Thr Pro Gly Val Phe Ile Asn Ser Lys His Phe Asn Ala Ser Gly Gly
                325                 330                 335

Ser Ser Leu Glu Phe Arg Thr Glu Gly Ser Thr Lys Val Gly Phe Leu
                340                 345                 350

Ile Asn Asn Asp Leu Thr Leu Asn Ala Thr Gly Gly Asn Ile Ser Leu
            355                 360                 365

Leu Gln Val Glu Gly Ile Asp Gly Met Ile Gly Lys Gly Val Val Ala
    370                 375                 380

Lys Lys Asn Ile Thr Phe Ala Gly Gly Asn Ile Thr Phe Gly Ser Lys
385                 390                 395                 400

Lys Ala Ile Thr Glu Ile Glu Gly Asn Ala Thr Ile Asn Asn Asn Ala
                405                 410                 415

Asn Val Thr Leu Ile Gly Ser Asp Phe Asp Asn His Gln Lys Pro Leu
            420                 425                 430

Thr Ile Lys Lys Asp Val Ile Ile Asn Ser Gly Asn Leu Thr Ala Gly
        435                 440                 445

Gly Asn Val Ile Asn Ile Asn Gly Asn Leu Thr Val Asn Asn Gly Ala
    450                 455                 460

Asn Leu Lys Ala Ile Thr Asn Phe Thr Phe Asn Val Gly Gly Leu Phe
465                 470                 475                 480

Asp Asn Lys Gly Asn Ser Asn Ile Ser Ile Ala Arg Gly Gly Ala Lys
                485                 490                 495

Phe Lys Asp Ile Asn Asn Thr Ser Ser Leu Asn Ile Thr Thr Asn Ser
            500                 505                 510

Asp Thr Thr Tyr Arg Thr Ile Ile Glu Gly Asn Ile Thr Asn Lys Ala
        515                 520                 525

Gly Asp Leu Asn Ile Ile Asp Asn Lys Gly Asn Ala Glu Ile Gln Ile
    530                 535                 540

Gly Gly Asn Ile Ser Gln Lys Glu Gly Asn Leu Thr Ile Ser Ser Asp
545                 550                 555                 560

Lys Ile Asn Ile Thr Asn Gln Ile Thr Ile Lys Lys Gly Val Asn Lys
                565                 570                 575
```

-continued

```
Glu Asp Ser Asp Ser Thr Ala Asn Asn Ala Asn Leu Thr Ile Lys
                580                 585                 590

Thr Lys Glu Leu Gln Leu Thr Gly Asp Leu Asn Ile Ser Gly Phe Asp
            595                 600                 605

Lys Ala Glu Ile Thr Ala Lys Glu Gly Ala Asp Leu Ile Ile Gly Asn
        610                 615                 620

Ser Asp Asn Asn Asn Ala Asn Ala Lys Lys Val Thr Phe Asn Gln
625                 630                 635                 640

Val Lys Asp Ser Lys Ile Ser Ala Gly Ser His Asn Val Thr Leu Asn
                645                 650                 655

Ser Lys Val Glu Thr Ser Asn Gly Asn Asn Asp Ala Glu Ser Asn Asn
            660                 665                 670

Gly Asp Ser Thr Ser Leu Thr Ile Asn Ala Lys Asn Val Thr Val Asn
        675                 680                 685

Asn Asn Ile Thr Ser His Lys Thr Val Asn Ile Thr Ala Ser Glu Asn
690                 695                 700

Val Thr Thr Lys Ala Gly Thr Thr Ile Asn Ala Thr Ile Gly Ser Val
705                 710                 715                 720

Glu Val Thr Ala Lys Thr Gly Asp Ile Lys Gly Ile Glu Ser Asn
                725                 730                 735

Ser Gly Asn Val Asn Ile Thr Ala Ser Gly Asp Thr Leu Asn Val Ser
            740                 745                 750

Asn Ile Thr Gly Gln Asn Val Thr Val Ala Ala Ser Gly Ala Val
        755                 760                 765

Thr Thr Thr Lys Gly Ser Thr Ile Asn Ala Thr Thr Gly Asn Ala Asn
770                 775                 780

Ile Thr Thr Lys Thr Gly Glu Ile Asn Gly Glu Val Lys Ser Ala Ser
785                 790                 795                 800

Gly Asn Val Asn Ile Thr Ala Ser Gly Asn Thr Leu Asn Val Ser Asn
                805                 810                 815

Ile Thr Gly Gln Asn Val Thr Val Thr Ala Asn Ser Gly Ala Ile Thr
            820                 825                 830

Thr Thr Glu Gly Ser Thr Ile Asn Ala Thr Thr Gly Asp Ala Asn Ile
        835                 840                 845

Thr Thr Gln Thr Gly Asn Ile Asn Gly Lys Val Glu Ser Ser Ser Gly
850                 855                 860

Ser Val Thr Leu Ile Ala Thr Gly Gln Thr Leu Ala Val Gly Asn Ile
865                 870                 875                 880

Ser Gly Asp Thr Val Thr Ile Thr Ala Asp Lys Gly Lys Leu Thr Thr
                885                 890                 895

Gln Thr Ser Ser Lys Ile Asn Gly Thr Lys Ser Val Thr Thr Ser Ser
            900                 905                 910

Gln Ser Gly Asp Ile Ser Gly Thr Ile Ser Gly Asn Thr Val Ser Val
        915                 920                 925

Ser Ala Thr Gly Ser Leu Thr Thr Gln Ala Gly Ser Lys Ile Glu Ala
930                 935                 940

Lys Thr Gly Glu Ala Asn Val Thr Ser Ala Thr Gly Thr Ile Gly Gly
945                 950                 955                 960

Thr Ile Ser Gly Asn Thr Val Asn Val Thr Ala Asn Thr Asp Asn Leu
                965                 970                 975

Thr Ile Lys Asp Gly Ala Arg Ile Lys Ala Thr Gly Gly Ala Val Thr
            980                 985                 990

Leu Thr Ala Thr Gly Gly Thr Leu Thr Thr Glu Thr Ser Ser Asp Ile
```

-continued

```
                995                 1000                1005
Thr Ser Ser Asn Gly Gln Thr Thr Leu Thr Ala Lys Asp Ser Ser Ile
   1010                1015                1020
Ala Gly Ser Ile Asn Ala Ala Asn Val Thr Leu Asn Thr Thr Gly Thr
1025                1030                1035                1040
Leu Thr Thr Val Ala Gly Ser Lys Ile Glu Ala Ala Ser Gly Thr Leu
           1045                1050                1055
Val Ile Asn Ala Lys Asp Ala Gln Leu Asp Gly Ala Ala Leu Gly Asp
           1060                1065                1070
Arg Thr Glu Val Asn Val Thr Asn Ala Asn Gly Ser Gly Ser Val Ile
   1075                1080                1085
Ala Thr Thr Ser Ser Arg Val Asn Ile Thr Gly Asp Leu Ile Thr Ile
   1090                1095                1100
Asn Gly Leu Asn Ile Ile Ser Lys Asn Gly Lys Asn Thr Val Leu Leu
1105                1110                1115                1120
Lys Gly Val Glu Ile Asp Val Lys Tyr Ile Gln Pro Gly Ile Ala Ser
           1125                1130                1135
Val Tyr Glu Val Ile Glu Ala Lys Arg Ala Leu Glu Lys Val Lys Asp
           1140                1145                1150
Leu Ser Asp Glu Glu Arg Glu Ala Leu Ala Lys Leu Gly Val Ser Ala
           1155                1160                1165
Val Arg Phe Ile Glu Pro Asn Asn Thr Ile Thr Val Asp Thr Gln Asn
   1170                1175                1180
Glu Phe Ala Thr Arg Pro Leu Ser Arg Ile Val Ile Ser Glu Gly Arg
1185                1190                1195                1200
Ala Cys Phe Ser Asn Ser Asp Gly Ala Thr Val Cys Val Asn Ile Ala
           1205                1210                1215
Asp Asn Gly Arg
         1220

<210> SEQ ID NO 29
<211> LENGTH: 2928
<212> TYPE: DNA
<213> ORGANISM: Haemophilus influenzae

<400> SEQUENCE: 29
aaagagtggt tgttagaccc ggataatgta tccattgaaa atccttcaac tgaacgcaat     60
gattccaatg aagacctaga gtatacagga acagggaaa atataaacaa ccctaaggta    120
aataatcagt ctaaaaaaac actaacaagc tcaatccttg agaacatcct gaaaaaaggc    180
tcttttgtta acattactgc cactgataac atctacgtta atagctctat caacatcgga    240
gacagtggtc acttaattct ctcaggtgga ggcaggaacg gcggcggtgt taagattaat    300
aaaaatatta cttccacggg cggaagttta accattaatt ccaaggatgg ggttgatatt    360
cactccaata tttcacttgg tacgggtttt ttgaacatta cctctaatgg ttccgtggct    420
tttgagaagg cagacaaaga taaggcacgt agcgcggcag atgctcaaat tgtcgcacaa    480
ggcatcataa acctcacagg ggaaaacaaa acctttaggc ttaacaatgt gtctttaaat    540
ggagtgggtc aagtctatc catcacgtca aatgtgggca atcaaactca taaattcgat    600
ggtgaaatta acataactgg aaatgtaaca attaatcaaa ctgcacctgc gacaaccgca    660
tattggaatt ttagctacga ttcatattgg aacgtcagta ctcttaacgt acaaaaaaac    720
tcaagcttta ccttattaa gcgcactgaa agtaatcgct ttggcccaac aacaccactt    780
cgaagctccg gagggtatt ctttaacggc acgaatggca acatggtgct taacgtcgga    840
```

```
actaattcga gagttttgtt taatttgaag ccaaatgaga atacaaacaa cagcaagcct      900
ttaccgcttc aatttaacgc caatattaca gccattggtg gaggctctgt gtcttttgat      960
atacacgcca atcattccgg cagagggct gaattaaaaa tgaacacaat taatatctct     1020
gacggcacca gcctcaccct acaatcccat gttcgcaaag atagtgcttt tataatcagt     1080
aaagatttaa caataaacgc aaccggttca aattttactc ttgagcaatc accagacagt     1140
tttactgaca aatacccccgg aagagctatt agttcaacta aaaatataac catctcaggt     1200
ggcaacgtct ctcttggtgg gcaaaattca agcagtgaca tcaagggaaa tattaccatc     1260
aaaagctcaa caaatgttac actgaaagcc cataacagcc ctcgcgactt tgcttccaga     1320
accttaaccc ttggcaactt gaatgttgaa ggaaatttaa ccctaaccgg ctcagttgcg     1380
gatattaaag gtaacctttc cattcttaac gatgctactt ttaaaggaga gaccagtgaa     1440
aacctaaaca tcaccggcaa cttcaccaat aatggcaccg ccgacattaa tataaaacaa     1500
ggggtggtaa acatccaagg taatattacc aataaaggtg gtttaaacat taccactaat     1560
gcccaaaaca atcaaaaaac cattattaac ggaaatataa ctaacgaagg cggagattta     1620
aacatcaagg atagtaacaa taatgctgaa atccaaattg gcggcaatat ctcgcaaaaa     1680
aaaggcaatc tcacaatttc ttctgataaa atcaatatta ccaagaagat aacaatcaaa     1740
gcaggcgttg atgaaggtgg ttctgactca agcccagcaa gtaatgctaa tctaaccatt     1800
aaaaccaaaa cgctagaatt aacaggagac ctaaatattt caggctttaa taaagcagaa     1860
attacagcta aaaatggcaa cgatttaact attggcaagg ctagtgatgg taatgctaat     1920
gctaaaaaag tgacttttga caaggttaaa gattcaaaaa tctcagctaa cggtcacaat     1980
gtaacactaa atagcaaagt ggaaacgtct aatagtgata gtagtgctga tgatagtaat     2040
gataacaaca ctggtttaac catttccgca aaagatgtaa cagtaaacaa tgacgtcacc     2100
tcccacaaga caataaatat ctctgccaca acaggaaatg taacaaccaa agaaagcaca     2160
accattaatg cggccacagg tagcgtggaa gtaactgcta aaacaggcga tattagtggc     2220
acaatttctg gtaatacagt aaatgttaca gcaactgata gcttaaccac ccaagcaagc     2280
tctagcatta cctcaagtaa tggtcagaca actcttacag ccaagaatgg cagtatcgca     2340
ggaagtattg atgccgctaa tgtgacatta aataccacag gcaccttaac tactgtagcg     2400
ggttcaaaca ttaaggcaac cagtggcact ttagctatta acgcaaaaga tgctaagtta     2460
gatggtactg catcaggtga ccgcacagta gtaaatgcaa ctaacgcaag tggctctggt     2520
agtgtgactg cggcaacctc aagtaacgtg aatatcactg gagatttaag cacaataaat     2580
ggattaaata tcatttcgaa aaatggtaaa acaccgtag tgttaaaagg tgctgaaatt     2640
gatgtgaaat atattcaacc aggtgtagca agtgcgaatg aggttattga agcgaagcgt     2700
gcccttgaaa agtaaaaga tttatctgat gaagaaagag aaacattagc taaacttggt     2760
gtaagtgctg tacgttttgt tgagccaaat aatacaatta cagtcaatac acaaaatgaa     2820
tttacaacca gaccgtcaag tcaagtgaca atttctgaag acaaggcgtg tttctcaagt     2880
ggtaatggtg cagcagtatg tactaatgtt actgacgata gacagtaa                 2928
```

<210> SEQ ID NO 30
<211> LENGTH: 975
<212> TYPE: PRT
<213> ORGANISM: Haemophilus influenzae

<400> SEQUENCE: 30

-continued

```
Lys Glu Trp Leu Leu Asp Pro Asp Asn Val Ser Ile Glu Asn Pro Ser
 1               5                  10                  15

Thr Glu Arg Asn Asp Ser Asn Glu Asp Leu Glu Tyr Thr Gly Thr Gly
                 20                  25                  30

Glu Asn Ile Asn Asn Pro Lys Val Asn Gln Ser Lys Lys Thr Leu
             35                  40                  45

Thr Ser Ser Ile Leu Glu Asn Ile Leu Lys Lys Gly Ser Phe Val Asn
 50                  55                  60

Ile Thr Ala Thr Asp Asn Ile Tyr Val Asn Ser Ser Ile Asn Ile Gly
 65                  70                  75                  80

Asp Ser Gly His Leu Ile Leu Ser Gly Gly Arg Asn Gly Gly Gly
                 85                  90                  95

Val Lys Ile Asn Lys Asn Ile Thr Ser Thr Gly Gly Ser Leu Thr Ile
                100                 105                 110

Asn Ser Lys Gly Trp Val Asp Ile His Ser Asn Ile Ser Leu Gly Thr
             115                 120                 125

Gly Phe Leu Asn Ile Thr Ser Asn Gly Ser Val Ala Phe Glu Lys Ala
         130                 135                 140

Asp Lys Asp Lys Ala Arg Ser Ala Ala Asp Ala Gln Ile Val Ala Gln
145                 150                 155                 160

Gly Ile Ile Asn Leu Thr Gly Glu Asn Lys Thr Phe Arg Leu Asn Asn
                165                 170                 175

Val Ser Leu Asn Gly Val Gly Gln Gly Leu Ser Ile Thr Ser Asn Val
             180                 185                 190

Gly Asn Gln Thr His Lys Phe Asp Gly Glu Ile Asn Ile Thr Gly Asn
         195                 200                 205

Val Thr Ile Asn Gln Thr Ala Pro Ala Thr Thr Ala Tyr Trp Asn Phe
    210                 215                 220

Ser Tyr Asp Ser Tyr Trp Asn Val Ser Thr Leu Asn Val Gln Lys Asn
225                 230                 235                 240

Ser Ser Phe Thr Phe Ile Lys Arg Thr Glu Ser Asn Arg Phe Gly Pro
                245                 250                 255

Thr Thr Pro Leu Arg Ser Ser Gly Val Phe Phe Asn Gly Thr Asn
             260                 265                 270

Gly Asn Met Val Leu Asn Val Gly Thr Asn Ser Arg Val Leu Phe Asn
         275                 280                 285

Leu Lys Pro Asn Glu Asn Thr Asn Asn Ser Lys Pro Leu Pro Leu Gln
    290                 295                 300

Phe Asn Ala Asn Ile Thr Ala Ile Gly Gly Gly Ser Val Ser Phe Asp
305                 310                 315                 320

Ile His Ala Asn His Ser Gly Arg Gly Ala Glu Leu Lys Met Asn Thr
                325                 330                 335

Ile Asn Ile Ser Asp Gly Thr Ser Leu Thr Leu Gln Ser His Val Arg
             340                 345                 350

Lys Asp Ser Ala Phe Ile Ile Ser Lys Asp Leu Thr Ile Asn Ala Thr
         355                 360                 365

Gly Ser Asn Phe Thr Leu Glu Gln Ser Pro Asp Ser Phe Thr Asp Lys
    370                 375                 380

Tyr Pro Gly Arg Ala Ile Ser Ser Thr Lys Asn Ile Thr Ile Ser Gly
385                 390                 395                 400

Gly Asn Val Ser Leu Gly Gly Gln Asn Ser Ser Ser Asp Ile Lys Gly
                405                 410                 415

Asn Ile Thr Ile Lys Ser Ser Thr Asn Val Thr Leu Lys Ala His Asn
```

```
                    420              425              430
Ser Pro Arg Asp Phe Ala Ser Arg Thr Leu Thr Leu Gly Asn Leu Asn
        435                  440                  445
Val Glu Gly Asn Leu Thr Leu Thr Gly Ser Val Ala Asp Ile Lys Gly
    450                  455                  460
Asn Leu Ser Ile Leu Asn Asp Ala Thr Phe Lys Gly Glu Thr Ser Glu
465                  470                  475                  480
Asn Leu Asn Ile Thr Gly Asn Phe Thr Asn Asn Gly Thr Ala Asp Ile
                485                  490                  495
Asn Ile Lys Gln Gly Val Val Asn Ile Gln Gly Asn Ile Thr Asn Lys
            500                  505                  510
Gly Gly Leu Asn Ile Thr Thr Asn Ala Gln Asn Asn Gln Lys Thr Ile
        515                  520                  525
Ile Asn Gly Asn Ile Thr Asn Glu Gly Gly Asp Leu Asn Ile Lys Asp
    530                  535                  540
Ser Asn Asn Asn Ala Glu Ile Gln Ile Gly Asn Ile Ser Gln Lys
545                  550                  555                  560
Lys Gly Asn Leu Thr Ile Ser Ser Asp Lys Ile Asn Ile Thr Lys Lys
                565                  570                  575
Ile Thr Ile Lys Ala Gly Val Asp Glu Gly Gly Ser Asp Ser Ser Pro
            580                  585                  590
Ala Ser Asn Ala Asn Leu Thr Ile Lys Thr Lys Thr Leu Glu Leu Thr
        595                  600                  605
Gly Asp Leu Asn Ile Ser Gly Phe Asn Lys Ala Glu Ile Thr Ala Lys
    610                  615                  620
Asn Gly Asn Asp Leu Thr Ile Gly Lys Ala Ser Asp Gly Asn Ala Asn
625                  630                  635                  640
Ala Lys Lys Val Thr Phe Asp Lys Val Lys Asp Ser Lys Ile Ser Ala
                645                  650                  655
Asn Gly His Asn Val Thr Leu Asn Ser Lys Val Glu Thr Ser Asn Ser
            660                  665                  670
Asp Ser Ser Ala Asp Asp Ser Asn Asp Asn Thr Gly Leu Thr Ile
        675                  680                  685
Ser Ala Lys Asp Val Thr Val Asn Asn Asp Val Thr Ser His Lys Thr
    690                  695                  700
Ile Asn Ile Ser Ala Thr Thr Gly Asn Val Thr Thr Lys Glu Ser Thr
705                  710                  715                  720
Thr Ile Asn Ala Ala Thr Gly Ser Val Glu Val Thr Ala Lys Thr Gly
                725                  730                  735
Asp Ile Ser Gly Thr Ile Ser Gly Asn Thr Val Asn Val Thr Ala Thr
            740                  745                  750
Asp Ser Leu Thr Thr Gln Ala Ser Ser Ile Thr Ser Asn Gly
        755                  760                  765
Gln Thr Thr Leu Thr Ala Lys Asn Gly Ser Ile Ala Gly Ser Ile Asp
    770                  775                  780
Ala Ala Asn Val Thr Leu Asn Thr Thr Gly Thr Leu Thr Thr Val Ala
785                  790                  795                  800
Gly Ser Asn Ile Lys Ala Thr Ser Gly Thr Leu Ala Ile Asn Ala Lys
                805                  810                  815
Asp Ala Lys Leu Asp Gly Thr Ala Ser Gly Asp Arg Thr Val Val Asn
            820                  825                  830
Ala Thr Asn Ala Ser Gly Ser Gly Ser Val Thr Ala Ala Thr Ser Ser
        835                  840                  845
```

```
Asn Val Asn Ile Thr Gly Asp Leu Ser Thr Ile Asn Gly Leu Asn Ile
        850                 855                 860

Ile Ser Lys Asn Gly Lys Asn Thr Val Val Leu Lys Gly Ala Glu Ile
865                 870                 875                 880

Asp Val Lys Tyr Ile Gln Pro Gly Val Ala Ser Ala Asn Glu Val Ile
                885                 890                 895

Glu Ala Lys Arg Ala Leu Glu Lys Val Lys Asp Leu Ser Asp Glu Glu
                900                 905                 910

Arg Glu Thr Leu Ala Lys Leu Gly Val Ser Ala Val Arg Phe Val Glu
                915                 920                 925

Pro Asn Asn Thr Ile Thr Val Asn Thr Gln Asn Glu Phe Thr Thr Arg
        930                 935                 940

Pro Ser Ser Gln Val Thr Ile Ser Glu Asp Lys Ala Cys Phe Ser Ser
945                 950                 955                 960

Gly Asn Gly Ala Ala Val Cys Thr Asn Val Thr Asp Asp Arg Gln
                965                 970                 975

<210> SEQ ID NO 31
<211> LENGTH: 2910
<212> TYPE: DNA
<213> ORGANISM: Haemophilus influenzae

<400> SEQUENCE: 31
```

| | | | | | |
|---|---|---|---|---|---|
| ccggataatg | tatccattga | aaatccttca | actgaacgca | atgattccaa | tgaagaccta | 60 |
| gagtatacag | gaacagggga | aaatataaac | aaccctaagg | taaataatca | gtctaaaaaa | 120 |
| acactaacaa | gctcaatcct | tgagaacatc | ctgaaaaaag | gctcttttgt | taacattact | 180 |
| gccactgata | acatctacgt | taatagctct | atcaacatcg | gagacagtgg | tcacttaatt | 240 |
| ctctcaggtg | gaggcaggaa | cggcggcggt | gttaagatta | taaaaatat | tacttccacg | 300 |
| ggcggaagtt | taaccattaa | ttccaaagga | tgggttgata | ttcactccaa | tatttcactt | 360 |
| ggtacgggtt | ttttgaacat | tacctctaat | ggttccgtgg | cttttgagaa | ggcagacaaa | 420 |
| gataaggcac | gtagcgcggc | agatgctcaa | attgtcgcac | aaggcatcat | aaacctcaca | 480 |
| ggggaaaaca | aaacctttag | gcttaacaat | gtgtctttaa | atggagtggg | tcaaggtcta | 540 |
| tccatcacgt | caaatgtggg | caatcaaact | cataaattcg | atggtgaaat | taacataact | 600 |
| ggaaatgtaa | caattaatca | aactgcacct | gcgacaaccg | catattggaa | ttttagctac | 660 |
| gattcatatt | ggaacgtcag | tactcttaac | gtacaaaaaa | actcaagctt | tacctttatt | 720 |
| aagcgcactg | aaagtaatcg | ctttggccca | acaacaccac | ttcgaagctc | cggagggta | 780 |
| ttctttaacg | gcacgaatgg | caacatggtg | cttaacgtcg | gaactaattc | gagagttttg | 840 |
| tttaatttga | agccaaatga | gaatacaaac | aacagcaagc | ctttaccgct | tcaatttaac | 900 |
| gccaatatta | cagccattgg | tggaggctct | gtgtcttttg | atatacacgc | caatcattcc | 960 |
| ggcagagggg | ctgaattaaa | aatgaacaca | attaatatct | ctgacggcac | cagcctcacc | 1020 |
| ctacaatccc | atgttcgcaa | agatagtgct | tttataatca | gtaaagattt | aacaataaac | 1080 |
| gcaaccggtt | caaattttac | tcttgagcaa | tcaccagaca | gtttactga | caaatacccc | 1140 |
| ggaagagcta | ttagttcaac | taaaaatata | accatctcag | gtggcaacgt | ctctcttggt | 1200 |
| gggcaaaatt | caagcagtga | catcaaggga | aatattacca | tcaaaagctc | aacaaatgtt | 1260 |
| acactgaaag | cccataacag | ccctcgcgac | tttgcttcca | gaaccttaac | ccttggcaac | 1320 |
| ttgaatgttg | aaggaaattt | aaccctaacc | ggctcagttg | cggatattaa | aggtaacctt | 1380 |

-continued

```
tccattctta acgatgctac ttttaaagga gagaccagtg aaaacctaaa catcaccggc    1440
aacttcacca ataatggcac cgccgacatt aatataaaac aaggggtggt aaacatccaa    1500
ggtaatatta ccaataaagg tggtttaaac attaccacta atgcccaaaa caatcaaaaa    1560
accattatta acgaaatat aactaacgaa ggcggagatt taaacatcaa ggatagtaac     1620 ataatgctg aaatccaaat tggcggcaat atctcgcaaa aaaaggcaa tctcacaatt      1680 tcttctgata aatcaatat taccaagaag ataacaatca aagcaggcgt tgatgaaggt     1740
ggttctgact caagcccagc aagtaatgct aatctaacca ttaaaaccaa aacgctagaa    1800
ttaacaggag acctaaatat ttcaggcttt aataaagcag aaattacagc taaaaatggc    1860
aacgatttaa ctattggcaa ggctagtgat ggtaatgcta atgctaaaaa agtgactttt    1920
gacaaggtta aagattcaaa aatctcagct aacggtcaca atgtaacact aaatagcaaa    1980
gtggaaacgt ctaatagtga tagtagtgct gatgatagta atgataacaa cactggttta    2040
accatttccg caaagatgt aacagtaaac aatgacgtca cctcccacaa gacaataaat     2100
atctctgcca aacaggaaa tgtaacaacc aaagaaagca caaccattaa tgcggccaca     2160
ggtagcgtgg aagtaactgc taaaacaggc gatattagtg gcacaatttc tggtaataca    2220
gtaaatgtta cagcaactga tagcttaacc acccaagcaa gctctagcat tacctcaagt    2280
aatggtcaga caactcttac agccaagaat ggcagtatcg caggaagtat tgatgccgct    2340
aatgtgacat taaataccac aggcacctta actactgtag cgggttcaaa cattaaggca    2400
accagtggca ctttagctat taacgcaaaa gatgctaagt tagatggtac tgcatcaggt    2460
gaccgcacag tagtaaatgc aactaacgca agtggctctg gtagtgtgac tgcggcaacc    2520
tcaagtaacg tgaatatcac tggagattta agcacaataa atggattaaa tatcatttcg    2580
aaaaatggta aaacaccgt agtgttaaaa ggtgctgaaa ttgatgtgaa atatattcaa     2640
ccaggtgtag caagtgcgaa tgaggttatt gaagcgaagc gtgcccttga aaaagtaaaa    2700
gatttatctg atgaagaaag agaaacatta gctaaacttg gtgtaagtgc tgtacgtttt    2760
gttgagccaa ataatacaat tacagtcaat acacaaaatg aatttacaac cagaccgtca    2820
agtcaagtga caattctga agacaaggcg tgtttctcaa gtggtaatgg tgcagcagta     2880
tgtactaatg ttactgacga tagacagtaa                                     2910
```

<210> SEQ ID NO 32
<211> LENGTH: 969
<212> TYPE: PRT
<213> ORGANISM: Haemophilus influenzae

<400> SEQUENCE: 32

```
Pro Asp Asn Val Ser Ile Glu Asn Pro Ser Thr Glu Arg Asn Asp Ser
  1               5                  10                  15

Asn Glu Asp Leu Glu Tyr Thr Gly Thr Gly Glu Asn Ile Asn Asn Pro
             20                  25                  30

Lys Val Asn Asn Gln Ser Lys Lys Thr Leu Thr Ser Ser Ile Leu Glu
         35                  40                  45

Asn Ile Leu Lys Lys Gly Ser Phe Val Asn Ile Thr Ala Thr Asp Asn
     50                  55                  60

Ile Tyr Val Asn Ser Ser Ile Asn Ile Gly Asp Ser Gly His Leu Ile
 65                  70                  75                  80

Leu Ser Gly Gly Gly Arg Asn Gly Gly Gly Val Lys Ile Asn Lys Asn
                 85                  90                  95

Ile Thr Ser Thr Gly Gly Ser Leu Thr Ile Asn Ser Lys Gly Trp Val
```

-continued

```
            100                 105                 110
Asp Ile His Ser Asn Ile Ser Leu Gly Thr Gly Phe Leu Asn Ile Thr
        115                 120                 125
Ser Asn Gly Ser Val Ala Phe Glu Lys Ala Asp Lys Asp Lys Ala Arg
    130                 135                 140
Ser Ala Ala Asp Ala Gln Ile Val Ala Gln Gly Ile Ile Asn Leu Thr
145                 150                 155                 160
Gly Glu Asn Lys Thr Phe Arg Leu Asn Asn Val Ser Leu Asn Gly Val
                165                 170                 175
Gly Gln Gly Leu Ser Ile Thr Ser Asn Val Gly Asn Gln Thr His Lys
            180                 185                 190
Phe Asp Gly Glu Ile Asn Ile Thr Gly Asn Val Thr Ile Asn Gln Thr
        195                 200                 205
Ala Pro Ala Thr Thr Ala Tyr Trp Asn Phe Ser Tyr Asp Ser Tyr Trp
210                 215                 220
Asn Val Ser Thr Leu Asn Val Gln Lys Asn Ser Ser Phe Thr Phe Ile
225                 230                 235                 240
Lys Arg Thr Glu Ser Asn Arg Phe Gly Pro Thr Thr Pro Leu Arg Ser
                245                 250                 255
Ser Gly Gly Val Phe Asn Gly Thr Asn Gly Asn Met Val Leu Asn
            260                 265                 270
Val Gly Thr Asn Ser Arg Val Leu Phe Asn Leu Lys Pro Asn Glu Asn
        275                 280                 285
Thr Asn Asn Ser Lys Pro Leu Pro Leu Gln Phe Asn Ala Asn Ile Thr
    290                 295                 300
Ala Ile Gly Gly Gly Ser Val Ser Phe Asp Ile His Ala Asn His Ser
305                 310                 315                 320
Gly Arg Gly Ala Glu Leu Lys Met Asn Thr Ile Asn Ile Ser Asp Gly
                325                 330                 335
Thr Ser Leu Thr Leu Gln Ser His Val Arg Lys Asp Ser Ala Phe Ile
            340                 345                 350
Ile Ser Lys Asp Leu Thr Ile Asn Ala Thr Gly Ser Asn Phe Thr Leu
        355                 360                 365
Glu Gln Ser Pro Asp Ser Phe Thr Asp Lys Tyr Pro Gly Arg Ala Ile
    370                 375                 380
Ser Ser Thr Lys Asn Ile Thr Ile Ser Gly Gly Asn Val Ser Leu Gly
385                 390                 395                 400
Gly Gln Asn Ser Ser Asp Ile Lys Gly Asn Ile Thr Ile Lys Ser
                405                 410                 415
Ser Thr Asn Val Thr Leu Lys Ala His Asn Ser Pro Arg Asp Phe Ala
            420                 425                 430
Ser Arg Thr Leu Thr Leu Gly Asn Leu Asn Val Glu Gly Asn Leu Thr
        435                 440                 445
Leu Thr Gly Ser Val Ala Asp Ile Lys Gly Asn Leu Ser Ile Leu Asn
    450                 455                 460
Asp Ala Thr Phe Lys Gly Glu Thr Ser Glu Asn Leu Asn Ile Thr Gly
465                 470                 475                 480
Asn Phe Thr Asn Asn Gly Thr Ala Asp Ile Asn Ile Lys Gln Gly Val
                485                 490                 495
Val Asn Ile Gln Gly Asn Ile Thr Asn Lys Gly Gly Leu Asn Ile Thr
            500                 505                 510
Thr Asn Ala Gln Asn Asn Gln Lys Thr Ile Ile Asn Gly Asn Ile Thr
        515                 520                 525
```

```
Asn Glu Gly Gly Asp Leu Asn Ile Lys Asp Ser Asn Asn Ala Glu
        530                 535                 540

Ile Gln Ile Gly Gly Asn Ile Ser Gln Lys Lys Gly Asn Leu Thr Ile
545                 550                 555                 560

Ser Ser Asp Lys Ile Asn Ile Thr Lys Lys Ile Thr Ile Lys Ala Gly
                565                 570                 575

Val Asp Glu Gly Gly Ser Asp Ser Ser Pro Ala Ser Asn Ala Asn Leu
            580                 585                 590

Thr Ile Lys Thr Lys Thr Leu Glu Leu Thr Gly Asp Leu Asn Ile Ser
        595                 600                 605

Gly Phe Asn Lys Ala Glu Ile Thr Ala Lys Asn Gly Asn Asp Leu Thr
    610                 615                 620

Ile Gly Lys Ala Ser Asp Gly Asn Ala Asn Ala Lys Lys Val Thr Phe
625                 630                 635                 640

Asp Lys Val Lys Asp Ser Lys Ile Ser Ala Asn Gly His Asn Val Thr
                645                 650                 655

Leu Asn Ser Lys Val Glu Thr Ser Asn Ser Asp Ser Ser Ala Asp Asp
            660                 665                 670

Ser Asn Asp Asn Asn Thr Gly Leu Thr Ile Ser Ala Lys Asp Val Thr
        675                 680                 685

Val Asn Asn Asp Val Thr Ser His Lys Thr Ile Asn Ile Ser Ala Thr
    690                 695                 700

Thr Gly Asn Val Thr Thr Lys Glu Ser Thr Thr Ile Asn Ala Ala Thr
705                 710                 715                 720

Gly Ser Val Glu Val Thr Ala Lys Thr Gly Asp Ile Ser Gly Thr Ile
                725                 730                 735

Ser Gly Asn Thr Val Asn Val Thr Ala Thr Asp Ser Leu Thr Thr Gln
            740                 745                 750

Ala Ser Ser Ser Ile Thr Ser Ser Asn Gly Gln Thr Thr Leu Thr Ala
        755                 760                 765

Lys Asn Gly Ser Ile Ala Gly Ser Ile Asp Ala Ala Asn Val Thr Leu
    770                 775                 780

Asn Thr Thr Gly Thr Leu Thr Thr Val Ala Gly Ser Asn Ile Lys Ala
785                 790                 795                 800

Thr Ser Gly Thr Leu Ala Ile Asn Ala Lys Asp Ala Lys Leu Asp Gly
                805                 810                 815

Thr Ala Ser Gly Asp Arg Thr Val Val Asn Ala Thr Asn Ala Ser Gly
            820                 825                 830

Ser Gly Ser Val Thr Ala Ala Thr Ser Ser Asn Val Asn Ile Thr Gly
        835                 840                 845

Asp Leu Ser Thr Ile Asn Gly Leu Asn Ile Ile Ser Lys Asn Gly Lys
    850                 855                 860

Asn Thr Val Val Leu Lys Gly Ala Glu Ile Asp Val Lys Tyr Ile Gln
865                 870                 875                 880

Pro Gly Val Ala Ser Ala Asn Glu Val Ile Glu Ala Lys Arg Ala Leu
                885                 890                 895

Glu Lys Val Lys Asp Leu Ser Asp Glu Glu Arg Glu Thr Leu Ala Lys
            900                 905                 910

Leu Gly Val Ser Ala Val Arg Phe Val Glu Pro Asn Asn Thr Ile Thr
        915                 920                 925

Val Asn Thr Gln Asn Glu Phe Thr Thr Arg Pro Ser Ser Gln Val Thr
    930                 935                 940
```

Ile Ser Glu Asp Lys Ala Cys Phe Ser Ser Gly Asn Gly Ala Ala Val
945                 950                 955                 960

Cys Thr Asn Val Thr Asp Asp Arg Gln
                965

<210> SEQ ID NO 33
<211> LENGTH: 3686
<212> TYPE: DNA
<213> ORGANISM: Haemophilus influenzae

<400> SEQUENCE: 33

| | | | | | |
|---|---|---|---|---|---|
| aaagagtggt | tgttagaccc | ggataatgta | tctattaatg | cacccgcact | tggacgtact | 60 |
| gagagtaccc | caaataacaa | tgagtacgac | tcgccaaatc | aaattaacta | taaaaacaaa | 120 |
| ccatccctaa | gtacactaac | aaacacaaca | cttgagagaa | tattaaaaag | aaacacctct | 180 |
| gttaatatca | ctgccaccaa | acaatcaca | gttaatagtg | atatcaatat | tggagacagc | 240 |
| tcccacttaa | ccctttggag | tgagggtcag | gggagaggcg | gcgttaatgt | tacaggcaat | 300 |
| attacttcta | ctaccaacgg | aaacttaacc | atttactctg | gcggatgggt | tgatgttcat | 360 |
| aaaaacatta | cacttaaatc | agggtactta | aacattacaa | ctaaacaagg | agacatcgcc | 420 |
| ttcgaagaca | aaccagggct | gagcaaccta | accattacag | ctaaagggac | cattgccgtg | 480 |
| aacaacaaga | aaggctttag | gtttgataat | gtcactctaa | atggaacggg | aggagggctc | 540 |
| tcttttaaat | acatcgaaac | cggaaataga | gatagcaatt | tcgaaaccca | ttttagagga | 600 |
| agattaaata | tttcagggaa | agtagatatc | ttaatgcaag | caaggcagga | gaactggaac | 660 |
| cgcagacact | ggggacgctc | ccactggaat | gtaacccgat | tgaacgtttc | tgaaaacagt | 720 |
| tattttaacg | tcactattga | tagcagtggc | agtgcctctt | ccctggcgc | tggccctctg | 780 |
| aatgcccaat | cgggtttaaa | tggcatatcg | tttaataatg | cactgttttt | taatattgca | 840 |
| gcaagttcgg | cggttaactt | taacatcaaa | ccaccaatag | tagacaaagt | aaccaacggg | 900 |
| aatcacacat | tattcaaagg | gaatatttca | gttttagggg | ggggatgtc | aactttcatt | 960 |
| ttaacgcctc | ctccagcaac | taccagactt | atggcgtgat | tatagagtca | caaaacttta | 1020 |
| gtgcctcagg | agggtcaagc | ttaaaattca | aaagcgaagg | ttcgacacac | gccgctttta | 1080 |
| caataaaaaa | tgatttaatt | ttaaatgcca | ctgggggcaa | tatatcattg | aaccaagttg | 1140 |
| caggtattga | tagtaatctc | aaaaaaagcc | ttatagccaa | taaaaacata | acctttgaag | 1200 |
| ggggcaatat | caccttgca | gccgataaaa | aaccaataga | aatcaaaggt | aatattactg | 1260 |
| ttaaagaagg | agccaatgtc | acccttcgta | gcgcgaatta | tggtaatgac | aaatcagctt | 1320 |
| taagtataag | aggaaatgtc | actaataaag | gcaatctcac | cgttaccggc | tccgctatca | 1380 |
| atatagaaaa | aaatcttacc | gttgaaggta | gtgctaagtt | tttagctaat | ccaaattaca | 1440 |
| gctttaacgt | atccggccta | tttgacaacc | aaggcaagtc | aaacatttcc | atcgctaagg | 1500 |
| gaggagctat | ttttaaagat | atcgagaata | ctggcagtct | gaatattacc | actaaatccg | 1560 |
| actccaacca | ccatactatt | ataaagggta | atataactaa | cagaaaaggt | gatttaaata | 1620 |
| tcacgaataa | tggtgataat | actgaaatcc | aaattggcgg | caatatctcg | caaaaagaag | 1680 |
| gcaatctcac | aatttcttct | gataaagtca | atattaccga | gcggataaca | atcaaagcag | 1740 |
| gcgttaatgg | ggataactct | gattcaaatg | aggcaacaag | tgctaaccta | accattaaaa | 1800 |
| ccaaagagtt | aaaattaaca | aacgacctaa | atatttcagg | ttttaataaa | gcagaaatta | 1860 |
| cagctaaaga | taacagtaat | ttaactattg | gcgataacag | tgacgctggc | aatactgacg | 1920 |
| ctaaaaaagt | aaccttagc | aatgttaaag | attcaaaaat | ctctgctagc | gaccataatg | 1980 |

```
taacgctaaa cagcaaagtg gaaacatctg gcgatactga cagcactgaa gatggcggca   2040
acaataacac cggcttaact attactgcaa aaaatgtaac agtaaacaac aatattactt   2100
ctcacaaaac agtaaatatc actgcgtcag aaaatgttac caccaaagcg ggcacaacca   2160
ttaatgcaac cacaggtagc gtagaagtaa cagccaaaac aggtgatatt aaaggtggaa   2220
ttgaatccaa ttccggtaat gtaaatatta cagcgagcgg cgacacgctt aatgtaagta   2280
acatcacagg tcaaaatgtg acagtggcag cagcctcagg tgccgtaaca accacaaaag   2340
gatcaactat taatgcaaca actggtaatg caaatattac aaccaaaaca ggtgaaatta   2400
atggcgaagt taaatcagct tccggtaatg taaatattac agcgagcggc aatacactta   2460
atgtaagtaa catcactggt caaaatgtaa cagtaacagc aaactcaggt gccataacaa   2520
ccacagaagg ctcaactatt aacgcgacaa caggtgatgc aaatattaca acccaaacag   2580
gtaatattaa tggtaaagtt gaatccagtt ctggttctgt gacgcttatt gcaactggac   2640
aaactcttgc tgtaggtaat atttcaggtg acactgttac cattactgcg gataaaggta   2700
aattaaccac acaaacaagc tctaagatta acggaactaa gagtgtaacc acctcaagcc   2760
aatcaggtga tattagtggc acaatttctg gtaatacggt aagcgttagt gcgaccggta   2820
gcttgaccac tcaagcaggc tcaaaaattg aagcaaaaac aggtgaggct aatgtaacaa   2880
gcgcaacagg tacaattggc ggtacaatct ctggcaatac agtaaatgtt acagcaaata   2940
ctgataattt aactattaaa gatggcgcaa gaattaaagc aacgggcgga gctgtgactt   3000
taaccgcaac aggaggtact ttaaccaccg aaacaagttc tgatattacc tcaagcaatg   3060
gtcagacaac tctcacggcc aaggatagca gtatcgcagg aagcatcaat gccgccaatg   3120
tgacattaaa taccacaggc actttaacta ctgtggcagg ttcaaaaatc gaggcagcca   3180
gtggcaccct ggttattaat gcaaagatg ctcagttgga cggcgcggca tcaggtgacc   3240
acacagtagt aaatgcaacc aacgcaaacg gctccggcag cgtaatcgcg acaacctcaa   3300
gcagagtgaa catcactggg gatttaatca aataaatgg attaaatatc atttcaaaaa   3360
acggtaaaaa caccgtgctg ttaaaaggtg ttgaaattga tgtgaaatac attcaaccgg   3420
gcatagcgag cgtaaatgaa gtaattgaag cgaaacgcgc ccttgagaaa gtaaaagatt   3480
tatctgacga agaaagagaa acattagcta aacttggcgt gagcgctgta cgttttgctg   3540
agccaaataa tgccattacg attaatacac aaaatgagtt tacaaccaga ccattaagtc   3600
aagtgacaat ttctgaaggt aaggtatgtt tcttaatcgg caatggcgca acaatatgca   3660
ccaatattgc tgatattgag cggtag                                       3686
```

<210> SEQ ID NO 34
<211> LENGTH: 1228
<212> TYPE: PRT
<213> ORGANISM: Haemophilus influenzae

<400> SEQUENCE: 34

Lys Glu Trp Leu Leu Asp Pro Asp Asn Val Ser Ile Asn Ala Pro Ala
 1               5                  10                  15

Leu Gly Arg Thr Glu Ser Thr Pro Asn Asn Asn Glu Tyr Asp Ser Pro
             20                  25                  30

Asn Gln Ile Asn Tyr Lys Asn Lys Pro Ser Leu Ser Thr Leu Thr Asn
         35                  40                  45

Thr Thr Leu Glu Arg Ile Leu Lys Arg Asn Thr Ser Val Asn Ile Thr
     50                  55                  60

-continued

```
Ala Thr Lys Thr Ile Thr Val Asn Ser Asp Ile Asn Ile Gly Asp Ser
 65                  70                  75                  80

Ser His Leu Thr Leu Trp Ser Glu Gly Gln Gly Arg Gly Gly Val Asn
                 85                  90                  95

Val Thr Gly Asn Ile Thr Ser Thr Thr Asn Gly Asn Leu Thr Ile Tyr
                100                 105                 110

Ser Gly Gly Trp Val Asp Val His Lys Asn Ile Thr Leu Lys Ser Gly
             115                 120                 125

Tyr Leu Asn Ile Thr Thr Lys Gln Gly Asp Ile Ala Phe Glu Asp Lys
130                 135                 140

Pro Gly Leu Ser Asn Leu Thr Ile Thr Ala Lys Gly Thr Ile Ala Val
145                 150                 155                 160

Asn Asn Lys Lys Gly Phe Arg Phe Asp Asn Val Thr Leu Asn Gly Thr
                165                 170                 175

Gly Gly Gly Leu Ser Phe Lys Tyr Ile Glu Thr Gly Asn Arg Asp Ser
            180                 185                 190

Asn Phe Glu Thr His Phe Arg Gly Arg Leu Asn Ile Ser Gly Lys Val
            195                 200                 205

Asp Ile Leu Met Gln Ala Arg Gln Glu Asn Trp Asn Arg Arg His Trp
210                 215                 220

Gly Arg Ser His Trp Asn Val Thr Arg Leu Asn Val Ser Glu Asn Ser
225                 230                 235                 240

Tyr Phe Asn Val Thr Ile Asp Ser Ser Gly Ser Ala Ser Ser Pro Gly
                245                 250                 255

Ala Gly Pro Leu Asn Ala Gln Ser Gly Leu Asn Gly Ile Ser Phe Asn
            260                 265                 270

Asn Asp Thr Val Phe Asn Ile Ala Ala Ser Ser Ala Val Asn Phe Asn
            275                 280                 285

Ile Lys Pro Pro Ile Val Asp Lys Val Thr Asn Gly Asn His Thr Leu
290                 295                 300

Phe Lys Gly Asn Ile Ser Val Leu Gly Gly Gly Met Ser Thr Phe Ile
305                 310                 315                 320

Phe Asn Ala Ser Ser Asn Tyr Gln Thr Tyr Gly Val Ile Ile Glu
                325                 330                 335

Ser Gln Asn Phe Ser Ala Ser Gly Gly Ser Ser Leu Lys Phe Lys Ser
            340                 345                 350

Glu Gly Ser Thr His Ala Ala Phe Thr Ile Lys Asn Asp Leu Ile Leu
            355                 360                 365

Asn Ala Thr Gly Gly Asn Ile Ser Leu Asn Gln Val Ala Gly Ile Asp
            370                 375                 380

Ser Asn Leu Lys Lys Ser Leu Ile Ala Asn Lys Asn Ile Thr Phe Glu
385                 390                 395                 400

Gly Gly Asn Ile Thr Leu Ala Ala Asp Lys Lys Pro Ile Glu Ile Lys
                405                 410                 415

Gly Asn Ile Thr Val Lys Glu Gly Ala Asn Val Thr Leu Arg Ser Ala
            420                 425                 430

Asn Tyr Gly Asn Asp Lys Ser Ala Leu Ser Ile Arg Gly Asn Val Thr
            435                 440                 445

Asn Lys Gly Asn Leu Thr Val Thr Gly Ser Ala Ile Asn Ile Glu Lys
450                 455                 460

Asn Leu Thr Val Glu Gly Ser Ala Lys Phe Leu Ala Asn Pro Asn Tyr
465                 470                 475                 480

Ser Phe Asn Val Ser Gly Leu Phe Asp Asn Gln Gly Lys Ser Asn Ile
```

-continued

```
                485                 490                 495
Ser Ile Ala Lys Gly Gly Ala Ile Phe Lys Asp Ile Glu Asn Thr Gly
            500                 505                 510
Ser Leu Asn Ile Thr Thr Lys Ser Asp Ser Asn His His Thr Ile Ile
        515                 520                 525
Lys Gly Asn Ile Thr Asn Arg Lys Gly Asp Leu Asn Ile Thr Asn Asn
    530                 535                 540
Gly Asp Asn Thr Glu Ile Gln Ile Gly Gly Asn Ile Ser Gln Lys Glu
545                 550                 555                 560
Gly Asn Leu Thr Ile Ser Ser Asp Lys Val Asn Ile Thr Glu Arg Ile
                565                 570                 575
Thr Ile Lys Ala Gly Val Asn Gly Asp Asn Ser Asp Ser Asn Glu Ala
            580                 585                 590
Thr Ser Ala Asn Leu Thr Ile Lys Thr Lys Glu Leu Lys Leu Thr Asn
        595                 600                 605
Asp Leu Asn Ile Ser Gly Phe Asn Lys Ala Glu Ile Thr Ala Lys Asp
    610                 615                 620
Asn Ser Asn Leu Thr Ile Gly Asp Asn Ser Asp Ala Gly Asn Thr Asp
625                 630                 635                 640
Ala Lys Lys Val Thr Phe Ser Asn Val Lys Asp Ser Lys Ile Ser Ala
                645                 650                 655
Ser Asp His Asn Val Thr Leu Asn Ser Lys Val Glu Thr Ser Gly Asp
            660                 665                 670
Thr Asp Ser Thr Glu Asp Gly Gly Asn Asn Thr Gly Leu Thr Ile
        675                 680                 685
Thr Ala Lys Asn Val Thr Val Asn Asn Ile Thr Ser His Lys Thr
    690                 695                 700
Val Asn Ile Thr Ala Ser Glu Asn Val Thr Thr Lys Ala Gly Thr Thr
705                 710                 715                 720
Ile Asn Ala Thr Thr Gly Ser Val Glu Val Thr Ala Lys Thr Gly Asp
                725                 730                 735
Ile Lys Gly Gly Ile Glu Ser Asn Ser Gly Asn Val Asn Ile Thr Ala
            740                 745                 750
Ser Gly Asp Thr Leu Asn Val Ser Asn Ile Thr Gly Gln Asn Val Thr
        755                 760                 765
Val Ala Ala Ala Ser Gly Ala Val Thr Thr Lys Gly Ser Thr Ile
    770                 775                 780
Asn Ala Thr Thr Gly Asn Ala Asn Ile Thr Thr Lys Thr Gly Glu Ile
785                 790                 795                 800
Asn Gly Glu Val Lys Ser Ala Ser Gly Asn Val Asn Ile Thr Ala Ser
                805                 810                 815
Gly Asn Thr Leu Asn Val Ser Asn Ile Thr Gly Gln Asn Val Thr Val
            820                 825                 830
Thr Ala Asn Ser Gly Ala Ile Thr Thr Glu Gly Ser Thr Ile Asn
        835                 840                 845
Ala Thr Thr Gly Asp Ala Asn Ile Thr Gln Thr Gly Asn Ile Asn
    850                 855                 860
Gly Lys Val Glu Ser Ser Gly Ser Val Thr Leu Ile Ala Thr Gly
865                 870                 875                 880
Gln Thr Leu Ala Val Gly Asn Ile Ser Gly Asp Thr Val Thr Ile Thr
                885                 890                 895
Ala Asp Lys Gly Lys Leu Thr Thr Gln Thr Ser Ser Lys Ile Asn Gly
            900                 905                 910
```

```
Thr Lys Ser Val Thr Thr Ser Ser Gln Ser Gly Asp Ile Ser Gly Thr
        915                 920                 925

Ile Ser Gly Asn Thr Val Ser Val Ser Ala Thr Gly Ser Leu Thr Thr
        930                 935                 940

Gln Ala Gly Ser Lys Ile Glu Ala Lys Thr Gly Glu Ala Asn Val Thr
945                 950                 955                 960

Ser Ala Thr Gly Thr Ile Gly Gly Thr Ile Ser Gly Asn Thr Val Asn
                965                 970                 975

Val Thr Ala Asn Thr Asp Asn Leu Thr Ile Lys Asp Gly Ala Arg Ile
            980                 985                 990

Lys Ala Thr Gly Gly Ala Val Thr Leu Thr Ala Thr Gly Gly Thr Leu
        995                 1000                1005

Thr Thr Glu Thr Ser Ser Asp Ile Thr Ser Ser Asn Gly Gln Thr Thr
    1010                1015                1020

Leu Thr Ala Lys Asp Ser Ser Ile Ala Gly Ser Ile Asn Ala Ala Asn
1025                1030                1035                1040

Val Thr Leu Asn Thr Thr Gly Thr Leu Thr Thr Val Ala Gly Ser Lys
        1045                1050                1055

Ile Glu Ala Ala Ser Gly Thr Leu Val Ile Asn Ala Lys Asp Ala Gln
        1060                1065                1070

Leu Asp Gly Ala Ala Ser Gly Asp His Thr Val Val Asn Ala Thr Asn
        1075                1080                1085

Ala Asn Gly Ser Gly Ser Val Ile Ala Thr Thr Ser Ser Arg Val Asn
        1090                1095                1100

Ile Thr Gly Asp Leu Ile Thr Ile Asn Gly Leu Asn Ile Ile Ser Lys
1105                1110                1115                1120

Asn Gly Lys Asn Thr Val Leu Leu Lys Gly Val Glu Ile Asp Val Lys
                1125                1130                1135

Tyr Ile Gln Pro Gly Ile Ala Ser Val Asn Glu Val Ile Glu Ala Lys
            1140                1145                1150

Arg Ala Leu Glu Lys Val Lys Asp Leu Ser Asp Glu Glu Arg Glu Thr
        1155                1160                1165

Leu Ala Lys Leu Gly Val Ser Ala Val Arg Phe Ala Glu Pro Asn Asn
    1170                1175                1180

Ala Ile Thr Ile Asn Thr Gln Asn Glu Phe Thr Thr Arg Pro Leu Ser
1185                1190                1195                1200

Gln Val Thr Ile Ser Glu Gly Lys Val Cys Phe Leu Ile Gly Asn Gly
            1205                1210                1215

Ala Thr Ile Cys Thr Asn Ile Ala Asp Ile Glu Arg
        1220                1225

<210> SEQ ID NO 35
<211> LENGTH: 915
<212> TYPE: PRT
<213> ORGANISM: Haemophilus influenzae

<400> SEQUENCE: 35

Gly Gly Asp Val Asn Phe His Phe Asn Ala Ser Ser Ser Asn Tyr Gln
1               5                   10                  15

Thr Tyr Gly Val Ile Ile Glu Ser Gln Asn Phe Ser Ala Ser Gly Gly
            20                  25                  30

Ser Ser Leu Lys Phe Lys Ser Glu Gly Ser Thr His Ala Ala Phe Thr
        35                  40                  45

Ile Lys Asn Asp Leu Ile Leu Asn Ala Thr Gly Gly Asn Ile Ser Leu
```

-continued

```
                 50                  55                  60
Asn Gln Val Ala Gly Ile Asp Ser Asn Leu Lys Lys Ser Leu Ile Ala
 65                  70                  75                  80

Asn Lys Asn Ile Thr Phe Glu Gly Gly Asn Ile Thr Leu Ala Ala Asp
                 85                  90                  95

Lys Lys Pro Ile Glu Ile Lys Gly Asn Ile Thr Val Lys Glu Gly Ala
                100                 105                 110

Asn Val Thr Leu Arg Ser Ala Asn Tyr Gly Asn Asp Lys Ser Ala Leu
                115                 120                 125

Ser Ile Arg Gly Asn Val Thr Asn Lys Gly Asn Leu Thr Val Thr Gly
130                 135                 140

Ser Ala Ile Asn Ile Glu Lys Asn Leu Thr Val Glu Gly Ser Ala Lys
145                 150                 155                 160

Phe Leu Ala Asn Pro Asn Tyr Ser Phe Asn Val Ser Gly Leu Phe Asp
                165                 170                 175

Asn Gln Gly Lys Ser Asn Ile Ser Ile Ala Lys Gly Gly Ala Ile Phe
                180                 185                 190

Lys Asp Ile Glu Asn Thr Gly Ser Leu Asn Ile Thr Thr Lys Ser Asp
                195                 200                 205

Ser Asn His His Thr Ile Ile Lys Gly Asn Ile Thr Asn Arg Lys Gly
                210                 215                 220

Asp Leu Asn Ile Thr Asn Asn Gly Asp Asn Thr Glu Ile Gln Ile Gly
225                 230                 235                 240

Gly Asn Ile Ser Gln Lys Glu Gly Asn Leu Thr Ile Ser Ser Asp Lys
                245                 250                 255

Val Asn Ile Thr Glu Arg Ile Thr Ile Lys Ala Gly Val Asn Gly Asp
                260                 265                 270

Asn Ser Asp Ser Asn Glu Ala Thr Ser Ala Asn Leu Thr Ile Lys Thr
                275                 280                 285

Lys Glu Leu Lys Leu Thr Asn Asp Leu Asn Ile Ser Gly Phe Asn Lys
                290                 295                 300

Ala Glu Ile Thr Ala Lys Asp Asn Ser Asn Leu Thr Ile Gly Asp Asn
305                 310                 315                 320

Ser Asp Ala Gly Asn Thr Asp Ala Lys Lys Val Thr Phe Ser Asn Val
                325                 330                 335

Lys Asp Ser Lys Ile Ser Ala Ser Asp His Asn Val Thr Leu Asn Ser
                340                 345                 350

Lys Val Glu Thr Ser Gly Asp Thr Asp Ser Thr Glu Asp Gly Gly Asn
                355                 360                 365

Asn Asn Thr Gly Leu Thr Ile Thr Ala Lys Asn Val Thr Val Asn Asn
                370                 375                 380

Asn Ile Thr Ser His Lys Thr Val Asn Ile Thr Ala Ser Glu Asn Val
385                 390                 395                 400

Thr Thr Lys Ala Gly Thr Thr Ile Asn Ala Thr Thr Gly Ser Val Glu
                405                 410                 415

Val Thr Ala Lys Thr Gly Asp Ile Lys Gly Gly Ile Glu Ser Asn Ser
                420                 425                 430

Gly Asn Val Asn Ile Thr Ala Ser Gly Asp Thr Leu Asn Val Ser Asn
                435                 440                 445

Ile Thr Gly Gln Asn Val Thr Val Ala Ala Ala Ser Gly Ala Val Thr
                450                 455                 460

Thr Thr Lys Gly Ser Thr Ile Asn Ala Thr Thr Gly Asn Ala Asn Ile
465                 470                 475                 480
```

```
Thr Thr Lys Thr Gly Glu Ile Asn Gly Glu Val Lys Ser Ala Ser Gly
            485                 490                 495

Asn Val Asn Ile Thr Ala Ser Gly Asn Thr Leu Asn Val Ser Asn Ile
            500                 505                 510

Thr Gly Gln Asn Val Thr Val Thr Ala Asn Ser Gly Ala Ile Thr Thr
            515                 520                 525

Thr Glu Gly Ser Thr Ile Asn Ala Thr Thr Gly Asp Ala Asn Ile Thr
            530                 535                 540

Thr Gln Thr Gly Asn Ile Asn Gly Lys Val Glu Ser Ser Ser Gly Ser
545                 550                 555                 560

Val Thr Leu Ile Ala Thr Gly Gln Thr Leu Ala Val Gly Asn Ile Ser
            565                 570                 575

Gly Asp Thr Val Thr Ile Thr Ala Asp Lys Gly Lys Leu Thr Thr Gln
            580                 585                 590

Thr Ser Ser Lys Ile Asn Gly Thr Lys Ser Val Thr Thr Ser Ser Gln
            595                 600                 605

Ser Gly Asp Ile Ser Gly Thr Ile Ser Gly Asn Thr Val Ser Val Ser
            610                 615                 620

Ala Thr Gly Ser Leu Thr Thr Gln Ala Gly Ser Lys Ile Glu Ala Lys
625                 630                 635                 640

Thr Gly Glu Ala Asn Val Thr Ser Ala Thr Gly Thr Ile Gly Gly Thr
            645                 650                 655

Ile Ser Gly Asn Thr Val Asn Val Thr Ala Asn Thr Asp Asn Leu Thr
            660                 665                 670

Ile Lys Asp Gly Ala Arg Ile Lys Ala Thr Gly Gly Ala Val Thr Leu
            675                 680                 685

Thr Ala Thr Gly Gly Thr Leu Thr Thr Glu Thr Ser Ser Asp Ile Thr
            690                 695                 700

Ser Ser Asn Gly Gln Thr Thr Leu Thr Ala Lys Asp Ser Ser Ile Ala
705                 710                 715                 720

Gly Ser Ile Asn Ala Ala Asn Val Thr Leu Asn Thr Thr Gly Thr Leu
            725                 730                 735

Thr Thr Val Ala Gly Ser Lys Ile Glu Ala Ala Ser Gly Thr Leu Val
            740                 745                 750

Ile Asn Ala Lys Asp Ala Gln Leu Asp Gly Ala Ala Ser Gly Asp His
            755                 760                 765

Thr Val Val Asn Ala Thr Asn Ala Asn Gly Ser Gly Ser Val Ile Ala
            770                 775                 780

Thr Thr Ser Ser Arg Val Asn Ile Thr Gly Asp Leu Ile Thr Ile Asn
785                 790                 795                 800

Gly Leu Asn Ile Ile Ser Lys Asn Gly Lys Asn Thr Val Leu Leu Lys
            805                 810                 815

Gly Val Glu Ile Asp Val Lys Tyr Ile Gln Pro Gly Ile Ala Ser Val
            820                 825                 830

Asn Glu Val Ile Glu Ala Lys Arg Ala Leu Glu Lys Val Lys Asp Leu
            835                 840                 845

Ser Asp Glu Glu Arg Glu Thr Leu Ala Lys Leu Gly Val Ser Ala Val
850                 855                 860

Arg Phe Ala Glu Pro Asn Asn Ala Ile Thr Ile Asn Thr Gln Asn Glu
865                 870                 875                 880

Phe Thr Thr Arg Pro Leu Ser Gln Val Thr Ile Ser Glu Gly Lys Val
            885                 890                 895
```

```
Cys Phe Leu Ile Gly Asn Gly Ala Thr Ile Cys Thr Asn Ile Ala Asp
            900                 905                 910
Ile Glu Arg
        915

<210> SEQ ID NO 36
<211> LENGTH: 3668
<212> TYPE: DNA
<213> ORGANISM: Haemophilus influenzae

<400> SEQUENCE: 36
ccggataatg tatctattaa tgcacccgca cttggacgta ctgagagtac cccaaataac      60
aatgagtacg actcgccaaa tcaaattaac tataaaaaca aaccatccct aagtacacta     120
acaaacacaa cacttgagag aatattaaaa agaaacacct ctgttaatat cactgccacc     180
aaaacaatca cagttaatag tgatatcaat attggagaca gctcccactt aacccttttgg    240 agtgagggtc aggggagagg cggcgttaat gttacaggca atattacttc tactaccaac     300
ggaaacttaa ccatttactc tggcggatgg gttgatgttc ataaaaacat tacacttaaa     360
tcagggtact aaacattac aactaaacaa ggagacatcg ccttcgaaga caaaccaggg     420
ctgagcaacc taaccattac agctaaaggg accattgccg tgaacaacaa gaaaggcttt     480
aggtttgata atgtcactct aaatggaacg ggaggagggc tctcttttaa atacatcgaa     540
accggaaata gagatagcaa tttcgaaacc cattttagag aagattaaa atttcaggg     600 aaagtagata tcttaatgca agcaaggcag gagaactgga accgcagaca ctggggacgc     660
tcccactgga atgtaacccg attgaacgtt tctgaaaaca gttatttaa cgtcactatt     720 gatagcagtg gcagtgcctc ttcccctggc gctggccctc tgaatgccca atcgggttta     780
aatggcatat cgtttaataa tgcacactgtt tttaatattg cagcaagttc ggcggttaac     840
tttaacatca aaccaccaat agtagacaaa gtaaccaacg ggaatcacac attattcaaa     900
gggaatattt cagttttagg gggggggatg tcaactttca ttttaacgcc tcctccagca     960
actaccagac ttatggcgtg attatagagt cacaaaactt tagtgcctca ggagggtcaa    1020
gcttaaaatt caaaagcgaa ggttcgacac acgccgcttt tacaataaaa aatgatttaa    1080
ttttaaatgc cactggggc aatatatcat tgaaccaagt tgcaggtatt gatagtaatc    1140 tcaaaaaag ccttatagcc aataaaaaca taaccttgga agggggcaat atcacccttg    1200
cagccgataa aaaccaata gaaatcaaag gtaatattac tgttaaagaa ggagccaatg    1260
tcacccttcg tagcgcgaat tatggtaatg acaaatcagc tttaagtata agaggaaatg    1320
tcactaataa aggcaatctc accgttaccg gctccgctat caatatagaa aaaaatctta    1380
ccgttgaagg tagtgctaag tttttagcta atccaaatta cagctttaac gtatccggcc    1440
tatttgacaa ccaaggcaag tcaaacattt ccatcgctaa gggaggagct atttttaaag    1500
atatcgagaa tactggcagt ctgaatatta ccactaaatc cgactccaac caccatacta    1560
ttataaaggg taatataact aacagaaaag gtgatttaaa tatcacgaat aatggtgata    1620
atactgaaat ccaaattggc ggcaatatct cgcaaaaaga aggcaatctc acaatttctt    1680
ctgataaagt caatattacc gagcggataa caatcaaagc aggcgttaat ggggataact    1740
ctgattcaaa tgaggcaaca agtgctaacc taaccattaa aaccaaagag ttaaaattaa    1800
caaacgacct aaatatttca ggttttaata agcagaaat tacagctaaa gataacagta    1860
atttaactat tggcgataac agtgacgctg gcaatactga cgctaaaaaa gtaaccttta    1920
gcaatgttaa agattcaaaa atctctgcta gcgaccataa tgtaacgcta aacagcaaag    1980
```

-continued

```
tggaaacatc tggcgatact gacagcactg aagatggcgg caacaataac accggcttaa    2040
ctattactgc aaaaaatgta acagtaaaca acaatattac ttctcacaaa acagtaaata    2100
tcactgcgtc agaaaatgtt accaccaaag cgggcacaac cattaatgca accacaggta    2160
gcgtagaagt aacagccaaa acaggtgata ttaaaggtgg aattgaatcc aattccggta    2220
atgtaaatat tacagcgagc ggcgacacgc ttaatgtaag taacatcaca ggtcaaaatg    2280
tgacagtggc agcagcctca ggtgccgtaa caaccacaaa aggatcaact attaatgcaa    2340
caactggtaa tgcaaatatt acaaccaaaa caggtgaaat taatggcgaa gttaaatcag    2400
cttccggtaa tgtaaatatt acagcgagcg gcaatacact taatgtaagt aacatcactg    2460
gtcaaaatgt aacagtaaca gcaaactcag gtgccataac aaccacagaa ggctcaacta    2520
ttaacgcgac aacaggtgat gcaaatatta caacccaaac aggtaatatt aatggtaaag    2580
ttgaatccag ttctggttct gtgacgctta ttgcaactgg acaaactctt gctgtaggta    2640
atatttcagg tgacactgtt accattactg cggataaagg taaattaacc acacaaacaa    2700
gctctaagat taacggaact aagagtgtaa ccacctcaag ccaatcaggt gatattagtg    2760
gcacaatttc tggtaatacg gtaagcgtta gtgcgaccgg tagcttgacc actcaagcag    2820
gctcaaaaat tgaagcaaaa acaggtgagg ctaatgtaac aagcgcaaca ggtacaattg    2880
gcggtacaat ctctggcaat acagtaaatg ttacagcaaa tactgataat ttaactatta    2940 agatggcgc aagaattaaa gcaacgggcg gagctgtgac tttaaccgca acaggaggta    3000 cttttaaccac cgaaacaagt tctgatatta cctcaagcaa tggtcagaca actctcacgg    3060
ccaaggatag cagtatcgca ggaagcatca atgccgccaa tgtgacatta aataccacag    3120
gcactttaac tactgtggca ggttcaaaaa tcgaggcagc cagtggcacc ctggttatta    3180
atgcaaaaga tgctcagttg gacggcgcgg catcaggtga ccacacagta gtaaatgcaa    3240
ccaacgcaaa cggctccggc agcgtaatcg cgacaacctc aagcagagtg aacatcactg    3300
gggatttaat cacaataaat ggattaaata tcatttcaaa aaacggtaaa acaccgtgc    3360 tgttaaaagg tgttgaaatt gatgtgaaat acattcaacc gggcatagcg agcgtaaatg    3420
aagtaattga agcgaaacgc gcccttgaga agtaaaaga tttatctgac gaagaaagag    3480
aaacattagc taaacttggc gtgagcgctg tacgtttgc tgagccaaat aatgccatta    3540
cgattaatac acaaaatgag tttacaacca gaccattaag tcaagtgaca atttctgaag    3600
gtaaggtatg tttcttaatc ggcaatggcg caacaatatg caccaatatt gctgatattg    3660
agcggtag                                                              3668
```

<210> SEQ ID NO 37
<211> LENGTH: 1222
<212> TYPE: PRT
<213> ORGANISM: Haemophilus influenzae

<400> SEQUENCE: 37

```
Pro Asp Asn Val Ser Ile Asn Ala Pro Ala Leu Gly Arg Thr Glu Ser
  1               5                  10                  15

Thr Pro Asn Asn Asn Glu Tyr Asp Ser Pro Asn Gln Ile Asn Tyr Lys
             20                  25                  30

Asn Lys Pro Ser Leu Ser Thr Leu Thr Asn Thr Thr Leu Glu Arg Ile
         35                  40                  45

Leu Lys Arg Asn Thr Ser Val Asn Ile Thr Ala Thr Lys Thr Ile Thr
     50                  55                  60
```

```
Val Asn Ser Asp Ile Asn Ile Gly Asp Ser Ser His Leu Thr Leu Trp
 65                  70                  75                  80

Ser Glu Gly Gln Gly Arg Gly Gly Val Asn Val Thr Gly Asn Ile Thr
                 85                  90                  95

Ser Thr Thr Asn Gly Asn Leu Thr Ile Tyr Ser Gly Gly Trp Val Asp
            100                 105                 110

Val His Lys Asn Ile Thr Leu Lys Ser Gly Tyr Leu Asn Ile Thr Thr
            115                 120                 125

Lys Gln Gly Asp Ile Ala Phe Glu Asp Lys Pro Gly Leu Ser Asn Leu
130                 135                 140

Thr Ile Thr Ala Lys Gly Thr Ile Ala Val Asn Asn Lys Lys Gly Phe
145                 150                 155                 160

Arg Phe Asp Asn Val Thr Leu Asn Gly Thr Gly Gly Leu Ser Phe
                165                 170                 175

Lys Tyr Ile Glu Thr Gly Asn Arg Asp Ser Asn Phe Glu Thr His Phe
            180                 185                 190

Arg Gly Arg Leu Asn Ile Ser Gly Lys Val Asp Ile Leu Met Gln Ala
            195                 200                 205

Arg Gln Glu Asn Trp Asn Arg Arg His Trp Gly Arg Ser His Trp Asn
210                 215                 220

Val Thr Arg Leu Asn Val Ser Glu Asn Ser Tyr Phe Asn Val Thr Ile
225                 230                 235                 240

Asp Ser Ser Gly Ser Ala Ser Ser Pro Gly Ala Gly Pro Leu Asn Ala
                245                 250                 255

Gln Ser Gly Leu Asn Gly Ile Ser Phe Asn Asn Asp Thr Val Phe Asn
            260                 265                 270

Ile Ala Ala Ser Ser Ala Val Asn Phe Asn Ile Lys Pro Pro Ile Val
            275                 280                 285

Asp Lys Val Thr Asn Gly Asn His Thr Leu Phe Lys Gly Asn Ile Ser
290                 295                 300

Val Leu Gly Gly Gly Met Ser Thr Phe Ile Phe Asn Ala Ser Ser Ser
305                 310                 315                 320

Asn Tyr Gln Thr Tyr Gly Val Ile Ile Glu Ser Gln Asn Phe Ser Ala
                325                 330                 335

Ser Gly Gly Ser Ser Leu Lys Phe Lys Ser Glu Gly Ser Thr His Ala
            340                 345                 350

Ala Phe Thr Ile Lys Asn Asp Leu Ile Leu Asn Ala Thr Gly Gly Asn
            355                 360                 365

Ile Ser Leu Asn Gln Val Ala Gly Ile Asp Ser Asn Leu Lys Lys Ser
370                 375                 380

Leu Ile Ala Asn Lys Asn Ile Thr Phe Glu Gly Gly Asn Ile Thr Leu
385                 390                 395                 400

Ala Ala Asp Lys Lys Pro Ile Glu Ile Lys Gly Asn Ile Thr Val Lys
                405                 410                 415

Glu Gly Ala Asn Val Thr Leu Arg Ser Ala Asn Tyr Gly Asn Asp Lys
            420                 425                 430

Ser Ala Leu Ser Ile Arg Gly Asn Val Thr Asn Lys Gly Asn Leu Thr
            435                 440                 445

Val Thr Gly Ser Ala Ile Asn Ile Glu Lys Asn Leu Thr Val Glu Gly
450                 455                 460

Ser Ala Lys Phe Leu Ala Asn Pro Asn Tyr Ser Phe Asn Val Ser Gly
465                 470                 475                 480

Leu Phe Asp Asn Gln Gly Lys Ser Asn Ile Ser Ile Ala Lys Gly Gly
```

-continued

```
            485                 490                 495
Ala Ile Phe Lys Asp Ile Glu Asn Thr Gly Ser Leu Asn Ile Thr Thr
            500                 505                 510
Lys Ser Asp Ser Asn His His Thr Ile Ile Lys Gly Asn Ile Thr Asn
            515                 520                 525
Arg Lys Gly Asp Leu Asn Ile Thr Asn Asn Gly Asp Asn Thr Glu Ile
            530                 535                 540
Gln Ile Gly Gly Asn Ile Ser Gln Lys Glu Gly Asn Leu Thr Ile Ser
545                 550                 555                 560
Ser Asp Lys Val Asn Ile Thr Glu Arg Ile Thr Ile Lys Ala Gly Val
            565                 570                 575
Asn Gly Asp Asn Ser Asp Ser Asn Glu Ala Thr Ser Ala Asn Leu Thr
            580                 585                 590
Ile Lys Thr Lys Glu Leu Lys Leu Thr Asn Asp Leu Asn Ile Ser Gly
            595                 600                 605
Phe Asn Lys Ala Glu Ile Thr Ala Lys Asp Asn Ser Asn Leu Thr Ile
            610                 615                 620
Gly Asp Asn Ser Asp Ala Gly Asn Thr Asp Ala Lys Lys Val Thr Phe
625                 630                 635                 640
Ser Asn Val Lys Asp Ser Lys Ile Ser Ala Ser Asp His Asn Val Thr
            645                 650                 655
Leu Asn Ser Lys Val Glu Thr Ser Gly Asp Thr Asp Ser Thr Glu Asp
            660                 665                 670
Gly Gly Asn Asn Asn Thr Gly Leu Thr Ile Thr Ala Lys Asn Val Thr
            675                 680                 685
Val Asn Asn Asn Ile Thr Ser His Lys Thr Val Asn Ile Thr Ala Ser
            690                 695                 700
Glu Asn Val Thr Thr Lys Ala Gly Thr Thr Ile Asn Ala Thr Thr Gly
705                 710                 715                 720
Ser Val Glu Val Thr Ala Lys Thr Gly Asp Ile Lys Gly Gly Ile Glu
            725                 730                 735
Ser Asn Ser Gly Asn Val Asn Ile Thr Ala Ser Gly Asp Thr Leu Asn
            740                 745                 750
Val Ser Asn Ile Thr Gly Gln Asn Val Thr Val Ala Ala Ser Gly
            755                 760                 765
Ala Val Thr Thr Thr Lys Gly Ser Thr Ile Asn Ala Thr Thr Gly Asn
            770                 775                 780
Ala Asn Ile Thr Thr Lys Thr Gly Glu Ile Asn Gly Glu Val Lys Ser
785                 790                 795                 800
Ala Ser Gly Asn Val Asn Ile Thr Ala Ser Gly Asn Thr Leu Asn Val
            805                 810                 815
Ser Asn Ile Thr Gly Gln Asn Val Thr Val Thr Ala Asn Ser Gly Ala
            820                 825                 830
Ile Thr Thr Thr Glu Gly Ser Thr Ile Asn Ala Thr Thr Gly Asp Ala
            835                 840                 845
Asn Ile Thr Thr Gln Thr Gly Asn Ile Asn Gly Lys Val Glu Ser Ser
            850                 855                 860
Ser Gly Ser Val Thr Leu Ile Ala Thr Gly Gln Thr Leu Ala Val Gly
865                 870                 875                 880
Asn Ile Ser Gly Asp Thr Val Thr Ile Thr Ala Asp Lys Gly Lys Leu
            885                 890                 895
Thr Thr Gln Thr Ser Ser Lys Ile Asn Gly Thr Lys Ser Val Thr Thr
            900                 905                 910
```

Ser Ser Gln Ser Gly Asp Ile Ser Gly Thr Ile Ser Gly Asn Thr Val
            915                 920                 925

Ser Val Ser Ala Thr Gly Ser Leu Thr Thr Gln Ala Gly Ser Lys Ile
        930                 935                 940

Glu Ala Lys Thr Gly Glu Ala Asn Val Thr Ser Ala Thr Gly Thr Ile
945                 950                 955                 960

Gly Gly Thr Ile Ser Gly Asn Thr Val Asn Val Thr Ala Asn Thr Asp
                965                 970                 975

Asn Leu Thr Ile Lys Asp Gly Ala Arg Ile Lys Ala Thr Gly Gly Ala
            980                 985                 990

Val Thr Leu Thr Ala Thr Gly Gly Thr Leu Thr Thr Glu Thr Ser Ser
        995                 1000                1005

Asp Ile Thr Ser Ser Asn Gly Gln Thr Thr Leu Thr Ala Lys Asp Ser
    1010                1015                1020

Ser Ile Ala Gly Ser Ile Asn Ala Ala Asn Val Thr Leu Asn Thr Thr
1025                1030                1035                1040

Gly Thr Leu Thr Thr Val Ala Gly Ser Lys Ile Glu Ala Ala Ser Gly
            1045                1050                1055

Thr Leu Val Ile Asn Ala Lys Asp Ala Gln Leu Asp Gly Ala Ala Ser
        1060                1065                1070

Gly Asp His Thr Val Val Asn Ala Thr Asn Ala Asn Gly Ser Gly Ser
        1075                1080                1085

Val Ile Ala Thr Thr Ser Ser Arg Val Asn Ile Thr Gly Asp Leu Ile
        1090                1095                1100

Thr Ile Asn Gly Leu Asn Ile Ile Ser Lys Asn Gly Lys Asn Thr Val
1105                1110                1115                1120

Leu Leu Lys Gly Val Glu Ile Asp Val Lys Tyr Ile Gln Pro Gly Ile
            1125                1130                1135

Ala Ser Val Asn Glu Val Ile Glu Ala Lys Arg Ala Leu Glu Lys Val
            1140                1145                1150

Lys Asp Leu Ser Asp Glu Glu Arg Glu Thr Leu Ala Lys Leu Gly Val
        1155                1160                1165

Ser Ala Val Arg Phe Ala Glu Pro Asn Asn Ala Ile Thr Ile Asn Thr
    1170                1175                1180

Gln Asn Glu Phe Thr Thr Arg Pro Leu Ser Gln Val Thr Ile Ser Glu
1185                1190                1195                1200

Gly Lys Val Cys Phe Leu Ile Gly Asn Gly Ala Thr Ile Cys Thr Asn
            1205                1210                1215

Ile Ala Asp Ile Glu Arg
            1220

<210> SEQ ID NO 38
<211> LENGTH: 3036
<212> TYPE: DNA
<213> ORGANISM: Haemophilus influenzae

<400> SEQUENCE: 38
aaagagtggt tgttagaccc ggatgatata aatattgtca acggaagtaa tattgatgct     60
caattacagc caggtagagg cgatacaccc aacaaggttt cagcagaagg cttaacatcc    120
attaacaatg ccacattatc caccgcttta caaagggta ttgaggtcaa catttctgcc    180
acaaaaaatg taaccgtcaa cgcggatgtt gatgttaaaa acggaacatt agtattacat    240
tcacaaagga atggagttaa aattaacggt aatattacct caacacaaaa tggtaattta    300

```
accattaaaa caggtggcaa ggttgatgtt cataaaaata tcacacttgg tatgggtttt      360
ttgaatatta cttccgataa taacatcacc tttgaaaaag gtgataatct aaccattacc      420
gcccaaggaa atataatctc taatcaagag aataaacaac ttagatttag taatgtatct      480
ttaaatggga tgggtgcggg tttaactttt actgcaaata aaggtaatca tacccataag      540
tttgatggca cgcttaacat ttccggaaag gtagtaatta atcaaaccac acctcacaac      600
attgctccat ggaatgcaag tgcagactct tactggaatg taactactct tactttaggt      660
aataatgcgc aatttacctt tattaaattt gtcgatagca accgctcggt agctcttaat      720
agcggttcaa gaagttttgc gggggtaaag ttctacggca agaataatga aatgaaattt      780
aatattggtg ataatgctaa tgttgaattc aagttaaaat caaatgataa tacaagcaac      840
aacaaaccac taccaattca gtttttatct aatatctcag ccactggtaa tggcactgta      900
tcttttgata tacatgccaa cttgtcagca aggtcaactg agttaaatat gagtttaatt      960
aacatttcta tggggttaa tttttccata aactcccatg ttcgcggtaa taatgctttt     1020
gaaatcaaaa aagatttaat tataaatgca actggctcga attttaatct taagcaaacg     1080
aaagataaat ttgacaatag ttacgaaaaa acgccatttt tctcaactca taacctaacc     1140
attcttggcg gcaatgttac tctaggtggg gaaaattcaa gtagtaatat taaaggaaat     1200
atcaacatca atagcaaggc aaatgttaca ttacaagctc atgccggcac gagtcacctt     1260
gataaaaaag aaagaaccct aacccttggc aatgtatctg ttgggggaaa tttaaacata     1320
attggctcaa atgcacatat tgacggcaat cttctattg cagaaagtgc taaatttcaa     1380
ggaaaaacca ataacaacct aaatattacc ggcacccttta ccaacaacgg caccgccgac     1440
attaatataa acaaggagt ggtaaaactc caaggtgata ttaccaataa cggtaattta     1500
aatatcacta ctaacgcctc agtcaatcaa aaaaccatta ttaacggaaa tataactaac     1560
aaaaaaggcg acttaaacat caaggatatt aaagccaacg ccgaaatcca aattggcggc     1620
aatatctcgc aaaaagaagg taatctcacg atttcttctg acaaaattaa tatcaccaaa     1680
cggatagaaa ttaaggcaga tactgatcaa gggaattctg attcaggcgt agcaagtaat     1740
gctaatctaa ccattaaaac caaagagtta acattaacag acaatctaaa catttcaggt     1800
tttaataaag cagaaattac agctaaagat aacagtgatt taattattgg caaggctagc     1860
agtgacaaca gtaatgctaa acaaataacc tttgacaagg ttaaagattc aaaaatctca     1920
gctggcaatc acaatgtaac actaaatagc aaagtggaaa cgtctaatag cgatggtagc     1980
accggaaacg gtagcgatga caacaatatc ggcttaacta tttccgcaaa agatgtaacg     2040
gtaaatagta atatcacctc tcacaaaaca gtaaatatct ctgcatcaga aggaggtatc     2100
actactaaag caggcacaac cattaatgcg accacaggta gcgtggaagt aactgctaaa     2160
acaggcgata ttagcggtac gatttccggt aagacagtaa gtgttacagc aaccaccgac     2220
agtttaactg ttaaaggtgg cgcaaaaatt aatgcgacga aaggaactgc aaccttaact     2280
gcatcatcgg gcaaattaac caccgaggcc aactctgcga ttagcggggc taacggtgta     2340
actgcctcaa gtcaatcagg cgatattagc ggtacgattt ccggtaagac agtaagtgtt     2400
acagcaagct ctggcagttt aactgttgga ggtgacgcaa aaattaatgc gacagaagga     2460
gctgcgactt taactgcaac aaaaggcact ttaactaccg tgaagggttc aaacattgac     2520
gcaaacgaag gcaccttagt tattaacgca caagacgcca cactaaatgg tgatgcatca     2580
ggcgaccgta cagaagtgaa tgcagtcaac gcaagcggct ctggtaacgt aactgcgaaa     2640
acctcaagca gtgtgaatat cactggagat ttaagcacaa taaatggatt aaatatcatt     2700
```

-continued

```
tcgaaaaatg gtaaaaacac cgtagtgtta aaaggtgctg aaattgatgt gaaatatatt    2760
caaccaggtg tagcaagtgc gaatgaggtt attgaagcga agcgtgccct tgaaaaagta    2820
aaagatttat ctgatgaaga aagagaaaca ttagctaaac ttggtgtaag tgctgtacgt    2880
tttattgaac caaataatac cattacggtt aacacacaaa atgagtttac aaccagacca    2940
tcaagtcaag tgacaatttc tgaaggtaag gcgtgtttct caagtggtaa tggcgcagca    3000
gtatgtacca atgttgctga cgatggacag cagtag                              3036
```

<210> SEQ ID NO 39
<211> LENGTH: 1011
<212> TYPE: PRT
<213> ORGANISM: Haemophilus influenzae

<400> SEQUENCE: 39

```
Lys Glu Trp Leu Leu Asp Pro Asp Asp Ile Asn Ile Val Asn Gly Ser
 1               5                  10                  15

Asn Ile Asp Ala Gln Leu Gln Pro Gly Arg Gly Asp Thr Pro Asn Lys
            20                  25                  30

Val Ser Ala Glu Gly Leu Thr Ser Ile Asn Asn Ala Thr Leu Ser Thr
        35                  40                  45

Ala Leu Gln Lys Gly Ile Glu Val Asn Ile Ser Ala Thr Lys Asn Val
    50                  55                  60

Thr Val Asn Ala Asp Val Asp Val Lys Asn Gly Thr Leu Val Leu His
65                  70                  75                  80

Ser Gln Arg Asn Gly Val Lys Ile Asn Gly Asn Ile Thr Ser Thr Gln
                85                  90                  95

Asn Gly Asn Leu Thr Ile Lys Thr Gly Gly Lys Val Asp Val His Lys
            100                 105                 110

Asn Ile Thr Leu Gly Met Gly Phe Leu Asn Ile Thr Ser Asp Asn Asn
        115                 120                 125

Ile Thr Phe Glu Lys Gly Asp Asn Leu Thr Ile Thr Ala Gln Gly Asn
    130                 135                 140

Ile Ile Ser Asn Gln Glu Asn Lys Gln Leu Arg Phe Ser Asn Val Ser
145                 150                 155                 160

Leu Asn Gly Met Gly Ala Gly Leu Thr Phe Thr Ala Asn Lys Gly Asn
                165                 170                 175

His Thr His Lys Phe Asp Gly Thr Leu Asn Ile Ser Gly Lys Val Val
            180                 185                 190

Ile Asn Gln Thr Thr Pro His Asn Ile Ala Pro Trp Asn Ala Ser Ala
        195                 200                 205

Asp Ser Tyr Trp Asn Val Thr Thr Leu Thr Leu Gly Asn Asn Ala Gln
    210                 215                 220

Phe Thr Phe Ile Lys Phe Val Asp Ser Asn Arg Ser Val Ala Leu Asn
225                 230                 235                 240

Ser Gly Ser Arg Ser Phe Ala Gly Val Lys Phe Tyr Gly Lys Asn Asn
                245                 250                 255

Glu Met Lys Phe Asn Ile Gly Asp Ala Asn Val Glu Phe Lys Leu
            260                 265                 270

Lys Ser Asn Asp Asn Thr Ser Asn Asn Lys Pro Leu Pro Ile Gln Phe
        275                 280                 285

Leu Ser Asn Ile Ser Ala Thr Gly Asn Gly Thr Val Ser Phe Asp Ile
    290                 295                 300

His Ala Asn Leu Ser Ala Arg Ser Thr Glu Leu Asn Met Ser Leu Ile
```

-continued

```
            305                 310                 315                 320
Asn Ile Ser Asn Gly Val Asn Phe Ser Ile Asn Ser His Val Arg Gly
                325                 330                 335
Asn Asn Ala Phe Glu Ile Lys Lys Asp Leu Ile Ile Asn Ala Thr Gly
                340                 345                 350
Ser Asn Phe Asn Leu Lys Gln Thr Lys Asp Lys Phe Asp Asn Ser Tyr
                355                 360                 365
Glu Lys Asn Ala Ile Phe Ser Thr His Asn Leu Thr Ile Leu Gly Gly
                370                 375                 380
Asn Val Thr Leu Gly Gly Glu Asn Ser Ser Asn Ile Lys Gly Asn
385                 390                 395                 400
Ile Asn Ile Asn Ser Lys Ala Asn Val Thr Leu Gln Ala His Ala Gly
                405                 410                 415
Thr Ser His Leu Asp Lys Lys Glu Arg Thr Leu Thr Leu Gly Asn Val
                420                 425                 430
Ser Val Gly Gly Asn Leu Asn Ile Ile Gly Ser Asn Ala His Ile Asp
                435                 440                 445
Gly Asn Leu Ser Ile Ala Glu Ser Ala Lys Phe Gln Gly Lys Thr Asn
    450                 455                 460
Asn Asn Leu Asn Ile Thr Gly Thr Phe Thr Asn Asn Gly Thr Ala Asp
465                 470                 475                 480
Ile Asn Ile Lys Gln Gly Val Val Lys Leu Gln Gly Asp Ile Thr Asn
                485                 490                 495
Asn Gly Asn Leu Asn Ile Thr Thr Asn Ala Ser Val Asn Gln Lys Thr
                500                 505                 510
Ile Ile Asn Gly Asn Ile Thr Asn Lys Lys Gly Asp Leu Asn Ile Lys
                515                 520                 525
Asp Ile Lys Ala Asn Ala Glu Ile Gln Ile Gly Gly Asn Ile Ser Gln
                530                 535                 540
Lys Glu Gly Asn Leu Thr Ile Ser Ser Asp Lys Ile Asn Ile Thr Lys
545                 550                 555                 560
Arg Ile Glu Ile Lys Ala Asp Thr Asp Gln Gly Asn Ser Asp Ser Gly
                565                 570                 575
Val Ala Ser Asn Ala Asn Leu Thr Ile Lys Thr Lys Glu Leu Thr Leu
                580                 585                 590
Thr Asp Asn Leu Asn Ile Ser Gly Phe Asn Lys Ala Glu Ile Thr Ala
                595                 600                 605
Lys Asp Asn Ser Asp Leu Ile Ile Gly Lys Ala Ser Ser Asp Asn Ser
                610                 615                 620
Asn Ala Lys Gln Ile Thr Phe Asp Lys Val Lys Asp Ser Lys Ile Ser
625                 630                 635                 640
Ala Gly Asn His Asn Val Thr Leu Asn Ser Lys Val Glu Thr Ser Asn
                645                 650                 655
Ser Asp Gly Ser Thr Gly Asn Gly Ser Asp Asp Asn Asn Ile Gly Leu
                660                 665                 670
Thr Ile Ser Ala Lys Asp Val Thr Val Asn Ser Asn Ile Thr Ser His
                675                 680                 685
Lys Thr Val Asn Ile Ser Ala Ser Glu Gly Gly Ile Thr Thr Lys Ala
                690                 695                 700
Gly Thr Thr Ile Asn Ala Thr Thr Gly Ser Val Glu Val Thr Ala Lys
705                 710                 715                 720
Thr Gly Asp Ile Ser Gly Thr Ile Ser Gly Lys Thr Val Ser Val Thr
                725                 730                 735
```

```
Ala Thr Thr Asp Ser Leu Thr Val Lys Gly Gly Ala Lys Ile Asn Ala
            740                 745                 750

Thr Glu Gly Thr Ala Thr Leu Thr Ala Ser Ser Gly Lys Leu Thr Thr
            755                 760                 765

Glu Ala Asn Ser Ala Ile Ser Gly Ala Asn Gly Val Thr Ala Ser Ser
            770                 775                 780

Gln Ser Gly Asp Ile Ser Gly Thr Ile Ser Gly Lys Thr Val Ser Val
785                 790                 795                 800

Thr Ala Ser Ser Gly Ser Leu Thr Val Gly Gly Asp Ala Lys Ile Asn
                805                 810                 815

Ala Thr Glu Gly Ala Ala Thr Leu Thr Ala Thr Lys Gly Thr Leu Thr
            820                 825                 830

Thr Val Lys Gly Ser Asn Ile Asp Ala Asn Glu Gly Thr Leu Val Ile
            835                 840                 845

Asn Ala Gln Asp Ala Thr Leu Asn Gly Asp Ala Ser Gly Asp Arg Thr
            850                 855                 860

Glu Val Asn Ala Val Asn Ala Ser Gly Ser Gly Asn Val Thr Ala Lys
865                 870                 875                 880

Thr Ser Ser Val Asn Ile Thr Gly Asp Leu Ser Thr Ile Asn Gly
                885                 890                 895

Leu Asn Ile Ile Ser Lys Asn Gly Lys Asn Thr Val Val Leu Lys Gly
            900                 905                 910

Ala Glu Ile Asp Val Lys Tyr Ile Gln Pro Gly Val Ala Ser Ala Asn
            915                 920                 925

Glu Val Ile Glu Ala Lys Arg Ala Leu Glu Lys Val Lys Asp Leu Ser
            930                 935                 940

Asp Glu Glu Arg Glu Thr Leu Ala Lys Leu Gly Val Ser Ala Val Arg
945                 950                 955                 960

Phe Ile Glu Pro Asn Asn Thr Ile Thr Val Asn Thr Gln Asn Glu Phe
                965                 970                 975

Thr Thr Arg Pro Ser Ser Gln Val Thr Ile Ser Glu Gly Lys Ala Cys
            980                 985                 990

Phe Ser Ser Gly Asn Gly Ala Ala Val Cys Thr Asn Val Ala Asp Asp
            995                 1000                1005

Gly Gln Gln
    1010

<210> SEQ ID NO 40
<211> LENGTH: 3018
<212> TYPE: DNA
<213> ORGANISM: Haemophilus influenzae

<400> SEQUENCE: 40
ccggatgata taaatattgt caacggaagt aatattgatg ctcaattaca gccaggtaga      60
ggcgatacac ccaacaaggt ttcagcagaa ggcttaacat ccattaacaa tgccacatta     120
tccaccgctt tacaaaaggg tattgaggtc aacatttctg ccacaaaaaa tgtaaccgtc     180
aacgcggatg ttgatgttaa aaacggaaca ttagtattac attcacaaag gaatggagtt     240
aaaattaacg gtaatattac ctcaacacaa aatggtaatt taaccattaa acaggtggc     300 aaggttgatg ttcataaaaa tatcacactt ggtatgggtt ttttgaatat tacttccgat     360
aataacatca cctttgaaaa aggtgataat ctaaccatta ccgcccaagg aaatataatc     420
tctaatcaag agaataaaca acttagattt agtaatgtat ctttaaatgg gatgggtgcg     480
```

```
ggtttaactt ttactgcaaa taaaggtaat catacccata agtttgatgg cacgcttaac    540
atttccggaa aggtagtaat taatcaaacc acacctcaca acattgctcc atggaatgca    600
agtgcagact cttactggaa tgtaactact cttactttag gtaataatgc gcaatttacc    660
tttattaaat ttgtcgatag caaccgctcg gtagctctta atagcggttc aagaagtttt    720
gcggggtaa agttctacgg caagaataat gaaatgaaat ttaatattgg tgataatgct    780
aatgttgaat tcaagttaaa atcaaatgat aatacaagca caacaaaccc actaccaatt    840
cagtttttat ctaatatctc agccactggt aatggcactg tatcttttga tatacatgcc    900
aacttgtcag caaggtcaac tgagtttaat atgagtttaa ttaacatttc taatggggtt    960
aatttttcca taaactccca tgttcgcggt aataatgctt ttgaaatcaa aaagattta    1020
attataaatg caactggctc gaatttaat cttaagcaaa cgaaagataa atttgacaat    1080
agttacgaaa aaacgccat tttctcaact cataacctaa ccattcttgg cggcaatgtt    1140
actctaggtg gggaaaattc aagtagtaat attaaaggaa atatcaacat caatagcaag    1200
gcaaatgtta cattacaagc tcatgccggc acgagtcacc ttgataaaaa agaaagaacc    1260
ctaacccttg gcaatgtatc tgttggggga aattaaaca taattggctc aaatgcacat    1320
attgacggca atctttctat tgcagaaagt gctaaatttc aaggaaaaac caataacaac    1380
ctaaatatta ccggcaccct taccaacaac ggcaccgccg acattaatat aaaacaagga    1440
gtggtaaaac tccaaggtga tattaccaat aacggtaatt taaatatcac tactaacgcc    1500
tcagtcaatc aaaaaaccat tattaacgga aatataacta caaaaaagg cgacttaaac    1560
atcaaggata ttaaagccaa cgccgaaatc caaattggcg gcaatatctc gcaaaaagaa    1620
ggtaatctca cgatttcttc tgacaaaatt aatatcacca acggatagaa attaaggca    1680
gatactgatc aagggaattc tgattcaggc gtagcaagta atgctaatct aaccattaaa    1740
accaaagagt taacattaac agacaatcta aacatttcag gttttaataa agcagaaatt    1800
acagctaaag ataacagtga tttaattatt ggcaaggcta gcagtgacaa cagtaatgct    1860
aaacaaataa cctttgacaa ggttaaagat tcaaaaatct cagctggcaa tcacaatgta    1920
acactaaata gcaaagtgga aacgtctaat agcgatggta gcaccggaaa cggtagcgat    1980
gacaacaata tcggcttaac tatttccgca aaagatgtaa cggtaaatag taatatcacc    2040
tctcacaaaa cagtaaatat ctctgcatca gaaggaggta tcactactaa agcaggcaca    2100
accattaatg cgaccacagg tagcgtggaa gtaactgcta aaacaggcga tattagcggt    2160
acgatttccg gtaagacagt aagtgttaca gcaaccaccg acagtttaac tgttaaaggt    2220
ggcgcaaaaa ttaatgcgac agaaggaact gcaaccttaa ctgcatcatc gggcaaatta    2280
accaccgagg ccaactctgc gattagcggg gctaacggtg taactgcctc aagtcaatca    2340
ggcgatatta gcggtacgat ttccggtaag acagtaagtg ttacagcaag ctctggcagt    2400
ttaactgttg gaggtgacgc aaaaattaat gcgacagaag gagctgcgac tttaactgca    2460
acaaaaggca ctttaactac cgtgaagggt tcaaacattg acgcaaacga aggcacctta    2520
gttattaacg cacaagacgc cacactaaat ggtgatgcat caggcgaccg tacagaagtg    2580
aatgcagtca acgcaagcgg ctctggtaac gtaactgcga aacctcaag cagtgtgaat    2640
atcactggag atttaagcac aataaatgga ttaaatatca tttcgaaaaa tggtaaaaac    2700
accgtagtgt taaaggtgc tgaaattgat gtgaaatata ttcaaccagg tgtagcaagt    2760
gcgaatgagg ttattgaagc gaagcgtgcc cttgaaaaag taaagatttt atctgatgaa    2820
gaaagagaaa cattagctaa acttggtgta agtgctgtac gttttattga accaaataat    2880
```

```
accattacgg ttaacacaca aaatgagttt acaaccagac catcaagtca agtgacaatt    2940
tctgaaggta aggcgtgttt ctcaagtggt aatggcgcag cagtatgtac caatgttgct    3000
gacgatggac agcagtag                                                  3018
```

<210> SEQ ID NO 41
<211> LENGTH: 1005
<212> TYPE: PRT
<213> ORGANISM: Haemophilus influenzae

<400> SEQUENCE: 41

```
Pro Asp Asp Ile Asn Ile Val Asn Gly Ser Asn Ile Asp Ala Gln Leu
 1               5                  10                  15

Gln Pro Gly Arg Gly Asp Thr Pro Asn Lys Val Ser Ala Glu Gly Leu
            20                  25                  30

Thr Ser Ile Asn Asn Ala Thr Leu Ser Thr Ala Leu Gln Lys Gly Ile
        35                  40                  45

Glu Val Asn Ile Ser Ala Thr Lys Asn Val Thr Val Asn Ala Asp Val
    50                  55                  60

Asp Val Lys Asn Gly Thr Leu Val Leu His Ser Gln Arg Asn Gly Val
65                  70                  75                  80

Lys Ile Asn Gly Asn Ile Thr Ser Thr Gln Asn Gly Asn Leu Thr Ile
                85                  90                  95

Lys Thr Gly Gly Lys Val Asp Val His Lys Asn Ile Thr Leu Gly Met
           100                 105                 110

Gly Phe Leu Asn Ile Thr Ser Asp Asn Asn Ile Thr Phe Glu Lys Gly
       115                 120                 125

Asp Asn Leu Thr Ile Thr Ala Gln Gly Asn Ile Ile Ser Asn Gln Glu
   130                 135                 140

Asn Lys Gln Leu Arg Phe Ser Asn Val Ser Leu Asn Gly Met Gly Ala
145                 150                 155                 160

Gly Leu Thr Phe Thr Ala Asn Lys Gly Asn His Thr His Lys Phe Asp
                165                 170                 175

Gly Thr Leu Asn Ile Ser Gly Lys Val Ile Asn Gln Thr Thr Pro
            180                 185                 190

His Asn Ile Ala Pro Trp Asn Ala Ser Ala Asp Ser Tyr Trp Asn Val
        195                 200                 205

Thr Thr Leu Thr Leu Gly Asn Asn Ala Gln Phe Thr Phe Ile Lys Phe
    210                 215                 220

Val Asp Ser Asn Arg Ser Val Ala Leu Asn Ser Gly Ser Arg Ser Phe
225                 230                 235                 240

Ala Gly Val Lys Phe Tyr Gly Lys Asn Asn Glu Met Lys Phe Asn Ile
                245                 250                 255

Gly Asp Asn Ala Asn Val Glu Phe Lys Leu Lys Ser Asn Asp Asn Thr
            260                 265                 270

Ser Asn Asn Lys Pro Leu Pro Ile Gln Phe Leu Ser Asn Ile Ser Ala
        275                 280                 285

Thr Gly Asn Gly Thr Val Ser Phe Asp Ile His Ala Asn Leu Ser Ala
    290                 295                 300

Arg Ser Thr Glu Leu Asn Met Ser Leu Ile Asn Ile Ser Asn Gly Val
305                 310                 315                 320

Asn Phe Ser Ile Asn Ser His Val Arg Gly Asn Asn Ala Phe Glu Ile
                325                 330                 335

Lys Lys Asp Leu Ile Ile Asn Ala Thr Gly Ser Asn Phe Asn Leu Lys
```

-continued

```
              340                 345                 350
Gln Thr Lys Asp Lys Phe Asp Asn Ser Tyr Glu Lys Asn Ala Ile Phe
            355                 360                 365
Ser Thr His Asn Leu Thr Ile Leu Gly Gly Asn Val Thr Leu Gly Gly
        370                 375                 380
Glu Asn Ser Ser Ser Asn Ile Lys Gly Asn Ile Asn Ile Asn Ser Lys
385                 390                 395                 400
Ala Asn Val Thr Leu Gln Ala His Ala Gly Thr Ser His Leu Asp Lys
                405                 410                 415
Lys Glu Arg Thr Leu Thr Leu Gly Asn Val Ser Val Gly Gly Asn Leu
            420                 425                 430
Asn Ile Ile Gly Ser Asn Ala His Ile Asp Gly Asn Leu Ser Ile Ala
        435                 440                 445
Glu Ser Ala Lys Phe Gln Gly Lys Thr Asn Asn Leu Asn Ile Thr
        450                 455                 460
Gly Thr Phe Thr Asn Asn Gly Thr Ala Asp Ile Asn Ile Lys Gln Gly
465                 470                 475                 480
Val Val Lys Leu Gln Gly Asp Ile Thr Asn Asn Gly Asn Leu Asn Ile
                485                 490                 495
Thr Thr Asn Ala Ser Val Asn Gln Lys Thr Ile Ile Asn Gly Asn Ile
                500                 505                 510
Thr Asn Lys Lys Gly Asp Leu Asn Ile Lys Asp Ile Lys Ala Asn Ala
            515                 520                 525
Glu Ile Gln Ile Gly Gly Asn Ile Ser Gln Lys Glu Gly Asn Leu Thr
        530                 535                 540
Ile Ser Ser Asp Lys Ile Asn Ile Thr Lys Arg Ile Glu Ile Lys Ala
545                 550                 555                 560
Asp Thr Asp Gln Gly Asn Ser Asp Ser Gly Val Ala Ser Asn Ala Asn
                565                 570                 575
Leu Thr Ile Lys Thr Lys Glu Leu Thr Leu Thr Asp Asn Leu Asn Ile
            580                 585                 590
Ser Gly Phe Asn Lys Ala Glu Ile Thr Ala Lys Asp Asn Ser Asp Leu
        595                 600                 605
Ile Ile Gly Lys Ala Ser Ser Asp Asn Ser Asn Ala Lys Gln Ile Thr
    610                 615                 620
Phe Asp Lys Val Lys Asp Ser Lys Ile Ser Ala Gly Asn His Asn Val
625                 630                 635                 640
Thr Leu Asn Ser Lys Val Glu Thr Ser Asn Ser Asp Gly Ser Thr Gly
                645                 650                 655
Asn Gly Ser Asp Asp Asn Asn Ile Gly Leu Thr Ile Ser Ala Lys Asp
                660                 665                 670
Val Thr Val Asn Ser Asn Ile Thr Ser His Lys Thr Val Asn Ile Ser
            675                 680                 685
Ala Ser Glu Gly Gly Ile Thr Thr Lys Ala Gly Thr Thr Ile Asn Ala
        690                 695                 700
Thr Thr Gly Ser Val Glu Val Thr Ala Lys Thr Gly Asp Ile Ser Gly
705                 710                 715                 720
Thr Ile Ser Gly Lys Thr Val Ser Val Thr Ala Thr Asp Ser Leu
                725                 730                 735
Thr Val Lys Gly Gly Ala Lys Ile Asn Ala Thr Glu Gly Thr Ala Thr
            740                 745                 750
Leu Thr Ala Ser Ser Gly Lys Leu Thr Thr Glu Ala Asn Ser Ala Ile
        755                 760                 765
```

| | | | | | | | | | | |
|---|---|---|---|---|---|---|---|---|---|---|
| Ser | Gly | Ala | Asn | Gly | Val | Thr | Ala | Ser | Ser | Gln | Ser | Gly | Asp | Ile | Ser |
| | | 770 | | | | | 775 | | | | | 780 | | | |

Ser Gly Ala Asn Gly Val Thr Ala Ser Ser Gln Ser Gly Asp Ile Ser
   770     775     780

Gly Thr Ile Ser Gly Lys Thr Val Ser Val Thr Ala Ser Ser Gly Ser
785     790     795     800

Leu Thr Val Gly Gly Asp Ala Lys Ile Asn Ala Thr Glu Gly Ala Ala
     805     810     815

Thr Leu Thr Ala Thr Lys Gly Thr Leu Thr Thr Val Lys Gly Ser Asn
   820     825     830

Ile Asp Ala Asn Glu Gly Thr Leu Val Ile Asn Ala Gln Asp Ala Thr
   835     840     845

Leu Asn Gly Asp Ala Ser Gly Asp Arg Thr Glu Val Asn Ala Val Asn
850     855     860

Ala Ser Gly Ser Gly Asn Val Thr Ala Lys Thr Ser Ser Ser Val Asn
865     870     875     880

Ile Thr Gly Asp Leu Ser Thr Ile Asn Gly Leu Asn Ile Ile Ser Lys
     885     890     895

Asn Gly Lys Asn Thr Val Val Leu Lys Gly Ala Glu Ile Asp Val Lys
   900     905     910

Tyr Ile Gln Pro Gly Val Ala Ser Ala Asn Glu Val Ile Glu Ala Lys
   915     920     925

Arg Ala Leu Glu Lys Val Lys Asp Leu Ser Asp Glu Arg Glu Thr
   930     935     940

Leu Ala Lys Leu Gly Val Ser Ala Val Arg Phe Ile Glu Pro Asn Asn
945     950     955     960

Thr Ile Thr Val Asn Thr Gln Asn Glu Phe Thr Thr Arg Pro Ser Ser
     965     970     975

Gln Val Thr Ile Ser Glu Gly Lys Ala Cys Phe Ser Ser Gly Asn Gly
   980     985     990

Ala Ala Val Cys Thr Asn Val Ala Asp Asp Gly Gln Gln
   995     1000     1005

<210> SEQ ID NO 42
<211> LENGTH: 3240
<212> TYPE: DNA
<213> ORGANISM: Haemophilus influenzae

<400> SEQUENCE: 42

```
aaagagtggt tgttagaccc ggatgatgta tccattgacg caccttcggc tgaacgcact    60
gacactggcg aagacgtgga ataccggga acagggctg atattaacca tcaaaaacaa   120
aacagcgaaa ccaagtcaac attaacaaac acaactcttg agggatgtt aaaaggggg    180
cttttttgtta atatcaccgc cagaaataaa atccgagtta atagcaccat caatatcggg   240
gatagcggcc atttaaccct ttacaaaaaa agaaaaaatc gtagcgatgg tattcaaatt   300
aacaaggata ttacttctac aggcggaagt ttaactatta ctccgacga ctgggttgat    360
attcatggaa atatcacgct tggtgagggc tttttaaata ttacctctag tgattccgtg   420
gctttcgagg gtggaaacgg caataaagga cgtagctcag caagtgctca aattatcgcg   480
cagggtacta taactcttac tggagaaaat aaaaccttta gactcaacaa tgtgtcttta   540
aatgggacgg gtaatggtct aagtattatt caacagcaa gcaatttatc tcatagactt   600
gacggtgaaa ttaatgtatc tggaaatgta acaattaatc aaaccacgca gcaaaacatt   660
gaatactgga aggctagcag cgattcttat tggaatgtcc ttctttaa tttgagagaa    720
gattcaaagt ttacctttat caaatacgtt aactctgcca gaaatggtga tgtaagagga   780
```

-continued

| | |
|---|---|
| agaagttttg caggtgtgat atttaatgct aaaggtctca ctacaagctt taacgtcaag | 840 |
| aaaggctcga cagttgattt taaattaaag ccaaattcag gctataattc acaaaaaagg | 900 |
| attccaattc aattccaatc caacatctcg gtctcaggag gaggaagggt aaacattaac | 960 |
| acgctcgcca atcttacagg cggaggagtt gagataagat cgagttcaat taatgtttct | 1020 |
| gatggctcaa ccctctctat gacagctcag gctcgcgaca ggaatgcctt tgaaattacc | 1080 |
| aaagatttag ttataaacgc aagcaattca aacctatcta ttatacagca aaatgatgga | 1140 |
| tttgataata atcaaaaggc aaatgccatt aactcaaaat ataacgtaac tattcaaggt | 1200 |
| ggtaatgtta cccttggcgg gcaaaattca agcagtacaa tcacagggag tgttaatatt | 1260 |
| ggcgctaatg caaatgttac tttgcaagcc cacaatggca atgatagaaa taaaaagcta | 1320 |
| accttcggta atgtatctgt tgaaggagaa ttaaggctag ttggcgcaag tgcaaacatt | 1380 |
| aacaacaatc ttagtgttaa gagcggtgct aaattcaaag cagaaacaaa tgacaaccta | 1440 |
| aacattaccg gcacctttac caacaacggc acctccataa ttgatgtaaa aaaaggggcg | 1500 |
| gcaaaactag gcaatattac caatgatggt aatttaaata tcactactaa tgctaaaaac | 1560 |
| ggtcaaaaaa gcgttatcaa cggaaatata actaacaata aaggtgcttt aaatattacg | 1620 |
| aataatggta atgacactga atccaaatt ggcggcaata tctcgcaaaa agaaggtaat | 1680 |
| ctcacgattt cttctgacaa aattaatatc accaaacgga tagaaattaa ggcaggtact | 1740 |
| gatcaaggga attctgattc aggcgtagca agtaatgcta atctaaccat taaaaccaaa | 1800 |
| gaattgaaat taacagaaaa cctaaatatt tcaggttttg ataaagcaga aattgtagcc | 1860 |
| aaagagaata acaatttaat tattggcaat aataatggcg acaatgctaa cgccaaaaca | 1920 |
| gtaactttta acaatgttaa agattcaaaa atctctgcta acggtcacaa tgtgacacta | 1980 |
| aatagcaaag tggaaacatc tgatggaaac agtaacactg aaggtaatag tgacaataac | 2040 |
| gccggcttaa ctatcgatgc aaaaaatgta acagtaaaca acgatatcac ttctcacaaa | 2100 |
| acagtaaaata tcactgcgtc agaaaggatt gatactaaag ctgatacaac cattaatgca | 2160 |
| accaccggca acgtgaaact aacagctgta acaagtgata tccaaggtgg aattaaatct | 2220 |
| aattctggtg atgtaaatat cacaaccagc acaggtagca ttaacggtaa aattgaatcc | 2280 |
| aagtctggct ctgtaacact taccgcaacc gaaaaaactc ttactgtagg caatgtttcg | 2340 |
| ggcaacaccg ttactgttac tgcaaataga ggtgcattaa ccactttggc aggctctacg | 2400 |
| attaacggga ctaacggtgt aactacctca agtcaatcag cgagattgg cggtgaggtt | 2460 |
| actggtaaga cagtaagtgt tacagcaact gccggcagct taactgttaa aggtggcgca | 2520 |
| aaaattaatg cgacagaagg aactgcaacc ttaactgcat catcgggcaa attaaccacc | 2580 |
| gaggctagct caaacatcac ttcagccaaa ggtcaggtag acctttcagc tcaggatggt | 2640 |
| agcattgcag acaaattag tgcagctaat gtaacactga atactacagg cactctaact | 2700 |
| accgtagagg gttcaagcat taacgcaaac gaaggcacct tggttattaa cgcaaacgac | 2760 |
| gccaagttag atggtaaggc atcaggtaac cgtacagaag taaatgcaac taacgcaagc | 2820 |
| ggctctggta gcgtgactgc gaaaacctca agcagcgtga atatcaccgg ggatttaaac | 2880 |
| acaataaatg ggttaaatat catttcggaa aatggtagaa acactgtgcg cttaagaggc | 2940 |
| aaggaaattg aggtgaaata tatccagcca ggtgtagcaa gtgtagaaga agtaattgaa | 3000 |
| gcgaaacgcg tccttgagaa agtgaaagat ttatctgatg aagaaagaga aacattagct | 3060 |
| aaacttggtg taagtgctgt acgttttatt gaaccaaata ataccattac ggttaacaca | 3120 |

-continued

```
caaaatgagt ttacaaccag accatcaagt caagtgacaa tttctgaagg taaggcgtgt    3180
ttctcaagtg gtaatggcgc agcagtatgt accaatgttg ctgacgatgg acagcagtag    3240
```

<210> SEQ ID NO 43
<211> LENGTH: 1079
<212> TYPE: PRT
<213> ORGANISM: Haemophilus influenzae

<400> SEQUENCE: 43

```
Lys Glu Trp Leu Leu Asp Pro Asp Val Ser Ile Asp Ala Pro Ser
  1               5                  10                  15

Ala Glu Arg Thr Asp Thr Gly Glu Asp Val Glu Tyr Thr Gly Thr Gly
                 20                  25                  30

Ala Asp Ile Asn His Gln Lys Gln Asn Ser Glu Thr Lys Ser Thr Leu
             35                  40                  45

Thr Asn Thr Thr Leu Glu Gly Met Leu Lys Arg Gly Leu Phe Val Asn
         50                  55                  60

Ile Thr Ala Arg Asn Lys Ile Arg Val Asn Ser Thr Ile Asn Ile Gly
 65                  70                  75                  80

Asp Ser Gly His Leu Thr Leu Tyr Lys Lys Arg Lys Asn Arg Ser Asp
                 85                  90                  95

Gly Ile Gln Ile Asn Lys Asp Ile Thr Ser Thr Gly Ser Leu Thr
            100                 105                 110

Ile Asn Ser Asp Asp Trp Val Asp Ile His Gly Asn Ile Thr Leu Gly
            115                 120                 125

Glu Gly Phe Leu Asn Ile Thr Ser Ser Asp Ser Val Ala Phe Glu Gly
        130                 135                 140

Gly Asn Gly Asn Lys Gly Arg Ser Ser Ala Ser Ala Gln Ile Ile Ala
145                 150                 155                 160

Gln Gly Thr Ile Thr Leu Thr Gly Glu Asn Lys Thr Phe Arg Leu Asn
                165                 170                 175

Asn Val Ser Leu Asn Gly Thr Gly Asn Gly Leu Ser Ile Ile Ser Thr
            180                 185                 190

Ala Ser Asn Leu Ser His Arg Leu Asp Gly Glu Ile Asn Val Ser Gly
        195                 200                 205

Asn Val Thr Ile Asn Gln Thr Thr Gln Gln Asn Ile Glu Tyr Trp Lys
    210                 215                 220

Ala Ser Ser Asp Ser Tyr Trp Asn Val Thr Ser Phe Asn Leu Arg Glu
225                 230                 235                 240

Asp Ser Lys Phe Thr Phe Ile Lys Tyr Val Asn Ser Ala Arg Asn Gly
                245                 250                 255

Asp Val Arg Gly Arg Ser Phe Ala Gly Val Ile Phe Asn Ala Lys Gly
            260                 265                 270

Leu Thr Thr Ser Phe Asn Val Lys Lys Gly Ser Thr Val Asp Phe Lys
        275                 280                 285

Leu Lys Pro Asn Ser Gly Tyr Asn Ser Gln Lys Arg Ile Pro Ile Gln
    290                 295                 300

Phe Gln Ser Asn Ile Ser Val Ser Gly Gly Arg Val Asn Ile Asn
305                 310                 315                 320

Thr Leu Ala Asn Leu Thr Gly Gly Val Glu Ile Arg Ser Ser
                325                 330                 335

Ile Asn Val Ser Asp Gly Ser Thr Leu Ser Met Thr Ala Gln Ala Arg
            340                 345                 350

Asp Arg Asn Ala Phe Glu Ile Thr Lys Asp Leu Val Ile Asn Ala Ser
```

-continued

```
              355                 360                 365
Asn Ser Asn Leu Ser Ile Ile Gln Gln Asn Asp Gly Phe Asp Asn Asn
        370                 375                 380
Gln Lys Ala Asn Ala Ile Asn Ser Lys Tyr Asn Val Thr Ile Gln Gly
385                 390                 395                 400
Gly Asn Val Thr Leu Gly Gly Gln Asn Ser Ser Thr Ile Thr Gly
                405                 410                 415
Ser Val Asn Ile Gly Ala Asn Ala Asn Val Thr Leu Gln Ala His Asn
                420                 425                 430
Gly Asn Asp Arg Asn Lys Lys Leu Thr Phe Gly Asn Val Ser Val Glu
        435                 440                 445
Gly Glu Leu Arg Leu Val Gly Ala Ser Ala Asn Ile Asn Asn Asn Leu
    450                 455                 460
Ser Val Lys Ser Gly Ala Lys Phe Lys Ala Glu Thr Asn Asp Asn Leu
465                 470                 475                 480
Asn Ile Thr Gly Thr Phe Thr Asn Asn Gly Thr Ser Ile Ile Asp Val
                485                 490                 495
Lys Lys Gly Ala Ala Lys Leu Gly Asn Ile Thr Asn Asp Gly Asn Leu
                500                 505                 510
Asn Ile Thr Thr Asn Ala Lys Asn Gly Gln Lys Ser Val Ile Asn Gly
            515                 520                 525
Asn Ile Thr Asn Asn Lys Gly Ala Leu Asn Ile Thr Asn Asn Gly Asn
        530                 535                 540
Asp Thr Glu Ile Gln Ile Gly Gly Asn Ile Ser Gln Lys Glu Gly Asn
545                 550                 555                 560
Leu Thr Ile Ser Ser Asp Lys Ile Asn Ile Thr Lys Arg Ile Glu Ile
                565                 570                 575
Lys Ala Gly Thr Asp Gln Gly Asn Ser Asp Ser Gly Val Ala Ser Asn
                580                 585                 590
Ala Asn Leu Thr Ile Lys Thr Lys Glu Leu Lys Leu Thr Glu Asn Leu
            595                 600                 605
Asn Ile Ser Gly Phe Asp Lys Ala Glu Ile Val Ala Lys Glu Asn Asn
        610                 615                 620
Asn Leu Ile Ile Gly Asn Asn Gly Asp Asn Ala Asn Ala Lys Thr
625                 630                 635                 640
Val Thr Phe Asn Asn Val Lys Asp Ser Lys Ile Ser Ala Asn Gly His
                645                 650                 655
Asn Val Thr Leu Asn Ser Lys Val Glu Thr Ser Asp Gly Asn Ser Asn
                660                 665                 670
Thr Glu Gly Asn Ser Asp Asn Asn Ala Gly Leu Thr Ile Asp Ala Lys
            675                 680                 685
Asn Val Thr Val Asn Asn Asp Ile Thr Ser His Lys Thr Val Asn Ile
        690                 695                 700
Thr Ala Ser Glu Arg Ile Asp Thr Lys Ala Asp Thr Thr Ile Asn Ala
705                 710                 715                 720
Thr Thr Gly Asn Val Lys Leu Thr Ala Val Thr Ser Asp Ile Gln Gly
                725                 730                 735
Gly Ile Lys Ser Asn Ser Gly Asp Val Asn Ile Thr Thr Ser Thr Gly
                740                 745                 750
Ser Ile Asn Gly Lys Ile Glu Ser Lys Ser Gly Ser Val Thr Leu Thr
            755                 760                 765
Ala Thr Glu Lys Thr Leu Thr Val Gly Asn Val Ser Gly Asn Thr Val
770                 775                 780
```

-continued

```
Thr Val Thr Ala Asn Arg Gly Ala Leu Thr Thr Leu Ala Gly Ser Thr
785                 790                 795                 800

Ile Asn Gly Thr Asn Gly Val Thr Thr Ser Ser Gln Ser Gly Glu Ile
                805                 810                 815

Gly Gly Glu Val Thr Gly Lys Thr Val Ser Val Thr Ala Thr Ala Gly
            820                 825                 830

Ser Leu Thr Val Lys Gly Gly Ala Lys Ile Asn Ala Thr Glu Gly Thr
        835                 840                 845

Ala Thr Leu Thr Ala Ser Ser Gly Lys Leu Thr Thr Glu Ala Ser Ser
850                 855                 860

Asn Ile Thr Ser Ala Lys Gly Gln Val Asp Leu Ser Ala Gln Asp Gly
865                 870                 875                 880

Ser Ile Ala Gly Gln Ile Ser Ala Ala Asn Val Thr Leu Asn Thr Thr
                885                 890                 895

Gly Thr Leu Thr Thr Val Glu Gly Ser Ser Ile Asn Ala Asn Glu Gly
            900                 905                 910

Thr Leu Val Ile Asn Ala Asn Asp Ala Lys Leu Asp Gly Lys Ala Ser
        915                 920                 925

Gly Asn Arg Thr Glu Val Asn Ala Thr Asn Ala Ser Gly Ser Gly Ser
930                 935                 940

Val Thr Ala Lys Thr Ser Ser Val Asn Ile Thr Gly Asp Leu Asn
945                 950                 955                 960

Thr Ile Asn Gly Leu Asn Ile Ile Ser Glu Asn Gly Arg Asn Thr Val
                965                 970                 975

Arg Leu Arg Gly Lys Glu Ile Glu Val Lys Tyr Ile Gln Pro Gly Val
            980                 985                 990

Ala Ser Val Glu Glu Val Ile Glu Ala Lys Arg Val Leu Glu Lys Val
        995                 1000                1005

Lys Asp Leu Ser Asp Glu Glu Arg Glu Thr Leu Ala Lys Leu Gly Val
    1010                1015                1020

Ser Ala Val Arg Phe Ile Glu Pro Asn Asn Thr Ile Thr Val Asn Thr
1025                1030                1035                1040

Gln Asn Glu Phe Thr Thr Arg Pro Ser Ser Gln Val Thr Ile Ser Glu
                1045                1050                1055

Gly Lys Ala Cys Phe Ser Ser Gly Asn Gly Ala Ala Val Cys Thr Asn
            1060                1065                1070

Val Ala Asp Asp Gly Gln Gln
        1075

<210> SEQ ID NO 44
<211> LENGTH: 3222
<212> TYPE: DNA
<213> ORGANISM: Haemophilus influenzae

<400> SEQUENCE: 44
ccggatgatg tatccattga cgcaccttcg gctgaacgca ctgacactgg cgaagacgtg    60
gaatacaccg gaacagggc tgatattaac catcaaaaac aaaacagcga accaagtca    120 acattaacaa acacaactct tgaggggatg ttaaaaaggg ggcttttttgt taatatcacc    180 gccagaaata aaatccgagt taatagcacc atcaatatcg gggatagcgg ccatttaacc    240
ctttacaaaa aaagaaaaaa tcgtagcgat ggtattcaaa ttaacaagga tattacttct    300
acaggcggaa gtttaactat taactccgac gactgggttg atattcatgg aaatatcacg    360
cttggtgagg gctttttaaa tattaccctct agtgattccg tggctttcga gggtggaaac    420
```

-continued

```
ggcaataaag gacgtagctc agcaagtgct caaattatcg cgcagggtac tataactctt      480
actggagaaa ataaaacctt tagactcaac aatgtgtctt taaatgggac gggtaatggt      540
ctaagtatta tttcaacagc aagcaattta tctcatagac ttgacggtga aattaatgta      600
tctggaaatg taacaattaa tcaaaccacg cagcaaaaca ttgaatactg aaggctagc       660 agcgattctt attggaatgt cacttctttt aatttgagag aagattcaaa gtttaccttt      720
atcaaatacg ttaactctgc cagaaatggt gatgtaagag gaagaagttt tgcaggtgtg      780
atatttaatg ctaaaggtct cactacaagc tttaacgtca agaaaggctc gacagttgat      840
tttaaattaa agccaaattc aggctataat tcacaaaaaa ggattccaat tcaattccaa      900
tccaacatct cggtctcagg aggaggaagg gtaaacatta acacgctcgc caatcttaca      960
ggcggaggag ttgagataag atcgagttca attaatgttt ctgatggctc aaccctctct     1020 atgcagctc aggctcgcga caggaatgcc tttgaaatta ccaaagatt agttataaac       1080 gcaagcaatt caaacctatc tattatacag caaaatgatg gatttgataa taatcaaaag     1140
gcaaatgcca ttaactcaaa atataacgta actattcaag gtggtaatgt tacccttggc     1200
gggcaaaatt caagcagtac aatcacaggg agtgttaata ttggcgctaa tgcaaatgtt     1260
actttgcaag cccacaatgg caatgataga aataaaaagc taaccttcgg taatgtatct     1320
gttgaaggag aattaaggct agttggcgca agtgcaaaca ttaacaacaa tcttagtgtt     1380
aagagcggtg ctaaattcaa agcagaaaca aatgacaacc taaacattac cggcacctt     1440 accaacaacg gcacctccat aattgatgta aaaaaagggg cggcaaaact aggcaatatt     1500
accaatgatg gtaatttaaa tatcactact aatgctaaaa acggtcaaaa aagcgttatc     1560
aacgaaaata taactaacaa taaggtgctt ttaaatatta cgaataatgg taatgacact     1620
gaaatccaaa ttggcggcaa tatctcgcaa aaagaaggta atctcacgat ttcttctgac     1680
aaaattaata tcaccaaacg gatagaaatt aaggcaggta ctgatcaagg gaattctgat     1740
tcaggcgtag caagtaatgc taatctaacc attaaaacca aagaattgaa attaacagaa     1800
aacctaaata tttcaggttt tgataaagca gaaattgtag ccaaagagaa taacaattta     1860
attattggca ataataatgg cgacaatgct aacgccaaaa cagtaacttt taacaatgtt     1920
aaagattcaa aaatctctgc taacggtcac aatgtgacac taaatagcaa agtgaaaaca     1980
tctgatggaa acagtaacac tgaaggtaat agtgacaata acgccggctt aactatcgat     2040
gcaaaaaatg taacagtaaa caacgatatc acttctcaca aaacagtaaa tatcactgcg     2100
tcagaaagga ttgatactaa agctgataca accattaatg caaccaccgg caacgtgaaa     2160
ctaacagctg taacaagtga tatccaaggt ggaattaaat ctaattctgg tgatgtaaat     2220
atcacaacca gcacaggtag cattaacggt aaaattgaat ccaagtctgg ctctgtaaca     2280
cttaccgcaa ccgaaaaaac tcttactgta ggcaatgttt cgggcaacac cgttactgtt     2340
actgcaaata gaggtgcatt aaccactttg gcaggctcta cgattaacgg gactaacggt     2400
gtaactacct caagtcaatc aggcgagatt ggcggtgagg ttactggtaa gacagtaagt     2460
gttacagcaa ctgccggcag cttaactgtt aaaggtggcg caaaaattaa tgcgacagaa     2520
ggaactgcaa ccttaactgc atcatcgggc aaattaacca ccgaggctag ctcaaacatc     2580
acttcagcca aaggtcaggt agacctttca gctcaggatg gtagcattgc aggacaaatt     2640
agtgcagcta atgtaacact gaatactaca ggcactctaa ctaccgtaga gggttcaagc     2700
attaacgcaa acgaaggcac cttggttatt aacgcaaacg acgccaagtt agatggtaag     2760
```

-continued

```
gcatcaggta accgtacaga agtaaatgca actaacgcaa gcggctctgg tagcgtgact      2820
gcgaaaacct caagcagcgt gaatatcacc ggggatttaa acacaataaa tgggttaaat      2880
atcatttcgg aaaatggtag aaacactgtg cgcttaagag gcaaggaaat tgaggtgaaa      2940
tatatccagc caggtgtagc aagtgtagaa gaagtaattg aagcgaaacg cgtccttgag      3000
aaagtgaaag atttatctga tgaagaaaga gaaacattag ctaaacttgg tgtaagtgct      3060
gtacgtttta ttgaaccaaa taataccatt acggttaaca cacaaaatga gtttacaacc      3120
agaccatcaa gtcaagtgac aatttctgaa ggtaaggcgt gtttctcaag tggtaatggc      3180
gcagcagtat gtaccaatgt tgctgacgat ggacagcagt ag                        3222
```

<210> SEQ ID NO 45
<211> LENGTH: 1073
<212> TYPE: PRT
<213> ORGANISM: Haemophilus influenzae

<400> SEQUENCE: 45

```
Pro Asp Asp Val Ser Ile Asp Ala Pro Ser Ala Glu Arg Thr Asp Thr
 1               5                  10                  15

Gly Glu Asp Val Glu Tyr Thr Gly Thr Gly Ala Asp Ile Asn His Gln
            20                  25                  30

Lys Gln Asn Ser Glu Thr Lys Ser Thr Leu Thr Asn Thr Thr Leu Glu
        35                  40                  45

Gly Met Leu Lys Arg Gly Leu Phe Val Asn Ile Thr Ala Arg Asn Lys
    50                  55                  60

Ile Arg Val Asn Ser Thr Ile Asn Ile Gly Asp Ser Gly His Leu Thr
65                  70                  75                  80

Leu Tyr Lys Lys Arg Lys Asn Arg Ser Asp Gly Ile Gln Ile Asn Lys
                85                  90                  95

Asp Ile Thr Ser Thr Gly Gly Ser Leu Thr Ile Asn Ser Asp Asp Trp
            100                 105                 110

Val Asp Ile His Gly Asn Ile Thr Leu Gly Glu Gly Phe Leu Asn Ile
        115                 120                 125

Thr Ser Ser Asp Ser Val Ala Phe Glu Gly Gly Asn Gly Asn Lys Gly
    130                 135                 140

Arg Ser Ser Ala Ser Ala Gln Ile Ile Ala Gln Gly Thr Ile Thr Leu
145                 150                 155                 160

Thr Gly Glu Asn Lys Thr Phe Arg Leu Asn Asn Val Ser Leu Asn Gly
                165                 170                 175

Thr Gly Asn Gly Leu Ser Ile Ile Ser Thr Ala Ser Asn Leu Ser His
            180                 185                 190

Arg Leu Asp Gly Glu Ile Asn Val Ser Gly Asn Val Thr Ile Asn Gln
        195                 200                 205

Thr Thr Gln Gln Asn Ile Glu Tyr Trp Lys Ala Ser Ser Asp Ser Tyr
    210                 215                 220

Trp Asn Val Thr Ser Phe Asn Leu Arg Glu Asp Ser Lys Phe Thr Phe
225                 230                 235                 240

Ile Lys Tyr Val Asn Ser Ala Arg Asn Gly Asp Val Arg Gly Arg Ser
                245                 250                 255

Phe Ala Gly Val Ile Phe Asn Ala Lys Gly Leu Thr Thr Ser Phe Asn
            260                 265                 270

Val Lys Lys Gly Ser Thr Val Asp Phe Lys Leu Lys Pro Asn Ser Gly
        275                 280                 285

Tyr Asn Ser Gln Lys Arg Ile Pro Ile Gln Phe Gln Ser Asn Ile Ser
```

-continued

```
            290                 295                 300
Val Ser Gly Gly Arg Val Asn Ile Asn Thr Leu Ala Asn Leu Thr
305                 310                 315                 320

Gly Gly Gly Val Glu Ile Arg Ser Ser Ile Asn Val Ser Asp Gly
                325                 330                 335

Ser Thr Leu Ser Met Thr Ala Gln Ala Arg Asp Arg Asn Ala Phe Glu
                340                 345                 350

Ile Thr Lys Asp Leu Val Ile Asn Ala Ser Asn Ser Asn Leu Ser Ile
                355                 360                 365

Ile Gln Gln Asn Asp Gly Phe Asp Asn Asn Gln Lys Ala Asn Ala Ile
370                 375                 380

Asn Ser Lys Tyr Asn Val Thr Ile Gln Gly Gly Asn Val Thr Leu Gly
385                 390                 395                 400

Gly Gln Asn Ser Ser Ser Thr Ile Thr Gly Ser Val Asn Ile Gly Ala
                405                 410                 415

Asn Ala Asn Val Thr Leu Gln Ala His Asn Gly Asn Asp Arg Asn Lys
                420                 425                 430

Lys Leu Thr Phe Gly Asn Val Ser Val Glu Gly Glu Leu Arg Leu Val
                435                 440                 445

Gly Ala Ser Ala Asn Ile Asn Asn Leu Ser Val Lys Ser Gly Ala
450                 455                 460

Lys Phe Lys Ala Glu Thr Asn Asp Asn Leu Asn Ile Thr Gly Thr Phe
465                 470                 475                 480

Thr Asn Asn Gly Thr Ser Ile Ile Asp Val Lys Lys Gly Ala Ala Lys
                485                 490                 495

Leu Gly Asn Ile Thr Asn Asp Gly Asn Leu Asn Ile Thr Thr Asn Ala
                500                 505                 510

Lys Asn Gly Gln Lys Ser Val Ile Asn Gly Asn Ile Thr Asn Asn Lys
                515                 520                 525

Gly Ala Leu Asn Ile Thr Asn Asn Gly Asn Asp Thr Glu Ile Gln Ile
                530                 535                 540

Gly Gly Asn Ile Ser Gln Lys Glu Gly Asn Leu Thr Ile Ser Ser Asp
545                 550                 555                 560

Lys Ile Asn Ile Thr Lys Arg Ile Glu Ile Lys Ala Gly Thr Asp Gln
                565                 570                 575

Gly Asn Ser Asp Ser Gly Val Ala Ser Asn Ala Asn Leu Thr Ile Lys
                580                 585                 590

Thr Lys Glu Leu Lys Leu Thr Glu Asn Leu Asn Ile Ser Gly Phe Asp
                595                 600                 605

Lys Ala Glu Ile Val Ala Lys Glu Asn Asn Leu Ile Ile Gly Asn
610                 615                 620

Asn Asn Gly Asp Asn Ala Asn Ala Lys Thr Val Thr Phe Asn Asn Val
625                 630                 635                 640

Lys Asp Ser Lys Ile Ser Ala Asn Gly His Asn Val Thr Leu Asn Ser
                645                 650                 655

Lys Val Glu Thr Ser Asp Gly Asn Ser Asn Thr Glu Gly Asn Ser Asp
                660                 665                 670

Asn Asn Ala Gly Leu Thr Ile Asp Ala Lys Asn Val Thr Val Asn Asn
                675                 680                 685

Asp Ile Thr Ser His Lys Thr Val Asn Ile Thr Ala Ser Glu Arg Ile
                690                 695                 700

Asp Thr Lys Ala Asp Thr Thr Ile Asn Ala Thr Thr Gly Asn Val Lys
705                 710                 715                 720
```

```
Leu Thr Ala Val Thr Ser Asp Ile Gln Gly Gly Ile Lys Ser Asn Ser
                725                 730                 735

Gly Asp Val Asn Ile Thr Thr Ser Thr Gly Ser Ile Asn Gly Lys Ile
            740                 745                 750

Glu Ser Lys Ser Gly Ser Val Thr Leu Thr Ala Thr Glu Lys Thr Leu
        755                 760                 765

Thr Val Gly Asn Val Ser Gly Asn Thr Val Thr Val Thr Ala Asn Arg
    770                 775                 780

Gly Ala Leu Thr Thr Leu Ala Gly Ser Thr Ile Asn Gly Thr Asn Gly
785                 790                 795                 800

Val Thr Thr Ser Ser Gln Ser Gly Glu Ile Gly Gly Glu Val Thr Gly
                805                 810                 815

Lys Thr Val Ser Val Thr Ala Thr Ala Gly Ser Leu Thr Val Lys Gly
            820                 825                 830

Gly Ala Lys Ile Asn Ala Thr Glu Gly Thr Ala Thr Leu Thr Ala Ser
        835                 840                 845

Ser Gly Lys Leu Thr Thr Glu Ala Ser Ser Asn Ile Thr Ser Ala Lys
    850                 855                 860

Gly Gln Val Asp Leu Ser Ala Gln Asp Gly Ser Ile Ala Gly Gln Ile
865                 870                 875                 880

Ser Ala Ala Asn Val Thr Leu Asn Thr Thr Gly Thr Leu Thr Thr Val
                885                 890                 895

Glu Gly Ser Ser Ile Asn Ala Asn Glu Gly Thr Leu Val Ile Asn Ala
            900                 905                 910

Asn Asp Ala Lys Leu Asp Gly Lys Ala Ser Gly Asn Arg Thr Glu Val
        915                 920                 925

Asn Ala Thr Asn Ala Ser Gly Ser Gly Ser Val Thr Ala Lys Thr Ser
    930                 935                 940

Ser Ser Val Asn Ile Thr Gly Asp Leu Asn Thr Ile Asn Gly Leu Asn
945                 950                 955                 960

Ile Ile Ser Glu Asn Gly Arg Asn Thr Val Arg Leu Arg Gly Lys Glu
                965                 970                 975

Ile Glu Val Lys Tyr Ile Gln Pro Gly Val Ala Ser Val Glu Glu Val
            980                 985                 990

Ile Glu Ala Lys Arg Val Leu Glu Lys Val Lys Asp Leu Ser Asp Glu
        995                 1000                1005

Glu Arg Glu Thr Leu Ala Lys Leu Gly Val Ser Ala Val Arg Phe Ile
    1010                1015                1020

Glu Pro Asn Asn Thr Ile Thr Val Asn Thr Gln Asn Glu Phe Thr Thr
1025                1030                1035                1040

Arg Pro Ser Ser Gln Val Thr Ile Ser Glu Gly Lys Ala Cys Phe Ser
                1045                1050                1055

Ser Gly Asn Gly Ala Ala Val Cys Thr Asn Val Ala Asp Asp Gly Gln
            1060                1065                1070

Gln

<210> SEQ ID NO 46
<211> LENGTH: 2952
<212> TYPE: DNA
<213> ORGANISM: Haemophilus influenzae

<400> SEQUENCE: 46
aaagagtggt tgttagaccc ggataatgtc aatattgtta aaggaaccga attacagaat      60
```

-continued

```
gatttggttg ttaggggcga tagtattgag aaaaagaatg cccctaccaa gactacaatt     120
catgcaggct ctatagaaca atctttgatg aagggtggtg cagttaatat ttctgctaca     180
aataaagtaa atgttactac agatattaat gtttataatg gagcattaac gttacactca     240
gaacgagatg gagttgaaat taacggtaat attacctcag aaaaaaatgg taatttaacc     300
attaaagcag gtagctgggt tgatgttcat aaaaatatca cacttggcga gggttttttg     360
aatattactt ccggtgatat cgccttcgaa aaaggtaata atctaaccat taccgctcaa     420
ggaaatataa cctctaataa agacggaaaa caacttagac ttaataatgt atctttaaat     480
ggaacaggtg caggtttaaa ctttattgca atcaaaata attttacaca caacattagt     540
ggcgcgatta acatttccgg agtagtaacg attaatcaaa ctacgaaaaa aaacgctaag     600
gcatggaata caagctatga ctcttactgg aacgtatcta ctcttacttt aagcaatgat     660
gcgaaattta cctttattaa atatgtcgac agcaatcatt cgacaaactc cagtgattca     720
cgaagttttg cgggagtaaa gttccacggc aagaataatg aaatgaaatt taatattggt     780
aataatgcca aggctgaatt taggttaaaa ccaaatgaga gacaactcc taacagacca      840 ctaccaattc agttttatc taatatttcg gtcactggcg gaggttctgt gttttcgat       900 atatacgcta acctttgggg taaagggact gagctaaaga tggattcaat taacgtttct     960
agcggctcta atcttacctt aaattcccat gttcgcaagt ataatgcttt tgaaatcaat     1020
aaagacttaa ctataaacgc aactaattca aatttcaacc tcagacagac gtcagatagt     1080
tttcgtaacg ggtaccgcaa taatgccatc aattcaaccc acaacatatc catcttgggc     1140
ggcaacgtca ctctcggcgg acaaaactca agcagcagca ttatggggaa tatcatcatc     1200
aagcgagcag caaatgttac gctagaagcc gataatagtc acaattctga caacgtaaag     1260
gatagaacta taaatcttgg caacttgacc gttgagggga atttaagttt aattggcgaa     1320
aatgcaaata ttaacggcaa tctctccatt gaaaaagaag ccatctttaa aggaaaaacc     1380
aaggacagcc taaacatcac cggcaacttt accaataatg gcactgccga aattaatata     1440
agccaaggag tggtaagtct tggcgatatt accaatgatg gcaaattaaa catcaccact     1500
cacgccaaga gcggtcaaaa aagcattatc cgcggagata taattaacaa acaagggaat     1560
ttaaatatta cggacaataa tagtaatgct gaaattgaaa ttggcggcaa tatctcgcaa     1620
aaagaaggta atctcaccat ttcttctgat aaagtcaata ttaccaaaca gataacaatc     1680
aaagcaggcg ttgatgggga gagttctagt tcaagcacag caagtgatgc caatctaacc     1740
attaaaacca aagagttaac attaacagac aatctaaaca tttcaggttt taataaagca     1800
gaaattacag ctaaagataa cagtgattta attattggca aggctagcag tgacaacagt     1860
aatgctaaac aagtaacctt tgacaaggtt aaagattcaa aaatctcagc tggcaatcac     1920
aatgtaacac taaatagcaa agtggaaacg tctaatagcg atggtagcac cggaaacggt     1980
agcgatgaca caaatatcgg cttaactatt tccgcaaaag atgtaacggt aaatagtaat     2040
atcacctctc acaaaacagt aaatatctct gcatcagaag gaggtatcac tactaaagca     2100
ggcacaacca ttaatgcgac cacaggtagc gtggaagtaa ctgctaaaac aggcgatatt     2160
agcggtacga tttccggtaa gacagtaagt gttacagcaa gcactggcga tttaactgtt     2220
aggaaagctg caaccattag tgcgacagaa ggagctgcaa ccttaccgc aacagggaat      2280 accttgacta ctgaagccgg ttctagcatc acttcaacta agggtcaggt agacctttca     2340
gctcaggatg gtagcattgc aggacaaatt agtgcagcta atgtgacatt aaataccaca     2400
ggcaccttaa ctactgtaga aggttcaaac attaaggcaa ccagtggcac cttagctatt     2460
```

-continued

```
aacgcaaaag acgctaagct agatggtacg gcatcaggta accgtacaga agtaaatgca   2520
actaacgcaa gtggttctgg tagcgtgact gcgaaaacct caagtaatgt gaatatcacc   2580
ggggatttaa gcacaataaa tgggttaaat atcatttcgg aaaatggtag aaacactgtg   2640
cgcttaagag gcaaggaaat tgatgtgaaa tatatccaac caggtgtagc aagcgtagaa   2700
gaggtaattg aagcgaaacg cgtccttgag aaagtaaaag atttatctga cgaagaaaga   2760
gaaacactag ccaaacttgg tgtaagtgct gtacgtttcg ttgagccaaa taatgccatt   2820
acgattaata cacaaaatga atttacaacc agaccgtcaa gtcaagtgat aatttctgaa   2880
ggtaaggcgt gtttctcaag tggtaatggc gcagcagtat gtaccaatgt tgctgacgat   2940
ggacagccgt ag                                                       2952
```

<210> SEQ ID NO 47
<211> LENGTH: 983
<212> TYPE: PRT
<213> ORGANISM: Haemophilus influenzae

<400> SEQUENCE: 47

```
Lys Glu Trp Leu Leu Asp Pro Asp Asn Val Asn Ile Val Lys Gly Thr
  1               5                  10                  15

Glu Leu Gln Asn Asp Leu Val Val Arg Gly Asp Ser Ile Glu Lys Lys
             20                  25                  30

Asn Ala Pro Thr Lys Thr Thr Ile His Ala Gly Ser Ile Glu Gln Ser
         35                  40                  45

Leu Met Lys Gly Gly Ala Val Asn Ile Ser Ala Thr Asn Lys Val Asn
     50                  55                  60

Val Thr Thr Asp Ile Asn Val Tyr Asn Gly Ala Leu Thr Leu His Ser
 65                  70                  75                  80

Glu Arg Asp Gly Val Glu Ile Asn Gly Asn Ile Thr Ser Glu Lys Asn
                 85                  90                  95

Gly Asn Leu Thr Ile Lys Ala Gly Ser Trp Val Asp Val His Lys Asn
            100                 105                 110

Ile Thr Leu Gly Glu Gly Phe Leu Asn Ile Thr Ser Gly Asp Ile Ala
        115                 120                 125

Phe Glu Lys Gly Asn Asn Leu Thr Ile Thr Ala Gln Gly Asn Ile Thr
    130                 135                 140

Ser Asn Lys Asp Gly Lys Gln Leu Arg Leu Asn Asn Val Ser Leu Asn
145                 150                 155                 160

Gly Thr Gly Ala Gly Leu Asn Phe Ile Ala Asn Gln Asn Asn Phe Thr
                165                 170                 175

His Asn Ile Ser Gly Ala Ile Asn Ile Ser Gly Val Val Thr Ile Asn
            180                 185                 190

Gln Thr Thr Lys Lys Asn Ala Lys Ala Trp Asn Thr Ser Tyr Asp Ser
        195                 200                 205

Tyr Trp Asn Val Ser Thr Leu Thr Leu Ser Asn Asp Ala Lys Phe Thr
    210                 215                 220

Phe Ile Lys Tyr Val Asp Ser Asn His Ser Thr Asn Ser Ser Asp Ser
225                 230                 235                 240

Arg Ser Phe Ala Gly Val Lys Phe His Gly Lys Asn Asn Glu Met Lys
                245                 250                 255

Phe Asn Ile Gly Asn Asn Ala Lys Ala Glu Phe Arg Leu Lys Pro Asn
            260                 265                 270

Glu Lys Thr Thr Pro Asn Arg Pro Leu Pro Ile Gln Phe Leu Ser Asn
```

```
                275                 280                 285
Ile Ser Val Thr Gly Gly Ser Val Phe Phe Asp Ile Tyr Ala Asn
290                 295                 300
Leu Trp Gly Lys Gly Thr Glu Leu Lys Met Asp Ser Ile Asn Val Ser
305                 310                 315                 320
Ser Gly Ser Asn Leu Thr Leu Asn Ser His Val Arg Lys Tyr Asn Ala
                325                 330                 335
Phe Glu Ile Asn Lys Asp Leu Thr Ile Asn Ala Thr Asn Ser Asn Phe
                340                 345                 350
Asn Leu Arg Gln Thr Ser Asp Ser Phe Arg Asn Gly Tyr Arg Asn Asn
                355                 360                 365
Ala Ile Asn Ser Thr His Asn Ile Ser Ile Leu Gly Asn Val Thr
370                 375                 380
Leu Gly Gly Gln Asn Ser Ser Ser Ile Met Gly Asn Ile Ile Ile
385                 390                 395                 400
Lys Arg Ala Ala Asn Val Thr Leu Glu Ala Asp Asn Ser His Asn Ser
                405                 410                 415
Asp Asn Val Lys Asp Arg Thr Ile Asn Leu Gly Asn Leu Thr Val Glu
                420                 425                 430
Gly Asn Leu Ser Leu Ile Gly Glu Asn Ala Asn Ile Asn Gly Asn Leu
                435                 440                 445
Ser Ile Glu Lys Glu Ala Ile Phe Lys Gly Lys Thr Lys Asp Ser Leu
                450                 455                 460
Asn Ile Thr Gly Asn Phe Thr Asn Asn Gly Thr Ala Glu Ile Asn Ile
465                 470                 475                 480
Ser Gln Gly Val Val Ser Leu Gly Asp Ile Thr Asn Asp Gly Lys Leu
                485                 490                 495
Asn Ile Thr Thr His Ala Lys Ser Gly Gln Lys Ser Ile Ile Arg Gly
                500                 505                 510
Asp Ile Ile Asn Lys Gln Gly Asn Leu Asn Ile Thr Asp Asn Asn Ser
                515                 520                 525
Asn Ala Glu Ile Glu Ile Gly Gly Asn Ile Ser Gln Lys Glu Gly Asn
530                 535                 540
Leu Thr Ile Ser Ser Asp Lys Val Asn Ile Thr Lys Gln Ile Thr Ile
545                 550                 555                 560
Lys Ala Gly Val Asp Gly Glu Ser Ser Ser Ser Thr Ala Ser Asp
                565                 570                 575
Ala Asn Leu Thr Ile Lys Thr Lys Glu Leu Thr Leu Thr Asp Asn Leu
                580                 585                 590
Asn Ile Ser Gly Phe Asn Lys Ala Glu Ile Thr Ala Lys Asp Asn Ser
                595                 600                 605
Asp Leu Ile Ile Gly Lys Ala Ser Asp Asn Ser Asn Ala Lys Gln
                610                 615                 620
Val Thr Phe Asp Lys Val Lys Asp Ser Lys Ile Ser Ala Gly Asn His
625                 630                 635                 640
Asn Val Thr Leu Asn Ser Lys Val Glu Thr Ser Asn Ser Asp Gly Ser
                645                 650                 655
Thr Gly Asn Gly Ser Asp Asp Asn Ile Gly Leu Thr Ile Ser Ala
                660                 665                 670
Lys Asp Val Thr Val Asn Ser Asn Ile Thr Ser His Lys Thr Val Asn
                675                 680                 685
Ile Ser Ala Ser Glu Gly Gly Ile Thr Thr Lys Ala Gly Thr Thr Ile
690                 695                 700
```

```
Asn Ala Thr Thr Gly Ser Val Glu Val Thr Ala Lys Thr Gly Asp Ile
705                 710                 715                 720

Ser Gly Thr Ile Ser Gly Lys Thr Val Ser Val Thr Ala Ser Thr Gly
            725                 730                 735

Asp Leu Thr Val Arg Lys Ala Ala Thr Ile Ser Ala Thr Glu Gly Ala
        740                 745                 750

Ala Thr Leu Thr Ala Thr Gly Asn Thr Leu Thr Thr Glu Ala Gly Ser
    755                 760                 765

Ser Ile Thr Ser Thr Lys Gly Gln Val Asp Leu Ser Ala Gln Asp Gly
770                 775                 780

Ser Ile Ala Gly Gln Ile Ser Ala Ala Asn Val Thr Leu Asn Thr Thr
785                 790                 795                 800

Gly Thr Leu Thr Thr Val Glu Gly Ser Asn Ile Lys Ala Thr Ser Gly
                805                 810                 815

Thr Leu Ala Ile Asn Ala Lys Asp Ala Lys Leu Asp Gly Thr Ala Ser
                820                 825                 830

Gly Asn Arg Thr Glu Val Asn Ala Thr Asn Ala Ser Gly Ser Gly Ser
        835                 840                 845

Val Thr Ala Lys Thr Ser Ser Asn Val Asn Ile Thr Gly Asp Leu Ser
850                 855                 860

Thr Ile Asn Gly Leu Asn Ile Ile Ser Glu Asn Gly Arg Asn Thr Val
865                 870                 875                 880

Arg Leu Arg Gly Lys Glu Ile Asp Val Lys Tyr Ile Gln Pro Gly Val
            885                 890                 895

Ala Ser Val Glu Glu Val Ile Glu Ala Lys Arg Val Leu Glu Lys Val
            900                 905                 910

Lys Asp Leu Ser Asp Glu Glu Arg Glu Thr Leu Ala Lys Leu Gly Val
        915                 920                 925

Ser Ala Val Arg Phe Val Glu Pro Asn Asn Ala Ile Thr Ile Asn Thr
    930                 935                 940

Gln Asn Glu Phe Thr Thr Arg Pro Ser Ser Gln Val Ile Ile Ser Glu
945                 950                 955                 960

Gly Lys Ala Cys Phe Ser Ser Gly Asn Gly Ala Ala Val Cys Thr Asn
                965                 970                 975

Val Ala Asp Asp Gly Gln Pro
            980

<210> SEQ ID NO 48
<211> LENGTH: 2934
<212> TYPE: DNA
<213> ORGANISM: Haemophilus influenzae

<400> SEQUENCE: 48
ccggataatg tcaatattgt taaaggaacc gaattacaga atgatttggt tgttaggggc      60
gatagtattg agaaaaagaa tgcccctacc aagactacaa ttcatgcagg ctctatagaa     120
caatctttga tgaagggtgg tgcagttaat atttctgcta caaataaagt aaatgttact     180
acagatatta atgtttataa tggagcatta acgttacact cagaacgaga tggagttgaa     240
attaacggta atattacctc agaaaaaaat ggtaatttaa ccattaaagc aggtagctgg     300
gttgatgttc ataaaaatat cacacttggc gagggttttt tgaatattac ttccggtgat     360
atcgccttcg aaaaggtaa taatctaacc attaccgctc aaggaaatat aacctctaat     420
aaagacggaa acaacttag acttaataat gtatctttaa atggaacagg tgcaggttta     480
```

```
aacttrattg caaatcaaaa taatttraca cacaacatta gtggcgcgat taacatttcc    540
ggagtagtaa cgattaatca aactacgaaa aaaaacgcta aggcatggaa tacaagctat    600
gactcttact ggaacgtatc tactcttact ttaagcaatg atgcgaaatt taccttratt    660
aaatatgtcg acagcaatca ttcgacaaac tccagtgatt cacgaagttt tgcgggagta    720
aagttccacg gcaagaataa tgaaatgaaa tttaatattg gtaataatgc caaggctgaa    780
tttaggttaa aaccaaatga aagacaact  cctaacagac cactaccaat tcagttttta    840
tctaatattt cggtcactgg cggaggttct gtgttttrcg atatatacgc taacctttgg    900
ggtaaaggga ctgagctaaa gatggattca attaacgttt ctagcggctc taatcttacc    960
ttaaattccc atgttcgcaa gtataatgct tttgaaatca ataaagactt aactataaac   1020
gcaactaatt caaatttcaa cctcagacag acgtcagata gttttcgtaa cgggtaccgc   1080
aataatgcca tcaattcaac ccacaacata tccatcttgg gcggcaacgt cactctcggc   1140
ggacaaaact caagcagcag cattatgggg aatatcatca tcaagcgagc agcaaatgtt   1200
acgctagaag ccgataatag tcacaattct gacaacgtaa aggatagaac tataaatctt   1260
ggcaacttga ccgttgaggg gaatttaagt ttaattggcg aaaatgcaaa tattaacggc   1320
aatctctcca ttgaaaaaga agccatcttt aaaggaaaaa ccaaggacag cctaaacatc   1380
accggcaact ttaccaataa tggcactgcc gaaattaata taagccaagg agtggtaagt   1440
cttggcgata ttaccaatga tggcaaatta acatcacca  ctcacgccaa gagcggtcaa   1500
aaaagcatta tccgcggaga tataattaac aaacaaggga atttaaatat tacgacaat   1560 aatagtaatg ctgaaattga aattggcggc aatatctcgc aaaaagaagg taatctcacc   1620
atttcttctg ataaagtcaa tattaccaaa cagataacaa tcaaagcagg cgttgatggg   1680
gagagttcta gttcaagcac agcaagtgat gccaatctaa ccattaaaac caaagagtta   1740
acattaacag acaatctaaa catttcaggt tttaataaag cagaaattac agctaaagat   1800
aacagtgatt taattattgg caaggctagc agtgacaaca gtaatgctaa acaagtaacc   1860
tttgacaagg ttaaagattc aaaaatctca gctggcaatc acaatgtaac actaaatagc   1920
aaagtggaaa cgtctaatag cgatggtagc accggaaacg gtagcgatga caacaatatc   1980
ggcttaacta tttccgcaaa agatgtaacg gtaaatagta atatcaccct  tcacaaaaca  2040
gtaaatatct ctgcatcaga aggaggtatc actactaaag caggcacaac cattaatgcg   2100
accacaggta gcgtggaagt aactgctaaa acaggcgata ttagcggtac gatttccggt   2160
aagacagtaa gtgttacagc aagcactggc gatttaactg ttaggaaagc tgcaaccatt   2220
agtgcgacag aaggagctgc aaccttaacc gcaacaggga ataccttgac tactgaagcc   2280
ggttctagca tcacttcaac taagggtcag gtagaccttt cagctcagga tggtagcatt   2340
gcaggacaaa ttagtgcagc taatgtgaca ttaaatacca caggcacctt aactactgta   2400
gaaggttcaa acattaaggc aaccagtggc accttagcta ttaacgcaaa agacgctaag   2460
ctagatggta cggcatcagg taaccgtaca gaagtaaatg caactaacgc aagtggttct   2520
ggtagcgtga ctgcgaaaac ctcaagtaat gtgaatatca ccggggattt aagcacaata   2580
aatgggttaa atatcatttc ggaaaatggt agaaacactg tgcgcttaag aggcaaggaa   2640
attgatgtga aatatatcca accaggtgta gcaagcgtag aagaggtaat tgaagcgaaa   2700
cgcgtccttg agaaagtaaa agatttatct gacgaagaaa gagaaacact agccaaactt   2760
ggtgtaagtg ctgtacgttt cgttgagcca ataatgccca ttacgattaa tacacaaaat   2820
gaatttacaa ccagaccgtc aagtcaagtg ataatttctg aaggtaaggc gtgtttctca   2880
```

```
agtggtaatg gcgcagcagt atgtaccaat gttgctgacg atggacagcc gtag        2934
```

<210> SEQ ID NO 49
<211> LENGTH: 977
<212> TYPE: PRT
<213> ORGANISM: Haemophilus influenzae

<400> SEQUENCE: 49

| | | | | | | | | | | | | | | | |
|---|---|---|---|---|---|---|---|---|---|---|---|---|---|---|---|
| Pro | Asp | Asn | Val | Asn | Ile | Val | Lys | Gly | Thr | Glu | Leu | Gln | Asn | Asp | Leu |
| 1 | | | | 5 | | | | | 10 | | | | | 15 | |
| Val | Val | Arg | Gly | Asp | Ser | Ile | Glu | Lys | Lys | Asn | Ala | Pro | Thr | Lys | Thr |
| | | | 20 | | | | | 25 | | | | | 30 | | |
| Thr | Ile | His | Ala | Gly | Ser | Ile | Glu | Gln | Ser | Leu | Met | Lys | Gly | Gly | Ala |
| | | | 35 | | | | 40 | | | | | 45 | | | |
| Val | Asn | Ile | Ser | Ala | Thr | Asn | Lys | Val | Asn | Val | Thr | Thr | Asp | Ile | Asn |
| | 50 | | | | | 55 | | | | | 60 | | | | |
| Val | Tyr | Asn | Gly | Ala | Leu | Thr | Leu | His | Ser | Glu | Arg | Asp | Gly | Val | Glu |
| 65 | | | | | 70 | | | | | 75 | | | | | 80 |
| Ile | Asn | Gly | Asn | Ile | Thr | Ser | Glu | Lys | Asn | Gly | Asn | Leu | Thr | Ile | Lys |
| | | | | 85 | | | | | 90 | | | | | 95 | |
| Ala | Gly | Ser | Trp | Val | Asp | Val | His | Lys | Asn | Ile | Thr | Leu | Gly | Glu | Gly |
| | | | 100 | | | | | 105 | | | | | 110 | | |
| Phe | Leu | Asn | Ile | Thr | Ser | Gly | Asp | Ile | Ala | Phe | Glu | Lys | Gly | Asn | Asn |
| | | | 115 | | | | | 120 | | | | | 125 | | |
| Leu | Thr | Ile | Thr | Ala | Gln | Gly | Asn | Ile | Thr | Ser | Asn | Lys | Asp | Gly | Lys |
| | 130 | | | | | 135 | | | | | 140 | | | | |
| Gln | Leu | Arg | Leu | Asn | Asn | Val | Ser | Leu | Asn | Gly | Thr | Gly | Ala | Gly | Leu |
| 145 | | | | | 150 | | | | | 155 | | | | | 160 |
| Asn | Phe | Ile | Ala | Asn | Gln | Asn | Asn | Phe | Thr | His | Asn | Ile | Ser | Gly | Ala |
| | | | | 165 | | | | | 170 | | | | | 175 | |
| Ile | Asn | Ile | Ser | Gly | Val | Val | Thr | Ile | Asn | Gln | Thr | Thr | Lys | Lys | Asn |
| | | | 180 | | | | | 185 | | | | | 190 | | |
| Ala | Lys | Ala | Trp | Asn | Thr | Ser | Tyr | Asp | Ser | Tyr | Trp | Asn | Val | Ser | Thr |
| | | | 195 | | | | | 200 | | | | | 205 | | |
| Leu | Thr | Leu | Ser | Asn | Asp | Ala | Lys | Phe | Thr | Phe | Ile | Lys | Tyr | Val | Asp |
| | 210 | | | | | 215 | | | | | 220 | | | | |
| Ser | Asn | His | Ser | Thr | Asn | Ser | Ser | Asp | Ser | Arg | Ser | Phe | Ala | Gly | Val |
| 225 | | | | | 230 | | | | | 235 | | | | | 240 |
| Lys | Phe | His | Gly | Lys | Asn | Asn | Glu | Met | Lys | Phe | Asn | Ile | Gly | Asn | Asn |
| | | | | 245 | | | | | 250 | | | | | 255 | |
| Ala | Lys | Ala | Glu | Phe | Arg | Leu | Lys | Pro | Asn | Glu | Lys | Thr | Thr | Pro | Asn |
| | | | 260 | | | | | 265 | | | | | 270 | | |
| Arg | Pro | Leu | Pro | Ile | Gln | Phe | Leu | Ser | Asn | Ile | Ser | Val | Thr | Gly | Gly |
| | | | 275 | | | | | 280 | | | | | 285 | | |
| Gly | Ser | Val | Phe | Phe | Asp | Ile | Tyr | Ala | Asn | Leu | Trp | Gly | Lys | Gly | Thr |
| | 290 | | | | | 295 | | | | | 300 | | | | |
| Glu | Leu | Lys | Met | Asp | Ser | Ile | Asn | Val | Ser | Ser | Gly | Ser | Asn | Leu | Thr |
| 305 | | | | | 310 | | | | | 315 | | | | | 320 |
| Leu | Asn | Ser | His | Val | Arg | Lys | Tyr | Asn | Ala | Phe | Glu | Ile | Asn | Lys | Asp |
| | | | | 325 | | | | | 330 | | | | | 335 | |
| Leu | Thr | Ile | Asn | Ala | Thr | Asn | Ser | Asn | Phe | Asn | Leu | Arg | Gln | Thr | Ser |
| | | | 340 | | | | | 345 | | | | | 350 | | |
| Asp | Ser | Phe | Arg | Asn | Gly | Tyr | Arg | Asn | Asn | Ala | Ile | Asn | Ser | Thr | His |
| | | | 355 | | | | | 360 | | | | | 365 | | |

```
Asn Ile Ser Ile Leu Gly Gly Asn Val Thr Leu Gly Gly Gln Asn Ser
    370                 375                 380

Ser Ser Ser Ile Met Gly Asn Ile Ile Ile Lys Arg Ala Ala Asn Val
385                 390                 395                 400

Thr Leu Glu Ala Asp Asn Ser His Asn Ser Asp Asn Val Lys Asp Arg
                405                 410                 415

Thr Ile Asn Leu Gly Asn Leu Thr Val Glu Gly Asn Leu Ser Leu Ile
            420                 425                 430

Gly Glu Asn Ala Asn Ile Asn Gly Asn Leu Ser Ile Glu Lys Glu Ala
                435                 440                 445

Ile Phe Lys Gly Lys Thr Lys Asp Ser Leu Asn Ile Thr Gly Asn Phe
        450                 455                 460

Thr Asn Asn Gly Thr Ala Glu Ile Asn Ile Ser Gln Gly Val Val Ser
465                 470                 475                 480

Leu Gly Asp Ile Thr Asn Asp Gly Lys Leu Asn Ile Thr Thr His Ala
                485                 490                 495

Lys Ser Gly Gln Lys Ser Ile Ile Arg Gly Asp Ile Ile Asn Lys Gln
            500                 505                 510

Gly Asn Leu Asn Ile Thr Asp Asn Asn Ser Asn Ala Glu Ile Glu Ile
            515                 520                 525

Gly Gly Asn Ile Ser Gln Lys Glu Gly Asn Leu Thr Ile Ser Ser Asp
        530                 535                 540

Lys Val Asn Ile Thr Lys Gln Ile Thr Ile Lys Ala Gly Val Asp Gly
545                 550                 555                 560

Glu Ser Ser Ser Ser Thr Ala Ser Asp Ala Asn Leu Thr Ile Lys
                565                 570                 575

Thr Lys Glu Leu Thr Leu Thr Asp Asn Leu Asn Ile Ser Gly Phe Asn
            580                 585                 590

Lys Ala Glu Ile Thr Ala Lys Asp Asn Ser Asp Leu Ile Ile Gly Lys
        595                 600                 605

Ala Ser Ser Asp Asn Ser Asn Ala Lys Gln Val Thr Phe Asp Lys Val
        610                 615                 620

Lys Asp Ser Lys Ile Ser Ala Gly Asn His Asn Val Thr Leu Asn Ser
625                 630                 635                 640

Lys Val Glu Thr Ser Asn Ser Asp Gly Ser Thr Gly Asn Gly Ser Asp
                645                 650                 655

Asp Asn Asn Ile Gly Leu Thr Ile Ser Ala Lys Asp Val Thr Val Asn
            660                 665                 670

Ser Asn Ile Thr Ser His Lys Thr Val Asn Ile Ser Ala Ser Glu Gly
            675                 680                 685

Gly Ile Thr Thr Lys Ala Gly Thr Thr Ile Asn Ala Thr Thr Gly Ser
        690                 695                 700

Val Glu Val Thr Ala Lys Thr Gly Asp Ile Ser Gly Thr Ile Ser Gly
705                 710                 715                 720

Lys Thr Val Ser Val Thr Ala Ser Thr Gly Asp Leu Thr Val Arg Lys
                725                 730                 735

Ala Ala Thr Ile Ser Ala Thr Glu Gly Ala Ala Thr Leu Thr Ala Thr
                740                 745                 750

Gly Asn Thr Leu Thr Thr Glu Ala Gly Ser Ser Ile Thr Ser Thr Lys
            755                 760                 765

Gly Gln Val Asp Leu Ser Ala Gln Asp Gly Ser Ile Ala Gly Gln Ile
        770                 775                 780
```

-continued

```
Ser Ala Ala Asn Val Thr Leu Asn Thr Thr Gly Thr Leu Thr Thr Val
785                 790                 795                 800

Glu Gly Ser Asn Ile Lys Ala Thr Ser Gly Thr Leu Ala Ile Asn Ala
            805                 810                 815

Lys Asp Ala Lys Leu Asp Gly Thr Ala Ser Gly Asn Arg Thr Glu Val
        820                 825                 830

Asn Ala Thr Asn Ala Ser Gly Ser Gly Ser Val Thr Ala Lys Thr Ser
    835                 840                 845

Ser Asn Val Asn Ile Thr Gly Asp Leu Ser Thr Ile Asn Gly Leu Asn
850                 855                 860

Ile Ile Ser Glu Asn Gly Arg Asn Thr Val Arg Leu Arg Gly Lys Glu
865                 870                 875                 880

Ile Asp Val Lys Tyr Ile Gln Pro Gly Val Ala Ser Val Glu Glu Val
            885                 890                 895

Ile Glu Ala Lys Arg Val Leu Glu Lys Val Lys Asp Leu Ser Asp Glu
        900                 905                 910

Glu Arg Glu Thr Leu Ala Lys Leu Gly Val Ser Ala Val Arg Phe Val
    915                 920                 925

Glu Pro Asn Asn Ala Ile Thr Ile Asn Thr Gln Asn Glu Phe Thr Thr
930                 935                 940

Arg Pro Ser Ser Gln Val Ile Ile Ser Glu Gly Lys Ala Cys Phe Ser
945                 950                 955                 960

Ser Gly Asn Gly Ala Ala Val Cys Thr Asn Val Ala Asp Asp Gly Gln
            965                 970                 975

Pro
```

```
<210> SEQ ID NO 50
<211> LENGTH: 3033
<212> TYPE: DNA
<213> ORGANISM: Haemophilus influenzae

<400> SEQUENCE: 50
aaagagtggt tgttagaccc ggatgatgta actattgccg caggcgcgcc aggacgtaac    60
gatggttcag tagacgactt ttttcccact ggaagagggg atgatgctag taatgcaaaa   120
acaaaccatc cagacaagcc gacattaaca aacacaactg ttgagaacgc attaaaaaac   180
aacacctttg ttaacataac cgccaaaaat aaaatcacag ttaatagcga catcaatatc   240
aaaggtggcg cccacctaac cctctatagc aaaaacaata aaaaaagtag cgttaagatt   300
aatggcaata ttacttctac cactaacgga aacttaacta tttactccag cggctgggtt   360
gatatccata aaacattac gcttaacaca ggttacctga atattaccgc tgggggttct   420
gtagccttcg agaaagccgg aaatgagaaa gggcgccaag tatcagaatc tgtaatcaaa   480
gcccagggag ttatcacctc aggtgtaggg aaggcttta ggtttaataa cgtctcccta   540
aatggcgttg cgcaggact gcgcttcgtt ggtcagaaaa atatcagtag caactcttgg   600
agagaaaaca ccatcaaaaa cagattcgat gggaatttaa atatctcagg aaaggtaaat   660
gtttcaatgg atgtatccgg acaaagtgg catacaagaa ttaacgggcg cacctactgg   720
aatgtaacca ctctaaacgt tgcctcaggt agtagtttca atctcagtat cgacgccagt   780
ggaatttctt caggtaacca ggacgacata acaaataggg gtttaaatgg cataacattt   840
aatggagaaa acactttaa tatcgcacag ggctcaacag ctaactttca tatcaaaacg   900
tcagtaatga cccctaaacc caactcgaac tacgcattat ttaatggaaa tatttcagtt   960
ttaggaggag gaactgtcaa ctttgaactt aatgcctcat ctagcaccca cacaacttct  1020
```

```
ggcgcaatta taaattctca aaattttaat gtctcaggtg ggtcaaaatt aaatctcaag    1080
gcttcaggct caacaaatac cgctttttta ataaaaaata atttaacttt aaacgctact    1140
ggaggtaata tagaaattaa acaggttgag ggtaccgatt cgcgcattca aaaaggtgtt    1200
gtagccgaac aaaacataat ttttgaaggg ggtaacatca cccttggctc ccaaaaagcc    1260
ccaacagaaa taaaaggcga tgttaccgtc aaacaaggaa ccaacgccac tctcagaagc    1320
gcgaattttg acaaccacaa aggtgcctta attgtgaatg gaaacgttac cgccaatggc    1380
aaccttactg cggacggcga cactattaaa ataaaaggca atcttgatgt tgcacaaggc    1440
gctaaattta acggcagcac aaaaaacaac ctaaacatta ctggcacctt taccaacaac    1500
ggcacttcta taatcgatat aacacaaggg gtggtaaacc ttggtaatgt taccaatgac    1560
ggcaaattaa acatcaccac tcacgccaag agcggtcaaa aaagcattat ccgcggagat    1620
ataattaaca acaagggaa tttaaatatt acggacaata atagtaatgc tgaaattgaa    1680
attggcggca atatctcgca aaaagaaggt aatctcacca tttcttctga taaagtcaat    1740
attaccaaac agataacaat caaagcaggc gttgatgggg agagttctag ttcaagcaca    1800
gcaagtgatg ccaatctaac cattaaaacc aaagagttaa cattcacaga caatctaaac    1860
atttcaggtt ttaataaagc agaaattaca gctaaagata acagtgatttt aattattggc    1920 aaggctagca gtgacaacag taatgctaaa caagtaacct ttgacaaggt taaagattca    1980
aaaatctcag ctggcaatca caatgtaaca ctaaatagca aagtggaaac gtctaatagc    2040
gatggtagca ccgaaacgg tagcgatgac aacaatatcg gcttaactat ttccgcaaaa    2100
gatgtaacgg taaatagtaa tatcaccctct cacaaaacag taaatatctc tgcatcagaa    2160
ggaggtatca ctactaaagc aggcacaacc attaatgcga ccacaggtag cgtggaagta    2220
actgctaaaa caggcgatat tagcggtacg atttccggta agacagtaag tgttacagca    2280
agcactggcg atttaactgt taggaaagct gcaaccatta gtgtgacaga aggagctgca    2340
accttaaccg caacagggaa taccttgact actgaagccg gttctagcat cacttcaact    2400
aagggtcagg tagaccttc agctcaggat ggtagcattg caggacaaat tagtgcagct    2460
aatgtgacat taaataccac aggcaccta actactgtag aaggttcaaa cattaaggca    2520
accagtggca ccttagctat taacgcaaaa gacgctaagc tagatggtac ggcatcaggt    2580
aaccgtacag aagtaaatgc aactaacgca agtggttctg gtagcgtgac tgcgaaaacc    2640
tcaagtaatg tgaatatcac cggggattta agcacaataa atgggttaaa tatcatttcg    2700
gaaaatggta gaaacactgt gcgcttaaga ggcaaggaaa ttgatgtgaa atatatccaa    2760
ccaggtgtag caagcgtaga agaggtaatt gaagcgaaac gcgtccttga aaagtaaaa    2820 gatttatctg acgaagaaag agaaacacta gccaaacttg gtgtaagtgc tgtacgtttc    2880
gttgagccaa ataatgccat tacgattaat acacaaaatg aatttacaac cagaccgtca    2940
agtcaagtga taatttctga aggtaaggcg tgtttctcaa gtggtaatgg cgcagcagta    3000
tgtaccaatg ttgctgacga tggacagccg tag                                 3033
```

<210> SEQ ID NO 51
<211> LENGTH: 1010
<212> TYPE: PRT
<213> ORGANISM: Haemophilus influenzae

<400> SEQUENCE: 51

Lys Glu Trp Leu Leu Asp Pro Asp Asp Val Thr Ile Ala Ala Gly Ala
 1               5                  10                  15

```
Pro Gly Arg Asn Asp Gly Ser Val Asp Asp Phe Phe Pro Thr Gly Arg
            20                  25                  30

Gly Asp Asp Ala Ser Asn Ala Lys Thr Asn His Pro Asp Lys Pro Thr
        35                  40                  45

Leu Thr Asn Thr Thr Val Glu Asn Ala Leu Lys Asn Asn Thr Phe Val
     50                  55                  60

Asn Ile Thr Ala Lys Asn Lys Ile Thr Val Asn Ser Asp Ile Asn Ile
 65                  70                  75                  80

Lys Gly Gly Ala His Leu Thr Leu Tyr Ser Lys Asn Asn Lys Lys Ser
                 85                  90                  95

Ser Val Lys Ile Asn Gly Asn Ile Thr Ser Thr Asn Gly Asn Leu
            100                 105                 110

Thr Ile Tyr Ser Ser Gly Trp Val Asp Ile His Lys Asn Ile Thr Leu
             115                 120                 125

Asn Thr Gly Tyr Leu Asn Ile Thr Ala Gly Ser Val Ala Phe Glu
    130                 135                 140

Lys Ala Gly Asn Glu Lys Gly Arg Gln Val Ser Glu Ser Val Ile Lys
145                 150                 155                 160

Ala Gln Gly Val Ile Thr Ser Gly Val Gly Glu Gly Phe Arg Phe Asn
                165                 170                 175

Asn Val Ser Leu Asn Gly Val Gly Ala Gly Leu Arg Phe Val Gly Gln
            180                 185                 190

Lys Asn Ile Ser Ser Asn Ser Trp Arg Glu Asn Thr Ile Lys Asn Arg
            195                 200                 205

Phe Asp Gly Asn Leu Asn Ile Ser Gly Lys Val Asn Val Ser Met Asp
    210                 215                 220

Val Ser Gly Thr Lys Trp His Thr Arg Ile Asn Gly Arg Thr Tyr Trp
225                 230                 235                 240

Asn Val Thr Thr Leu Asn Val Ala Ser Gly Ser Ser Phe Asn Leu Ser
                245                 250                 255

Ile Asp Ala Ser Gly Ile Ser Ser Gly Asn Gln Asp Asp Ile Thr Asn
            260                 265                 270

Arg Gly Leu Asn Gly Ile Thr Phe Asn Gly Glu Asn Thr Phe Asn Ile
        275                 280                 285

Ala Gln Gly Ser Thr Ala Asn Phe His Ile Lys Thr Ser Val Met Thr
    290                 295                 300

Pro Lys Pro Asn Ser Asn Tyr Ala Leu Phe Asn Gly Asn Ile Ser Val
305                 310                 315                 320

Leu Gly Gly Gly Thr Val Asn Phe Glu Leu Asn Ala Ser Ser Ser Thr
                325                 330                 335

His Thr Thr Ser Gly Ala Ile Ile Asn Ser Gln Asn Phe Asn Val Ser
            340                 345                 350

Gly Gly Ser Lys Leu Asn Leu Lys Ala Ser Gly Ser Thr Asn Thr Ala
        355                 360                 365

Phe Leu Ile Lys Asn Asn Leu Thr Leu Asn Ala Thr Gly Gly Asn Ile
    370                 375                 380

Glu Ile Lys Gln Val Glu Gly Thr Asp Ser Arg Ile Gln Lys Gly Val
385                 390                 395                 400

Val Ala Glu Gln Asn Ile Ile Phe Glu Gly Gly Asn Ile Thr Leu Gly
                405                 410                 415

Ser Gln Lys Ala Pro Thr Glu Ile Lys Gly Asp Val Thr Val Lys Gln
            420                 425                 430
```

-continued

```
Gly Thr Asn Ala Thr Leu Arg Ser Ala Asn Phe Asp Asn His Lys Gly
            435                 440                 445

Ala Leu Ile Val Asn Gly Asn Val Thr Ala Asn Gly Asn Leu Thr Ala
        450                 455                 460

Asp Gly Asp Thr Ile Lys Ile Lys Gly Asn Leu Asp Val Ala Gln Gly
465                 470                 475                 480

Ala Lys Phe Asn Gly Ser Thr Lys Asn Asn Leu Asn Ile Thr Gly Thr
                485                 490                 495

Phe Thr Asn Asn Gly Thr Ser Ile Ile Asp Ile Thr Gln Gly Val Val
                500                 505                 510

Asn Leu Gly Asn Val Thr Asn Asp Gly Lys Leu Asn Ile Thr Thr His
            515                 520                 525

Ala Lys Ser Gly Gln Lys Ser Ile Ile Arg Gly Asp Ile Ile Asn Lys
        530                 535                 540

Gln Gly Asn Leu Asn Ile Thr Asp Asn Asn Ser Asn Ala Glu Ile Glu
545                 550                 555                 560

Ile Gly Gly Asn Ile Ser Gln Lys Glu Gly Asn Leu Thr Ile Ser Ser
                565                 570                 575

Asp Lys Val Asn Ile Thr Lys Gln Ile Thr Ile Lys Ala Gly Val Asp
            580                 585                 590

Gly Glu Ser Ser Ser Ser Ser Thr Ala Ser Asp Ala Asn Leu Thr Ile
        595                 600                 605

Lys Thr Lys Glu Leu Thr Phe Thr Asp Asn Leu Asn Ile Ser Gly Phe
610                 615                 620

Asn Lys Ala Glu Ile Thr Ala Lys Asp Asn Ser Asp Leu Ile Ile Gly
625                 630                 635                 640

Lys Ala Ser Ser Asp Asn Ser Asn Ala Lys Gln Val Thr Phe Asp Lys
                645                 650                 655

Val Lys Asp Ser Lys Ile Ser Ala Gly Asn His Asn Val Thr Leu Asn
            660                 665                 670

Ser Lys Val Glu Thr Ser Asn Ser Asp Gly Ser Thr Gly Asn Gly Ser
        675                 680                 685

Asp Asp Asn Asn Ile Gly Leu Thr Ile Ser Ala Lys Asp Val Thr Val
690                 695                 700

Asn Ser Asn Ile Thr Ser His Lys Thr Val Asn Ile Ser Ala Ser Glu
705                 710                 715                 720

Gly Gly Ile Thr Thr Lys Ala Gly Thr Thr Ile Asn Ala Thr Thr Gly
                725                 730                 735

Ser Val Glu Val Thr Ala Lys Thr Gly Asp Ile Ser Gly Thr Ile Ser
            740                 745                 750

Gly Lys Thr Val Ser Val Thr Ala Ser Thr Gly Asp Leu Thr Val Arg
        755                 760                 765

Lys Ala Ala Thr Ile Ser Val Thr Glu Gly Ala Ala Thr Leu Thr Ala
770                 775                 780

Thr Gly Asn Thr Leu Thr Thr Glu Ala Gly Ser Ser Ile Thr Ser Thr
785                 790                 795                 800

Lys Gly Gln Val Asp Leu Ser Ala Gln Asp Gly Ser Ile Ala Gly Gln
                805                 810                 815

Ile Ser Ala Ala Asn Val Thr Leu Asn Thr Thr Gly Thr Leu Thr Thr
            820                 825                 830

Val Glu Gly Ser Asn Ile Lys Ala Thr Ser Gly Thr Leu Ala Ile Asn
        835                 840                 845

Ala Lys Asp Ala Lys Leu Asp Gly Thr Ala Ser Gly Asn Arg Thr Glu
```

```
              850            855            860
Val Asn Ala Thr Asn Ala Ser Gly Ser Gly Ser Val Thr Ala Lys Thr
865                 870                 875                 880

Ser Ser Asn Val Asn Ile Thr Gly Asp Leu Ser Thr Ile Asn Gly Leu
                885                 890                 895

Asn Ile Ile Ser Glu Asn Gly Arg Asn Thr Val Arg Leu Arg Gly Lys
            900                 905                 910

Glu Ile Asp Val Lys Tyr Ile Gln Pro Gly Val Ala Ser Val Glu Glu
        915                 920                 925

Val Ile Glu Ala Lys Arg Val Leu Glu Lys Val Lys Asp Leu Ser Asp
930                 935                 940

Glu Glu Arg Glu Thr Leu Ala Lys Leu Gly Val Ser Ala Val Arg Phe
945                 950                 955                 960

Val Glu Pro Asn Asn Ala Ile Thr Ile Asn Thr Gln Asn Glu Phe Thr
                965                 970                 975

Thr Arg Pro Ser Ser Gln Val Ile Ile Ser Glu Gly Lys Ala Cys Phe
            980                 985                 990

Ser Ser Gly Asn Gly Ala Ala Val Cys Thr Asn Val Ala Asp Asp Gly
        995                 1000                1005

Gln Pro
   1010
```

<210> SEQ ID NO 52
<211> LENGTH: 3015
<212> TYPE: DNA
<213> ORGANISM: Haemophilus influenzae

<400> SEQUENCE: 52

| | | | | | |
|---|---|---|---|---|---|
| ccggatgatg | taactattgc | cgcaggcgcg | ccaggacgta | acgatggttc | agtagacgac | 60 |
| ttttttccca | ctggaagagg | ggatgatgct | agtaatgcaa | aaacaaacca | tccagacaag | 120 |
| ccgacattaa | caaacacaac | tgttgagaac | gcattaaaaa | acaacacctt | tgttaacata | 180 |
| accgccaaaa | ataaaatcac | agttaatagc | gacatcaata | tcaaaggtgg | cgcccaccta | 240 |
| accctctata | gcaaaaacaa | taaaaaaagt | agcgttaaga | ttaatggcaa | tattacttct | 300 |
| accactaacg | gaaacttaac | tatttactcc | agcggctggg | ttgatatcca | taaaaacatt | 360 |
| acgcttaaca | caggttacct | gaatattacc | gctgggggtt | ctgtagcctt | cgagaaagcc | 420 |
| ggaaatgaga | aagggcgcca | agtatcagaa | tctgtaatca | agcccagggg | agttatcacc | 480 |
| tcaggtgtag | gggaaggctt | taggtttaat | aacgtctccc | taaatggcgt | tggcgcagga | 540 |
| ctgcgcttcg | ttggtcagaa | aaatatcagt | agcaactctt | ggagagaaaa | caccatcaaa | 600 |
| aacagattcg | atgggaattt | aaatatctca | ggaaaggtaa | atgtttcaat | ggatgtatcc | 660 |
| gggacaaagt | ggcatacaag | aattaacggg | cgcacctact | ggaatgtaac | cactctaaac | 720 |
| gttgcctcag | gtagtagttt | caatctcagt | atcgacgcca | gtggaatttc | ttcaggtaac | 780 |
| caggacgaca | taacaaatag | gggtttaaat | ggcataacat | ttaatggaga | aaacactttt | 840 |
| aatatcgcac | agggctcaac | agctaacttt | catatcaaaa | cgtcagtaat | gacccctaaa | 900 |
| cccaactcga | actacgcatt | atttaatgga | aatatttcag | ttttaggagg | aggaactgtc | 960 |
| actttgaac | ttatgcctc | atctagcacc | cacacaactt | ctggcgcaat | tataaattct | 1020 |
| aaaattttta | atgtctcagg | tgggtcaaaa | ttaaatctca | aggcttcagg | ctcaacaaat | 1080 |
| ccgcttttt | taataaaaaa | taatttaact | ttaaacgcta | ctggaggtaa | tatagaaatt | 1140 |
| aacaggttg | agggtaccga | ttcgcgcatt | caaaaaggtg | ttgtagccga | acaaaacata | 1200 |

-continued

```
tttttgaag ggggtaacat caccccttggc tcccaaaaag ccccaacaga aataaaaggc    1260 atgttaccg tcaaacaagg aaccaacgcc actctcagaa gcgcgaattt tgacaaccac    1320 aaggtgcct taattgtgaa tggaaacgtt accgccaatg caaccttac tgcggacggc     1380 acactatta aaataaaagg caatcttgat gttgcacaag cgctaaatt taacggcagc     1440 caaaaaaca acctaaacat tactggcacc tttaccaaca acggcacttc tataatcgat    1500 taacacaag gggtggtaaa ccttggtaat gttaccaatg acggcaaatt aaacatcacc    1560 ctcacgcca agagcggtca aaaaagcatt atccgcggag atataattaa caaacaaggg    1620 atttaaata ttacggacaa taatagtaat gctgaaattg aaattggcgg caatatctcg    1680 aaaaagaag gtaatctcac catttcttct gataaagtca atattaccaa acagataaca    1740 tcaaagcag gcgttgatgg ggagagttct agttcaagca cagcaagtga tgccaatcta    1800 ccattaaaa ccaaagagtt aacattcaca gacaatctaa acatttcagg ttttaataaa    1860 cagaaatta cagctaaaga taacagtgat ttaattattg gcaaggctag cagtgacaac    1920 gtaatgcta acaagtaac ctttgacaag gttaaagatt caaaaatctc agctggcaat    1980 acaatgtaa cactaaatag caaagtggaa acgtctaata gcgatggtag caccggaaac    2040 gtagcgatg acaacaatat cggcttaact atttccgcaa aagatgtaac ggtaaatagt    2100
atatcaccct ctcacaaaac agtaaatatc tctgcatcag aaggaggtat cactactaaa    2160 caggcacaa ccattaatgc gaccacaggt agcgtggaag taactgctaa acaggcgat     2220 ttagcggta cgatttccgg taagacagta agtgttacag caagcactgg cgatttaact    2280 ttaggaaag ctgcaaccat tagtgtgaca gaaggagctg caaccttaac cgcaacaggg    2340 ataccttga ctactgaagc cggttctagc atcacttcaa ctaagggtca ggtagacctt    2400 cagctcagg atggtagcat tgcaggacaa attagtgcag ctaatgtgac attaaatacc    2460 caggcacct taactactgt agaaggttca aacattaagg caaccagtgg caccttagct    2520 ttaacgcaa aagacgctaa gctagatggt acggcatcag gtaaccgtac agaagtaaat    2580 caactaacg caagtggttc tggtagcgtg actgcgaaaa cctcaagtaa tgtgaatatc    2640 ccggggatt taagcacaat aaatgggtta aatatcattt cggaaaatgg tagaaacact    2700 tgcgcttaa gaggcaagga aattgatgtg aaatatatcc aaccaggtgt agcaagcgta    2760 aagaggtaa ttgaagcgaa acgcgtcctt gagaaagtaa aagatttatc tgacgaagaa    2820 gagaaacac tagccaaact tggtgtaagt gctgtacgtt tcgttgagcc aaataatgcc    2880 ttacgatta atacacaaaa tgaatttaca accagaccgt caagtcaagt gataaatttct   2940 aaggtaagg cgtgttttctc aagtggtaat ggcgcagcag tatgtaccaa tgttgctgac    3000 atggacagc cgtag                                                     3015
```

<210> SEQ ID NO 53
<211> LENGTH: 1004
<212> TYPE: PRT
<213> ORGANISM: Haemophilus influenzae

<400> SEQUENCE: 53

| Pro | Asp | Asp | Val | Thr | Ile | Ala | Ala | Gly | Ala | Pro | Gly | Arg | Asn | Asp | Gly |
|-----|-----|-----|-----|-----|-----|-----|-----|-----|-----|-----|-----|-----|-----|-----|-----|
| 1 | | | | 5 | | | | | 10 | | | | | 15 | |

| Ser | Val | Asp | Asp | Phe | Phe | Pro | Thr | Gly | Arg | Gly | Asp | Asp | Ala | Ser | Asn |
| | | | 20 | | | | | 25 | | | | | 30 | | |

| Ala | Lys | Thr | Asn | His | Pro | Asp | Lys | Pro | Thr | Leu | Thr | Asn | Thr | Thr | Val |
| | | 35 | | | | | 40 | | | | | 45 | | | |

-continued

```
Glu Asn Ala Leu Lys Asn Asn Thr Phe Val Asn Ile Thr Ala Lys Asn
 50                  55                  60

Lys Ile Thr Val Asn Ser Asp Ile Asn Ile Lys Gly Ala His Leu
 65                  70                  75                  80

Thr Leu Tyr Ser Lys Asn Asn Lys Lys Ser Ser Val Lys Ile Asn Gly
                     85                  90                  95

Asn Ile Thr Ser Thr Asn Gly Asn Leu Thr Ile Tyr Ser Ser Gly
                100                 105                 110

Trp Val Asp Ile His Lys Asn Ile Thr Leu Asn Thr Gly Tyr Leu Asn
                115                 120                 125

Ile Thr Ala Gly Gly Ser Val Ala Phe Glu Lys Ala Gly Asn Glu Lys
    130                 135                 140

Gly Arg Gln Val Ser Glu Ser Val Ile Lys Ala Gln Gly Val Ile Thr
145                 150                 155                 160

Ser Gly Val Gly Glu Gly Phe Arg Phe Asn Asn Val Ser Leu Asn Gly
                165                 170                 175

Val Gly Ala Gly Leu Arg Phe Val Gly Gln Lys Asn Ile Ser Ser Asn
                180                 185                 190

Ser Trp Arg Glu Asn Thr Ile Lys Asn Arg Phe Asp Gly Asn Leu Asn
    195                 200                 205

Ile Ser Gly Lys Val Asn Val Ser Met Asp Val Ser Gly Thr Lys Trp
    210                 215                 220

His Thr Arg Ile Asn Gly Arg Thr Tyr Trp Asn Val Thr Thr Leu Asn
225                 230                 235                 240

Val Ala Ser Gly Ser Ser Phe Asn Leu Ser Ile Asp Ala Ser Gly Ile
                245                 250                 255

Ser Ser Gly Asn Gln Asp Asp Ile Thr Asn Arg Gly Leu Asn Gly Ile
                260                 265                 270

Thr Phe Asn Gly Glu Asn Thr Phe Asn Ile Ala Gln Gly Ser Thr Ala
                275                 280                 285

Asn Phe His Ile Lys Thr Ser Val Met Thr Pro Lys Pro Asn Ser Asn
290                 295                 300

Tyr Ala Leu Phe Asn Gly Asn Ile Ser Val Leu Gly Gly Thr Val
305                 310                 315                 320

Asn Phe Glu Leu Asn Ala Ser Ser Ser Thr His Thr Thr Ser Gly Ala
                325                 330                 335

Ile Ile Asn Ser Gln Asn Phe Asn Val Ser Gly Gly Ser Lys Leu Asn
            340                 345                 350

Leu Lys Ala Ser Gly Ser Thr Asn Thr Ala Phe Leu Ile Lys Asn Asn
        355                 360                 365

Leu Thr Leu Asn Ala Thr Gly Gly Asn Ile Glu Ile Lys Gln Val Glu
        370                 375                 380

Gly Thr Asp Ser Arg Ile Gln Lys Gly Val Val Ala Glu Gln Asn Ile
385                 390                 395                 400

Ile Phe Glu Gly Gly Asn Ile Thr Leu Gly Ser Gln Lys Ala Pro Thr
                405                 410                 415

Glu Ile Lys Gly Asp Val Thr Val Lys Gln Gly Thr Asn Ala Thr Leu
                420                 425                 430

Arg Ser Ala Asn Phe Asp Asn His Lys Gly Ala Leu Ile Val Asn Gly
        435                 440                 445

Asn Val Thr Ala Asn Gly Asn Leu Thr Ala Asp Gly Asp Thr Ile Lys
450                 455                 460
```

-continued

```
Ile Lys Gly Asn Leu Asp Val Ala Gln Gly Ala Lys Phe Asn Gly Ser
465                 470                 475                 480

Thr Lys Asn Asn Leu Asn Ile Thr Gly Thr Phe Thr Asn Asn Gly Thr
                485                 490                 495

Ser Ile Ile Asp Ile Thr Gln Gly Val Val Asn Leu Gly Asn Val Thr
            500                 505                 510

Asn Asp Gly Lys Leu Asn Ile Thr Thr His Ala Lys Ser Gly Gln Lys
        515                 520                 525

Ser Ile Ile Arg Gly Asp Ile Asn Lys Gln Gly Asn Leu Asn Ile
    530                 535                 540

Thr Asp Asn Asn Ser Asn Ala Glu Ile Glu Ile Gly Asn Ile Ser
545                 550                 555                 560

Gln Lys Glu Gly Asn Leu Thr Ile Ser Ser Asp Lys Val Asn Ile Thr
                565                 570                 575

Lys Gln Ile Thr Ile Lys Ala Gly Val Asp Gly Glu Ser Ser Ser Ser
            580                 585                 590

Ser Thr Ala Ser Asp Ala Asn Leu Thr Ile Lys Thr Lys Glu Leu Thr
        595                 600                 605

Phe Thr Asp Asn Leu Asn Ile Ser Gly Phe Asn Lys Ala Glu Ile Thr
610                 615                 620

Ala Lys Asp Asn Ser Asp Leu Ile Ile Gly Lys Ala Ser Ser Asp Asn
625                 630                 635                 640

Ser Asn Ala Lys Gln Val Thr Phe Asp Lys Val Lys Asp Ser Lys Ile
                645                 650                 655

Ser Ala Gly Asn His Asn Val Thr Leu Asn Ser Lys Val Glu Thr Ser
            660                 665                 670

Asn Ser Asp Gly Ser Thr Gly Asn Gly Ser Asp Asp Asn Asn Ile Gly
        675                 680                 685

Leu Thr Ile Ser Ala Lys Asp Val Thr Val Asn Ser Asn Ile Thr Ser
690                 695                 700

His Lys Thr Val Asn Ile Ser Ala Ser Glu Gly Gly Ile Thr Thr Lys
705                 710                 715                 720

Ala Gly Thr Thr Ile Asn Ala Thr Thr Gly Ser Val Glu Val Thr Ala
                725                 730                 735

Lys Thr Gly Asp Ile Ser Gly Thr Ile Ser Gly Lys Thr Val Ser Val
            740                 745                 750

Thr Ala Ser Thr Gly Asp Leu Thr Val Arg Lys Ala Ala Thr Ile Ser
        755                 760                 765

Val Thr Glu Gly Ala Ala Thr Leu Thr Ala Thr Gly Asn Thr Leu Thr
770                 775                 780

Thr Glu Ala Gly Ser Ser Ile Ser Thr Lys Gly Gln Val Asp Leu
785                 790                 795                 800

Ser Ala Gln Asp Gly Ser Ile Ala Gly Gln Ile Ser Ala Ala Asn Val
                805                 810                 815

Thr Leu Asn Thr Thr Gly Thr Leu Thr Thr Val Glu Gly Ser Asn Ile
            820                 825                 830

Lys Ala Thr Ser Gly Thr Leu Ala Ile Asn Ala Lys Asp Ala Lys Leu
        835                 840                 845

Asp Gly Thr Ala Ser Gly Asn Arg Thr Glu Val Asn Ala Thr Asn Ala
850                 855                 860

Ser Gly Ser Gly Ser Val Thr Ala Lys Thr Ser Ser Asn Val Asn Ile
865                 870                 875                 880

Thr Gly Asp Leu Ser Thr Ile Asn Gly Leu Asn Ile Ile Ser Glu Asn
```

```
                    885                 890                 895
Gly Arg Asn Thr Val Arg Leu Arg Gly Lys Glu Ile Asp Val Lys Tyr
                900                 905                 910
Ile Gln Pro Gly Val Ala Ser Val Glu Glu Val Ile Glu Ala Lys Arg
                915                 920                 925
Val Leu Glu Lys Val Lys Asp Leu Ser Asp Glu Arg Glu Thr Leu
                930                 935                 940
Ala Lys Leu Gly Val Ser Ala Val Arg Phe Val Glu Pro Asn Asn Ala
945                 950                 955                 960
Ile Thr Ile Asn Thr Gln Asn Glu Phe Thr Thr Arg Pro Ser Ser Gln
                965                 970                 975
Val Ile Ile Ser Glu Gly Lys Ala Cys Phe Ser Ser Gly Asn Gly Ala
                980                 985                 990
Ala Val Cys Thr Asn Val Ala Asp Asp Gly Gln Pro
                995                 1000
```

<210> SEQ ID NO 54
<211> LENGTH: 2997
<212> TYPE: DNA
<213> ORGANISM: Haemophilus influenzae

<400> SEQUENCE: 54

```
aaagagtggt tgttagaccc ggataatgta acaattgaag ccccttccta ttctcgcggt     60
aatgccggta tagatagtga attcccgggc ggttcgggca caaaggaaag ccctaaaaca    120
aacggcgaac agccgacagt attaaccaat gaaaccattt caaattatct gaaaagcggc    180
acctgggtaa tgaatataac agccaagaaa atcttaccg ttaacagctc aattaacatt    240
ggagacagct cccacttaat ccttcatagt gaaggcaaga taacggcgg tgttaagatt    300
aaagaagaca ttacctctaa tggcggaaac ttaaccattc aatccggcgg atgggttgat    360
gttcacaaaa atattacgct tggcacaggc accttgaata ttacagctaa aggatccata    420
gcctttgagg gaaacggtac agaaaaagcc cgcaacgcat caagcgctca aatcaccgcg    480
cagggaacta taaccaatac tggcgatcaa aaacaactca gacttaataa tgtatctatt    540
aatgggacgg gtataggttt aaattttgtt tcaattcagc ctaacacttc tcacagattt    600
gatgggagc ttattatttc agggagagta catgttaatc aaaccacacc taaaaacctg    660
tctttttgga aggtatccga tgaatcttat tggaatgtca gccatcttac cgtaaaagag    720
aagtcagcat tctcatttac caagtttgcg ttaaataaca atcatggccg agagacttcc    780
agataccgca aggtggagg tgtaatcttt cgctcaccta ccggtcacac aaatttcaca    840
gttaaacaag gctcagtggc taattttttca ttcaaggcaa aaaatgatac aaatcatgca    900
aatcaactcc cgattcagtt taactctaat atctcagtcg atggaggagg gaaagtcctt    960
ttttgtataa cctccaacta ctccggcaga tcagtgggga taggaatgtc tagcattaat   1020
gtttctgatg gctcaaacct tactttttaat tcttccattc gcggccagga agcctttaat   1080
atcagtaaag atttaaccat aaatgcaacc ggttcatttt ttgaacttgg caatactcg    1140
gatacctta atggtaatgg ctttaaccac gacgccatta atcaactca caatatatcc    1200
atcttaggtg gcaatgttac ccttggcggg caagattcaa gcagtaccat tacaggtaat   1260
atcaatatct ctcaggcagc aaatgttacc ttgcgagctt ataatggtaa cggtcgaaac   1320
aaacaactaa cccttggcaa tgtatctatt gaagggaatt taagtttaat cggtgcaagt   1380
gcaaatatta acggcaacct ttccgttaaa gaaaatgcta aatttaaagg ggaaacccaa   1440
```

-continued

```
gacaacttga acatcaccgg caccttatc aataacggcg actctaaaat caatatatct  1500
caaggagtgg taaaacttgg caatgttacc aatgatggta tttaaacat taccactcac  1560 gctaaacaca accaaagaag catcatcggc ggagatataa tcaacaaaaa aggaagctta  1620
aatattacag acagtaataa gaatgctgaa atccaaattg gcggcaatat ctcgcaaaaa  1680
gaaggcaatc tcacgatttc ttccgataaa atcaatatta ccaatcagat aacaatcaaa  1740
gcaggtgttg atggggagaa ttccgattca gacgcgacaa caatgccaa tctaaccatt  1800 aaaaccaaag aattgaaatt aacgcaagac ctaaatattt caggtttcaa taaagcagag  1860
attacagcta aagatggtag tgatttaact attggtaaca ccaatagtgc tgatagtact  1920
aatgccaaaa aagtaacctt taaccaggtt aaagattcaa aaatctctgc tggcgaccat  1980
aatgtgacac taaatagcaa agtggaaaca tctggtaata ctgacaacac tggagacggc  2040
agtggcaata atgccggctt aactattgcc gcgaaaaatg tagaagtaaa aaacaacatt  2100
acttctaaca aaacagtaaa tatcaccgcg tcagaaaaac ttaccaccaa agcggatgca  2160
accattaatg caaccactgg taacgtagaa gtgacagcca aaacaggtga tattaaggt  2220 gaagtcaaat ccacttccgg taatgtaaat attacagcaa acggcgacac gcttaatgta  2280
agtaatgttt caggcaatgc tgttaccatc actgcagata agggcaaatt aaccacccaa  2340
gcaagctcta gcattacctc aaacaatggc cagacaactc ttacagccaa ggatggcagt  2400
atcgcaggaa gcatcaatgc cgccaatgtg acattaaata ccacaggcac tttaactact  2460
gtagaaggtt caaacattaa cgcagccagt ggtaccttgg ttattaatgc aaaagatgct  2520
aagttgaacg gcgcggcatc aggtgaccac acagtagtaa atgcaactaa cgcaagtggc  2580
tctggtagtg tgactgcggt aacctcaagt aatgtgaata tcaccgggga tttaagtaca  2640
gtaaatggat taaatatcat ttcgaaaaat ggtagaaaca ccgtagtgtt aaaaggtact  2700
gaaattgagg tgaaatatat ccagccaggt gtagcaagtg tagaagaagt aattgaagcg  2760
aaacgcgtcc ttgagaaagt gaaagattta tctgatgaag aaagagaaac attagctaaa  2820
cttggtgtaa gtgctgtacg tttattgaa ccaaataata ccattacggt taacacacaa  2880
aatgagttta caaccagacc atcaagtcaa gtgacaattt ctgaaggtaa ggcgtgtttc  2940
tcaagtggta atggcgcagc agtatgtacc aatgttgctg acgatggaca gcagtag     2997
```

<210> SEQ ID NO 55
<211> LENGTH: 998
<212> TYPE: PRT
<213> ORGANISM: Haemophilus influenzae

<400> SEQUENCE: 55

```
Lys Glu Trp Leu Leu Asp Pro Asp Asn Val Thr Ile Glu Ala Pro Ser
  1               5                  10                  15

Tyr Ser Arg Gly Asn Ala Gly Ile Asp Ser Glu Phe Pro Gly Gly Ser
             20                  25                  30

Gly Thr Lys Glu Ser Pro Lys Thr Asn Gly Glu Gln Pro Thr Val Leu
         35                  40                  45

Thr Asn Glu Thr Ile Ser Asn Tyr Leu Lys Ser Gly Thr Trp Val Met
     50                  55                  60

Asn Ile Thr Ala Lys Lys Asn Leu Thr Val Asn Ser Ser Ile Asn Ile
 65                  70                  75                  80

Gly Asp Ser Ser His Leu Ile Leu His Ser Glu Gly Lys Asn Asn Gly
                 85                  90                  95

Gly Val Lys Ile Lys Glu Asp Ile Thr Ser Asn Gly Gly Asn Leu Thr
```

-continued

```
                100                 105                 110
Ile Gln Ser Gly Gly Trp Val Asp Val His Lys Asn Ile Thr Leu Gly
            115                 120                 125
Thr Gly Thr Leu Asn Ile Thr Ala Lys Gly Ser Ile Ala Phe Glu Gly
            130                 135                 140
Asn Gly Thr Glu Lys Ala Arg Asn Ala Ser Ala Gln Ile Thr Ala
145                 150                 155                 160
Gln Gly Thr Ile Thr Asn Thr Gly Asp Gln Lys Gln Leu Arg Leu Asn
            165                 170                 175
Asn Val Ser Ile Asn Gly Thr Gly Ile Gly Leu Asn Phe Val Ser Ile
            180                 185                 190
Gln Pro Asn Thr Ser His Arg Phe Asp Gly Glu Leu Ile Ile Ser Gly
            195                 200                 205
Arg Val His Val Asn Gln Thr Thr Pro Lys Asn Leu Ser Phe Trp Lys
            210                 215                 220
Val Ser Asp Glu Ser Tyr Trp Asn Val Ser His Leu Thr Val Lys Glu
225                 230                 235                 240
Lys Ser Ala Phe Ser Phe Thr Lys Phe Ala Leu Asn Asn Asn His Gly
            245                 250                 255
Arg Glu Thr Ser Arg Tyr Arg Lys Gly Gly Val Ile Phe Arg Ser
            260                 265                 270
Pro Thr Gly His Thr Asn Phe Thr Val Lys Gln Gly Ser Val Ala Asn
            275                 280                 285
Phe Ser Phe Lys Ala Lys Asn Asp Thr Asn His Ala Asn Gln Leu Pro
            290                 295                 300
Ile Gln Phe Asn Ser Asn Ile Ser Val Asp Gly Gly Lys Val Leu
305                 310                 315                 320
Phe Cys Ile Thr Ser Asn Tyr Ser Gly Arg Ser Val Gly Ile Gly Met
            325                 330                 335
Ser Ser Ile Asn Val Ser Asp Gly Ser Asn Leu Thr Phe Asn Ser Ser
            340                 345                 350
Ile Arg Gly Gln Glu Ala Phe Asn Ile Ser Lys Asp Leu Thr Ile Asn
            355                 360                 365
Ala Thr Gly Ser Phe Phe Glu Leu Gly Gln Tyr Ser Asp Thr Phe Asn
370                 375                 380
Gly Asn Gly Phe Asn His Asp Ala Ile Lys Ser Thr His Asn Ile Ser
385                 390                 395                 400
Ile Leu Gly Gly Asn Val Thr Leu Gly Gly Gln Asp Ser Ser Ser Thr
            405                 410                 415
Ile Thr Gly Asn Ile Asn Ile Ser Gln Ala Ala Asn Val Thr Leu Arg
            420                 425                 430
Ala Tyr Asn Gly Asn Gly Arg Asn Lys Gln Leu Thr Leu Gly Asn Val
            435                 440                 445
Ser Ile Glu Gly Asn Leu Ser Leu Ile Gly Ala Ser Ala Asn Ile Asn
            450                 455                 460
Gly Asn Leu Ser Val Lys Glu Asn Ala Lys Phe Lys Gly Glu Thr Gln
465                 470                 475                 480
Asp Asn Leu Asn Ile Thr Gly Thr Phe Ile Asn Asn Gly Asp Ser Lys
            485                 490                 495
Ile Asn Ile Ser Gln Gly Val Val Lys Leu Gly Asn Val Thr Asn Asp
            500                 505                 510
Gly Asp Leu Asn Ile Thr Thr His Ala Lys His Asn Gln Arg Ser Ile
            515                 520                 525
```

```
Ile Gly Gly Asp Ile Ile Asn Lys Lys Gly Ser Leu Asn Ile Thr Asp
    530                 535                 540

Ser Asn Lys Asn Ala Glu Ile Gln Ile Gly Gly Asn Ile Ser Gln Lys
545                 550                 555                 560

Glu Gly Asn Leu Thr Ile Ser Ser Asp Lys Ile Asn Ile Thr Asn Gln
                565                 570                 575

Ile Thr Ile Lys Ala Gly Val Asp Gly Glu Asn Ser Asp Ser Asp Ala
            580                 585                 590

Thr Asn Asn Ala Asn Leu Thr Ile Lys Thr Lys Glu Leu Lys Leu Thr
                595                 600                 605

Gln Asp Leu Asn Ile Ser Gly Phe Asn Lys Ala Glu Ile Thr Ala Lys
        610                 615                 620

Asp Gly Ser Asp Leu Thr Ile Gly Asn Thr Asn Ser Ala Asp Ser Thr
625                 630                 635                 640

Asn Ala Lys Lys Val Thr Phe Asn Gln Val Lys Asp Ser Lys Ile Ser
                645                 650                 655

Ala Gly Asp His Asn Val Thr Leu Asn Ser Lys Val Glu Thr Ser Gly
            660                 665                 670

Asn Thr Asp Asn Thr Gly Asp Gly Ser Gly Asn Asn Ala Gly Leu Thr
        675                 680                 685

Ile Ala Ala Lys Asn Val Glu Val Lys Asn Asn Ile Thr Ser Asn Lys
    690                 695                 700

Thr Val Asn Ile Thr Ala Ser Glu Lys Leu Thr Thr Lys Ala Asp Ala
705                 710                 715                 720

Thr Ile Asn Ala Thr Thr Gly Asn Val Glu Val Thr Ala Lys Thr Gly
                725                 730                 735

Asp Ile Lys Gly Glu Val Lys Ser Thr Ser Gly Asn Val Asn Ile Thr
            740                 745                 750

Ala Asn Gly Asp Thr Leu Asn Val Ser Asn Val Ser Gly Asn Ala Val
        755                 760                 765

Thr Ile Thr Ala Asp Lys Gly Lys Leu Thr Thr Gln Ala Ser Ser Ser
770                 775                 780

Ile Thr Ser Asn Asn Gly Gln Thr Thr Leu Thr Ala Lys Asp Gly Ser
785                 790                 795                 800

Ile Ala Gly Ser Ile Asn Ala Ala Asn Val Thr Leu Asn Thr Thr Gly
                805                 810                 815

Thr Leu Thr Thr Val Glu Gly Ser Asn Ile Asn Ala Ala Ser Gly Thr
            820                 825                 830

Leu Val Ile Asn Ala Lys Asp Ala Lys Leu Asn Gly Ala Ala Ser Gly
        835                 840                 845

Asp His Thr Val Val Asn Ala Thr Asn Ala Ser Gly Ser Gly Ser Val
    850                 855                 860

Thr Ala Val Thr Ser Ser Asn Val Asn Ile Thr Gly Asp Leu Ser Thr
865                 870                 875                 880

Val Asn Gly Leu Asn Ile Ile Ser Lys Asn Gly Arg Asn Thr Val Val
                885                 890                 895

Leu Lys Gly Thr Glu Ile Glu Val Lys Tyr Ile Gln Pro Gly Val Ala
            900                 905                 910

Ser Val Glu Glu Val Ile Glu Ala Lys Arg Val Leu Glu Lys Val Lys
        915                 920                 925

Asp Leu Ser Asp Glu Glu Arg Glu Thr Leu Ala Lys Leu Gly Val Ser
    930                 935                 940
```

```
Ala Val Arg Phe Ile Glu Pro Asn Asn Thr Ile Thr Val Asn Thr Gln
945                 950                 955                 960

Asn Glu Phe Thr Thr Arg Pro Ser Ser Gln Val Thr Ile Ser Glu Gly
            965                 970                 975

Lys Ala Cys Phe Ser Ser Gly Asn Gly Ala Ala Val Cys Thr Asn Val
        980                 985                 990

Ala Asp Asp Gly Gln Gln
        995

<210> SEQ ID NO 56
<211> LENGTH: 2979
<212> TYPE: DNA
<213> ORGANISM: Haemophilus influenzae

<400> SEQUENCE: 56
ccggataatg taacaattga agccccttcc tattctcgcg gtaatgccgg tatagatagt     60
gaattcccgg gcggttcggg cacaaaggaa agccctaaaa caaacggcga acagccgaca    120
gtattaacca atgaaaccat ttcaaattat ctgaaaagcg gcacctgggt aatgaatata    180
acagccaaga aaaatcttac cgttaacagc tcaattaaca ttggagacag ctcccactta    240
atccttcata gtgaaggcaa gaataacggc ggtgttaaga ttaaagaaga cattacctct    300
aatggcggaa acttaaccat tcaatccggc ggatgggttg atgttcacaa aaatattacg    360
cttggcacag gcaccttgaa tattacagct aaaggatcca tagcctttga gggaaacggt    420
acagaaaaag cccgcaacgc atcaagcgct caaatcaccg cgcagggaac tataaccaat    480
actggcgatc aaaaacaact cagacttaat aatgtatcta ttaatgggac gggtataggt    540
ttaaattttg tttcaattca gcctaacact tctcacagat tgatgggga gcttattatt    600
tcagggagag tacatgttaa tcaaaccaca cctaaaaacc tgtctttttg gaaggtatcc    660
gatgaatctt attggaatgt cagccatctt accgtaaaag agaagtcagc attctcattt    720
accaagtttg cgttaaataa caatcatggc cgagagactt ccagataccg caaggtgga    780
ggtgtaatct ttcgctcacc taccggtcac acaaatttca cagttaaaca aggctcagtg    840
gctaattttt cattcaaggc aaaaaatgat acaaatcatg caaatcaact cccgattcag    900
tttaactcta atatctcagt cgatggagga gggaaagtcc ttttttgtat aacctccaac    960
tactccggca gatcagtggg gataggaatg tctagcatta atgtttctga tggctcaaac   1020
cttacttta attcttccat tcgcggccag gaagccttta atatcagtaa agatttaacc   1080
ataaatgcaa ccgttcatt tttttgaactt gggcaatact cggataccttt aatggtaat   1140
ggctttaacc acgacgccat taaatcaact cacaatatat ccatcttagg tggcaatgtt   1200
acccttggcg ggcaagattc aagcagtacc attacaggta atatcaatat ctctcaggca   1260
gcaaatgtta ccttgcgagc ttataatggt aacggtcgaa acaaacaact aacccttggc   1320
aatgtatcta ttgaagggaa tttaagttta atcggtgcaa gtgcaaatat aacggcaac   1380
cttttccgtta agaaaatgc taaatttaaa ggggaaaccc aagacaactt gaacatcacc   1440
ggcaccttta tcaataacgg cgactctaaa atcaatatat ctcaaggagt ggtaaaactt   1500
ggcaatgtta ccaatgatgg tgatttaaac attaccactc acgctaaaca caaccaaaga   1560
agcatcatcg gcgagatat aatcaacaaa aaggaagct taaatattac agacagtaat   1620
aagaatgctg aaatccaaat tggcggcaat atctcgcaaa aagaaggcaa tctcacgatt   1680
tcttccgata aaatcaatat taccaatcag ataacaatca aagcaggtgt tgatggggag   1740
aattccgatt cagacgcgac aaacaatgcc aatctaacca ttaaaaccaa agaattgaaa   1800
```

```
ttaacgcaag acctaaatat ttcaggtttc aataaagcag agattacagc taaagatggt    1860
agtgatttaa ctattggtaa caccaatagt gctgatagta ctaatgccaa aaaagtaacc    1920
tttaaccagg ttaaagattc aaaaatctct gctggcgacc ataatgtgac actaaatagc    1980
aaagtggaaa catctggtaa tactgacaac actggagacg gcagtggcaa taatgccggc    2040
ttaactattg ccgcgaaaaa tgtagaagta aaaaacaaca ttacttctaa caaaacagta    2100
aatatcaccg cgtcagaaaa acttaccacc aaagcggatg caaccattaa tgcaaccact    2160
ggtaacgtag aagtgacagc caaaacaggt gatattaaag gtgaagtcaa atccacttcc    2220
ggtaatgtaa atattacagc aaacggcgac acgcttaatg taagtaatgt ttcaggcaat    2280
gctgttacca tcactgcaga taagggcaaa ttaaccaccc aagcaagctc tagcattacc    2340
tcaaacaatg ccagacaac  tcttacagcc aaggatggca gtatcgcagg aagcatcaat    2400
gccgccaatg tgacattaaa taccacaggc actttaacta ctgtagaagg ttcaaacatt    2460
aacgcagcca gtggtacctt ggttattaat gcaaaagatg ctaagttgaa cggcgcggca    2520
tcaggtgacc acacagtagt aaatgcaact aacgcaagtg gctctggtag tgtgactgcg    2580
gtaacctcaa gtaatgtgaa tatcaccggg gatttaagta cagtaaatgg attaaatatc    2640
atttcgaaaa atggtagaaa caccgtagtg ttaaaaggta ctgaaattga ggtgaaatat    2700
atccagccag gtgtagcaag tgtagaagaa gtaattgaag cgaaacgcgt ccttgagaaa    2760
gtgaaagatt tatctgatga agaaagagaa acattagcta aacttggtgt aagtgctgta    2820
cgttttattg aaccaaataa taccattacg gttaacacac aaaatgagtt tacaaccaga    2880
ccatcaagtc aagtgacaat ttctgaaggt aaggcgtgtt tctcaagtgg taatggcgca    2940
gcagtatgta ccaatgttgc tgacgatgga cagcagtag                           2979
```

<210> SEQ ID NO 57
<211> LENGTH: 992
<212> TYPE: PRT
<213> ORGANISM: Haemophilus influenzae

<400> SEQUENCE: 57

```
Pro Asp Asn Val Thr Ile Glu Ala Pro Ser Tyr Ser Arg Gly Asn Ala
  1               5                  10                  15

Gly Ile Asp Ser Glu Phe Pro Gly Gly Ser Gly Thr Lys Glu Ser Pro
             20                  25                  30

Lys Thr Asn Gly Glu Gln Pro Thr Val Leu Thr Asn Glu Thr Ile Ser
         35                  40                  45

Asn Tyr Leu Lys Ser Gly Thr Trp Val Met Asn Ile Thr Ala Lys Lys
     50                  55                  60

Asn Leu Thr Val Asn Ser Ser Ile Asn Ile Gly Asp Ser Ser His Leu
 65                  70                  75                  80

Ile Leu His Ser Glu Gly Lys Asn Asn Gly Val Lys Ile Lys Glu
                 85                  90                  95

Asp Ile Thr Ser Asn Gly Gly Asn Leu Thr Ile Gln Ser Gly Gly Trp
            100                 105                 110

Val Asp Val His Lys Asn Ile Thr Leu Gly Thr Gly Thr Leu Asn Ile
        115                 120                 125

Thr Ala Lys Gly Ser Ile Ala Phe Glu Gly Asn Gly Thr Glu Lys Ala
    130                 135                 140

Arg Asn Ala Ser Ser Ala Gln Ile Thr Ala Gln Gly Thr Ile Thr Asn
145                 150                 155                 160
```

-continued

Thr Gly Asp Gln Lys Gln Leu Arg Leu Asn Asn Val Ser Ile Asn Gly
                165                 170                 175

Thr Gly Ile Gly Leu Asn Phe Val Ser Ile Gln Pro Asn Thr Ser His
            180                 185                 190

Arg Phe Asp Gly Glu Leu Ile Ile Ser Gly Arg Val His Val Asn Gln
        195                 200                 205

Thr Thr Pro Lys Asn Leu Ser Phe Trp Lys Val Ser Asp Glu Ser Tyr
    210                 215                 220

Trp Asn Val Ser His Leu Thr Val Lys Glu Lys Ser Ala Phe Ser Phe
225                 230                 235                 240

Thr Lys Phe Ala Leu Asn Asn His Gly Arg Glu Thr Ser Arg Tyr
                245                 250                 255

Arg Lys Gly Gly Gly Val Ile Phe Arg Ser Pro Thr Gly His Thr Asn
                260                 265                 270

Phe Thr Val Lys Gln Gly Ser Val Ala Asn Phe Ser Phe Lys Ala Lys
            275                 280                 285

Asn Asp Thr Asn His Ala Asn Gln Leu Pro Ile Gln Phe Asn Ser Asn
    290                 295                 300

Ile Ser Val Asp Gly Gly Lys Val Leu Phe Cys Ile Thr Ser Asn
305                 310                 315                 320

Tyr Ser Gly Arg Ser Val Gly Ile Gly Met Ser Ser Ile Asn Val Ser
                325                 330                 335

Asp Gly Ser Asn Leu Thr Phe Asn Ser Ser Ile Arg Gly Gln Glu Ala
            340                 345                 350

Phe Asn Ile Ser Lys Asp Leu Thr Ile Asn Ala Thr Gly Ser Phe Phe
        355                 360                 365

Glu Leu Gly Gln Tyr Ser Asp Thr Phe Asn Gly Asn Gly Phe Asn His
    370                 375                 380

Asp Ala Ile Lys Ser Thr His Asn Ile Ser Ile Leu Gly Gly Asn Val
385                 390                 395                 400

Thr Leu Gly Gly Gln Asp Ser Ser Thr Ile Thr Gly Asn Ile Asn
                405                 410                 415

Ile Ser Gln Ala Ala Asn Val Thr Leu Arg Ala Tyr Asn Gly Asn Gly
            420                 425                 430

Arg Asn Lys Gln Leu Thr Leu Gly Asn Val Ser Ile Glu Gly Asn Leu
        435                 440                 445

Ser Leu Ile Gly Ala Ser Ala Asn Ile Asn Gly Asn Leu Ser Val Lys
450                 455                 460

Glu Asn Ala Lys Phe Lys Gly Glu Thr Gln Asp Asn Leu Asn Ile Thr
465                 470                 475                 480

Gly Thr Phe Ile Asn Asn Gly Asp Ser Lys Ile Asn Ile Ser Gln Gly
                485                 490                 495

Val Val Lys Leu Gly Asn Val Thr Asn Asp Gly Asp Leu Asn Ile Thr
            500                 505                 510

Thr His Ala Lys His Asn Gln Arg Ser Ile Ile Gly Asp Ile Ile
        515                 520                 525

Asn Lys Lys Gly Ser Leu Asn Ile Thr Asp Ser Asn Lys Asn Ala Glu
    530                 535                 540

Ile Gln Ile Gly Gly Asn Ile Ser Gln Lys Glu Gly Asn Leu Thr Ile
545                 550                 555                 560

Ser Ser Asp Lys Ile Asn Ile Thr Asn Gln Ile Thr Ile Lys Ala Gly
                565                 570                 575

Val Asp Gly Glu Asn Ser Asp Ser Asp Ala Thr Asn Asn Ala Asn Leu

-continued

```
            580                 585                 590
Thr Ile Lys Thr Lys Glu Leu Lys Leu Thr Gln Asp Leu Asn Ile Ser
        595                 600                 605

Gly Phe Asn Lys Ala Glu Ile Thr Ala Lys Asp Gly Ser Asp Leu Thr
        610                 615                 620

Ile Gly Asn Thr Asn Ser Ala Asp Ser Thr Asn Ala Lys Lys Val Thr
625                 630                 635                 640

Phe Asn Gln Val Lys Asp Ser Lys Ile Ser Ala Gly Asp His Asn Val
                645                 650                 655

Thr Leu Asn Ser Lys Val Glu Thr Ser Gly Asn Thr Asp Asn Thr Gly
            660                 665                 670

Asp Gly Ser Gly Asn Asn Ala Gly Leu Thr Ile Ala Ala Lys Asn Val
            675                 680                 685

Glu Val Lys Asn Asn Ile Thr Ser Asn Lys Thr Val Asn Ile Thr Ala
            690                 695                 700

Ser Glu Lys Leu Thr Thr Lys Ala Asp Ala Thr Ile Asn Ala Thr Thr
705                 710                 715                 720

Gly Asn Val Glu Val Thr Ala Lys Thr Gly Asp Ile Lys Gly Glu Val
                725                 730                 735

Lys Ser Thr Ser Gly Asn Val Asn Ile Thr Ala Asn Gly Asp Thr Leu
            740                 745                 750

Asn Val Ser Asn Val Ser Gly Asn Ala Val Thr Ile Thr Ala Asp Lys
            755                 760                 765

Gly Lys Leu Thr Thr Gln Ala Ser Ser Ile Thr Ser Asn Asn Gly
770                 775                 780

Gln Thr Thr Leu Thr Ala Lys Asp Gly Ser Ile Ala Gly Ser Ile Asn
785                 790                 795                 800

Ala Ala Asn Val Thr Leu Asn Thr Thr Gly Thr Leu Thr Thr Val Glu
                805                 810                 815

Gly Ser Asn Ile Asn Ala Ala Ser Gly Thr Leu Val Ile Asn Ala Lys
            820                 825                 830

Asp Ala Lys Leu Asn Gly Ala Ala Ser Gly Asp His Thr Val Val Asn
            835                 840                 845

Ala Thr Asn Ala Ser Gly Ser Gly Ser Val Thr Ala Val Thr Ser Ser
850                 855                 860

Asn Val Asn Ile Thr Gly Asp Leu Ser Thr Val Asn Gly Leu Asn Ile
865                 870                 875                 880

Ile Ser Lys Asn Gly Arg Asn Thr Val Val Leu Lys Gly Thr Glu Ile
                885                 890                 895

Glu Val Lys Tyr Ile Gln Pro Gly Val Ala Ser Val Glu Glu Val Ile
            900                 905                 910

Glu Ala Lys Arg Val Leu Glu Lys Val Lys Asp Leu Ser Asp Glu Glu
            915                 920                 925

Arg Glu Thr Leu Ala Lys Leu Gly Val Ser Ala Val Arg Phe Ile Glu
            930                 935                 940

Pro Asn Asn Thr Ile Thr Val Asn Thr Gln Asn Glu Phe Thr Thr Arg
945                 950                 955                 960

Pro Ser Ser Gln Val Thr Ile Ser Glu Gly Lys Ala Cys Phe Ser Ser
                965                 970                 975

Gly Asn Gly Ala Ala Val Cys Thr Asn Val Ala Asp Asp Gly Gln Gln
            980                 985                 990
```

<210> SEQ ID NO 58

-continued

<211> LENGTH: 3568
<212> TYPE: DNA
<213> ORGANISM: Haemophilus influenzae

<400> SEQUENCE: 58

```
gaattcggct tcgggatccc atatgccgga gaatgtatat attaatgcag gagacgcagg      60
gcgtagtgac actaatttag aaaacgaaga atacacagga acaggagaga gtgctgatac     120
tccaaaacga aacaataaca caaagacaac actaacaaac tcaacgcttg agaagatatt     180
agcaagaggc tcttttgtta atatcactgc caacaatgaa atcagagtta atagtgatat     240
caatatcgga ggcaactccc acctaaccct ctggagcagc aaaaataaaa acagtggcgt     300
tctgattaat ggcaatatca cttctactgc taacggaaac ttaaccattt actctagcgg     360
atgggttgat attcataaaa atattacgct tgaatcagga cgcttaaaca ttacaactaa     420
agaaggagat gtcgcctttg aaaagggaa taacctaacc attacaggtc aaggaactat     480
tacagcaggc aataataaag gctttagatt tgaaaatgtc tctctaaatg gcactgggac     540
tggcttgctt tttaatctca gtagaccaca aaaaacaat agtctcgtca caactatt      600
taatgggact ttaaatattt caggaagcgt aaatatctca atgattccac ctaatgctac     660
aagcaattgg tacagcagat acaaagggcg aacctattgg aatataaccc acttaaatgc     720
ctccgaagat agcaacttta accttactat tgactcctcg gcagaggatg gctcagcccc     780
tcttttatcc agttatacct aaacggcat atcattcacc acagatacca cctttaatgt     840
taataaaaat gcaaaagtca actttaacat caaagcacca ataggactaa taatcaata     900
caataacctg aattacgcat tattcaatgg gaacatttca gtttcaggag gggggaatgt     960
caccttcagg cttaacgctt catcctcaa ccagcaaacc cctggcgtaa ttataaattc    1020
taaacaccct tatgcttcaa aagggtcgag cttaagattt gaaactacag gttcaacaaa    1080
agtcggttt ttaatataa atgatttaac tttaaacgcc actggaggca atatatcgct    1140
cttgcaggtt gaaggcattg acgggatgat tggtgaaggc gttgtagcta aaaaaaacat    1200
aacctttact ggaggcaata tcacctttgg ctccaagaaa gccataacag aaatcaaagg    1260
caatgttact atcaatgaaa acaccaacgc cactcttatc ggttcggatt ttaacgatca    1320
taaaaaccct ttaaatataa aaggagatgt cgtcaataga ggcaacctta ccgctggcgg    1380
caatgttatc aatataggcg gaaatcttac cgttgaaaat ggcgccaatc ttaaagctat    1440
cacaaatttc acttttaatg taggcggctt gtttaacaac aaaggcaatt caaatatctc    1500
cattgctaga ggaggggcta aatttaaaga tatcaataac accagtagct taaatattac    1560
caccaactcc gacaccactt accgtaccat tatagaaggt aatataacca acaaagcagg    1620
tgatttgaat atcattgata taaaggtaa cgctgaaatc caaattggcg gcaacatctc    1680
gcaaaaagaa ggtaacctca cgatttcctc cgataaaatc aatattacca acagataac    1740
aatcaagaag ggtgttaacg gagagaactc tgattcaagt acgaaaagtc aagccaatct    1800
aaccattaaa accaaagaat tgaaattaac acaagaccta aatatttcag gcttcaacaa    1860
agcaaagatt gtagctaaag atagtagtaa tttaactatt ggtaatagtg atgatagcgg    1920
caatactagc gctaaaacag taacttttaa caatgttaaa gattcaaaaa tctctgctga    1980
cggtcacaag gtgacactaa atagcaaagt gaaaacactt agtgataatg ataacaacac    2040
tgaaggtggc agtgacaaca ataccggttt aactattact gcaaaagatg tagaagtaaa    2100
caacaatatt acttctcaca aaacagtgaa cgtctctgcg gcaaatggag ggattaccac    2160
taaaacaggt acaaccatta atgcaaccgc cggtaacgtg gagataaccg ctcatacagg    2220
```

-continued

```
cagtatccaa ggcggaattg agtccaagcc tggctctgtg acaattgtgg caggcggcga      2280
tactcttgct gtaggtaata tttcaggcaa cgccgttact gttactgcaa atagcggtgc      2340
attaaccact ttggcaggct ctacaattaa aggaaccgag agtataacca cttcaagtca      2400
atcaggtaat atcggcggta aaatttccgg caagacagta aacgttaaag caactaatag      2460
tttaaccacc caagcagact caaaaattga agcgactgaa ggcgaggcta atgtaacaag      2520
caaaacaagc ataattggcg gtacaatttc tggtggcaca gtagaagtta ccgcgaccga      2580
aggtttaacc acccaagcag gctctacgat tactggaacc gagagcgtga ccacttcaag      2640
ccaatcaggt aatatcggcg gcatgatttc tggtggcaaa gtagaagtta gcgcaaccaa      2700
agatttaatt actaaatccg gttcagagat taaagcaacg gcgggcgagg tgaatgtaac      2760
aagtgcaaca ggtacaattg acggtacgat ttccggtaat acggtaaatg ttacagcaaa      2820
tactggcgat ttaactgttg aagatgccgc aaaaattgat gcgacaggag gagccgcgac      2880
cctaactgca acatcgggca aattaaccac taaggctagt tcaagcatta cttcagctaa      2940
taaccaggta aacctttcag ctaaggatgg tagcattggg ggaaatatca atgctgctaa      3000
tgtaacactg aatactacag gcgctctaac taccgtgaag ggttcaagca ttaacgcaaa      3060
cagcggcacc ttggttatta acgcaaaaga cgctgagcta atggtgagg catcaggtaa      3120 ccatacagta gtgaatgcaa ccaacgcaaa tggctccggc agcgtaatcg cgacaacctc      3180
aagcagagtg aacatcactg gggatttaat cacaataaat ggattaaata tcatttcaaa      3240
aaacggtata aacaccgtac tgttaaaagg cgttaaaatt gatgtgaaat acattcaacc      3300
gggtatagca agcgtagatg aagtaattga agcgaaacgc atccttgaga aggtaaaaga      3360
tttatctgat gaagaaagag aagcgttagc taaacttggc gtaagcgctg tacgttttgc      3420
tgagccaaat aatgccatta cgattaatac acaaaatgag tttacaacca gaccatcaag      3480
tcaagtgaca atttctgaag gtaaggtatg tttcttaatc ggcaatggtg caacaatatg      3540
caccaatatt gctgatattg agcggtag                                         3568
```

<210> SEQ ID NO 59
<211> LENGTH: 1188
<212> TYPE: PRT
<213> ORGANISM: Haemophilus influenzae

<400> SEQUENCE: 59

```
Asn Ser Ala Ser Gly Ser His Met Pro Glu Asn Val Tyr Ile Asn Ala
  1               5                  10                  15

Gly Asp Ala Gly Arg Ser Asp Thr Asn Leu Glu Asn Glu Glu Tyr Thr
             20                  25                  30

Gly Thr Gly Glu Ser Ala Asp Thr Pro Lys Arg Asn Asn Asn Thr Lys
         35                  40                  45

Thr Thr Leu Thr Asn Ser Thr Leu Glu Lys Ile Leu Ala Arg Gly Ser
     50                  55                  60

Phe Val Asn Ile Thr Ala Asn Asn Glu Ile Arg Val Asn Ser Asp Ile
 65                  70                  75                  80

Asn Ile Gly Gly Asn Ser His Leu Thr Leu Trp Ser Ser Lys Asn Lys
                 85                  90                  95

Asn Ser Gly Val Leu Ile Asn Gly Asn Ile Thr Ser Thr Ala Asn Gly
            100                 105                 110

Asn Leu Thr Ile Tyr Ser Ser Gly Trp Val Asp Ile His Lys Asn Ile
        115                 120                 125
```

```
Thr Leu Glu Ser Gly Arg Leu Asn Ile Thr Thr Lys Glu Gly Asp Val
    130                 135                 140

Ala Phe Glu Lys Gly Asn Asn Leu Thr Ile Thr Gly Gln Gly Thr Ile
145                 150                 155                 160

Thr Ala Gly Asn Asn Lys Gly Phe Arg Phe Glu Asn Val Ser Leu Asn
                165                 170                 175

Gly Thr Gly Thr Gly Leu Leu Phe Asn Leu Ser Arg Pro Gln Lys Asn
            180                 185                 190

Asn Ser Leu Val Thr Asn Tyr Phe Asn Gly Thr Leu Asn Ile Ser Gly
            195                 200                 205

Ser Val Asn Ile Ser Met Ile Pro Pro Asn Ala Thr Ser Asn Trp Tyr
    210                 215                 220

Ser Arg Tyr Lys Gly Arg Thr Tyr Trp Asn Ile Thr His Leu Asn Ala
225                 230                 235                 240

Ser Glu Asp Ser Asn Phe Asn Leu Thr Ile Asp Ser Ser Ala Glu Asp
                245                 250                 255

Gly Ser Ala Pro Leu Leu Ser Ser Tyr Thr Leu Asn Gly Ile Ser Phe
            260                 265                 270

Thr Thr Asp Thr Thr Phe Asn Val Asn Lys Asn Ala Lys Val Asn Phe
    275                 280                 285

Asn Ile Lys Ala Pro Ile Gly Thr Ile Asn Gln Tyr Asn Asn Leu Asn
290                 295                 300

Tyr Ala Leu Phe Asn Gly Asn Ile Ser Val Ser Gly Gly Asn Val
305                 310                 315                 320

Thr Phe Arg Leu Asn Ala Ser Ser Asn Gln Gln Thr Pro Gly Val
                325                 330                 335

Ile Ile Asn Ser Lys His Leu Asn Ala Ser Lys Gly Ser Ser Leu Arg
            340                 345                 350

Phe Glu Thr Thr Gly Ser Thr Lys Val Gly Phe Leu Ile Asn Asn Asp
    355                 360                 365

Leu Thr Leu Asn Ala Thr Gly Gly Asn Ile Ser Leu Leu Gln Val Glu
370                 375                 380

Gly Ile Asp Gly Met Ile Gly Glu Gly Val Val Ala Lys Lys Asn Ile
385                 390                 395                 400

Thr Phe Thr Gly Gly Asn Ile Thr Phe Gly Ser Lys Lys Ala Ile Thr
                405                 410                 415

Glu Ile Lys Gly Asn Val Thr Ile Asn Glu Asn Thr Asn Ala Thr Leu
            420                 425                 430

Ile Gly Ser Asp Phe Asn Asp His Lys Lys Pro Leu Asn Ile Lys Gly
    435                 440                 445

Asp Val Val Asn Arg Gly Asn Leu Thr Ala Gly Asn Val Ile Asn
450                 455                 460

Ile Gly Gly Asn Leu Thr Val Glu Asn Gly Ala Asn Leu Lys Ala Ile
465                 470                 475                 480

Thr Asn Phe Thr Phe Asn Val Gly Leu Phe Asn Asn Lys Gly Asn
                485                 490                 495

Ser Asn Ile Ser Ile Ala Arg Gly Gly Ala Lys Phe Lys Asp Ile Asn
            500                 505                 510

Asn Thr Ser Ser Leu Asn Ile Thr Thr Asn Ser Asp Thr Thr Tyr Arg
    515                 520                 525

Thr Ile Ile Glu Gly Asn Ile Thr Asn Lys Ala Gly Asp Leu Asn Ile
530                 535                 540

Ile Asp Asn Lys Gly Asn Ala Glu Ile Gln Ile Gly Gly Asn Ile Ser
```

```
              545                 550                 555                 560
Gln Lys Glu Gly Asn Leu Thr Ile Ser Ser Asp Lys Ile Asn Ile Thr
                565                 570                 575
Lys Gln Ile Thr Ile Lys Lys Gly Val Asn Gly Glu Asn Ser Asp Ser
                580                 585                 590
Ser Thr Lys Ser Gln Ala Asn Leu Thr Ile Lys Thr Lys Glu Leu Lys
                595                 600                 605
Leu Thr Gln Asp Leu Asn Ile Ser Gly Phe Asn Lys Ala Lys Ile Val
                610                 615                 620
Ala Lys Asp Ser Ser Asn Leu Thr Ile Gly Asn Ser Asp Asp Ser Gly
625                 630                 635                 640
Asn Thr Ser Ala Lys Thr Val Thr Phe Asn Asn Val Lys Asp Ser Lys
                645                 650                 655
Ile Ser Ala Asp Gly His Lys Val Thr Leu Asn Ser Lys Val Lys Thr
                660                 665                 670
Leu Ser Asp Asn Asp Asn Thr Glu Gly Ser Asp Asn Asn Thr
                675                 680                 685
Gly Leu Thr Ile Thr Ala Lys Asp Val Glu Val Asn Asn Ile Thr
                690                 695                 700
Ser His Lys Thr Val Asn Val Ser Ala Ala Asn Gly Ile Thr Thr
705                 710                 715                 720
Lys Thr Gly Thr Thr Ile Asn Ala Thr Ala Gly Asn Val Glu Ile Thr
                725                 730                 735
Ala His Thr Gly Ser Ile Gln Gly Gly Ile Glu Ser Lys Pro Gly Ser
                740                 745                 750
Val Thr Ile Val Ala Gly Gly Asp Thr Leu Ala Val Gly Asn Ile Ser
                755                 760                 765
Gly Asn Ala Val Thr Val Thr Ala Asn Ser Gly Ala Leu Thr Thr Leu
                770                 775                 780
Ala Gly Ser Thr Ile Lys Gly Thr Glu Ser Ile Thr Thr Ser Ser Gln
785                 790                 795                 800
Ser Gly Asn Ile Gly Gly Lys Ile Ser Gly Lys Thr Val Asn Val Lys
                805                 810                 815
Ala Thr Asn Ser Leu Thr Thr Gln Ala Asp Ser Lys Ile Glu Ala Thr
                820                 825                 830
Glu Gly Glu Ala Asn Val Thr Ser Lys Thr Ser Ile Ile Gly Gly Thr
                835                 840                 845
Ile Ser Gly Gly Thr Val Glu Val Thr Ala Thr Glu Gly Leu Thr Thr
                850                 855                 860
Gln Ala Gly Ser Thr Ile Thr Gly Thr Glu Ser Val Thr Thr Ser Ser
865                 870                 875                 880
Gln Ser Gly Asn Ile Gly Gly Met Ile Ser Gly Lys Val Glu Val
                885                 890                 895
Ser Ala Thr Lys Asp Leu Ile Thr Lys Ser Gly Ser Glu Ile Lys Ala
                900                 905                 910
Thr Ala Gly Glu Val Asn Val Thr Ser Ala Thr Gly Thr Ile Asp Gly
                915                 920                 925
Thr Ile Ser Gly Asn Thr Val Asn Val Thr Ala Asn Thr Gly Asp Leu
                930                 935                 940
Thr Val Glu Asp Ala Ala Lys Ile Asp Ala Thr Gly Gly Ala Ala Thr
945                 950                 955                 960
Leu Thr Ala Thr Ser Gly Lys Leu Thr Thr Lys Ala Ser Ser Ser Ile
                965                 970                 975
```

-continued

```
Thr Ser Ala Asn Asn Gln Val Asn Leu Ser Ala Lys Asp Gly Ser Ile
            980                 985                 990
Gly Gly Asn Ile Asn Ala Ala Asn Val Thr Leu Asn Thr Thr Gly Ala
        995                1000                1005
Leu Thr Thr Val Lys Gly Ser Ser Ile Asn Ala Asn Ser Gly Thr Leu
   1010                1015                1020
Val Ile Asn Ala Lys Asp Ala Glu Leu Asn Gly Glu Ala Ser Gly Asn
1025                1030                1035                1040
His Thr Val Asn Ala Thr Asn Ala Asn Gly Ser Gly Ser Val Ile
            1045                1050                1055
Ala Thr Thr Ser Ser Arg Val Asn Ile Thr Gly Asp Leu Ile Thr Ile
        1060                1065                1070
Asn Gly Leu Asn Ile Ile Ser Lys Asn Gly Ile Asn Thr Val Leu Leu
   1075                1080                1085
Lys Gly Val Lys Ile Asp Val Lys Tyr Ile Gln Pro Gly Ile Ala Ser
1090                1095                1100
Val Asp Glu Val Ile Glu Ala Lys Arg Ile Leu Glu Lys Val Lys Asp
1105                1110                1115                1120
Leu Ser Asp Glu Glu Arg Glu Ala Leu Ala Lys Leu Gly Val Ser Ala
            1125                1130                1135
Val Arg Phe Ala Glu Pro Asn Asn Ala Ile Thr Ile Asn Thr Gln Asn
        1140                1145                1150
Glu Phe Thr Thr Arg Pro Ser Ser Gln Val Thr Ile Ser Glu Gly Lys
   1155                1160                1165
Val Cys Phe Leu Ile Gly Asn Gly Ala Thr Ile Cys Thr Asn Ile Ala
1170                1175                1180
Asp Ile Glu Arg
1185

<210> SEQ ID NO 60
<211> LENGTH: 3543
<212> TYPE: DNA
<213> ORGANISM: Haemophilus influenzae

<400> SEQUENCE: 60
ccggagaatg tatatattaa tgcaggagac gcagggcgta gtgacactaa tttagaaaac    60
gaagaataca caggaacagg agagagtgct gatactccaa acgaaacaa taacacaaag   120
acaacactaa caaactcaac gcttgagaag atattagcaa gaggctcttt tgttaatatc   180
actgccaaca atgaaatcag agttaatagt gatatcaata tcggaggcaa ctcccaccta   240
accctctgga gcagcaaaaa taaaacagt ggcgttctga ttaatggcaa tatcacttct   300
actgctaacg gaaacttaac catttactct agcggatggg ttgatattca taaaaatatt   360
acgcttgaat caggacgctt aaacattaca actaaagaag agatgtcgc ctttgaaaaa   420
gggaataacc taaccattac aggtcaagga actattacag caggcaataa taaaggcttt   480
agatttgaaa atgtctctct aaatggcact gggactggct tgctttttaa tctcagtaga   540
ccacaaaaaa acaatagtct cgtcacaaac tattttaatg ggactttaaa tatttcagga   600
agcgtaaata tctcaatgat tccacctaat gctacaagca attggtacag cagatacaaa   660
gggcgaacct attggaatat aacccactta aatgcctccg aagatagcaa ctttaacctt   720
actattgact cctcggcaga ggatggctca gcccctcttt tatccagtta taccttaaac   780
ggcatatcat tcaccacaga taccaccttt aatgttaata aaaatgcaaa agtcaacttt   840
```

```
aacatcaaag caccaatagg gactataaat caatacaata acctgaatta cgcattattc    900
aatgggaaca tttcagtttc aggaggggg aatgtcacct tcaggcttaa cgcttcatcc    960
tctaaccagc aaaccctgg cgtaattata aattctaaac accttaatgc ttcaaaaggg   1020
tcgagcttaa gatttgaaac tacaggttca acaaaagtcg gttttttaat aaataatgat   1080
ttaactttaa acgccactgg aggcaatata tcgctcttgc aggttgaagg cattgacggg   1140
atgattggtg aaggcgttgt agctaaaaaa aacataacct ttactggagg caatatcacc   1200
tttggctcca agaaagccat aacagaaatc aaaggcaatg ttactatcaa tgaaaacacc   1260
aacgccactc ttatcggttc ggattttaac gatcataaaa aacctttaaa tataaaagga   1320
gatgtcgtca atagaggcaa ccttaccgct ggcggcaatg ttatcaatat aggcggaaat   1380
cttaccgttg aaaatggcgc caatcttaaa gctatcacaa atttcacttt taatgtaggc   1440
ggcttgttta acaacaaagg caattcaaat atctccattg ctagaggagg ggctaaattt   1500
aaagatatca ataacaccag tagcttaaat attaccacca actccgacac cacttaccgt   1560
accattatag aagtaatat aaccaacaaa gcaggtgatt tgaatatcat tgataataaa   1620
ggtaacgctg aaatccaaat tggcggcaac atctcgcaaa aagaaggtaa cctcacgatt   1680
tcctccgata aaatcaatat taccaaacag ataacaatca agaagggtgt taacggagag   1740
aactctgatt caagtacgaa aagtcaagcc aatctaacca ttaaaaccaa agaattgaaa   1800
ttaacacaag acctaaatat ttcaggcttc aacaaagcaa agattgtagc taaagatagt   1860
agtaatttaa ctattggtaa tagtgatgat agcggcaata ctagcgctaa aacagtaact   1920
tttaacaatg ttaaagattc aaaaatctct gctgacggtc acaaggtgac actaaatagc   1980
aaagtgaaaa cacttagtga taatgataac aacactgaag gtggcagtga caacaatacc   2040
ggtttaacta ttactgcaaa agatgtagaa gtaaacaaca atattacttc tcacaaaaca   2100
gtgaacgtct ctgcggcaaa tggagggatt accactaaaa caggtacaac cattaatgca   2160
accgccggta acgtggagat aaccgctcat acaggcagta tccaaggcgg aattgagtcc   2220
aagcctggct ctgtgacaat tgtggcaggc ggcgatactc ttgctgtagg taatatttca   2280
ggcaacgccg ttactgttac tgcaaatagc ggtgcattaa ccactttggc aggctctaca   2340
attaaaggaa ccgagagtat aaccacttca agtcaatcag gtaatatcgg cggtaaaatt   2400
tccggcaaga cagtaaacgt taaagcaact aatagtttaa ccacccaagc agactcaaaa   2460
attgaagcga ctgaaggcga ggctaatgta acaagcaaaa caagcataat tggcggtaca   2520
atttctggtg gcacagtaga agttaccgcg accgaaggtt taaccaccca agcaggctct   2580
acgattactg gaaccgagag cgtgaccact tcaagccaat caggtaatat cggcggcatg   2640
atttctggtg gcaaagtaga agttagcgca accaaagatt taattactaa atccggttca   2700
gagattaaag caacggcggg cgaggtgaat gtaacaagtg caacaggtac aattgacggt   2760
acgatttccg gtaatacggt aaatgttaca gcaaatactg gcgatttaac tgttgaagat   2820
gccgcaaaaa ttgatgcgac aggaggagcc gcgaccctaa ctgcaacatc gggcaaatta   2880
accactaagg ctagttcaag cattacttca gctaataacc aggtaaacct ttcagctaag   2940
gatggtagca ttgggggaaa tatcaatgct gctaatgtaa cactgaatac tacaggcgct   3000
ctaactaccg tgaagggttc aagcattaac gcaaacagcg gcaccttggt tattaacgca   3060
aaagacgctg agctaaatgg tgaggcatca ggtaaccata cagtagtgaa tgcaaccaac   3120
gcaaatggct ccggcagcgt aatcgcgaca acctcaagca gagtgaacat cactggggat   3180
ttaatcacaa taaatggatt aaatatcatt tcaaaaaacg gtataaacac cgtactgtta   3240
```

```
aaaggcgtta aaattgatgt gaaatacatt caaccgggta tagcaagcgt agatgaagta      3300
attgaagcga aacgcatcct tgagaaggta aaagatttat ctgatgaaga agagaagcg       3360 ttagctaaac ttggcgtaag cgctgtacgt tttgctgagc caaataatgc cattacgatt      3420
aatacacaaa atgagtttac aaccagacca tcaagtcaag tgacaatttc tgaaggtaag      3480
gtatgtttct taatcggcaa tggtgcaaca atatgcacca atattgctga tattgagcgg      3540
tag                                                                    3543
```

<210> SEQ ID NO 61
<211> LENGTH: 1180
<212> TYPE: PRT
<213> ORGANISM: Haemophilus influenzae

<400> SEQUENCE: 61

```
Pro Glu Asn Val Tyr Ile Asn Ala Gly Asp Ala Gly Arg Ser Asp Thr
 1               5                  10                  15

Asn Leu Glu Asn Glu Glu Tyr Thr Gly Thr Gly Glu Ser Ala Asp Thr
            20                  25                  30

Pro Lys Arg Asn Asn Thr Lys Thr Thr Leu Thr Asn Ser Thr Leu
        35                  40                  45

Glu Lys Ile Leu Ala Arg Gly Ser Phe Val Asn Ile Thr Ala Asn Asn
    50                  55                  60

Glu Ile Arg Val Asn Ser Asp Ile Asn Ile Gly Gly Asn Ser His Leu
65                  70                  75                  80

Thr Leu Trp Ser Ser Lys Asn Lys Asn Ser Gly Val Leu Ile Asn Gly
                85                  90                  95

Asn Ile Thr Ser Thr Ala Asn Gly Asn Leu Thr Ile Tyr Ser Ser Gly
            100                 105                 110

Trp Val Asp Ile His Lys Asn Ile Thr Leu Glu Ser Gly Arg Leu Asn
        115                 120                 125

Ile Thr Thr Lys Glu Gly Asp Val Ala Phe Glu Lys Gly Asn Asn Leu
    130                 135                 140

Thr Ile Thr Gly Gln Gly Thr Ile Thr Ala Gly Asn Asn Lys Gly Phe
145                 150                 155                 160

Arg Phe Glu Asn Val Ser Leu Asn Gly Thr Gly Thr Gly Leu Leu Phe
                165                 170                 175

Asn Leu Ser Arg Pro Gln Lys Asn Asn Ser Leu Val Thr Asn Tyr Phe
            180                 185                 190

Asn Gly Thr Leu Asn Ile Ser Gly Ser Val Asn Ile Ser Met Ile Pro
        195                 200                 205

Pro Asn Ala Thr Ser Asn Trp Tyr Ser Arg Tyr Lys Gly Arg Thr Tyr
    210                 215                 220

Trp Asn Ile Thr His Leu Asn Ala Ser Glu Asp Ser Asn Phe Asn Leu
225                 230                 235                 240

Thr Ile Asp Ser Ser Ala Glu Asp Gly Ser Ala Pro Leu Leu Ser Ser
                245                 250                 255

Tyr Thr Leu Asn Gly Ile Ser Phe Thr Thr Asp Thr Phe Asn Val
            260                 265                 270

Asn Lys Asn Ala Lys Val Asn Phe Asn Ile Lys Ala Pro Ile Gly Thr
        275                 280                 285

Ile Asn Gln Tyr Asn Asn Leu Asn Tyr Ala Leu Phe Asn Gly Asn Ile
    290                 295                 300

Ser Val Ser Gly Gly Gly Asn Val Thr Phe Arg Leu Asn Ala Ser Ser
```

-continued

```
305                 310                 315                 320
Ser Asn Gln Gln Thr Pro Gly Val Ile Ile Asn Ser Lys His Leu Asn
                325                 330                 335

Ala Ser Lys Gly Ser Ser Leu Arg Phe Glu Thr Thr Gly Ser Thr Lys
                340                 345                 350

Val Gly Phe Leu Ile Asn Asn Asp Leu Thr Leu Asn Ala Thr Gly Gly
                355                 360                 365

Asn Ile Ser Leu Leu Gln Val Glu Gly Ile Asp Gly Met Ile Gly Glu
            370                 375                 380

Gly Val Val Ala Lys Lys Asn Ile Thr Phe Thr Gly Gly Asn Ile Thr
385                 390                 395                 400

Phe Gly Ser Lys Lys Ala Ile Thr Glu Ile Lys Gly Asn Val Thr Ile
                405                 410                 415

Asn Glu Asn Thr Asn Ala Thr Leu Ile Gly Ser Asp Phe Asn Asp His
                420                 425                 430

Lys Lys Pro Leu Asn Ile Lys Gly Asp Val Val Asn Arg Gly Asn Leu
            435                 440                 445

Thr Ala Gly Gly Asn Val Ile Asn Ile Gly Gly Asn Leu Thr Val Glu
450                 455                 460

Asn Gly Ala Asn Leu Lys Ala Ile Thr Asn Phe Thr Phe Asn Val Gly
465                 470                 475                 480

Gly Leu Phe Asn Asn Lys Gly Asn Ser Asn Ile Ser Ile Ala Arg Gly
                485                 490                 495

Gly Ala Lys Phe Lys Asp Ile Asn Asn Thr Ser Ser Leu Asn Ile Thr
                500                 505                 510

Thr Asn Ser Asp Thr Thr Tyr Arg Thr Ile Ile Glu Gly Asn Ile Thr
            515                 520                 525

Asn Lys Ala Gly Asp Leu Asn Ile Ile Asp Asn Lys Gly Asn Ala Glu
            530                 535                 540

Ile Gln Ile Gly Gly Asn Ile Ser Gln Lys Glu Gly Asn Leu Thr Ile
545                 550                 555                 560

Ser Ser Asp Lys Ile Asn Ile Thr Lys Gln Ile Thr Ile Lys Lys Gly
                565                 570                 575

Val Asn Gly Glu Asn Ser Asp Ser Ser Thr Lys Ser Gln Ala Asn Leu
            580                 585                 590

Thr Ile Lys Thr Lys Glu Leu Lys Leu Thr Gln Asp Leu Asn Ile Ser
        595                 600                 605

Gly Phe Asn Lys Ala Lys Ile Val Ala Lys Asp Ser Ser Asn Leu Thr
    610                 615                 620

Ile Gly Asn Ser Asp Asp Ser Gly Asn Thr Ser Ala Lys Thr Val Thr
625                 630                 635                 640

Phe Asn Asn Val Lys Asp Ser Lys Ile Ser Ala Asp Gly His Lys Val
                645                 650                 655

Thr Leu Asn Ser Lys Val Lys Thr Leu Ser Asp Asn Asp Asn Asn Thr
            660                 665                 670

Glu Gly Gly Ser Asp Asn Asn Thr Gly Leu Thr Ile Thr Ala Lys Asp
            675                 680                 685

Val Glu Val Asn Asn Asn Ile Thr Ser His Lys Thr Val Asn Val Ser
        690                 695                 700

Ala Ala Asn Gly Gly Ile Thr Thr Lys Thr Gly Thr Thr Ile Asn Ala
705                 710                 715                 720

Thr Ala Gly Asn Val Glu Ile Thr Ala His Thr Gly Ser Ile Gln Gly
                725                 730                 735
```

-continued

```
Gly Ile Glu Ser Lys Pro Gly Ser Val Thr Ile Val Ala Gly Gly Asp
            740                 745                 750
Thr Leu Ala Val Gly Asn Ile Ser Gly Asn Ala Val Thr Val Thr Ala
        755                 760                 765
Asn Ser Gly Ala Leu Thr Thr Leu Ala Gly Ser Thr Ile Lys Gly Thr
    770                 775                 780
Glu Ser Ile Thr Thr Ser Ser Gln Ser Gly Asn Ile Gly Gly Lys Ile
785                 790                 795                 800
Ser Gly Lys Thr Val Asn Val Lys Ala Thr Asn Ser Leu Thr Thr Gln
                805                 810                 815
Ala Asp Ser Lys Ile Glu Ala Thr Gly Glu Ala Asn Val Thr Ser
            820                 825                 830
Lys Thr Ser Ile Ile Gly Gly Thr Ile Ser Gly Gly Thr Val Glu Val
        835                 840                 845
Thr Ala Thr Glu Gly Leu Thr Thr Gln Ala Gly Ser Thr Ile Thr Gly
    850                 855                 860
Thr Glu Ser Val Thr Thr Ser Ser Gln Ser Gly Asn Ile Gly Gly Met
865                 870                 875                 880
Ile Ser Gly Gly Lys Val Glu Val Ser Ala Thr Lys Asp Leu Ile Thr
                885                 890                 895
Lys Ser Gly Ser Glu Ile Lys Ala Thr Ala Gly Glu Val Asn Val Thr
            900                 905                 910
Ser Ala Thr Gly Thr Ile Asp Gly Thr Ile Ser Gly Asn Thr Val Asn
        915                 920                 925
Val Thr Ala Asn Thr Gly Asp Leu Thr Val Glu Asp Ala Ala Lys Ile
    930                 935                 940
Asp Ala Thr Gly Gly Ala Ala Thr Leu Thr Ala Thr Ser Gly Lys Leu
945                 950                 955                 960
Thr Thr Lys Ala Ser Ser Ser Ile Thr Ser Ala Asn Asn Gln Val Asn
                965                 970                 975
Leu Ser Ala Lys Asp Gly Ser Ile Gly Gly Asn Ile Asn Ala Ala Asn
            980                 985                 990
Val Thr Leu Asn Thr Thr Gly Ala Leu Thr Thr Val Lys Gly Ser Ser
        995                 1000                1005
Ile Asn Ala Asn Ser Gly Thr Leu Val Ile Asn Ala Lys Asp Ala Glu
    1010                1015                1020
Leu Asn Gly Glu Ala Ser Gly Asn His Thr Val Val Asn Ala Thr Asn
1025                1030                1035                1040
Ala Asn Gly Ser Gly Ser Val Ile Ala Thr Thr Ser Ser Arg Val Asn
                1045                1050                1055
Ile Thr Gly Asp Leu Ile Thr Ile Asn Gly Leu Asn Ile Ile Ser Lys
            1060                1065                1070
Asn Gly Ile Asn Thr Val Leu Leu Lys Gly Val Lys Ile Asp Val Lys
        1075                1080                1085
Tyr Ile Gln Pro Gly Ile Ala Ser Val Asp Glu Val Ile Glu Ala Lys
    1090                1095                1100
Arg Ile Leu Glu Lys Val Lys Asp Leu Ser Asp Glu Glu Arg Glu Ala
1105                1110                1115                1120
Leu Ala Lys Leu Gly Val Ser Ala Val Arg Phe Ala Glu Pro Asn Asn
                1125                1130                1135
Ala Ile Thr Ile Asn Thr Gln Asn Glu Phe Thr Thr Arg Pro Ser Ser
            1140                1145                1150
```

```
Gln Val Thr Ile Ser Glu Gly Lys Val Cys Phe Leu Ile Gly Asn Gly
        1155                1160                1165

Ala Thr Ile Cys Thr Asn Ile Ala Asp Ile Glu Arg
 1170                1175                1180

<210> SEQ ID NO 62
<211> LENGTH: 5116
<212> TYPE: DNA
<213> ORGANISM: Haemophilus influenzae

<400> SEQUENCE: 62
acagcgttct cttaatacta gtacaaaccc acaataaaat atgacaaaca acaattacaa      60
cacctttttt gcagtctata tgcaaatatt ttaaaaaata gtataaatcc gccatataaa     120
atggtataat ctttcatctt tcatctttca tctttcatct ttcatctttc atctttcatc     180
tttcatcttt catctttcat ctttcatctt tcatctttca tctttcatct ttcatctttc     240
acatgccctg atgaaccgag ggaagggagg gaggggcaag aatgaagagg gagctgaacg     300
aacgcaaatg ataaagtaat ttaattgttc aactaacctt aggagaaaat atgaacaagc     360
tatatcgtct caaattcagc aaacgcctga atgctttggt tgctgtgtct gaattggcac     420
ggggttgtga ccattccaca gaaaaaggca gcgaaaaacc tgctcgcatg aaagtgcgtc     480
acttagcgtt aaagccactt tccgctatgt tactatccttt aggtgtaaca tctattccac     540
aatctgtttt agcaagcggc ttacaaggaa tggatgtagt acacggcaca gccactatgc     600
aagtagatgg taataaaacc attatccgca acagtgttga cgatatcatt aattggaaac     660
aatttaacat cgaccaaaat gaaatggtgc agttttttaca agaaaacaac aactccgccg     720
tattcaaccg tgttcatctc aaccaaatct cccaattaaa agggatttta gattctaacg     780
gacaagtctt tttaatcaac ccaaatggta tcacaatagg taaagacgca attattaaca     840
ctaatggctt tacggcttct acgctagaca tttctaacga aaacatcaag gcgcgtaatt     900
tcaccttcga gcaaaccaaa gataaagcgc tcgctgaaat tgtgaatcac ggtttaatta     960
ctgtcggtaa agacggcagt gtaaatctta ttggtggcaa agtgaaaaac gagggtgtga    1020
ttagcgtaaa tggtggcagc atttctttac tcgcagggca aaaaatcacc atcagcgata    1080
taataaaccc aaccattact tacagcattg ccgcgcctga aatgaagcg gtcaatctgg     1140 gcgatatttt tgccaaaggc ggtaacatta atgtccgtgc tgccactatt cgaaaccaag    1200
gtaaactttc tgctgattct gtaagcaaag ataaaagcgg caatattgtt ctttccgcca    1260
aagagggtga agcggaaatt ggcggtgtaa tttccgctca aaatcagcaa gctaaaggcg    1320
gcaagctgat gattacaggc gataaagtca cattaaaaaac aggtgcagtt atcgaccttt    1380
caggtaaaga aggggagaa acttaccttg gcggtgacga gcgcggcgaa ggtaaaaagg    1440
gcattcaatt agcaaagaaa acctctttag aaaaaggctc aaccatcaat gtatcaggca    1500
aagaaaaagg cggacgcgct attgtgtggg gcgatattgc gttaattgac ggcaatatta    1560
acgctcaagg tagtggtgat atcgctaaaa ccggtggttt tgtggagacg tcggggcatg    1620
atttattcat caaagacaat gcaattgttg acgccaaaga gtggttgtta gacccggata    1680
atgtatctat taatgcagaa acagcaggac gcagcaatac ttcagaagac gatgaataca    1740
cgggatccgg aatagtgcc agcacccaa acgaaacaa agaaaagaca acattaacaa    1800
acacaactct tgagagtata ctaaaaaaag gtaccctttgt taacatcact gctaatcaac    1860
gcatctatgt caatagctcc attaattat ccaatggcag cttaactctt tggagtgagg    1920
gtcggagcgg tggcggcgtt gagattaaca acgatattac caccggtgat gataccagag    1980
```

-continued

```
gtgcaaactt aacaatttac tcaggcggct gggttgatgt tcataaaaat atctcactcg   2040
gggcgcaagg taacataaac attacagcta acaagatat cgcctttgag aaaggaagca    2100
accaagtcat tacaggtcaa gggactatta cctcaggcaa tcaaaaaggt tttagattta   2160
ataatgtctc tctaaacggc actggcagcg gactgcaatt caccactaaa agaaccaata   2220
aatacgctat cacaaataaa tttgaaggga ctttaaatat ttcagggaaa gtgaacatct   2280
caatggtttt acctaaaaat gaaagtggat atgataaatt caaggacgc acttactgga    2340 atttaacctc cttaaatgtt tccgagagtg gcgagtttaa cctcactatt gactccagag   2400
gaagcgatag tgcaggcaca cttacccagc cttataattt aaacggtata tcattcaaca   2460
aagacactac ctttaatgtt gaacgaaatg caagagtcaa ctttgacatc aaggcaccaa   2520
tagggataaa taagtattct agtttgaatt acgcatcatt taatggaaac atttcagttt   2580
cgggaggggg gagtgttgat ttcacacttc tcgcctcatc ctctaacgtc caaaccccg    2640 gtgtagttat aaattctaaa tactttaatg tttcaacagg gtcaagttta agatttaaaa   2700
cttcaggctc aacaaaaact ggcttctcaa tagagaaaga tttaacttta aatgccaccg   2760
gaggcaacat aacacttttg caagttgaag gcaccgatgg aatgattggt aaaggcattg   2820
tagccaaaaa aaacataacc tttgaaggag gtaacatcac ctttggctcc aggaaagccg   2880
taacagaaat cgaaggcaat gttactatca ataacaacgc taacgtcact cttatcggtt   2940
cggattttga caaccatcaa aaacctttaa ctattaaaaa agatgtcatc attaatagcg   3000
gcaaccttac cgctggaggc aatattgtca atatagccgg aaatcttacc gttgaaagta   3060
acgctaattt caaagctatc acaaatttca cttttaatgt aggcggcttg tttgacaaca   3120
aaggcaattc aaatatttcc attgccaaag gagggctcg ctttaaagac attgataatt    3180
ccaagaattt aagcatcacc accaactcca gctccactta ccgcactatt ataagcggca   3240
atataaccaa taaaaacggt gatttaaata ttacgaacga aggtagtgat actgaaatgc   3300
aaattggcgg cgatgtctcg caaaaagaag gtaatctcac gatttcttct gacaaaatca   3360
atattaccaa acagataaca atcaaggcag gtgttgatgg ggagaattcc gattcagacg   3420
cgacaaacaa tgccaatcta accattaaaa ccaagaatt gaaattaacg caagacctaa    3480
atatttcagg tttcaataaa gcagagatta cagctaaaga tggtagtgat ttaactattg   3540
gtaacaccaa tagtgctgat ggtactaatg ccaaaaaagt aacctttaac caggttaaag   3600
attcaaaaat ctctgctgac ggtcacaagg tgacactaca cagcaaagtg gaaacatccg   3660
gtagtaataa caacactgaa gatagcagtg acaataatgc cggcttaact atcgatgcaa   3720
aaaatgtaac agtaaacaac aatattactt ctcacaaagc agtgagcatc tctgcgacaa   3780
gtggagaaat taccactaaa acaggtacaa ccattaacgc aaccactggt aacgtggaga   3840
taaccgctca aacaggtagt atcctaggtg gaattgagtc cagctctggc tctgtaacac   3900
ttactgcaac cgagggcgct cttgctgtaa gcaatatttc gggcaacacc gttactgtta   3960
ctgcaaatag cggtgcatta accactttgg caggctctac aattaaagga accgagagtg   4020
taaccacttc aagtcaatca ggcgatatcg gcggtacgat ttctggtggc acagtagagg   4080
ttaaagcaac cgaaagttta accactcaat ccaattcaaa aattaaagca acaacaggcg   4140
aggctaacgt aacaagtgca acaggtacaa ttggtggtac gatttccggt aatacggtaa   4200
atgttacggc aaacgctggc gatttaacag ttgggaatgg cgcagaaatt aatgcgacag   4260
aaggagctgc aaccttaact acatcatcgg gcaaattaac taccgaagct agttcacaca   4320
```

```
ttacttcagc caagggtcag gtaaatcttt cagctcagga tggtagcgtt gcaggaagta    4380
ttaatgccgc caatgtgaca ctaaatacta caggcacttt aactaccgtg aagggttcaa    4440
acattaatgc aaccagcggt accttggtta ttaacgcaaa agacgctgag ctaaatggcg    4500
cagcattggg taaccacaca gtggtaaatg caaccaacgc aaatggctcc ggcagcgtaa    4560
tcgcgacaac ctcaagcaga gtgaacatca ctggggattt aatcacaata aatggattaa    4620
atatcatttc aaaaaacggt ataaacaccg tactgttaaa aggcgttaaa attgatgtga    4680
aatacattca accgggtata gcaagcgtag atgaagtaat tgaagcgaaa cgcatccttg    4740
agaaggtaaa agatttatct gatgaagaaa gagaagcgtt agctaaactt ggagtaagtg    4800
ctgtacgttt tattgagcca aataatacaa ttacagtcga tacacaaaat gaatttgcaa    4860
ccagaccatt aagtcgaata gtgatttctg aaggcagggc gtgtttctca acagtgatg    4920
gcgcgacggt gtgcgttaat atcgctgata acgggcggta gcggtcagta attgacaagg    4980
tagatttcat cctgcaatga agtcattta ttttcgtatt atttactgtg tgggttaaag    5040
ttcagtacgg gctttaccca tcttgtaaaa aattacggag aatacaataa agtattttta    5100
acaggttatt attatg                                                    5116
```

<210> SEQ ID NO 63
<211> LENGTH: 1536
<212> TYPE: PRT
<213> ORGANISM: Haemophilus influenzae

<400> SEQUENCE: 63

```
Met Asn Lys Leu Tyr Arg Leu Lys Phe Ser Lys Arg Leu Asn Ala Leu
1               5                   10                  15

Val Ala Val Ser Glu Leu Ala Arg Gly Cys Asp His Ser Thr Glu Lys
            20                  25                  30

Gly Ser Glu Lys Pro Ala Arg Met Lys Val Arg His Leu Ala Leu Lys
        35                  40                  45

Pro Leu Ser Ala Met Leu Leu Ser Leu Gly Val Thr Ser Ile Pro Gln
    50                  55                  60

Ser Val Leu Ala Ser Gly Leu Gln Gly Met Asp Val Val His Gly Thr
65                  70                  75                  80

Ala Thr Met Gln Val Asp Gly Asn Lys Thr Ile Ile Arg Asn Ser Val
            85                  90                  95

Asp Asp Ile Ile Asn Trp Lys Gln Phe Asn Ile Asp Gln Asn Glu Met
            100                 105                 110

Val Gln Phe Leu Gln Glu Asn Asn Ser Ala Val Phe Asn Arg Val
        115                 120                 125

Thr Ser Asn Gln Ile Ser Gln Leu Lys Gly Ile Leu Asp Ser Asn Gly
    130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Phe Glu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
```

```
            225                 230                 235                 240

Ile Ser Asp Ile Ile Asn Pro Thr Ile Thr Tyr Ser Ile Ala Ala Pro
                245                 250                 255

Glu Asn Glu Ala Val Asn Leu Gly Asp Ile Phe Ala Lys Gly Gly Asn
                260                 265                 270

Ile Asn Val Arg Ala Ala Thr Ile Arg Asn Gln Gly Lys Leu Ser Ala
                275                 280                 285

Asp Ser Val Ser Lys Asp Lys Ser Gly Asn Ile Val Leu Ser Ala Lys
                290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Gly Glu Thr Tyr
                340                 345                 350

Leu Gly Gly Asp Glu Arg Gly Glu Gly Lys Lys Gly Ile Gln Leu Ala
                355                 360                 365

Lys Lys Thr Ser Leu Glu Lys Gly Ser Thr Ile Asn Val Ser Gly Lys
                370                 375                 380

Glu Lys Gly Gly Arg Ala Ile Val Trp Gly Asp Ile Ala Leu Ile Asp
385                 390                 395                 400

Gly Asn Ile Asn Ala Gln Gly Ser Gly Asp Ile Ala Lys Thr Gly Gly
                405                 410                 415

Phe Val Glu Thr Ser Gly His Asp Leu Phe Ile Lys Asp Asn Ala Ile
                420                 425                 430

Val Asp Ala Lys Glu Trp Leu Leu Asp Pro Asp Asn Val Ser Ile Asn
                435                 440                 445

Ala Glu Thr Ala Gly Arg Ser Asn Thr Ser Glu Asp Asp Glu Tyr Thr
                450                 455                 460

Gly Ser Gly Asn Ser Ala Ser Thr Pro Lys Arg Asn Lys Glu Lys Thr
465                 470                 475                 480

Thr Leu Thr Asn Thr Thr Leu Glu Ser Ile Leu Lys Lys Gly Thr Phe
                485                 490                 495

Val Asn Ile Thr Ala Asn Gln Arg Ile Tyr Val Asn Ser Ser Ile Asn
                500                 505                 510

Leu Ser Asn Gly Ser Leu Thr Leu Trp Ser Glu Gly Arg Ser Gly Gly
                515                 520                 525

Gly Val Glu Ile Asn Asn Asp Ile Thr Thr Gly Asp Asp Thr Arg Gly
                530                 535                 540

Ala Asn Leu Thr Ile Tyr Ser Gly Gly Trp Val Asp Val His Lys Asn
545                 550                 555                 560

Ile Ser Leu Gly Ala Gln Gly Asn Ile Asn Ile Thr Ala Lys Gln Asp
                565                 570                 575

Ile Ala Phe Glu Lys Gly Ser Asn Gln Val Ile Thr Gly Gln Gly Thr
                580                 585                 590

Ile Thr Ser Gly Asn Gln Lys Gly Phe Arg Phe Asn Asn Val Ser Leu
                595                 600                 605

Asn Gly Thr Gly Ser Gly Leu Gln Phe Thr Thr Lys Arg Thr Asn Lys
                610                 615                 620

Tyr Ala Ile Thr Asn Lys Phe Glu Gly Thr Leu Asn Ile Ser Gly Lys
625                 630                 635                 640

Val Asn Ile Ser Met Val Leu Pro Lys Asn Glu Ser Gly Tyr Asp Lys
                645                 650                 655
```

```
Phe Lys Gly Arg Thr Tyr Trp Asn Leu Thr Ser Leu Asn Val Ser Glu
            660                 665                 670

Ser Gly Glu Phe Asn Leu Thr Ile Asp Ser Arg Gly Ser Asp Ser Ala
            675                 680                 685

Gly Thr Leu Thr Gln Pro Tyr Asn Leu Asn Gly Ile Ser Phe Asn Lys
            690                 695                 700

Asp Thr Thr Phe Asn Val Glu Arg Asn Ala Arg Val Asn Phe Asp Ile
705                 710                 715                 720

Lys Ala Pro Ile Gly Ile Asn Lys Tyr Ser Ser Leu Asn Tyr Ala Ser
                725                 730                 735

Phe Asn Gly Asn Ile Ser Val Ser Gly Gly Ser Val Asp Phe Thr
            740                 745                 750

Leu Leu Ala Ser Ser Asn Val Gln Thr Pro Gly Val Val Ile Asn
            755                 760                 765

Ser Lys Tyr Phe Asn Val Ser Thr Gly Ser Ser Leu Arg Phe Lys Thr
            770                 775                 780

Ser Gly Ser Thr Lys Thr Gly Phe Ser Ile Glu Lys Asp Leu Thr Leu
785                 790                 795                 800

Asn Ala Thr Gly Gly Asn Ile Thr Leu Leu Gln Val Glu Gly Thr Asp
                805                 810                 815

Gly Met Ile Gly Lys Gly Ile Val Ala Lys Lys Asn Ile Thr Phe Glu
            820                 825                 830

Gly Gly Asn Ile Thr Phe Gly Ser Arg Lys Ala Val Thr Glu Ile Glu
            835                 840                 845

Gly Asn Val Thr Ile Asn Asn Asn Ala Asn Val Thr Leu Ile Gly Ser
850                 855                 860

Asp Phe Asp Asn His Gln Lys Pro Leu Thr Ile Lys Lys Asp Val Ile
865                 870                 875                 880

Ile Asn Ser Gly Asn Leu Thr Ala Gly Gly Asn Ile Val Asn Ile Ala
            885                 890                 895

Gly Asn Leu Thr Val Glu Ser Asn Ala Asn Phe Lys Ala Ile Thr Asn
            900                 905                 910

Phe Thr Phe Asn Val Gly Gly Leu Phe Asp Asn Lys Gly Asn Ser Asn
            915                 920                 925

Ile Ser Ile Ala Lys Gly Gly Ala Arg Phe Lys Asp Ile Asp Asn Ser
            930                 935                 940

Lys Asn Leu Ser Ile Thr Thr Asn Ser Ser Thr Tyr Arg Thr Ile
945                 950                 955                 960

Ile Ser Gly Asn Ile Thr Asn Lys Asn Gly Asp Leu Asn Ile Thr Asn
            965                 970                 975

Glu Gly Ser Asp Thr Glu Met Gln Ile Gly Gly Asp Val Ser Gln Lys
            980                 985                 990

Glu Gly Asn Leu Thr Ile Ser Ser Asp Lys Ile Asn Ile Thr Lys Gln
            995                 1000                1005

Ile Thr Ile Lys Ala Gly Val Asp Gly Glu Asn Ser Asp Ser Asp Ala
    1010                1015                1020

Thr Asn Asn Ala Asn Leu Thr Ile Lys Thr Lys Glu Leu Lys Leu Thr
1025                1030                1035                1040

Gln Asp Leu Asn Ile Ser Gly Phe Asn Lys Ala Glu Ile Thr Ala Lys
                1045                1050                1055

Asp Gly Ser Asp Leu Thr Ile Gly Asn Thr Asn Ser Ala Asp Gly Thr
            1060                1065                1070
```

-continued

```
Asn Ala Lys Lys Val Thr Phe Asn Gln Val Lys Asp Ser Lys Ile Ser
        1075                1080                1085
Ala Asp Gly His Lys Val Thr Leu His Ser Lys Val Glu Thr Ser Gly
1090                1095                1100
Ser Asn Asn Asn Thr Glu Asp Ser Ser Asp Asn Ala Gly Leu Thr
1105                1110                1115                1120
Ile Asp Ala Lys Asn Val Thr Val Asn Asn Ile Thr Ser His Lys
        1125                1130                1135
Ala Val Ser Ile Ser Ala Thr Ser Gly Glu Ile Thr Thr Lys Thr Gly
        1140                1145                1150
Thr Thr Ile Asn Ala Thr Thr Gly Asn Val Glu Ile Thr Ala Gln Thr
        1155                1160                1165
Gly Ser Ile Leu Gly Gly Ile Glu Ser Ser Gly Ser Val Thr Leu
        1170                1175                1180
Thr Ala Thr Glu Gly Ala Leu Ala Val Ser Asn Ile Ser Gly Asn Thr
1185                1190                1195                1200
Val Thr Val Thr Ala Asn Ser Gly Ala Leu Thr Thr Leu Ala Gly Ser
                1205                1210                1215
Thr Ile Lys Gly Thr Glu Ser Val Thr Thr Ser Ser Gln Ser Gly Asp
                1220                1225                1230
Ile Gly Gly Thr Ile Ser Gly Gly Thr Val Glu Val Lys Ala Thr Glu
        1235                1240                1245
Ser Leu Thr Thr Gln Ser Asn Ser Lys Ile Lys Ala Thr Thr Gly Glu
        1250                1255                1260
Ala Asn Val Thr Ser Ala Thr Gly Thr Ile Gly Gly Thr Ile Ser Gly
1265                1270                1275                1280
Asn Thr Val Asn Val Thr Ala Asn Ala Gly Asp Leu Thr Val Gly Asn
                1285                1290                1295
Gly Ala Glu Ile Asn Ala Thr Glu Gly Ala Ala Thr Leu Thr Thr Ser
        1300                1305                1310
Ser Gly Lys Leu Thr Thr Glu Ala Ser Ser His Ile Thr Ser Ala Lys
        1315                1320                1325
Gly Gln Val Asn Leu Ser Ala Gln Asp Gly Ser Val Ala Gly Ser Ile
        1330                1335                1340
Asn Ala Ala Asn Val Thr Leu Asn Thr Thr Gly Thr Leu Thr Thr Val
1345                1350                1355                1360
Lys Gly Ser Asn Ile Asn Ala Thr Ser Gly Thr Leu Val Ile Asn Ala
                1365                1370                1375
Lys Asp Ala Glu Leu Asn Gly Ala Ala Leu Gly Asn His Thr Val Val
        1380                1385                1390
Asn Ala Thr Asn Ala Asn Gly Ser Gly Ser Val Ile Ala Thr Thr Ser
        1395                1400                1405
Ser Arg Val Asn Ile Thr Gly Asp Leu Ile Thr Ile Asn Gly Leu Asn
        1410                1415                1420
Ile Ile Ser Lys Asn Gly Ile Asn Thr Val Leu Leu Lys Gly Val Lys
1425                1430                1435                1440
Ile Asp Val Lys Tyr Ile Gln Pro Gly Ile Ala Ser Val Asp Glu Val
                1445                1450                1455
Ile Glu Ala Lys Arg Ile Leu Glu Lys Val Lys Asp Leu Ser Asp Glu
        1460                1465                1470
Glu Arg Glu Ala Leu Ala Lys Leu Gly Val Ser Ala Val Arg Phe Ile
        1475                1480                1485
Glu Pro Asn Asn Thr Ile Thr Val Asp Thr Gln Asn Glu Phe Ala Thr
```

```
              1490                1495                1500
         Arg Pro Leu Ser Arg Ile Val Ile Ser Glu Gly Arg Ala Cys Phe Ser
         1505                1510                1515                1520

Asn Ser Asp Gly Ala Thr Val Cys Val Asn Ile Ala Asp Asn Gly Arg
                        1525                1530                1535

<210> SEQ ID NO 64
<211> LENGTH: 3285
<212> TYPE: DNA
<213> ORGANISM: Haemophilus influenzae

<400> SEQUENCE: 64
ccggataatg tatctattaa tgcagaaaca gcaggacgca gcaatacttc agaagacgat      60
gaatacacgg gatccgggaa tagtgccagc accccaaaac gaaacaaaga aaagacaaca     120
ttaacaaaca caactcttga gagtatacta aaaaaggta cctttgttaa catcactgct      180
aatcaacgca tctatgtcaa tagctccatt aatttatcca atggcagctt aactcttggg     240
agtgagggtc ggagcggtgg cggcgttgag attaacaacg atattaccac cggtgatgat     300
accagaggtg caaacttaac aatttactca ggcggctggg ttgatgttca taaaaatatc     360
tcactcgggg cgcaaggtaa cataaacatt acagctaaac aagatatcgc ctttgagaaa     420
ggaagcaacc aagtcattac aggtcaaggg actattacct caggcaatca aaaggtttt      480
agatttaata atgtctctct aaacggcact ggcagcggac tgcaattcac cactaaaaga     540
accaataaat acgctatcac aaataaattt gaagggactt aaatatttc agggaaagtg      600
aacatctcaa tggtttttacc taaaaatgaa agtggatatg ataaattcaa aggacgcact     660
tactggaatt taacctcctt aaatgtttcc gagagtggcg agtttaacct cactattgac     720
tccagaggaa gcgatagtgc aggcacactt acccagcctt ataatttaaa cggtatatca     780
ttcaacaaag acactacctt taatgttgaa cgaaatgcaa gagtcaactt tgacatcaag     840
gcaccaatag ggataaataa gtattctagt ttgaattacg catcatttaa tggaaacatt     900
tcagtttcgg gaggggggag tgttgatttc acacttctcg cctcatcctc taacgtccaa     960
acccccggtg tagttataaa ttctaaatac tttaatgttt caacagggtc aagtttaaga    1020
tttaaaactt caggctcaac aaaaactggc ttctcaatag agaaagattt aactttaaat    1080
gccaccggag gcaacataac acttttgcaa gttgaaggca ccgatggaat gattggtaaa    1140
ggcattgtag ccaaaaaaaa cataaccttt gaaggaggta acatcacctt tggctccagg    1200
aaagccgtaa cagaaatcga aggcaatgtt actatcaata caacgctaa cgtcactctt      1260
atcggttcgg attttgacaa ccatcaaaaa cctttaacta ttaaaaaaga tgtcatcatt    1320
aatagcggca accttaccgc tggaggcaat attgtcaata tagccggaaa tcttaccgtt    1380
gaaagtaacg ctaatttcaa agctatcaca aatttcactt ttaatgtagg cggcttgttt    1440
gacaacaaag gcaattcaaa tatttccatt gccaaaggag gggctcgctt taaagacatt    1500
gataattcca agaatttaag catcaccacc aactccagct ccacttaccg cactattata    1560
agcggcaata taaccaataa aaacggtgat ttaaatatta cgaacgaagg tagtgatact    1620
gaaatgcaaa ttggcggcga tgtctcgcaa aagaaggta atctcacgat ttcttctgac     1680
aaaatcaata ttaccaaaca gataacaatc aaggcaggtt tgatgggga gaattccgat     1740
tcagacgcga caaacaatgc caatctaacc attaaaacca agaattgaa attaacgcaa     1800
gacctaaata tttcaggttt caataaagca gagattacag ctaaagatgg tagtgattta    1860
actattggta acaccaatag tgctgatggt actaatgcca aaaaagtaac ctttaaccag    1920
```

-continued

```
gttaaagatt caaaaatctc tgctgacggt cacaaggtga cactacacag caaagtggaa    1980
acatccggta gtaataacaa cactgaagat agcagtgaca ataatgccgg cttaactatc    2040
gatgcaaaaa atgtaacagt aaacaacaat attacttctc acaaagcagt gagcatctct    2100
gcgacaagtg gagaaattac cactaaaaca ggtacaacca ttaacgcaac cactggtaac    2160
gtggagataa ccgctcaaac aggtagtatc ctaggtggaa ttgagtccag ctctggctct    2220
gtaacactta ctgcaaccga gggcgctctt gctgtaagca atatttcggg caacaccgtt    2280
actgttactg caaatagcgg tgcattaacc actttggcag gctctacaat taaaggaacc    2340
gagagtgtaa ccacttcaag tcaatcaggc gatatcggcg gtacgatttc tggtggcaca    2400
gtagaggtta aagcaaccga aagtttaacc actcaatcca attcaaaaat taaagcaaca    2460
acaggcgagg ctaacgtaac aagtgcaaca ggtacaattg gtggtacgat tccggtaat     2520 acggtaaatg ttacggcaaa cgctggcgat ttaacagttg ggaatggcgc agaaattaat    2580
gcgacagaag gagctgcaac cttaactaca tcatcgggca aattaactac cgaagctagt    2640
tcacacatta cttcagccaa gggtcaggta aatctttcag ctcaggatgg tagcgttgca    2700
ggaagtatta atgccgccaa tgtgacacta aatactacag gcactttaac taccgtgaag    2760
ggttcaaaca ttaatgcaac cagcggtacc ttggttatta acgcaaaaga cgctgagcta    2820
aatggcgcag cattgggtaa ccacacagtg gtaaatgcaa ccaacgcaaa tggctccggc    2880
agcgtaatcg cgacaacctc aagcagagtg aacatcactg gggatttaat cacaataaat    2940
ggattaaata tcatttcaaa aaacggtata acaccgtac tgttaaaagg cgttaaaatt     3000
gatgtgaaat acattcaacc gggtatagca agcgtagatg aagtaattga agcgaaacgc    3060
atccttgaga aggtaaaaga tttatctgat gaagaaagag aagcgttagc taaacttgga    3120
gtaagtgctg tacgttttat tgagccaaat aatacaatta cagtcgatac acaaaatgaa    3180
tttgcaacca gaccattaag tcgaatagtg atttctgaag gcagggcgtg tttctcaaac    3240
agtgatggcg cgacggtgtg cgttaatatc gctgataacg ggcgg                   3285
```

<210> SEQ ID NO 65
<211> LENGTH: 1095
<212> TYPE: PRT
<213> ORGANISM: Haemophilus influenzae

<400> SEQUENCE: 65

```
Pro Asp Asn Val Ser Ile Asn Ala Glu Thr Ala Gly Arg Ser Asn Thr
  1               5                  10                  15

Ser Glu Asp Asp Glu Tyr Thr Gly Ser Gly Asn Ser Ala Ser Thr Pro
                 20                  25                  30

Lys Arg Asn Lys Glu Lys Thr Thr Leu Thr Asn Thr Thr Leu Glu Ser
             35                  40                  45

Ile Leu Lys Lys Gly Thr Phe Val Asn Ile Thr Ala Asn Gln Arg Ile
         50                  55                  60

Tyr Val Asn Ser Ser Ile Asn Leu Ser Asn Gly Ser Leu Thr Leu Trp
 65                  70                  75                  80

Ser Glu Gly Arg Ser Gly Gly Val Glu Ile Asn Asn Asp Ile Thr
                 85                  90                  95

Thr Gly Asp Asp Thr Arg Gly Ala Asn Leu Thr Ile Tyr Ser Gly Gly
            100                 105                 110

Trp Val Asp Val His Lys Asn Ile Ser Leu Gly Ala Gln Gly Asn Ile
            115                 120                 125
```

```
Asn Ile Thr Ala Lys Gln Asp Ile Ala Phe Glu Lys Gly Ser Asn Gln
    130                 135                 140

Val Ile Thr Gly Gln Gly Thr Ile Thr Ser Gly Asn Gln Lys Gly Phe
145                 150                 155                 160

Arg Phe Asn Asn Val Ser Leu Asn Gly Thr Gly Ser Gly Leu Gln Phe
                165                 170                 175

Thr Thr Lys Arg Thr Asn Lys Tyr Ala Ile Thr Asn Lys Phe Glu Gly
            180                 185                 190

Thr Leu Asn Ile Ser Gly Lys Val Asn Ile Ser Met Val Leu Pro Lys
        195                 200                 205

Asn Glu Ser Gly Tyr Asp Lys Phe Lys Gly Arg Thr Tyr Trp Asn Leu
    210                 215                 220

Thr Ser Leu Asn Val Ser Glu Ser Gly Glu Phe Asn Leu Thr Ile Asp
225                 230                 235                 240

Ser Arg Gly Ser Asp Ser Ala Gly Thr Leu Thr Gln Pro Tyr Asn Leu
                245                 250                 255

Asn Gly Ile Ser Phe Asn Lys Asp Thr Thr Phe Asn Val Glu Arg Asn
            260                 265                 270

Ala Arg Val Asn Phe Asp Ile Lys Ala Pro Ile Gly Ile Asn Lys Tyr
        275                 280                 285

Ser Ser Leu Asn Tyr Ala Ser Phe Asn Gly Asn Ile Ser Val Ser Gly
    290                 295                 300

Gly Gly Ser Val Asp Phe Thr Leu Leu Ala Ser Ser Asn Val Gln
305                 310                 315                 320

Thr Pro Gly Val Val Ile Asn Ser Lys Tyr Phe Asn Val Ser Thr Gly
                325                 330                 335

Ser Ser Leu Arg Phe Lys Thr Ser Gly Ser Thr Lys Thr Gly Phe Ser
            340                 345                 350

Ile Glu Lys Asp Leu Thr Leu Asn Ala Thr Gly Gly Asn Ile Thr Leu
        355                 360                 365

Leu Gln Val Glu Gly Thr Asp Gly Met Ile Gly Lys Gly Ile Val Ala
    370                 375                 380

Lys Lys Asn Ile Thr Phe Glu Gly Gly Asn Ile Thr Phe Gly Ser Arg
385                 390                 395                 400

Lys Ala Val Thr Glu Ile Glu Gly Asn Val Thr Ile Asn Asn Asn Ala
                405                 410                 415

Asn Val Thr Leu Ile Gly Ser Asp Phe Asp Asn His Gln Lys Pro Leu
            420                 425                 430

Thr Ile Lys Lys Asp Val Ile Ile Asn Ser Gly Asn Leu Thr Ala Gly
        435                 440                 445

Gly Asn Ile Val Asn Ile Ala Gly Asn Leu Thr Val Glu Ser Asn Ala
    450                 455                 460

Asn Phe Lys Ala Ile Thr Asn Phe Thr Phe Asn Val Gly Gly Leu Phe
465                 470                 475                 480

Asp Asn Lys Gly Asn Ser Asn Ile Ser Ile Ala Lys Gly Gly Ala Arg
                485                 490                 495

Phe Lys Asp Ile Asp Asn Ser Lys Asn Leu Ser Ile Thr Thr Asn Ser
            500                 505                 510

Ser Ser Thr Tyr Arg Thr Ile Ile Ser Gly Asn Ile Thr Asn Lys Asn
        515                 520                 525

Gly Asp Leu Asn Ile Thr Asn Glu Gly Ser Asp Thr Glu Met Gln Ile
    530                 535                 540

Gly Gly Asp Val Ser Gln Lys Glu Gly Asn Leu Thr Ile Ser Ser Asp
```

-continued

```
             545                 550                 555                 560
Lys Ile Asn Ile Thr Lys Gln Ile Thr Ile Lys Ala Gly Val Asp Gly
                 565                 570                 575
Glu Asn Ser Asp Ser Asp Ala Thr Asn Asn Ala Asn Leu Thr Ile Lys
             580                 585                 590
Thr Lys Glu Leu Lys Leu Thr Gln Asp Leu Asn Ile Ser Gly Phe Asn
         595                 600                 605
Lys Ala Glu Ile Thr Ala Lys Asp Gly Ser Asp Leu Thr Ile Gly Asn
     610                 615                 620
Thr Asn Ser Ala Asp Gly Thr Asn Ala Lys Lys Val Thr Phe Asn Gln
625                 630                 635                 640
Val Lys Asp Ser Lys Ile Ser Ala Asp Gly His Lys Val Thr Leu His
                 645                 650                 655
Ser Lys Val Glu Thr Gly Ser Asn Asn Asn Thr Glu Asp Ser Ser
             660                 665                 670
Asp Asn Asn Ala Gly Leu Thr Ile Asp Ala Lys Asn Val Thr Val Asn
             675                 680                 685
Asn Asn Ile Thr Ser His Lys Ala Val Ser Ile Ser Ala Thr Ser Gly
         690                 695                 700
Glu Ile Thr Thr Lys Thr Gly Thr Thr Ile Asn Ala Thr Thr Gly Asn
705                 710                 715                 720
Val Glu Ile Thr Ala Gln Thr Gly Ser Ile Leu Gly Ile Glu Ser
                 725                 730                 735
Ser Ser Gly Ser Val Thr Leu Thr Ala Thr Glu Gly Ala Leu Ala Val
             740                 745                 750
Ser Asn Ile Ser Gly Asn Thr Val Thr Val Thr Ala Asn Ser Gly Ala
             755                 760                 765
Leu Thr Thr Leu Ala Gly Ser Thr Ile Lys Gly Thr Glu Ser Val Thr
         770                 775                 780
Thr Ser Ser Gln Ser Gly Asp Ile Gly Gly Thr Ile Ser Gly Gly Thr
785                 790                 795                 800
Val Glu Val Lys Ala Thr Glu Ser Leu Thr Thr Gln Ser Asn Ser Lys
                 805                 810                 815
Ile Lys Ala Thr Thr Gly Glu Ala Asn Val Thr Ser Ala Thr Gly Thr
             820                 825                 830
Ile Gly Gly Thr Ile Ser Gly Asn Thr Val Asn Val Thr Ala Asn Ala
         835                 840                 845
Gly Asp Leu Thr Val Gly Asn Gly Ala Glu Ile Asn Ala Thr Glu Gly
     850                 855                 860
Ala Ala Thr Leu Thr Thr Ser Ser Gly Lys Leu Thr Thr Glu Ala Ser
865                 870                 875                 880
Ser His Ile Thr Ser Ala Lys Gly Gln Val Asn Leu Ser Ala Gln Asp
                 885                 890                 895
Gly Ser Val Ala Gly Ser Ile Asn Ala Asn Val Thr Leu Asn Thr
             900                 905                 910
Thr Gly Thr Leu Thr Thr Val Lys Gly Ser Asn Ile Asn Ala Thr Ser
         915                 920                 925
Gly Thr Leu Val Ile Asn Ala Lys Asp Ala Glu Leu Asn Gly Ala Ala
     930                 935                 940
Leu Gly Asn His Thr Val Val Asn Ala Thr Asn Ala Asn Gly Ser Gly
945                 950                 955                 960
Ser Val Ile Ala Thr Thr Ser Ser Arg Val Asn Ile Thr Gly Asp Leu
                 965                 970                 975
```

```
Ile Thr Ile Asn Gly Leu Asn Ile Ile Ser Lys Asn Gly Ile Asn Thr
            980                 985                 990
Val Leu Leu Lys Gly Val Lys Ile Asp Val Lys Tyr Ile Gln Pro Gly
        995                 1000                1005
Ile Ala Ser Val Asp Glu Val Ile Glu Ala Lys Arg Ile Leu Glu Lys
    1010                1015                1020
Val Lys Asp Leu Ser Asp Glu Glu Arg Glu Ala Leu Ala Lys Leu Gly
1025                1030                1035                1040
Val Ser Ala Val Arg Phe Ile Glu Pro Asn Asn Thr Ile Thr Val Asp
            1045                1050                1055
Thr Gln Asn Glu Phe Ala Thr Arg Pro Leu Ser Arg Ile Val Ile Ser
        1060                1065                1070
Glu Gly Arg Ala Cys Phe Ser Asn Ser Asp Gly Ala Thr Val Cys Val
    1075                1080                1085
Asn Ile Ala Asp Asn Gly Arg
    1090                1095
```

<210> SEQ ID NO 66
<211> LENGTH: 4937
<212> TYPE: DNA
<213> ORGANISM: Haemophilus influenzae

<400> SEQUENCE: 66

| | |
|---|---:|
| taaatataca agataataaa aataaatcaa gattttgtg atgacaaaca acaattacaa | 60 |
| cacctttttt gcagtctata tgcaaatatt ttaaaaaaat agtataaatc cgccatataa | 120 |
| aatggtataa tctttcatct ttcatcttta atctttcatc tttcatcttt catctttcat | 180 |
| ctttcatctt tcatctttca tctttcatct ttcatctttc atctttcatc tttcatcttt | 240 |
| cacatgaaat gatgaaccga gggaagggag ggaggggcaa gaatgaagag ggagctgaac | 300 |
| gaacgcaaat gataaagtaa tttaattgtt caactaacct taggagaaaa tatgaacaag | 360 |
| atatatcgtc tcaaattcag caaacgcctg aatgctttgg ttgctgtgtc tgaattggca | 420 |
| cggggttgtg accattccac agaaaaaggc ttccgctatg ttactatctt taggtgtaac | 480 |
| cacttagcgt taaagccact ttccgctatg ttactatctt taggtgtaac atctattcca | 540 |
| caatctgttt tagcaagcgg cttacaagga atggatgtag tacacggcac agccactatg | 600 |
| caagtagatg gtaataaaac cattatccgc aacagtgttg acgctatcat taattggaaa | 660 |
| caatttaaca tcgaccaaaa tgaaatggtg cagtttttac aagaaaacaa caactccgcc | 720 |
| gtattcaacc gtgttacatc taaccaaatc tcccaattaa aagggatttt agattctaac | 780 |
| ggacaagtct ttttaatcaa cccaaatggt atcacaatag gtaaagacgc aattattaac | 840 |
| actaatggct ttacggcttc tacgctagac atttctaacg aaaacatcaa ggcgcgtaat | 900 |
| ttcaccttcg agcaaaccaa agataaagcg ctcgctgaaa ttgtgaatca cggtttaatt | 960 |
| actgtcggta agacggcag tgtaaatctt attggtggca aagtgaaaaa cgagggtgtg | 1020 |
| attagcgtaa atggtggcag catttcttta ctcgcagggc aaaaaatcac catcagcgat | 1080 |
| ataataaacc caaccattac ttacagcatt gccgcgcctg aaaatgaagc ggtcaatctg | 1140 |
| ggcgatattt ttgccaaagg cggtaacatt aatgtccgtg ctgccactat tcgaaaccaa | 1200 |
| ggtaaacttt ctgctgattc tgtaagcaaa gataaagcg gcaatattgt tctttccgcc | 1260 |
| aaagagggtg aagcggaaat tggcggtgta atttccgctc aaaatcagca agctaaaggc | 1320 |
| ggcaagctga tgattacagg cgataaagtc acattaaaaa caggtgcagt tatcgacctt | 1380 |

```
tcaggtaaag aaggggaga aacttacctt ggcggtgacg agcgcggcga aggtaaaaac    1440
ggcattcaat tagcaaagaa aacctcttta gaaaaaggct caaccatcaa tgtatcaggc    1500
aaagaaaaag gcggacgcgc tattgtgtgg ggcgatattg cgttaattga cggcaatatt    1560
aacgctcaag gtagtggtga tatcgctaaa accggtggtt ttgtggagac atcggggcat    1620
tatttatcca ttgacagcaa tgcaattgtt aaaacaaaag agtggttgct agaccctgat    1680
gatgtaacaa ttgaagccga agacccccct cgcaataata ccggtataaa tgatgaattc    1740
ccaacaggca ccggtgaagc aagcgaccct aaaaaaaata gcgaactcaa acaacgcta    1800 accaatacaa ctatttcaaa ttatctgaaa acgcctgga caatgaatat aacggcatca    1860
agaaaactta ccgttaatag ctcaatcaac atcggaagca actcccactt aattctccat    1920
agtaaaggtc agcgtggcgg aggcgttcag attgatggaa atattacttc taaaggcgga    1980
aatttaacca tttattctgg cggatgggtt gatgttcata aaatattac gcttgatcag    2040 ggttttttaa atattaccgc cgcttccgta gcttttgaag gtggaaataa caaagcacgc    2100
gacgcggcaa atgctaaaat tgtcgcccag ggcactgtaa ccattacagg agagggaaaa    2160
gatttcaggg ctaacaacgt atctttaaac ggaacgggta aagtctgaa tatcatttca    2220 tcagtgaata atttaaccca caatcttagt ggcacaatta acatatctgg gaatataaca    2280
attaaccaaa ctacgagaaa gaacacctcg tattggcaaa ccagccatga ttcgcactgg    2340
aacgtcagtg ctcttaatct agagacaggc gcaaattta cctttattaa atacatttca    2400
agcaatagca aaggcttaac aacacagtat agaagctctg cagggtgaa ttttaacggc    2460 gtaaatggca acatgtcatt caatctcaaa gaaggagcga agttaatttt caaattaaaa    2520
ccaaacgaga acatgaacac aagcaaacct ttaccaattc ggttttttagc caatatcaca    2580 gccactggtg ggggctctgt ttttttgat atatatgcca accattctgg cagagggggct    2640 gagttaaaaa tgagtgaaat taatatctct aacggcgcta attttacctt aaattcccat    2700
gttcgcggcg atgacgcttt taaaatcaac aaagacttaa ccataaatgc aaccaattca    2760
aatttcagcc tcagacagac gaaagatgat ttttatgacg ggtacgcacg caatgccatc    2820
aattcaacct acaacatatc cattctgggc ggtaatgtca cccttggtgg acaaaactca    2880
agcagcagca ttacgggaa tattactatc gagaaagcag caaatgttac gctagaagcc    2940
aataacgccc ctaatcagca aaacataagg gatagagtta taaaacttgg cagcttgctc    3000
gttaatggga gtttaagttt aactggcgaa aatgcagata ttaaaggcaa tctcactatt    3060
tcagaaagcg ccacttttaa aggaaagact agagataccc taaatatcac cggcaatttt    3120
accaataatg gcactgccga aattaatata acacaaggag tggtaaaact tggcaatgtt    3180
accaatgatg gtgatttaaa cattaccact cacgctaaac gcaaccaaag aagcatcatc    3240
ggcggagata taatcaacaa aaaggaagc ttaaatatta cagacagtaa taatgatgct    3300
gaaatccaaa ttggcggcaa tatctcgcaa aagaaggca acctcacgat tcttccgat    3360 aaaattaata tcaccaaaca gataacaatc aaaagggta ttgatggaga ggactctagt    3420
tcagatgcga caagtaatgc caacctaact attaaaacca aagaattgaa attgacagaa    3480
gacctaagta tttcaggttt caataaagca gagattacag ccaaagatgg tagagattta    3540
actattggca acagtaatga cggtaacagc ggtgccgaag ccaaaacagt aacttttaac    3600
aatgttaaag attcaaaaat ctctgctgac ggtcacaatg tgacactaaa tagcaaagtg    3660 aaacatcta gcagcaatgg cggacgtgaa agcaatagcg acaacgatac cggcttaact    3720
attactgcaa aaaatgtaga agtaaacaaa gatattactt ctctcaaaac agtaaatatc    3780
```

```
accgcgtcgg aaaaggttac caccacagca ggctcgacca ttaacgcaac aaatggcaaa   3840
gcaagtatta caaccaaaac aggtgatatc agcggtacga tttccggtaa cacggtaagt   3900
gttagcgcga ctggtgattt aaccactaaa tccggctcaa aaattgaagc gaaatcgggt   3960
gaggctaatg taacaagtgc aacaggtaca attggcggta caatttccgg taatacggta   4020
aatgttacgg caaacgctgg cgatttaaca gttgggaatg gcgcagaaat taatgcgaca   4080
gaaggagctg caaccttaac cgcaacaggg aataccttga ctactgaagc cggttctagc   4140
atcacttcaa ctaagggtca ggtagacctc ttggctcaga atggtagcat cgcaggaagc   4200
attaatgctg ctaatgtgac attaaatact acaggcacct taaccaccgt ggcaggctcg   4260
gatattaaag caaccagcgg caccttggtt attaacgcaa aagatgctaa gctaaatggt   4320
gatgcatcag gtgatagtac agaagtgaat gcagtcaacg caagcggctc tggtagtgtg   4380
actgcggcaa cctcaagcag tgtgaatatc actggggatt taaacacagt aaatgggtta   4440
aatatcattt cgaaagatgg tagaaacact gtgcgcttaa gaggcaagga aattgaggtg   4500
aaatatatcc agccaggtgt agcaagtgta gaagaagtaa ttgaagcgaa acgcgtcctt   4560 gaaaagtaa aagatttatc tgatgaagaa agagaaacat tagctaaact tggtgtaagt   4620
gctgtacgtt ttgttgagcc aaataataca attacagtca atacacaaaa tgaatttaca   4680
accagaccgt caagtcaagt gataaatttct gaaggtaagg cgtgtttctc aagtggtaat   4740
ggcgcacgag tatgtaccaa tgttgctgac gatggacagc cgtagtcagt aattgacaag   4800
gtagatttca tcctgcaatg aagtcatttt attttcgtat tatttactgt gtgggttaaa   4860
gttcagtacg ggctttaccc atcttgtaaa aaattacgga gaatacaata aagtatttt   4920 aacaggttat tattatg                                                  4937
```

<210> SEQ ID NO 67  
<211> LENGTH: 1477  
<212> TYPE: PRT  
<213> ORGANISM: Haemophilus influenzae

<400> SEQUENCE: 67

```
Met Asn Lys Ile Tyr Arg Leu Lys Phe Ser Lys Arg Leu Asn Ala Leu
  1               5                  10                  15

Val Ala Val Ser Glu Leu Ala Arg Gly Cys Asp His Ser Thr Glu Lys
                 20                  25                  30

Gly Phe Arg Tyr Val Thr Ile Phe Arg Cys Asn His Leu Ala Leu Lys
             35                  40                  45

Pro Leu Ser Ala Met Leu Leu Ser Leu Gly Val Thr Ser Ile Pro Gln
         50                  55                  60

Ser Val Leu Ala Ser Gly Leu Gln Gly Met Asp Val Val His Gly Thr
 65                  70                  75                  80

Ala Thr Met Gln Val Asp Gly Asn Lys Thr Ile Ile Arg Asn Ser Val
                 85                  90                  95

Asp Ala Ile Ile Asn Trp Lys Gln Phe Asn Ile Asp Gln Asn Glu Met
            100                 105                 110

Val Gln Phe Leu Gln Glu Asn Asn Ser Ala Val Phe Asn Arg Val
            115                 120                 125

Thr Ser Asn Gln Ile Ser Gln Leu Lys Gly Ile Leu Asp Ser Asn Gly
        130                 135                 140

Gln Val Phe Leu Ile Asn Pro Asn Gly Ile Thr Ile Gly Lys Asp Ala
145                 150                 155                 160
```

-continued

```
Ile Ile Asn Thr Asn Gly Phe Thr Ala Ser Thr Leu Asp Ile Ser Asn
            165                 170                 175

Glu Asn Ile Lys Ala Arg Asn Phe Thr Phe Glu Gln Thr Lys Asp Lys
            180                 185                 190

Ala Leu Ala Glu Ile Val Asn His Gly Leu Ile Thr Val Gly Lys Asp
            195                 200                 205

Gly Ser Val Asn Leu Ile Gly Gly Lys Val Lys Asn Glu Gly Val Ile
210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
            245                 250                 255

Glu Asn Glu Ala Val Asn Leu Gly Asp Ile Phe Ala Lys Gly Gly Asn
            260                 265                 270

Ile Asn Val Arg Ala Ala Thr Ile Arg Asn Gln Gly Lys Leu Ser Ala
            275                 280                 285

Asp Ser Val Ser Lys Asp Lys Ser Gly Asn Ile Val Leu Ser Ala Lys
            290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
            325                 330                 335

Thr Gly Ala Val Ile Asp Leu Ser Gly Lys Glu Gly Gly Glu Thr Tyr
            340                 345                 350

Leu Gly Gly Asp Glu Arg Gly Glu Gly Lys Asn Gly Ile Gln Leu Ala
            355                 360                 365

Lys Lys Thr Ser Leu Glu Lys Gly Ser Thr Ile Asn Val Ser Gly Lys
370                 375                 380

Glu Lys Gly Gly Arg Ala Ile Val Trp Gly Asp Ile Ala Leu Ile Asp
385                 390                 395                 400

Gly Asn Ile Asn Ala Gln Gly Ser Gly Asp Ile Ala Lys Thr Gly Gly
            405                 410                 415

Phe Val Glu Thr Ser Gly His Tyr Leu Ser Ile Asp Ser Asn Ala Ile
            420                 425                 430

Val Lys Thr Lys Glu Trp Leu Leu Asp Pro Asp Val Thr Ile Glu
            435                 440                 445

Ala Glu Asp Pro Leu Arg Asn Asn Thr Gly Ile Asn Asp Glu Phe Pro
450                 455                 460

Thr Gly Thr Gly Glu Ala Ser Asp Pro Lys Lys Asn Ser Glu Leu Lys
465                 470                 475                 480

Thr Thr Leu Thr Asn Thr Thr Ile Ser Asn Tyr Leu Lys Asn Ala Trp
            485                 490                 495

Thr Met Asn Ile Thr Ala Ser Arg Lys Leu Thr Val Asn Ser Ser Ile
            500                 505                 510

Asn Ile Gly Ser Asn Ser His Leu Ile Leu His Ser Lys Gly Gln Arg
            515                 520                 525

Gly Gly Gly Val Gln Ile Gly Asp Ile Thr Ser Lys Gly Gly Asn
            530                 535                 540

Leu Thr Ile Tyr Ser Gly Gly Trp Val Asp Val His Lys Asn Ile Thr
545                 550                 555                 560

Leu Asp Gln Gly Phe Leu Asn Ile Thr Ala Ala Ser Val Ala Phe Glu
            565                 570                 575

Gly Gly Asn Asn Lys Ala Arg Asp Ala Ala Asn Ala Lys Ile Val Ala
```

-continued

```
            580                 585                 590
Gln Gly Thr Val Thr Ile Thr Gly Glu Gly Lys Asp Phe Arg Ala Asn
            595                 600                 605
Asn Val Ser Leu Asn Gly Thr Gly Lys Gly Leu Asn Ile Ile Ser Ser
            610                 615                 620
Val Asn Asn Leu Thr His Asn Leu Ser Gly Thr Ile Asn Ile Ser Gly
625                 630                 635                 640
Asn Ile Thr Ile Asn Gln Thr Thr Arg Lys Asn Thr Ser Tyr Trp Gln
                    645                 650                 655
Thr Ser His Asp Ser His Trp Asn Val Ser Ala Leu Asn Leu Glu Thr
                660                 665                 670
Gly Ala Asn Phe Thr Phe Ile Lys Tyr Ile Ser Ser Asn Ser Lys Gly
            675                 680                 685
Leu Thr Thr Gln Tyr Arg Ser Ser Ala Gly Val Asn Phe Asn Gly Val
            690                 695                 700
Asn Gly Asn Met Ser Phe Asn Leu Lys Glu Gly Ala Lys Val Asn Phe
705                 710                 715                 720
Lys Leu Lys Pro Asn Glu Asn Met Asn Thr Ser Lys Pro Leu Pro Ile
                725                 730                 735
Arg Phe Leu Ala Asn Ile Thr Ala Thr Gly Gly Ser Val Phe Phe
                740                 745                 750
Asp Ile Tyr Ala Asn His Ser Gly Arg Gly Ala Glu Leu Lys Met Ser
            755                 760                 765
Glu Ile Asn Ile Ser Asn Gly Ala Asn Phe Thr Leu Asn Ser His Val
770                 775                 780
Arg Gly Asp Asp Ala Phe Lys Ile Asn Lys Asp Leu Thr Ile Asn Ala
785                 790                 795                 800
Thr Asn Ser Asn Phe Ser Leu Arg Gln Thr Lys Asp Asp Phe Tyr Asp
                805                 810                 815
Gly Tyr Ala Arg Asn Ala Ile Asn Ser Thr Tyr Asn Ile Ser Ile Leu
            820                 825                 830
Gly Gly Asn Val Thr Leu Gly Gly Gln Asn Ser Ser Ser Ser Ile Thr
            835                 840                 845
Gly Asn Ile Thr Ile Glu Lys Ala Ala Asn Val Thr Leu Glu Ala Asn
850                 855                 860
Asn Ala Pro Asn Gln Gln Asn Ile Arg Asp Arg Val Ile Lys Leu Gly
865                 870                 875                 880
Ser Leu Leu Val Asn Gly Ser Leu Ser Leu Thr Gly Glu Asn Ala Asp
                885                 890                 895
Ile Lys Gly Asn Leu Thr Ile Ser Glu Ser Ala Thr Phe Lys Gly Lys
                900                 905                 910
Thr Arg Asp Thr Leu Asn Ile Thr Gly Asn Phe Thr Asn Asn Gly Thr
            915                 920                 925
Ala Glu Ile Asn Ile Thr Gln Gly Val Val Lys Leu Gly Asn Val Thr
            930                 935                 940
Asn Asp Gly Asp Leu Asn Ile Thr Thr His Ala Lys Arg Asn Gln Arg
945                 950                 955                 960
Ser Ile Ile Gly Gly Asp Ile Asn Lys Lys Gly Ser Leu Asn Ile
                965                 970                 975
Thr Asp Ser Asn Asn Asp Ala Glu Ile Gln Ile Gly Gly Asn Ile Ser
            980                 985                 990
Gln Lys Glu Gly Asn Leu Thr Ile Ser Ser Asp Lys Ile Asn Ile Thr
            995                 1000                1005
```

-continued

```
Lys Gln Ile Thr Ile Lys Lys Gly Ile Asp Gly Glu Asp Ser Ser Ser
    1010                1015                1020
Asp Ala Thr Ser Asn Ala Asn Leu Thr Ile Lys Thr Lys Glu Leu Lys
1025                1030                1035                1040
Leu Thr Glu Asp Leu Ser Ile Ser Gly Phe Asn Lys Ala Glu Ile Thr
            1045                1050                1055
Ala Lys Asp Gly Arg Asp Leu Thr Ile Gly Asn Ser Asn Asp Gly Asn
            1060                1065                1070
Ser Gly Ala Glu Ala Lys Thr Val Thr Phe Asn Asn Val Lys Asp Ser
        1075                1080                1085
Lys Ile Ser Ala Asp Gly His Asn Val Thr Leu Asn Ser Lys Val Lys
    1090                1095                1100
Thr Ser Ser Ser Asn Gly Gly Arg Glu Ser Asn Ser Asp Asn Asp Thr
1105                1110                1115                1120
Gly Leu Thr Ile Thr Ala Lys Asn Val Glu Val Asn Lys Asp Ile Thr
            1125                1130                1135
Ser Leu Lys Thr Val Asn Ile Thr Ala Ser Glu Lys Val Thr Thr Thr
        1140                1145                1150
Ala Gly Ser Thr Ile Asn Ala Thr Asn Gly Lys Ala Ser Ile Thr Thr
        1155                1160                1165
Lys Thr Gly Asp Ile Ser Gly Thr Ile Ser Gly Asn Thr Val Ser Val
    1170                1175                1180
Ser Ala Thr Gly Asp Leu Thr Thr Lys Ser Gly Ser Lys Ile Glu Ala
1185                1190                1195                1200
Lys Ser Gly Glu Ala Asn Val Thr Ser Ala Thr Gly Thr Ile Gly Gly
            1205                1210                1215
Thr Ile Ser Gly Asn Thr Val Asn Val Thr Ala Asn Ala Gly Asp Leu
            1220                1225                1230
Thr Val Gly Asn Gly Ala Glu Ile Asn Ala Thr Glu Gly Ala Ala Thr
        1235                1240                1245
Leu Thr Ala Thr Gly Asn Thr Leu Thr Thr Glu Ala Gly Ser Ser Ile
        1250                1255                1260
Thr Ser Thr Lys Gly Gln Val Asp Leu Leu Ala Gln Asn Gly Ser Ile
1265                1270                1275                1280
Ala Gly Ser Ile Asn Ala Ala Asn Val Thr Leu Asn Thr Thr Gly Thr
            1285                1290                1295
Leu Thr Thr Val Ala Gly Ser Asp Ile Lys Ala Thr Ser Gly Thr Leu
            1300                1305                1310
Val Ile Asn Ala Lys Asp Ala Lys Leu Asn Gly Asp Ala Ser Gly Asp
        1315                1320                1325
Ser Thr Glu Val Asn Ala Val Asn Ala Ser Gly Ser Gly Ser Val Thr
        1330                1335                1340
Ala Ala Thr Ser Ser Ser Val Asn Ile Thr Gly Asp Leu Asn Thr Val
1345                1350                1355                1360
Asn Gly Leu Asn Ile Ile Ser Lys Asp Gly Arg Asn Thr Val Arg Leu
            1365                1370                1375
Arg Gly Lys Glu Ile Glu Val Lys Tyr Ile Gln Pro Gly Val Ala Ser
            1380                1385                1390
Val Glu Glu Val Ile Glu Ala Lys Arg Val Leu Glu Lys Val Lys Asp
        1395                1400                1405
Leu Ser Asp Glu Glu Arg Glu Thr Leu Ala Lys Leu Gly Val Ser Ala
    1410                1415                1420
```

```
Val Arg Phe Val Glu Pro Asn Asn Thr Ile Thr Val Asn Thr Gln Asn
1425                1430                1435                1440

Glu Phe Thr Thr Arg Pro Ser Ser Gln Val Ile Ile Ser Glu Gly Lys
            1445                1450                1455

Ala Cys Phe Ser Ser Gly Asn Gly Ala Arg Val Cys Thr Asn Val Ala
        1460                1465                1470

Asp Asp Gly Gln Pro
    1475

<210> SEQ ID NO 68
<211> LENGTH: 3108
<212> TYPE: DNA
<213> ORGANISM: Haemophilus influenzae

<400> SEQUENCE: 68
cctgatgatg taacaattga agccgaagac ccccttcgca ataataccgg tataaatgat      60
gaattcccaa caggcaccgg tgaagcaagc gaccctaaaa aaaatagcga actcaaaaca     120
acgctaacca atacaactat ttcaaattat ctgaaaaacg cctggacaat gaatataacg     180
gcatcaagaa aacttaccgt taatagctca atcaacatcg gaagcaactc ccacttaatt     240
ctccatagta aggtcagcg tggcggaggc gttcagattg atggagatat tacttctaaa      300
ggcggaaatt taaccattta ttctggcgga tgggttgatg ttcataaaaa tattacgctt     360
gatcagggtt ttttaaatat taccgccgct tccgtagctt ttgaaggtgg aaataacaaa     420
gcacgcgacg cggcaaatgc taaaattgtc gcccagggca ctgtaaccat tacaggagag     480
ggaaaagatt tcagggctaa caacgtatct ttaaacgaa cgggtaaagg tctgaatatc      540
atttcatcag tgaataattt aacccacaat cttagtggca caattaacat atctgggaat     600
ataacaatta accaaactac gagaaagaac acctcgtatt ggcaaaccag ccatgattcg     660
cactggaacg tcagtgctct taatctagag acaggcgcaa attttacctt tattaaatac     720
atttcaagca atagcaaagg cttaacaaca cagtatagaa gctctgcagg ggtgaatttt     780
aacggcgtaa atggcaacat gtcattcaat ctcaaagaag gagcgaaagt taatttcaaa     840
ttaaaaccaa acgagaacat gaacacaagc aaaccttttac caattcggtt tttagccaat     900
atcacagcca ctggtggggg ctctgttttt tttgatatat atgccaacca ttctggcaga     960
ggggctgagt taaaaatgag tgaaattaat atctctaacg gcgctaattt taccttaaat    1020
tcccatgttc gcggcgatga cgcttttaaa atcaacaaag acttaaccat aaatgcaacc    1080
aattcaaatt tcagcctcag acagacgaaa gatgattttt atgacgggta cgcacgcaat    1140
gccatcaatt caacctacaa catatccatt ctgggcggta atgtcaccct tggtggacaa    1200
aactcaagca gcagcattac ggggaatatt actatcgaga aagcagcaaa tgttacgcta    1260
gaagccaata acgcccctaa tcagcaaaac ataagggata gagttataaa acttggcagc    1320
ttgctcgtta atgggagttt aagtttaact ggcgaaaatg cagatattaa aggcaatctc    1380
actatttcag aaagcgccac ttttaaagga agactagag ataccctaaa tatcaccggc      1440
aattttacca ataatggcac tgccgaaatt aatataacac aaggagtggt aaaacttggc    1500
aatgttacca atgatggtga tttaaacatt accactcacg ctaaacgcaa ccaaagaagc    1560
atcatcggcg agatataat caacaaaaaa ggaagcttaa atattacaga cagtaataat     1620
gatgctgaaa tccaaattgg cggcaatatc tcgcaaaaag aaggcaaccct cacgatttct    1680
tccgataaaa ttaatatcac caaacagata acaatcaaaa agggtattga tggagaggac    1740
tctagttcag atgcgacaag taatgccaac ctaactatta aaccaaaga attgaaattg      1800
```

-continued

```
acagaagacc taagtatttc aggtttcaat aaagcagaga ttacagccaa agatggtaga    1860
gatttaacta ttggcaacag taatgacggt aacagcggtg ccgaagccaa acagtaact     1920 tttaacaatg ttaaagattc aaaaatctct gctgacggtc acaatgtgac actaaatagc    1980
aaagtgaaaa catctagcag caatggcgga cgtgaaagca atagcgacaa cgataccggc    2040
ttaactatta ctgcaaaaaa tgtagaagta acaaagata ttacttctct caaaacagta    2100
aatatcaccg cgtcggaaaa ggttaccacc acagcaggct cgaccattaa cgcaacaaat    2160
ggcaaagcaa gtattacaac caaaacaggt gatatcagcg gtacgatttc cggtaacacg    2220
gtaagtgtta gcgcgactgg tgatttaacc actaaatccg gctcaaaaat tgaagcgaaa    2280
tcgggtgagg ctaatgtaac aagtgcaaca ggtacaattg gcggtacaat ttccggtaat    2340
acggtaaatg ttacggcaaa cgctggcgat ttaacagttg ggaatggcgc agaaattaat    2400
gcgacagaag gagctgcaac cttaaccgca acagggaata ccttgactac tgaagccggt    2460
tctagcatca cttcaactaa gggtcaggta gacctcttgg ctcagaatgg tagcatcgca    2520
ggaagcatta atgctgctaa tgtgacatta aatactacag gcaccttaac caccgtggca    2580
ggctcggata ttaaagcaac cagcggcacc ttggttatta acgcaaaaga tgctaagcta    2640
aatggtgatg catcaggtga tagtacagaa gtgaatgcag tcaacgcaag cggctctggt    2700
agtgtgactg cggcaacctc aagcagtgtg aatatcactg gggatttaaa cacagtaaat    2760
gggttaaata tcatttcgaa agatggtaga acactgtgc gcttaagagg caaggaaatt    2820
gaggtgaaat atatccagcc aggtgtagca agtgtagaa aagtaattga agcgaaacgc    2880
gtccttgaaa aagtaaaaga tttatctgat gaagaaagag aaacattagc taaacttggt    2940
gtaagtgctg tacgttttgt tgagccaaat aatacaatta cagtcaatac acaaaatgaa    3000
tttacaacca gaccgtcaag tcaagtgata atttctgaag gtaaggcgtg tttctcaagt    3060
ggtaatggcg cacgagtatg taccaatgtt gctgacgatg gacagccg              3108
```

<210> SEQ ID NO 69
<211> LENGTH: 1036
<212> TYPE: PRT
<213> ORGANISM: Haemophilus influenzae

<400> SEQUENCE: 69

```
Pro Asp Asp Val Thr Ile Glu Ala Glu Asp Pro Leu Arg Asn Asn Thr
1               5                   10                  15

Gly Ile Asn Asp Glu Phe Pro Thr Gly Thr Gly Glu Ala Ser Asp Pro
            20                  25                  30

Lys Lys Asn Ser Glu Leu Lys Thr Thr Leu Thr Asn Thr Thr Ile Ser
        35                  40                  45

Asn Tyr Leu Lys Asn Ala Trp Thr Met Asn Ile Thr Ala Ser Arg Lys
    50                  55                  60

Leu Thr Val Asn Ser Ser Ile Asn Ile Gly Ser Asn Ser His Leu Ile
65                  70                  75                  80

Leu His Ser Lys Gly Gln Arg Gly Gly Val Gln Ile Asp Gly Asp
                85                  90                  95

Ile Thr Ser Lys Gly Gly Asn Leu Thr Ile Tyr Ser Gly Gly Trp Val
            100                 105                 110

Asp Val His Lys Asn Ile Thr Leu Asp Gln Gly Phe Leu Asn Ile Thr
        115                 120                 125

Ala Ala Ser Val Ala Phe Glu Gly Gly Asn Asn Lys Ala Arg Asp Ala
    130                 135                 140
```

-continued

```
Ala Asn Ala Lys Ile Val Ala Gln Gly Thr Val Thr Ile Thr Gly Glu
145                 150                 155                 160

Gly Lys Asp Phe Arg Ala Asn Asn Val Ser Leu Asn Gly Thr Gly Lys
                165                 170                 175

Gly Leu Asn Ile Ile Ser Ser Val Asn Asn Leu Thr His Asn Leu Ser
            180                 185                 190

Gly Thr Ile Asn Ile Ser Gly Asn Ile Thr Ile Asn Gln Thr Thr Arg
            195                 200                 205

Lys Asn Thr Ser Tyr Trp Gln Thr Ser His Asp Ser His Trp Asn Val
210                 215                 220

Ser Ala Leu Asn Leu Glu Thr Gly Ala Asn Phe Thr Phe Ile Lys Tyr
225                 230                 235                 240

Ile Ser Ser Asn Ser Lys Gly Leu Thr Thr Gln Tyr Arg Ser Ser Ala
                245                 250                 255

Gly Val Asn Phe Asn Gly Val Asn Gly Asn Met Ser Phe Asn Leu Lys
                260                 265                 270

Glu Gly Ala Lys Val Asn Phe Lys Leu Lys Pro Asn Glu Asn Met Asn
            275                 280                 285

Thr Ser Lys Pro Leu Pro Ile Arg Phe Leu Ala Asn Ile Thr Ala Thr
            290                 295                 300

Gly Gly Gly Ser Val Phe Phe Asp Ile Tyr Ala Asn His Ser Gly Arg
305                 310                 315                 320

Gly Ala Glu Leu Lys Met Ser Glu Ile Asn Ile Ser Asn Gly Ala Asn
                325                 330                 335

Phe Thr Leu Asn Ser His Val Arg Gly Asp Asp Ala Phe Lys Ile Asn
                340                 345                 350

Lys Asp Leu Thr Ile Asn Ala Thr Asn Ser Asn Phe Ser Leu Arg Gln
            355                 360                 365

Thr Lys Asp Asp Phe Tyr Asp Gly Tyr Ala Arg Asn Ala Ile Asn Ser
370                 375                 380

Thr Tyr Asn Ile Ser Ile Leu Gly Gly Asn Val Thr Leu Gly Gly Gln
385                 390                 395                 400

Asn Ser Ser Ser Ser Ile Thr Gly Asn Ile Thr Ile Glu Lys Ala Ala
                405                 410                 415

Asn Val Thr Leu Glu Ala Asn Asn Ala Pro Asn Gln Gln Asn Ile Arg
            420                 425                 430

Asp Arg Val Ile Lys Leu Gly Ser Leu Leu Val Asn Gly Ser Leu Ser
            435                 440                 445

Leu Thr Gly Glu Asn Ala Asp Ile Lys Gly Asn Leu Thr Ile Ser Glu
450                 455                 460

Ser Ala Thr Phe Lys Gly Lys Thr Arg Asp Thr Leu Asn Ile Thr Gly
465                 470                 475                 480

Asn Phe Thr Asn Asn Gly Thr Ala Glu Ile Asn Ile Thr Gln Gly Val
                485                 490                 495

Val Lys Leu Gly Asn Val Thr Asn Asp Gly Asp Leu Asn Ile Thr Thr
            500                 505                 510

His Ala Lys Arg Asn Gln Arg Ser Ile Ile Gly Gly Asp Ile Ile Asn
            515                 520                 525

Lys Lys Gly Ser Leu Asn Ile Thr Asp Ser Asn Asn Asp Ala Glu Ile
530                 535                 540

Gln Ile Gly Gly Asn Ile Ser Gln Lys Glu Gly Asn Leu Thr Ile Ser
545                 550                 555                 560
```

```
Ser Asp Lys Ile Asn Ile Thr Lys Gln Ile Thr Ile Lys Lys Gly Ile
            565                 570                 575

Asp Gly Glu Asp Ser Ser Asp Ala Thr Ser Asn Ala Asn Leu Thr
        580                 585                 590

Ile Lys Thr Lys Glu Leu Lys Leu Thr Glu Asp Leu Ser Ile Ser Gly
        595                 600                 605

Phe Asn Lys Ala Glu Ile Thr Ala Lys Asp Gly Arg Asp Leu Thr Ile
        610                 615                 620

Gly Asn Ser Asn Asp Gly Asn Ser Gly Ala Glu Ala Lys Thr Val Thr
625                 630                 635                 640

Phe Asn Asn Val Lys Asp Ser Lys Ile Ser Ala Asp Gly His Asn Val
                645                 650                 655

Thr Leu Asn Ser Lys Val Lys Thr Ser Ser Ser Asn Gly Gly Arg Glu
                660                 665                 670

Ser Asn Ser Asp Asn Asp Thr Gly Leu Thr Ile Thr Ala Lys Asn Val
                675                 680                 685

Glu Val Asn Lys Asp Ile Thr Ser Leu Lys Thr Val Asn Ile Thr Ala
        690                 695                 700

Ser Glu Lys Val Thr Thr Thr Ala Gly Ser Thr Ile Asn Ala Thr Asn
705                 710                 715                 720

Gly Lys Ala Ser Ile Thr Thr Lys Thr Gly Asp Ile Ser Gly Thr Ile
                725                 730                 735

Ser Gly Asn Thr Val Ser Val Ser Ala Thr Gly Asp Leu Thr Thr Lys
                740                 745                 750

Ser Gly Ser Lys Ile Glu Ala Lys Ser Gly Glu Ala Asn Val Thr Ser
        755                 760                 765

Ala Thr Gly Thr Ile Gly Gly Thr Ile Ser Gly Asn Thr Val Asn Val
        770                 775                 780

Thr Ala Asn Ala Gly Asp Leu Thr Val Gly Asn Gly Ala Glu Ile Asn
785                 790                 795                 800

Ala Thr Glu Gly Ala Ala Thr Leu Thr Ala Thr Gly Asn Thr Leu Thr
                805                 810                 815

Thr Glu Ala Gly Ser Ser Ile Thr Ser Thr Lys Gly Gln Val Asp Leu
                820                 825                 830

Leu Ala Gln Asn Gly Ser Ile Ala Gly Ser Ile Asn Ala Ala Asn Val
                835                 840                 845

Thr Leu Asn Thr Thr Gly Thr Leu Thr Thr Val Ala Gly Ser Asp Ile
        850                 855                 860

Lys Ala Thr Ser Gly Thr Leu Val Ile Asn Ala Lys Asp Ala Lys Leu
865                 870                 875                 880

Asn Gly Asp Ala Ser Gly Asp Ser Thr Glu Val Asn Ala Val Asn Ala
                885                 890                 895

Ser Gly Ser Gly Ser Val Thr Ala Ala Thr Ser Ser Val Asn Ile
                900                 905                 910

Thr Gly Asp Leu Asn Thr Val Asn Gly Leu Asn Ile Ile Ser Lys Asp
        915                 920                 925

Gly Arg Asn Thr Val Arg Leu Arg Gly Lys Glu Ile Glu Val Lys Tyr
        930                 935                 940

Ile Gln Pro Gly Val Ala Ser Val Glu Val Ile Glu Ala Lys Arg
945                 950                 955                 960

Val Leu Glu Lys Val Lys Asp Leu Ser Asp Glu Glu Arg Glu Thr Leu
                965                 970                 975

Ala Lys Leu Gly Val Ser Ala Val Arg Phe Val Glu Pro Asn Asn Thr
```

```
                980             985             990
Ile Thr Val Asn Thr Gln Asn Glu Phe Thr Thr Arg Pro Ser Ser Gln
            995             1000            1005

Val Ile Ile Ser Glu Gly Lys Ala Cys Phe Ser Ser Gly Asn Gly Ala
    1010            1015            1020

Arg Val Cys Thr Asn Val Ala Asp Asp Gly Gln Pro
1025            1030            1035

<210> SEQ ID NO 70
<211> LENGTH: 25
<212> TYPE: DNA
<213> ORGANISM: Haemophilus influenzae

<400> SEQUENCE: 70
tcttttgctg tggctgatgc cccta                                         25

<210> SEQ ID NO 71
<211> LENGTH: 25
<212> TYPE: DNA
<213> ORGANISM: Haemophilus influenzae

<400> SEQUENCE: 71
cactgatagg ttgctcatat tcgcc                                         25

<210> SEQ ID NO 72
<211> LENGTH: 6
<212> TYPE: PRT
<213> ORGANISM: Haemophilus influenzae

<400> SEQUENCE: 72

Val Gly Val His Lys Asn
 1               5

<210> SEQ ID NO 73
<211> LENGTH: 20
<212> TYPE: DNA
<213> ORGANISM: Haemophilus influenzae

<400> SEQUENCE: 73
ggtgatgttc ataaaaatat                                               20

<210> SEQ ID NO 74
<211> LENGTH: 21
<212> TYPE: DNA
<213> ORGANISM: Haemophilus influenzae

<400> SEQUENCE: 74
atatttttat gaacatcaac c                                             21

<210> SEQ ID NO 75
<211> LENGTH: 8
<212> TYPE: PRT
<213> ORGANISM: Haemophilus influenzae

<400> SEQUENCE: 75

Gly Gly Ser Leu Thr Ile Asn Ser
 1               5

<210> SEQ ID NO 76
<211> LENGTH: 22
<212> TYPE: DNA
<213> ORGANISM: Haemophilus influenzae
```

```
<400> SEQUENCE: 76
ggcggagttt aactattaac tc                                              22

<210> SEQ ID NO 77
<211> LENGTH: 23
<212> TYPE: DNA
<213> ORGANISM: Haemophilus influenzae

<400> SEQUENCE: 77
gagttaatag ttaaacttcc gcc                                             23

<210> SEQ ID NO 78
<211> LENGTH: 10
<212> TYPE: PRT
<213> ORGANISM: Haemophilus influenzae

<400> SEQUENCE: 78

Gly Val Asp Gly Glu Asn Ser Asp Ser Asp
 1               5                  10

<210> SEQ ID NO 79
<211> LENGTH: 31
<212> TYPE: DNA
<213> ORGANISM: Haemophilus influenzae

<400> SEQUENCE: 79
ggtgttgatg gggagaattc cgattcagac g                                    31

<210> SEQ ID NO 80
<211> LENGTH: 10
<212> TYPE: PRT
<213> ORGANISM: Haemophilus influenzae

<400> SEQUENCE: 80

Val Cys Val Asn Ile Ala Asp Asn Gly Arg
 1               5                  10

<210> SEQ ID NO 81
<211> LENGTH: 33
<212> TYPE: DNA
<213> ORGANISM: Haemophilus influenzae

<400> SEQUENCE: 81
gtgtgcgtta atatcgctga taacgggcgg tag                                  33

<210> SEQ ID NO 82
<211> LENGTH: 43
<212> TYPE: DNA
<213> ORGANISM: Haemophilus influenzae

<400> SEQUENCE: 82
ggcctctaga ctaccgcccg ttatcagcga tattaacgca cac                       43

<210> SEQ ID NO 83
<211> LENGTH: 41
<212> TYPE: DNA
<213> ORGANISM: Haemophilus influenzae

<400> SEQUENCE: 83
ggcctctaga cggtcagtaa ttgacaaggt agatttcatc c                         41

<210> SEQ ID NO 84
<211> LENGTH: 13
```

```
<212> TYPE: PRT
<213> ORGANISM: Haemophilus influenzae

<400> SEQUENCE: 84

Gly Arg Gln Trp Phe Asp Leu Arg Glu Phe Asn Met Ala
 1               5                  10

<210> SEQ ID NO 85
<211> LENGTH: 39
<212> TYPE: DNA
<213> ORGANISM: Haemophilus influenzae

<400> SEQUENCE: 85
ggtcgtcagt ggttcgattt gcgtgaattc aatatggca                            39

<210> SEQ ID NO 86
<211> LENGTH: 39
<212> TYPE: DNA
<213> ORGANISM: Haemophilus influenzae

<400> SEQUENCE: 86
tgccatattg aattcacgca atcgaacca ctgacgacc                             39

<210> SEQ ID NO 87
<211> LENGTH: 13
<212> TYPE: PRT
<213> ORGANISM: Haemophilus influenzae

<400> SEQUENCE: 87

Met Pro Asp Asp Val Ser Ile Asp Ala Pro Ser Ala Glu
 1               5                  10

<210> SEQ ID NO 88
<211> LENGTH: 50
<212> TYPE: DNA
<213> ORGANISM: Haemophilus influenzae

<400> SEQUENCE: 88
cgggatccca tatgccggat gatgtatcca ttgacgcacc ttcggctgaa                50

<210> SEQ ID NO 89
<211> LENGTH: 13
<212> TYPE: PRT
<213> ORGANISM: Haemophilus influenzae

<400> SEQUENCE: 89

Ala Ala Val Cys Thr Asn Val Ala Asp Asp Gly Gln Gln
 1               5                  10

<210> SEQ ID NO 90
<211> LENGTH: 43
<212> TYPE: DNA
<213> ORGANISM: Haemophilus influenzae

<400> SEQUENCE: 90
gcagcagtat gtaccaatgt tgctgacgat ggacagcagt agt                       43

<210> SEQ ID NO 91
<211> LENGTH: 49
```

-continued

```
<212> TYPE: DNA
<213> ORGANISM: Haemophilus influenzae

<400> SEQUENCE: 91
gtctagacta ctgctgtcca tcgtcagcaa cattggtaca tactgctgc           49
```

PROTECTIVE RECOMBINANT *HAEMOPHILUS INFLUENZAE* HIGH MOLECULAR WEIGHT PROTEINS

REFERENCE TO RELATED APPLICATION

This application is a continuation of U.S. patent application Ser. No. 09/167,568 filed Oct. 7, 1998 (now abandoned).

FIELD OF INVENTION

The present invention relates to the field of molecular genetics and, in particular, to the production of recombinant *Haemophilus influenzae* high molecular weight proteins and nucleic acid molecules and vectors employed therein.

BACKGROUND TO THE INVENTION

Encapsulated *Haemophilus influenzae* type b strains are a major cause of bacterial meningitis and other invasive infections in young children. However, the non-encapsulated or nontypeable *H. influenzae* (NTHi) are responsible for a wide range of human diseases, including otitis media, epiglottitis, pneumonia and tracheobronchitis. Vaccines based upon *H. influenzae* type b capsular polysaccharide conjugated to diphtheria toxoid (ref. 1. Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure), tetanus toxoid (ref. 2 and U.S. Pat. No. 4,496, 538), or *Neisseria meningitidis* outer membrane protein (ref. 3) have been effective in reducing *H. influenzae* type b-induced meningitis, but not NTHi-induced disease (ref. 4).

Otitis media is the most common illness of early childhood, with 60 to 70% of all children, of less than 2 years of age, experiencing between one and three ear infections (ref. 5). Chronic otitis media is responsible for hearing, speech and cognitive impairments in children. *H. influenzae* infections account for about 30% of the cases of acute otitis media and about 60% of chronic otitis media. In the United States alone, treatment of otitis media costs between 1 and 2 billion dollars per year for antibiotics and surgical procedures, such as tonsillectomies, adenoidectomies and insertion of tympanostomy tubes. It is estimated that an additional $30 billion is spent per annum on adjunct therapies, such as speech therapy and special education classes. Furthermore, many of the causative organisms of otitis media are becoming resistant to antibiotic treatment. An effective prophylactic vaccine against otitis media is thus desirable.

During natural infection by NTHi, surface-exposed outer membrane proteins that stimulate an antibody response are potentially important targets for bactericidal and/or protective antibodies and, therefore, potential vaccine candidates. Barenkamp and Bodor (ref. 6) demonstrated that convalescent sera from children suffering from otitis media due to NTHi contained antibodies to high molecular weight (HMW) proteins. About 70 to 75% of NTHi strains express the HMW proteins and most of these strains contain two gene clusters termed hmw1ABC and hmw2ABC. The hmwA genes encode the structural HMWA proteins and the hmwB and hmwC genes are accessory genes responsible for the processing and secretion of the HMWA proteins (refs. 7, 8, 9; U.S. Pat. No. 5,603,938; WO 97/36914). The HMWA proteins have been demonstrated to be adhesins mediating attachment to human epithelial cells (ref. 10) and only properly processed HMWA proteins appear to be effective adhesins (ref. 8). Immunization with a mixture of native HMW1A and HMW2A proteins resulted in protection in the chinchilla intrabulla challenge model of otitis media (ref. 11; WO 97/36914). The prototype hmw1 A gene from NTHi strain 12 encodes a 160 kDa HMW1A protein that is processed by cleavage of a 35 kDa amino terminal fragment, generating the mature 125 kDa HMW1A protein. Similarly, the NTHi strain 12 hmw2A gene encodes a 155 kDa HMW2A protein that is processed by cleavage of a nearly identical 35 kDa amino terminal fragment to produce the mature 120 kDa HMW2A protein.

Plasmid pHMW1-15 (ref. 8) has a pT7-7 backbone (ref. 12) and contains the complete NTHi strain 12 hmw1ABC operon with 5'- and 3'-flanking regions. There are about 400 bp of 5'-flanking sequences located between the T7 promoter and the start of the hmw1A structural gene. Plasmid pHMW2-21 (ref. 10) has a pT7-7 backbone and contains the complete hmw2ABC operon with 5'- and 3'-flanking sequences. There are about 800 bp of 5'-flanking sequences located between the T7 promoter and the start of the hmw2A structural gene. The rHMW1A and rHMW2A proteins are produced in relatively low yield from plasmids pHMW1-15 and pHMW2-21.

The *H. influenzae* hmw1 ABC or hmw2 ABC genes can be genetically engineered to produce the mature recombinant HMW1A or HMW2A proteins by deleting the sequence encoding the 35 kDa leader sequence, that is normally removed by processing in *H. influenzae*. Since the leader sequence has been deleted, there should be no necessity for the hmw1BC or hmw2BC genes which serve to process and secrete the mature HMW1A and HMW2A structural proteins in *H. influenzae* (ref. 9). The yield of rHMW1A or rHMW2A protein can be significantly increased by deletion of the leader sequence and processing genes, however, the purified recombinant proteins are not protective. As set forth herein, the hmw1BC and hmw2BC genes or their protein products apparently contribute to the protective ability of rHMW1A and rHMW2A proteins. Such a requirement for otherwise redundant accessory genes, is unexpected.

The *E. coli* cer gene is thought to stabilize plasmids by preventing multimerization (ref. 13). For expression vectors with large inserts, the cer gene may be used to stabilize the plasmids.

SUMMARY OF THE INVENTION

The present invention is directed towards the provision of recombinant non-typeable *H. influenzae* high molecular weight proteins that are protective by providing certain nucleic acid molecules and vectors containing the same.

It has now been found that, in order to obtain recombinant high molecular weight (HMW) proteins of non-typeable Haemophilus which are protective, it is necessary to provide a vector containing only the segment of the A portion of the operon which encodes the mature HMW protein, i.e. lacking the segment of the A gene which encodes the leader sequence, and the B and C portions of the operon. It has also been found that the level of expression of the mature protein may be enhanced by including in the vector at least one additional segment which encodes the mature protein, the cer gene from *E. coli* or both.

Accordingly, in one aspect of the present invention, there is provided a nucleic acid molecule comprising a promoter functional in *E. coli* and operatively coupled to a modified operon of a non-typeable strain of Haemophilus comprising A, B and C genes, wherein the A gene of the operon contains only a nucleic acid sequence which encodes a mature high molecular weight protein of the non-typeable strain of Haemophilus, and hence from which the portion of the A gene encoding the leader sequence is absent.

Any suitable promoter may be used to effect expression of the mature HMW protein in *E. coli*. However, it is preferred to use the T7 promoter.

The encoded mature high molecular weight protein may be HMW1 or HMW2 protein of the non-typeable Haemophilus strain. The non-typeable Haemophilus strain may be selected from the group consisting of strains 12, Joyc, K21, LCDC2, PMH1 and 15 of non-typeable *Haemophilus influenzae*.

The present invention also provides the nucleotide sequences for the hmw1A and/or hmw2A genes of certain non-typeable strains of *Haemophilus influenzae* which have not been previously isolated, purified and expressed, along with the deduced amino acid sequences of the corresponding HMW1 and HMW2 proteins of the non-typeable Haemophilus strains.

Accordingly, in another aspect of the invention, there is provided an isolated and purified nucleic acid molecule encoding a high molecular weight (HMW) protein of a non-typeable strain of *Haemophilus influenzae* having:

(a) a DNA sequence selected from the group consisting of those shown in FIGS. 18, 19, 20, 21, 22, 23, 24, 25 and 26 (SEQ ID NOS: 25, 27, 29, 32, 33, 36, 38, 40, 42, 44, 46, 48, 50, 52, 54, 56, 58, 60), or a sequence complementary thereto; or (b) a DNA sequence encoding a high molecular weight protein having an amino acid sequence selected from the group consisting of those shown in FIGS. 18, 19, 20, 21, 22, 23, 24, 25 and 26 (SEQ ID NOS: 26, 28, 30, 32, 34, 35, 37, 39, 41, 43, 45, 47, 49, 51, 53, 55, 57, 59, 61), or a sequence complementary thereto.

The modified operon in the first aspect of the invention may include the mature protein encoding sequences (SEQ ID NOS: 27, 31, 36, 40, 44, 48, 52, 56, 60, 64, 68) or a DNA molecule encoding the mature protein having the amino acid sequences (SEQ ID NOS: 28, 32, 37, 41, 45, 49, 53, 57, 61, 65, 69) shown in such FIGS. 18, 19, 20, 21, 22, 23, 24, 25, 26, 27 and 28.

The nucleic acid molecule provided in accordance with the first aspect of the invention may further comprise a sequence containing at least one additional copy of the mature encoding region only of the operon of a non-typeable strain of Haemophilus, the cer gene of *E. coli* or both such segments.

The nucleic acid molecules provided in accordance with the first aspect of the invention may be incorporated into a vector, usually a plasmid vector, for transformation of *E. coli* for the purpose of expression of the mature protective high molecular protein of a non-typeable strain of Haemophilus.

Plasmid vectors for the latter purpose may have the identifying characteristics of a plasmid which is selected from the group consisting of:

DS-1046-1-1
JB-2507-7
BK-86-1-1
BK-35-4
BK-76-1-1
DS-2334-5
DS-2400-13

Details of the structures and preparation of such plasmid is provided in the Figures and Examples.

The present invention extends, in a further aspect thereof, to a strain of *E. coli* transformed by the vectors provided herein and expressing a protective high molecular weight protein of a non-typeable strain of Haemophilus. The present invention further includes an isolated and purified recombinant protective high molecular weight protein of a non-typeable strain of Haemophilus immunogenic segment or analog thereof producible by the transformed *E. coli*.

The present invention further includes, in an additional aspect therein, a recombinant method for a production of a protective high molecular weight protein of a non-typeable strain of Haemophilus, which comprises:

transforming *E. coli* with a vector comprising the nucleic acid molecule provided in the first aspect of the invention, growing *E. coli* to express the encoded mature high molecular weight (HMW) protein, and isolating and purifying the expressed HMW protein.

The non-typeable strain of Haemophilus may be any of the strains referred to above and the high molecular weight protein may be the HMW1 protein or HMW2 protein, which is provided in a form free from contamination by the other protein. The purification steps may include separating the HMW A protein from the B and C protein.

The present invention, in an additional aspect thereof provides an isolated and purified protective HMW 1 protein of a strain of non-typeable Haemophilus which is free from contamination by the HMW2 protein of the same strain of non-typeable Haemophilus.

In a yet further aspect, the present invention provides an isolated and purified protective HMW2 protein of a strain of non-typeable Haemophilus which is free from contamination by the HMW 1 protein of the same strain of non-typeable Haemophilus.

The HMW1 or HMW2 protein may be from any of the non-typeable strain of Haemophilus mentioned above and may be one having SEQ ID NO: 28, 32, 37, 41, 45, 49, 53, 57, 61, 65 of 69.

In accordance with another aspect of the invention, an immunogenic composition is provided which comprises at least one immunologically-active component selected from the group consisting of at least one nucleic acid molecule as provided herein, at least one recombinant HMW protein as provided herein or at least one novel HMW protein as provided herein, and a pharmaceutically acceptable carrier therefor. The at least one active component produces an immune response when administered to a host.

The immunogenic compositions provided herein may be formulated as a vaccine for in vivo administration to a host to provide protection against disease caused by *H. influenzae*. For such purpose, the compositions may be formulated as a microparticle, ISCOM or liposome preparation. The immunogenic composition may be provided in combination with a targeting molecule for delivery to specific cells of the immune system or to mucosal surfaces. The immunogenic compositions of the invention (including vaccines) may further comprise at least one other immunogenic or immunostimulating material and the immunostimulating material may be at least one adjuvant or at least one cytokine.

Suitable adjuvants for use in the present invention include (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA and a lipoprotein and other adjuvants. Advantageous combination of adjuvants are described in copending U.S. patent applications Ser. No. 08/261,194 filed Jun. 16, 1994 and 08/483,856 filed Jun. 7, 1995, assigned to the assignee hereof and the disclosure of which is incorporated herein by reference (WO 95/34308, published Nov. 21, 1995).

In accordance with another aspect of the invention, there is provided a method for generating an immune response in a host, comprising the step of administering to a susceptible host, such as a human, an effective amount of the immunogenic composition as recited above. The immune response may be humoral or a cell-mediated immune response and may provide protection against disease caused by Haemophilus. Hosts in which protection against disease may be conferred include primates, including human.

It has been found that the nucleic acid sequences of the B and C portions of the operon encoding HMW1 and HMW2 proteins are highly conserved in nucleic acid sequence among species of non-typeable Haemophilus, enabling them to be provided on a universal plasmid vector for receipt of the nucleic acid sequence encoding the mature HMW1A or HMW2A protein from a variety of strains of non-typeable Haemophilus for the purpose of expression of the HMW1A or HMW2A from a transformed host, such as *E. coli*.

Accordingly, in a yet further aspect of the invention, there is provided a plasmid vector for expression of a high molecular weight protein of a non-typeable strain of Haemophilus and comprising the T7 promoter, a cloning site and the B and C portions of the hmw operon of a non-typeable Haemophilus strain. The plasmid may also contain the *E. coli* cer gene. The plasmid vector may be plasmid JB-2646-1.

The present invention, in its various aspects, permits the production of protective high molecular weight proteins of non-typeable Haemophilus which are useful in providing immunogenic compositions to confer protection against disease caused by infection by non-typeable Haemophilus strains.

BRIEF DESCRIPTION OF DRAWINGS

The present invention will be further understood from the following description with reference to the drawings, in which:

FIG. 1B shows the sequence of the oligonucleotides used in the construction scheme of FIG. 1A (SEQ ID NOS: 1, 2 and 3).

FIG. 3B shows the sequence of the oligonucleotides used in the construction scheme of FIG. 3A (SEQ ID NOS: 4, 5 and 6).

FIG. 4B shows the oligonucleotides used in the construction scheme of FIG. 4A (SEQ ID NOS: 7, 8 and 9).

FIG. 8A–8B shows the construction scheme to generate plasmids DS-2084-3 and DS-2084-1 that contain one or two copies of the T7 hmw2A gene cassette encoding the mature 120 kDa HMW2A protein. Restriction enzyme sites are: B, BamH I; Bg, Bgl II; H, Hind III; M, Mlu I; R, EcoR I; Xb, Xba I. Other abbreviations are: T7p, T7 promoter; ApR, ampicillin resistance gene; TcR, tetracycline resistance gene; CAP, calf alkaline phosphatase; tt1, transcription terminator 1; tt2, transcription terminator 2; MCS, multiple cloning site.

FIG. 8B shows the oligonucleotides used to PCR amplify the 3'-end of hmw2A in the construction scheme of FIG. 8A (SEQ ID NOS: 15, 16, 17, 18 and 19).

FIG. 15 contains an SDS-PAGE analysis showing the stability of rHMW1 from construct T7 hmwABC/cer/kanR stored at −20° C. in the presence of 20% glycerol.

FIG. 17 shows the sequences of oligonucleotides used to PCR amplify additional hmw genes from non-typable *H. influenzae* chromosomal DNA (SEQ ID NOS: 20, 21, 22, 23 and 24).

FIGS. 18A to 18R shows the nucleotide sequence (SEQ ID NO: 25) and deduced amino acid sequence (SEQ ID NO: 26) of the hmw1A gene from NTHi strain Joyc. The arrow marks the predicted start of the mature protein (mature protein: encoding sequence SEQ ID NO: 27; amino acid sequence SEQ ID NO: 28).

FIGS. 19A to 19O shows the nucleotide sequence (SEQ ID NO: 29) and deduced amino acid sequence (SEQ ID NO: 30) of the hmw2A gene from NTHi strain Joyc. The arrow marks the predicted start of the mature protein (mature protein: encoding sequence SEQ ID NO: 31; amino acid sequence SEQ ID NO: 32).

FIGS. 20A to 20R shows the nucleotide sequence (SEQ ID NO: 33) and deduced amino acid sequences (SEQ ID NO: 34, 35) of the defective hmw1A gene from NTHi strain K1. The arrow marks the predicted start of the mature protein (mature protein: encoding sequence SEQ ID NO: 36; amino acid sequence SEQ ID NOS: 37, 35).

FIGS. 21A to 21O show the nucleotide sequence (SEQ ID NO: 38) and deduced amino acid sequence (SEQ ID NO: 39) of the hmw2A gene from NTHi strain K21. The arrow marks the predicted start of the mature protein (mature protein: encoding sequence SEQ ID NO: 40; amino acid sequence SEQ ID NO: 41).

FIGS. 22A to 22P shows the nucleotide sequence (SEQ ID NO: 42) and deduced amino acid sequence (SEQ ID NO: 43) of the hmw2A gene from NTHi strain LCDC2. The arrow marks the predicted start of the mature protein (mature protein: encoding sequence SEQ ID NO: 44; amino acid sequence SEQ ID NO: 45).

FIGS. 23A to 23O shows the nucleotide sequence (SEQ ID NO: 46) and deduced amino acid sequence (SEQ ID NO: 47) of the hmw1A gene from NTHi strain PMH1. The arrow marks the predicted start of the mature protein (mature protein: encoding sequence SEQ ID NO: 48; amino acid sequence SEQ ID NO: 49).

FIGS. 24A to 24O shows the nucleotide sequence (SEQ ID NO: 50) and deduced amino acid sequence (SEQ ID NO: 51) of the hmw2A gene from NTHi strain PMH1. The arrow marks the predicted start of the mature protein (mature protein: encoding sequence SEQ ID NO: 52; amino acid sequence SEQ ID NO: 53).

FIGS. 25A to 25O shows the nucleotide sequence (SEQ ID NO: 54) and deduced amino acid sequence (SEQ ID NO: 55) of the hmw1A gene from NTHi strain 15. The arrow marks the predicted start of the mature protein (mature protein: encoding sequence SEQ ID NO: 56; amino acid sequence SEQ ID NO: 57).

FIGS. 26A to 26R shows the nucleotide sequence (SEQ ID NO: 58) and deduced amino acid sequence (SEQ ID NO: 59) of the hmw2A gene from NTHi strain 15. The arrow marks the predicted start of the mature protein (mature protein: encoding sequence SEQ ID NO: 60; amino acid sequence SEQ ID NO: 61).

FIGS. 27A to 27Q shows the nucleotide sequence (SEQ ID NO: 62) and deduced amino acid sequence (SEQ ID NO: 63 of the hmw1A gene from NTHi strain 12. The arrow marks the predicted start of the mature protein (mature protein: encoding sequence SEQ ID NO: 64; amino acid sequence SEQ ID NO: 65).

FIGS. 28A to 28N shows the nucleotide sequence (SEQ ID NO: 66) and deduced amino acid sequence (SEQ ID NO: 67 of the hmw2A gene from NTHi strain 12. The arrow marks the predicted start of the mature protein (mature protein: encoding sequence SEQ ID NO: 68; amino acid sequence SEQ ID NO: 69).

FIGS. 29A to 29L shows the alignment of the deduced HMW1A and HMW2A protein sequences (SEQ ID NOS: 26, 30, 34, 35, 39, 43, 47, 51, 55, 59) with the published strain 12 HMW1A and HMW2A protein sequences (U.S. Pat. No. 5,603,938) (SEQ ID NOS: 63, 67).

FIG. 30 shows the oligonucleotides (SEQ ID NOS: 70, 71, 72, 73, 74, 75, 76, 77) used to determine whether the PCR amplified hmwA genes were hmw1 or hmw2.

FIG. 31B—31B illustrates the oligonucleotides (SEQ ID NOS: 78, 79, 80, 81, 82, 83, 84, 85, 86) used to PCR amplify the 3'-end of hmw1A and the 5'-end of hmw1B in the construction scheme of FIG. 31A.

Figure 32A:
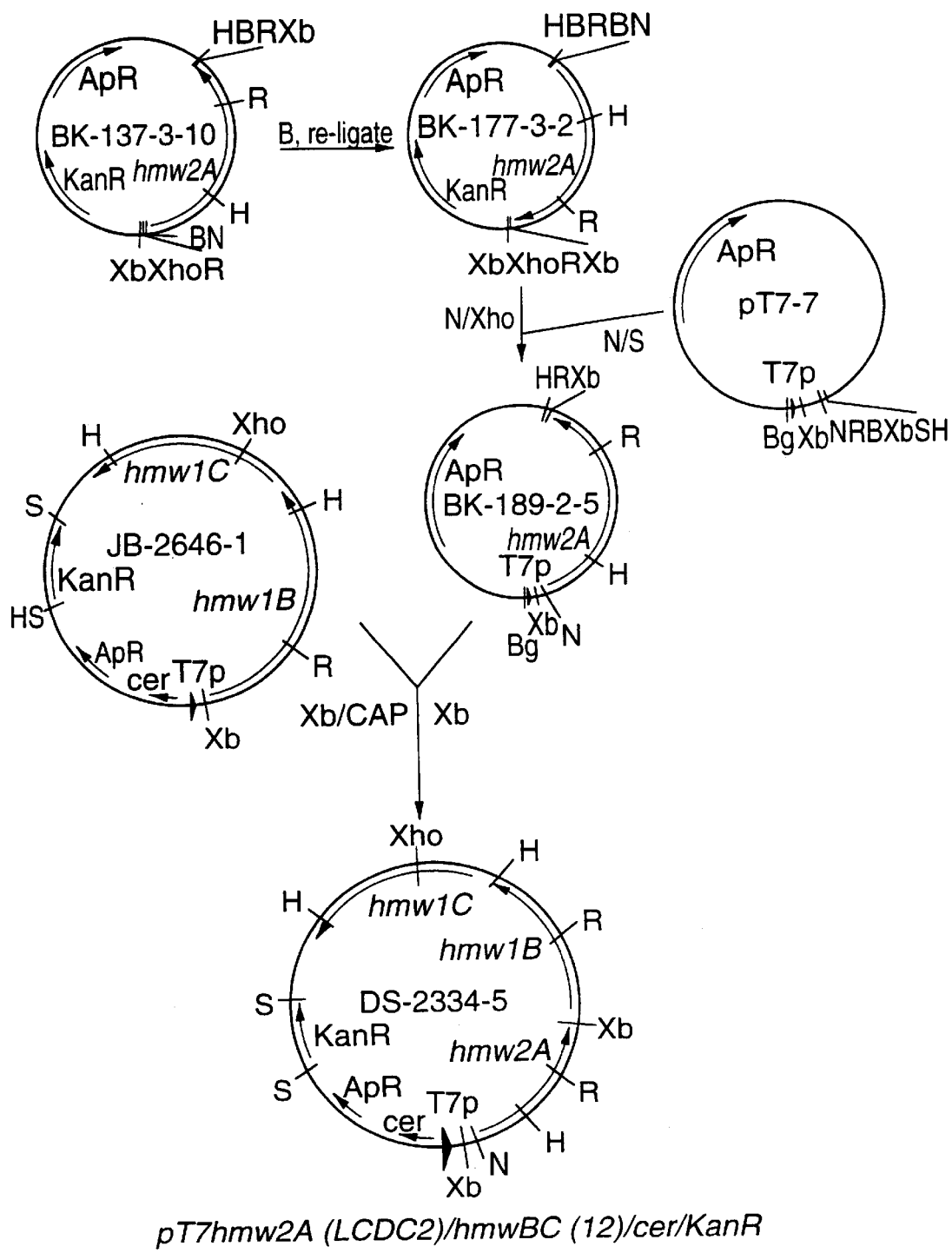
FIG. 32A shows the construction of DS-2334-5 that contains a chimeric T7 hmwABC gene of the LCDC2 hmw2A gene and NTHI 12 hmwBC genes. Restriction enzyme sites are: B, BamH I; Bg, Bgl II; H, Hind III; K, Kpn I; N, Nde I; R, EcoR I; S, Sal I; Xb, Xba I, Xho, Xho I. Other abbreviations are: T7p, T7 promoter; ApR, ampicillin resistance gene; KanR, kanamycin resistance gene; CAP, calf alkaline phosphatase.

FIG. 32B shows the oligonucleotides (SEQ ID NOS: 87, 88, 89, 90, 91) used to PCR amplify the LCDC2 hmw2A gene for expression in the generic expression vector constructed as shown in FIG. 30A.

Figure 33A:
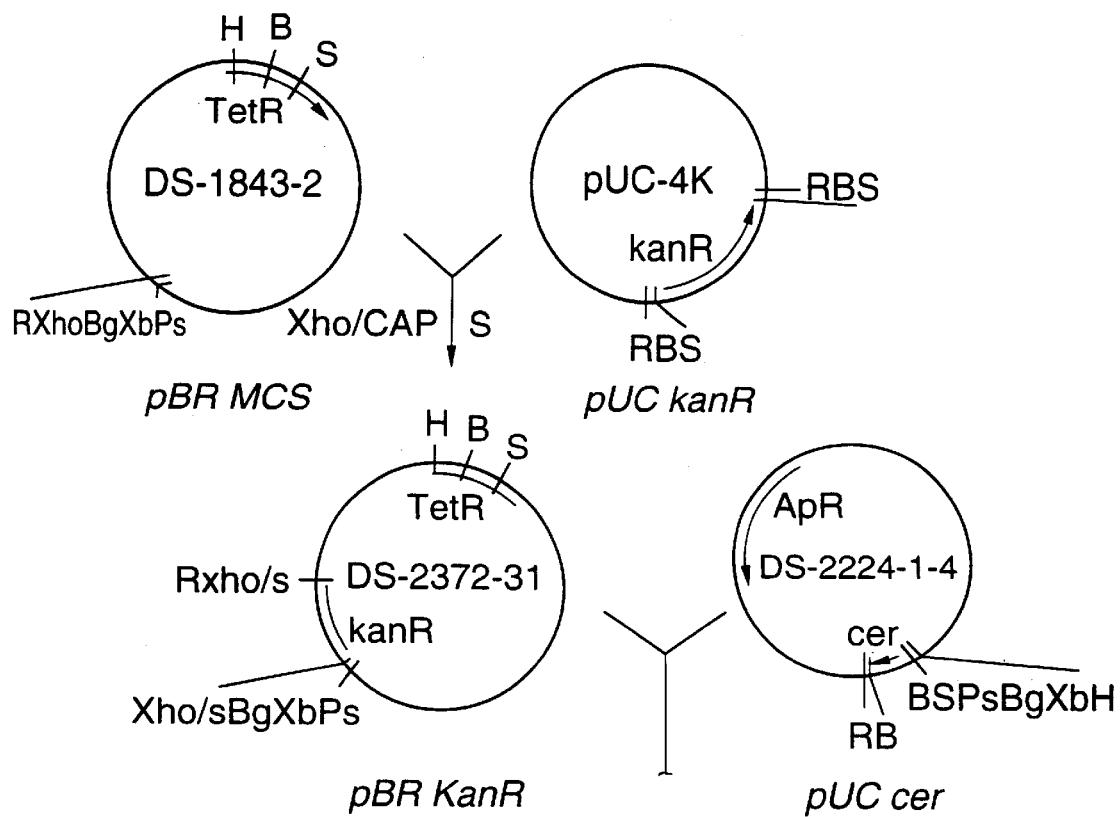

FIGS. 33A and 33A' shows the construction of DS-2400-13 that contains the T7 hmwA/T7 hmwABC genes and the E. coli cer gene. Restriction enzyme sites are: B, BamH I; Bg, Bgl II; H, Hind III; R, EcoR I; S, Sal I; Xb, Xba I, Xho, Xho I. Other abbreviations are: T7p, T7 promoter; ApR, ampicillin resistance gene; KanR, kanamycin resistance gene; TetR, tetracycline resistance gene; CAP, calf alkaline phosphatase.

GENERAL DESCRIPTION OF THE INVENTION

Any Haemophilus strain that has hmw genes may be conveniently used to provide the purified and isolated nucleic acid molecules (which may be in the form of DNA molecules), comprising at least a portion coding for a HMW1A, HMW1B, HMW1C, HMW2A, HMW2B, or HMW2C protein as typified by embodiments of the present invention. Such strains are generally available from clinical sources and from bacterial culture collections, such as the American Type Culture Collection. Appropriate strains of non-typeable Haemophilus include:

Non-typeable H.influenzae strain 12

Non-typeable H. influenzae strain Joyc;

Non-typeable H. influenzae strain K1;

Non-typeable H. influenzae strain K21;

Non-typeable H. influenzae strain LCDC2;

Non-typeable H. influenzae strain PMH1; or

Non-typeable H. influenzae strain 15.

In this application, the term "HMW protein" is used to define a family of HMW proteins which includes those having naturally occurring variations in their amino acid sequences as found in various strains of non-typeable Haemophilus and characterized by an apparent molecular weight of about 100 to about 150.

Reference will now be made in detail to the presently preferred embodiments of the invention, which together with the following Examples, serve to explain the principle of the invention. For clarity of disclosure, and not by way of limitation, the detailed description of the invention is divided into the following sections:

Improved Production of Recombinant HMW Proteins from E. coli

The production of native HMW1A or HMW2A proteins in H. influenzae is very low. The plasmids pHMW1-15 and pHMW2-21 (refs. 8, 10) contain the complete hmw1ABC and hmw2ABC operons from NTHi strain 12 cloned into the expression vector pT7-7. The production of the recombinant rHMW1A or rHMW2A proteins is low from these plasmids, possibly due to the 5'-flanking and hmw promoter sequences inserted between the T7 promoter and the start codon of the hmwA genes. By removal of the 5'-flanking and hmw promoter sequences, the yield of rHMW1A and rHMW2A proteins produced from plasmids DS-1091-2 and DS-1094-2 (FIGS. 1 and 2), was marginally improved.

When produced in H. influenzae, the native HMWA proteins are processed and secreted, with a 35 kDa N-terminal fragment removed. Rather than relying upon the correct processing and secretion of the rHMWA proteins by E. coli, the gene sequences encoding the N-terminal 35 kDa fragments were removed genetically from the hmw1ABC and hmw2ABC genes. The production of the mature rHMW1A and rHMW2A proteins was enhanced in the new constructs, DS-1046-1-1 and DS-1174-4 (FIGS. 3 and 4). The rHMW BC proteins were also overproduced. The hmw1ABC and hmw2ABC gene inserts in the pT7-7 vector were still approximately 8.6 kb and approximately 8.3 kb, respectively. Since the HMWA proteins are the structural and protective proteins, it was thought that the size of the gene insert could be reduced by deleting part or all of the hmwBC genes. Expression vectors with smaller inserts are generally more efficient at producing recombinant proteins and the overproduction of the rHMWBC proteins was thought to be undesirable.

The production of rHMWA proteins was marginally improved when the hmwBC genes were deleted in vectors DS-1200-3, DS-1122-2, JB-2330-7 and DS-2084-3 (FIGS. 4, 5, 6 and 8). However, the production of rHMWB and rHMWC proteins was eliminated, which simplified the protein purification process. When tandem copies of T7 hmwA gene cassettes were used to express rHMWA proteins from vectors JB-2369-6 and DS-2084-1 (FIGS. 7 and 8), the production was marginally improved.

The construction of this series of expression vectors demonstrated that it was possible to increase the production of rHMW1 and rHMW2 proteins from E. coli. However, when tested in a nasopharyngeal colonization model for protection, the rHMWA proteins produced from the improved vectors were not protective. Only mixtures of native HMW1A+HMW2A proteins or rHMWA proteins produced from the lower yield vectors containing complete hmwABC genes were protective.

Modification of Expression Vectors to Produce Protective Recombinant HMW Proteins The expression vectors that contained hmwABC genes encoding full-length HMW1A (DS-1091-2) or HMW2A (DS-1094-2) proteins and which relied upon E. coli to process them, did not produce enough protein to test in animal models. The expression vectors that contained hmwABC genes encoding mature HMW1A (DS-1046-1-1) or HMW2A (DS-1174-4) proteins, expressed protective rHMWA proteins in moderate yield. The vectors that overproduced rHMWA proteins alone did not yield protective antigens.

Two approaches were tried to enhance the yield of protective rHMWA protein. To the vector that contained the T7 hmwABC gene cassette expressing mature rHMW1A protein, was introduced the E. coli cer gene. The cer gene is thought to stabilize plasmids by preventing multimerization and its presence may stabilize expression vectors containing the large hmwABC gene cassettes. We had also found that sometimes the presence of cer also increased the production of recombinant proteins. The rHMW1A antigen that was overproduced from T7 hmw1ABC/cer constructs (FIG. 10) was protective in the nasopharyngeal colonization model (Table 2).

The second approach to overproduce protective rHMWA protein was to construct a vector in which the rHMWA protein was overproduced in the presence of rHMWBC proteins. To the vector that contained the T7 hmwABC gene cassette expressing mature rHMW1A protein, was added an additional T7 hmwA gene cassette. The rHMW1A antigen that was overproduced from T7 hmw1A/T7 hmw1ABC constructs (FIG. 9) was protective in the nasopharyngeal colonization model (Table 2).

Figure 33A:
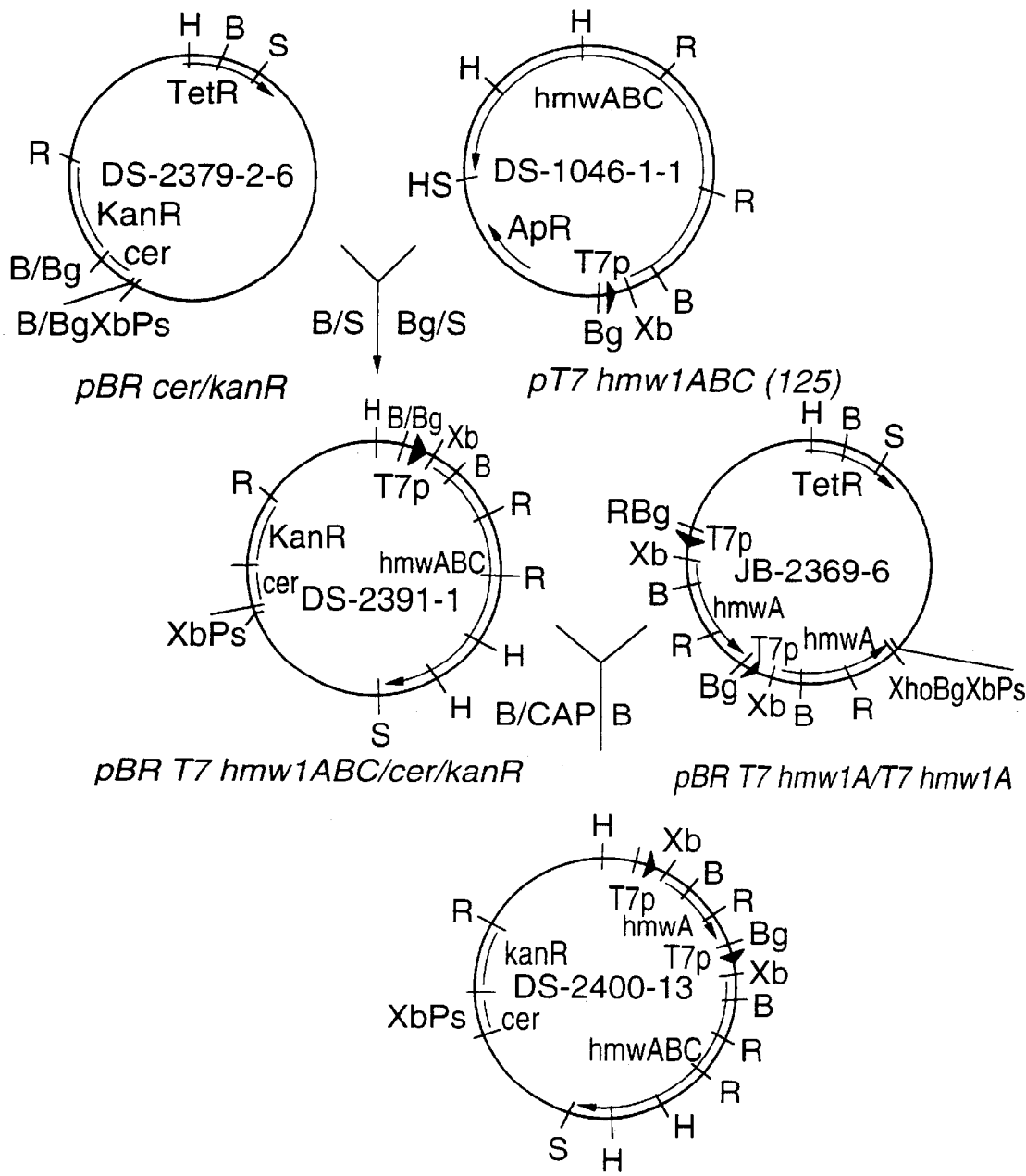

The two approaches can be combined so that tandem copies of the T7 hmwA/T7 hmwABC genes are co-expressed with the E. coli cer gene on the same plasmid, DS-2400-13 (FIG. 33).

Cloning and Sequence Analysis of Additional hmwA Genes

The hmwA genes and encoded proteins have variable sequences. In order to produce a completely effective vaccine, it may be necessary to use rHMWA proteins generated from multiple strains of non-typeable Haemophilus. The hmw1A and/or hmw2A genes were PCR amplified and sequenced from several strains of non-typeable *Haemophilus influenzae*. FIGS. 18 to 26 illustrate the nucleotide and deduced amino acid sequences for the hmw1A gene from strain Joyc, the hmw2A gene from strain Joyc, the defective hmw1A gene from strain K1, the hmw2A gene from strain K21, the hmw2A gene from strain LCDC2, the hmw1A gene from strain PMH1, the hmw2A gene from strain PMH1, the hmw1A gene from strain 15, and the hmw2A gene from strain 15, respectively. The alignment of the deduced protein sequences with the previously described strain 12 HMW1A and HMW2A protein sequences (FIGS. 27 and 28) identifies both regions of sequence conservation and divergence (FIG. 29). Such information may be useful in the identification of potential epitopes to generate peptides for vaccination or diagnostic purposes. The molecular weights of the mature HMW proteins from the various non-typeable Haemophilus strains is contained in Table 3.

Construction of a Generic Expression Vector for Production of Protective Recombinant HMW Proteins New hmwA genes can be PCR amplified from strains of non-typeable Haemophilus and sequenced as described above. However, in order to produce protective rHMWA antigens, the hmwA genes must be expressed in the presence of hmwBC genes. The deduced sequences of the accessory HMW1B and HMW2B proteins from the prototype strain 12 were found to be 99% identical, while the deduced HMW1C and HMW2C proteins from the same strain were 96% identical (ref. 8, U.S. Pat. No. 5,603,938). The highly conserved nature of the hmwBC genes lead to the possibility of constructing a generic expression vector using the hmwBC genes from a prototype strain, and introducing any hmwA gene to the vector for expression therein. FIG. 31 illustrates the construction of a generic expression vector (JB-2646-1) that contains the T7 promoter, an Xba I cloning site for introduction of hmwA genes, the strain 12 hmw1BC genes, and the E. coli cer gene. FIG. 32 illustrates the construction of a chimeric T7 hmwABC gene cassette in the generic expression vector, wherein a PCR amplified LCDC2 hmw2A gene is combined with the strain 12 hmw1BC genes to produce plasmid DS-2334-5. The expression of the genes from the chimeric construct was as seen for T7 hmw1ABC or T7 hmw2ABC constructs based on NTHi strain 12 hmw1A and hmw2A genes.

It is clearly apparent to one skilled in the art, that the various embodiments of the present invention have use in applications in the fields of vaccination, diagnosis, treatment of Haemophilus infection and the generation of immunological agents. A further non-limiting discussion of such uses is further presented below.

5. Vaccine Preparation and Use

Immunogenic compositions, suitable to be used as vaccines, may be prepared from immunogenic high molecular weight (HMW) proteins of non-typeable Haemophilus strains, immunogenic analogs and fragments thereof and/or immunogenic peptides as disclosed herein. The vaccine elicits an immune response which produces antibodies, including anti-HMW antibodies and antibodies that are opsonizing or bactericidal. Immunogenic compositions, including vaccines, may be prepared as injectables, as liquid solutions or emulsions. The HMW protein, immunogenic analogs and fragments thereof and/or immunogenic peptides may be mixed with pharmaceutically acceptable excipients which are compatible with the HMW protein, immunogenic fragments analogs or immunogenic peptides. Such excipients may include, water, saline, dextrose, glycerol, ethanol and combinations thereof. The immunogenic compositions and vaccines may further contain auxiliary substances such as wetting or emulsifying agents, pH buffering agents, or adjuvants to enhance the effectiveness of the vaccines. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. The immunogenic composition may be provided in combination with a targeting molecule for delivery to specific cells of the immune system or to mucosal surfaces. Some such targeting molecules include vitamin B12 and fragments of bacterial toxins, as described in WO 92/17167 (Biotech Australia Pty. Ltd.), and monoclonal antibodies, as described in U.S. Pat. No. 5,194,254 (Barber et al). Alternatively, other modes of administration including suppositories and oral formulations may be desirable. For suppositories, binders and carriers may include, for example polyalkalene glycols or triglycerides. Oral formulations may include normally employed incipients such as, for example pharmaceutical grades of saccharine, cellulose and magnesium carbonate. These compositions take the form of solutions, suspensions, tablets, pills, capsules, sustained release formulations or powders and contain about 1 to 95% of the HMW protein, fragment analogs and/or peptides.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the high molecular weight protein, analogs and fragments thereof and/or peptides. Suitable regimes for initial administration and booster doses are also variable, but may include an initial administration followed by subsequent administrations. The dosage of the vaccine may also depend on the route of administration and will vary according to the size of the host.

The nucleic acid molecules encoding the HMW proteins of non-typeable Haemophilus may also be used directly for immunization by administration of the DNA directly, for example by injection for genetic immunization or by constructing a live vector, such as Salmonella, BCG, adenovirus, poxvirus, vaccinia or poliovirus, containing the nucleic acid molecule. A discussion of some live vectors that have been used to carry heterologous antigens to the immune system are discussed in, for example, O'Hagan (1992) (ref. 17). Processes for the direct injection of DNA into test subjects for genetic immunization are described in, for example, Ulmer et al., 1993 (ref. 18).

Immunogenicity can be significantly improved if the antigens are co-administered with adjuvants, commonly used as an 0.05 to 1.0 percent solution in phosphate—buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established.

A wide range of extrinsic adjuvants can provoke potent immune responses to antigens. These include saponins complexed to membrane protein antigens (immune stimulating complexes), pluronic polymers with mineral oil, killed mycobacteria and mineral oil, Freund's complete adjuvants, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. 1991 (ref. 19) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. 1990 (ref. 20), reported that octadecyl esters of aromatic amino acids complexed with a recombinant hepatitis B surface antigen, enhanced the host immune responses against hepatitis B virus.

6. Immunoassays

The HMW protein of a non-typeable strain of Haemophilus, analogs and fragments thereof and/or peptides of the present invention are useful as immunogens, as antigens in immunoassays including enzyme-linked immunosorbent assay (ELISA), RIAs and other non-enzyme linked antibody binding assays or procedures known in the art for the detection of anti-bacterial, Haemophilus, HMW and/or peptide antibodies. In ELISA assays, the HMW protein, analogs, fragments and/or peptides corresponding to portions of HMW protein are immobilized onto a selected surface, for example a surface capable of binding proteins or peptides, such as the wells of a polystyrene microtiter plate. After washing to remove incompletely adsorbed HMW protein, analogs fragments and/or peptides, a nonspecific protein such as a solution of bovine serum albumin (BSA) or casein that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents such as BSA, bovine gamma globulin (BGG) and/or phosphate buffered saline (PBS)/Tween. The sample is then allowed to incubate for from about 2 to about 4 hours, at temperature such as of the order of about 25° to about 37° C. Following incubation, the sample-contacted surface is washed to remove non-immunocomplexed material. The washing procedure may include washing with a solution such as PBS/Tween, or a borate buffer.

Following formation of specific immunocomplexes between the test sample and the bound HMW protein, analogs, fragments and/or peptide, and subsequent washing, the occurrence, and even amount, of immunocomplex formation may be determined by subjecting the immunocomplex to a second antibody having specificity for the first antibody. If the test sample is of human origin, the second antibody is an antibody having, specificity for human immunoglobulins and in general IgG. To provide detecting means, the second antibody may have an associated activity, such as an enzymatic activity, that will generate, for example, a color development, upon incubating with an appropriate chromogenic substrate. Quantification may then achieved by measuring the degree of color generation using, for example, a visible spectra spectrophotometer.

7. Use of Sequences as Hybridization Probes

The nucleotide sequences of the present invention, comprising the newly-isolated and characterized sequences of the hmw genes, allow for the identification and cloning of the hmw genes from other non-typeable strains of Haemophilus.

The nucleotide sequences comprising the sequence of hmw genes of the present invention are useful for their ability to selectively from duplex molecules with complementary stretches of other hmw genes. Depending on the application, a variety of hybridization conditions may be employed to achieve varying degrees of selectivity of the probe toward the other hmw genes. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between 20° C. to 55° C. Hybridization conditions can also be rendered more stringent by the addition of increasing amount of formamide, to destabilize the hybrid duplex. Thus, particular hybridization conditions can be readily manipulated, and will generally be a method of choice depending on the desired results. In general convenient hybridization temperatures in the presence of 50% formamide and 0.15 M NaCl are: 42° C. for an hmw gene which is about 95 to 100% homologous to the target nucleic acid fragment, 37° C. for about 90 to 95 homology and 32° C. for about 85 to 90% homology.

In a clinical diagnostic embodiment, the nucleic acid sequences of the hmw genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag, such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridization with samples containing hmw genes sequences.

The nucleic acid sequences of hmw genes of the present invention are useful as hybridization probes in solution hybridizations and in embodiments employing solid-phase procedures. In embodiments involving solid-phase procedures the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the hmw genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. It is preferred to select nucleic acid sequence portions which are conserved among species of Haemophilus. The selected probe may be at least 18 bp in length and may be in the range of 30 bp to 90 bp long.

8. Expression of the High Molecular Weight Protein Genes

Plasmid vectors containing replicon and control sequences which are derived from species compatible with the host cell may be used for the expression of the high molecular weight protein genes in expression systems. The vector ordinarily carries a replication site, as well as marking sequences which are capable of providing phenotypic selection in transformed cells. For example, E. coli may be transformed using pBR322 which contains genes for ampicillin and tetracycline resistance and thus provides easy means for identifying transformed cells. The pBR322 plasmid, or other microbial plasmid or phage, must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as E. coli LE392.

Promoters commonly used in recombinant DNA construction include the β-lactamase (penicillinase) and lactose promoter systems and other microbial promoters such as the T7 promoter system employed herein in preferred embodiments (U.S. Pat. No. 4,952,496). Details concerning the nucleotide sequences of promoters are known, enabling a skilled worker to ligate them functionally with genes. The particular promoter used will generally be a matter of choice depending upon the desired results. Hosts that are appropriate for expression of the HMW protein and immunological fragments or analogs thereof include E. coli, Bordetella species, Bacillus species, Haemophilus, fungi, yeast or the baculovirus expression system may be used. E. coli is the preferred host used herein.

In accordance with this invention, it is preferred to produce the HMW proteins by recombinant methods, particularly when the naturally occurring HMW protein as purified from a culture of a species of Haemophilus may include trace amounts of toxic materials or other contaminants. This problem can be avoided by using recombinantly produced HMW protein in heterologous systems which can be isolated from the host in a manner to minimize contaminants in the purified materials, specifically employing the constructs described herein. Furthermore, recombinant method of production permit the manufacture of HMW1 or HMW2 or immunogenic fragments and analogs thereof separate from one another and in highly-purified form, which is distinct from the normal combined proteins present in Haemophilus.

Biological Deposits

Certain vectors that contain nucleic acid coding for a high molecular weight protein of a non-typeable strain of Haemophilus that are described and referred to herein have been deposited with the America Type Culture Collection (ATCC) located at 10801 University Boulevard, Manassas, Va. 20110-2209, USA, pursuant the Budapest Treaty and prior to the filing of this application. Samples of the deposited vectors will become available to the public and all restrictions imposed on access to the deposits will be received upon grant of a patent based on this United States patent application. In addition, the deposit will be replaced if viable samples cannot be dispensed by the Depository. The invention described and claimed herein is not limited in scope by the biological materials deposited, since the deposited embodiment is intended only as an illustration of the invention. Any equivalent or similar vectors that contain nucleic acid which encodes equivalent or similar antigens as described in this application are within the scope of the invention.

Deposit Summary

| Plasmid | | ATCC | Date Deposited |
|---|---|---|---|
| DS-1046-1-1 | (pT7 hmw1ABC(125)) | 203263 | 25 Sep. 1998 |
| JB-2507-7 | (pT7 hmw1A(125)/ T7 hmw1ABC(125)) | 203262 | 25 Sep. 1998 |
| BK-86-1-1 | (pT7 hmw1A(125)/ T7 hmw1ABC(125)/Kan$^R$) | 203258 | 25 Sep. 1998 |
| BK-35-4 | (pT7 hmw1ABC(125)/cer) | 203259 | 25 Sep. 1998 |
| BK-76-1-1 | (pT7 hmw1ABC(125)/cer/Kan$^R$) | 203263 | 25 Sep. 1998 |
| DS-2334-5 | (pT7 hmw2A(LCDC2)/ hmw1BC(12)/cer/Kan$^R$) | 203260 | 25 Sep. 1998 |
| JB-2646-1 | (pT7 hmw1BC(12)/cer/Kan$^R$) | 203256 | 25 Sep. 1998 |
| DS-2400-13 | (pBRT7 hmw1A/T7 hmw1ABC/ cer/Kan$^R$) | 203263 | 25 Sep. 1998 |

EXAMPLES

The above disclosure generally describes the present invention. A more complete understanding can be obtained by reference to the following specific Examples. These Examples are described solely for the purposes of illustration and are not intended to limit the scope of the invention. Changes in form and substitution of equivalents are contemplated as circumstances may suggest or render expedient. Although specific terms have been employed herein, such terms are intended in a descriptive sense and not for the purposes of limitations.

Methods of molecular genetics, protein biochemistry, immunology and fermentation technology used, but not explicitly described in this disclosure and these Examples, are amply reported in the scientific literature and are well within the ability of those skilled in the art.

Example 1

This Example describes the construction of plasmid DS-1091-2 that expresses the hmw1ABC genes encoding the full-length 160 kDa HMW1A protein.

Figure 1A:
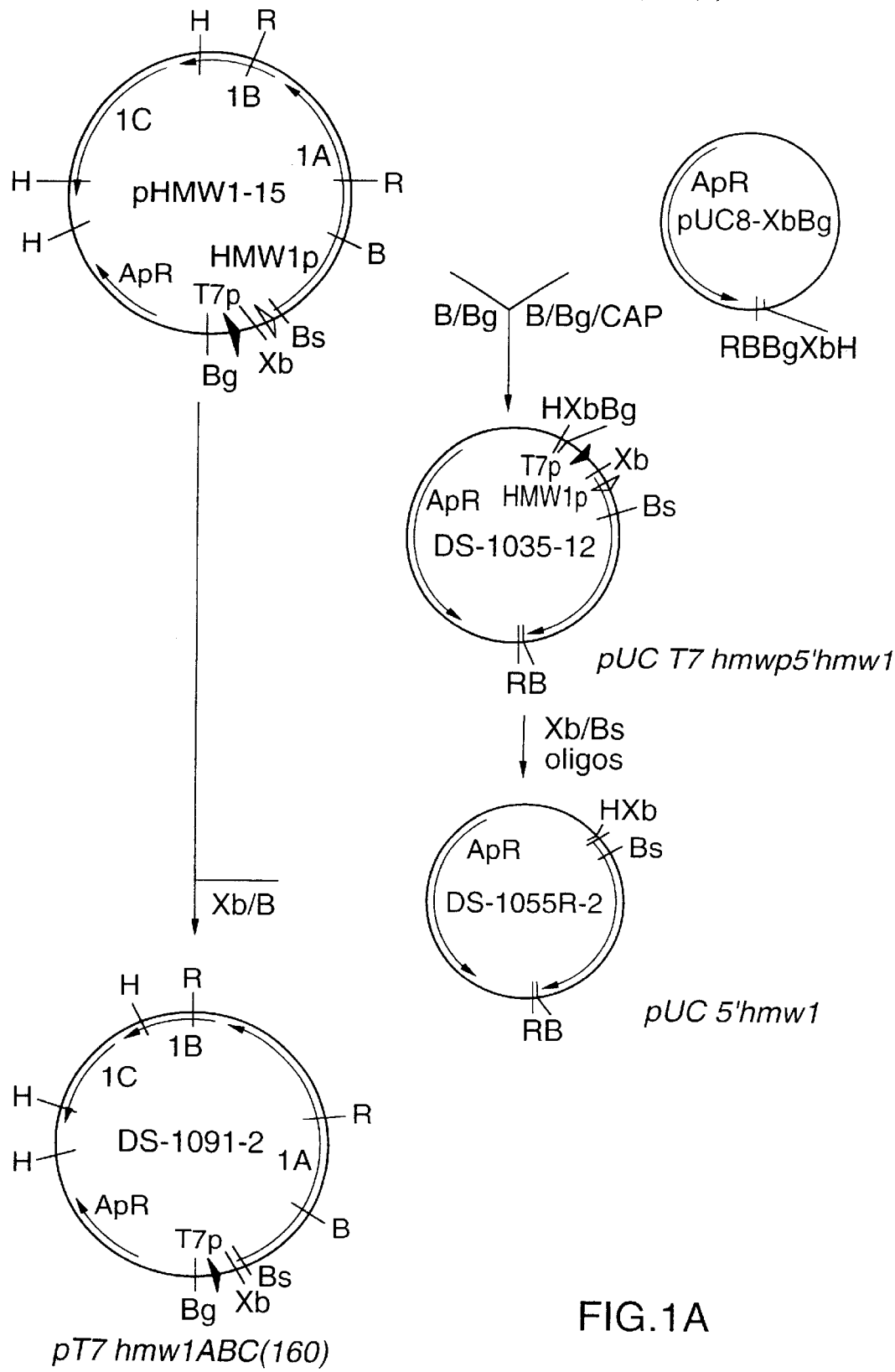
FIG. 1A shows the construction scheme to generate plasmid DS-1091-2 that expresses the hmw1ABC genes encoding the full-length 160 kDa HMW1A protein. Restriction enzyme sites are: B, BamH I; Bg, Bgl II; Bs, Bsm I; H, Hind III; R, EcoR I; Xb, Xba I. Other abbreviations are: T7p, T7 promoter; HMW1p, hmw1 promoter; ApR, ampicillin resistance gene; CAP, calf alkaline phosphatase.

Plasmid pHMW1-15 (ref. 8) contains about 400 bp of 5'-flanking region, including the hmw1 promoter, inserted between the T7 promoter and the start of the hmw1ABC coding region (FIG. 1). There is a unique Bgl II site in the multiple cloning site of pHMW1-15 and a unique BamH I site in the coding region of hmw1A. The 2.2 kb Bgl II-BamH I fragment was subcloned for further manipulation, generating plasmid DS-1035-12. A 400 bp Xba I-Bsm I fragment containing the 5'-flanking region was replaced by approximately 86 bp oligonucleotides (FIG. 1B) that joined the T7 promoter directly to the ATG start codon of the hmw1A gene in plasmid DS-1055R-2. The 1.5 kb Xba I-BamH I fragment from DS-1055R-2 was inserted into pHMW1-15 that had been digested with the same enzymes to generate plasmid DS-1091-2.

Example 2

This Example describes the construction of plasmid DS-1094-2 that expresses the hmw2ABC genes encoding the full-length 155 kDa HMW2A protein.

Figure 2:
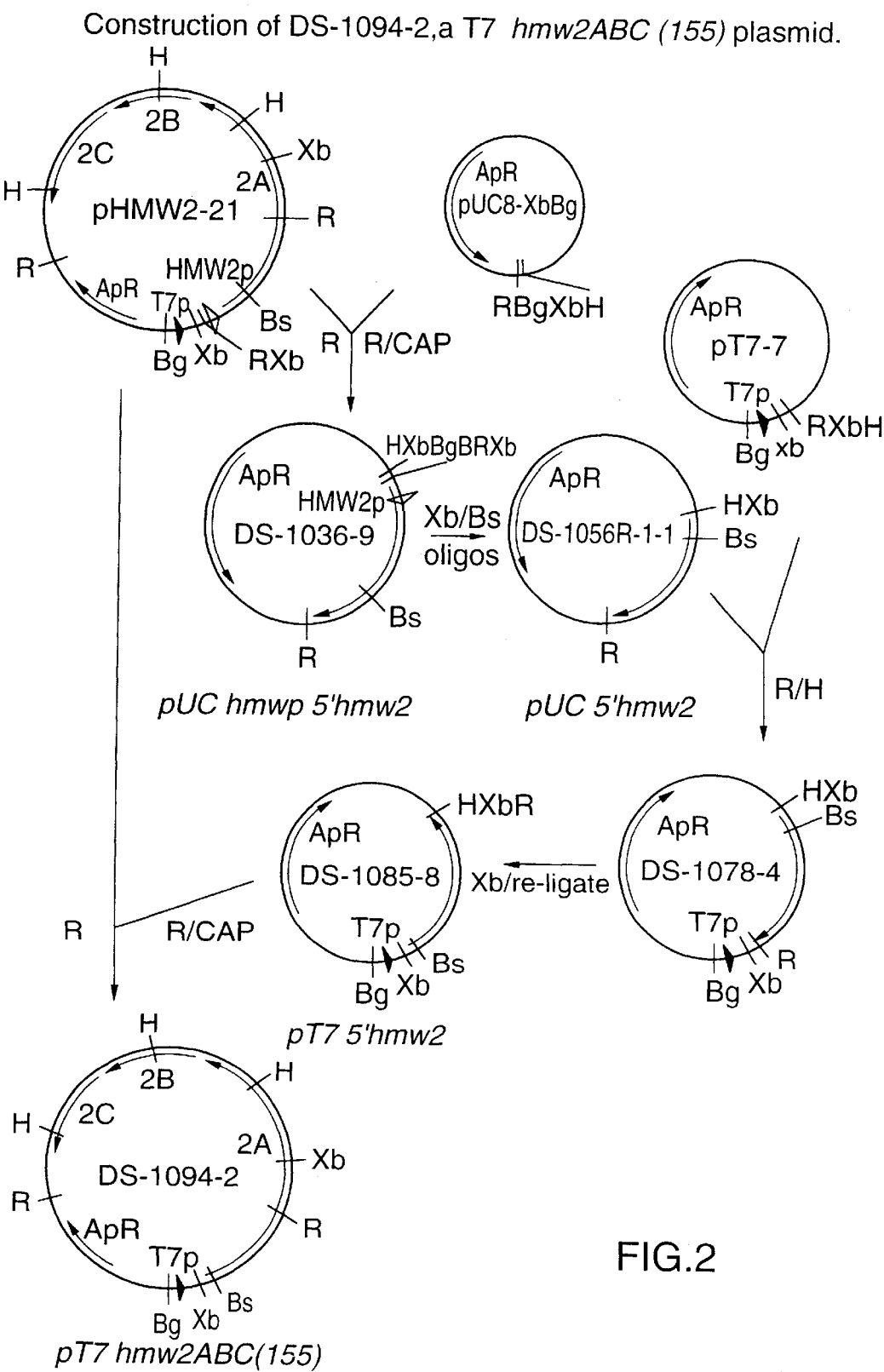
FIG. 2 shows the construction scheme to generate plasmid DS-1094-2 that expresses the hmw2ABC genes encoding the full-length 155 kDa HMW2A protein. Restriction enzyme sites are: Bg, Bgl II; Bs, Bsm I; H, Hind III; R, EcoR I; Xb, Xba I. Other abbreviations are: T7p, T7 promoter; HMW2p, hmw2 promoter; ApR, ampicillin resistance gene; CAP, calf alkaline phosphatase.

Plasmid pHMW2-21 (ref. 10) contains about 800 bp of 5'-flanking sequence, including the hmw2 promoter, between the T7 promoter and the start of the hmw2ABC coding sequence (FIG. 2). Plasmid pHMW2-21 has two EcoR I sites, one in the multiple cloning site, and one within the coding sequence of the hmw2A gene. The 2.5 kb EcoR I fragment was subcloned for further manipulation, generating plasmid DS-1036-9. The approximately 800 bp Xba I-Bsm I fragment containing the 5'-flanking sequences, was replaced by the same approximately 86 bp oligonucleotides that were used for hmw1 (FIG. 1B), to join the T7 promoter directly to the ATG start codon of hmw2A, generating plasmid DS-1056R-1-1. An intermediate plasmid (DS-1078-4) was necessary to introduce convenient restriction enzyme sites, and the Xba I insert was excised, then re-ligated to change orientation for plasmid DS-1085-8. Plasmid DS-1085-8 was linearized with EcoR I, dephosphorylated, and ligated with the 8 kb EcoR I fragment from pHMW2-21, to generate plasmid DS-1094-2 that contains the T7 promoter joined directly, to the coding sequence of hmw2ABC.

Example 3

This Example illustrates the construction of plasmid DS-1046-1-1 that expresses the hmw1ABC genes encoding the mature 125 kDa HMW1A protein.

Figure 3A:
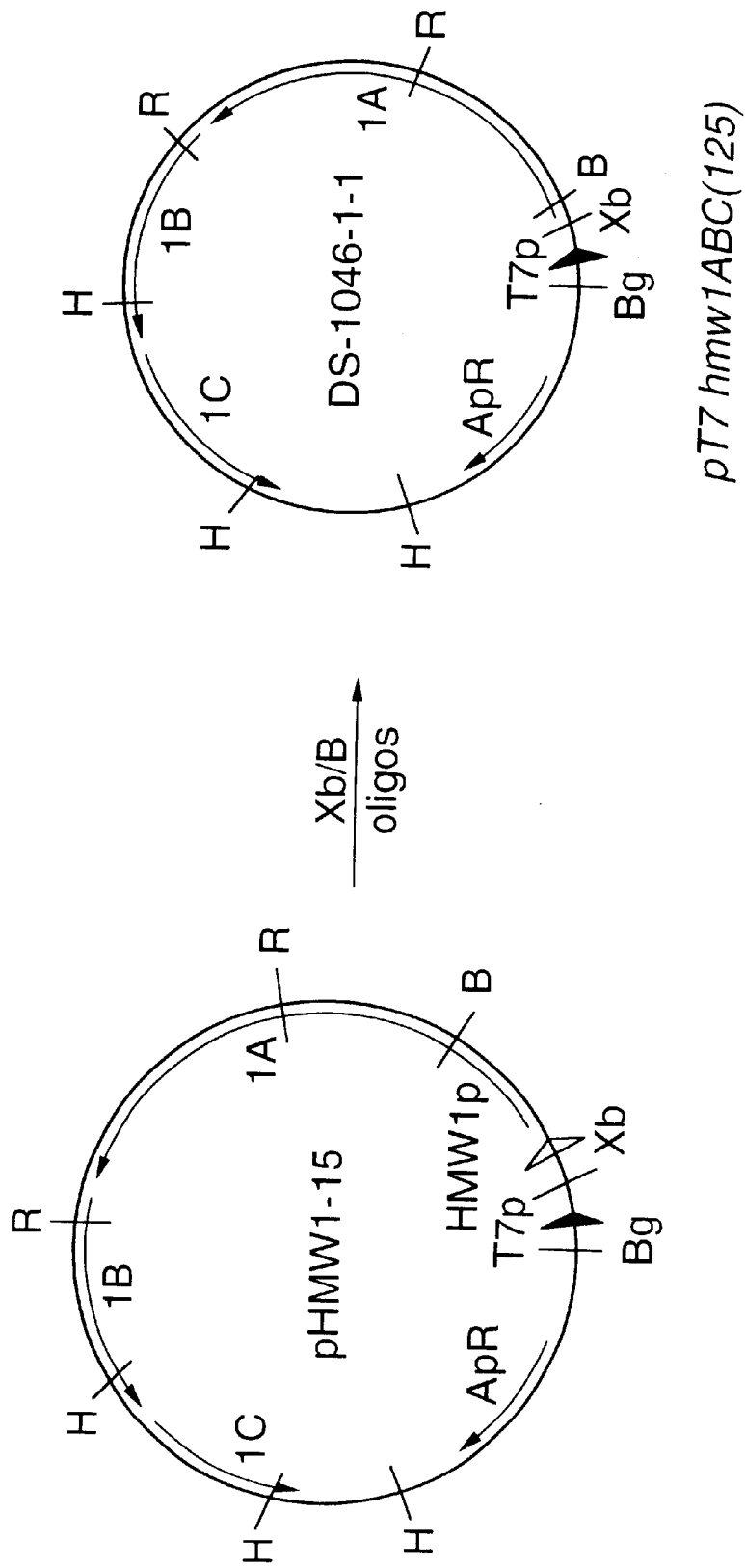
FIG. 3A shows the construction scheme to generate plasmid DS-1046-1-1 that expresses the hmw1ABC genes encoding the mature 125 kDa HMW1A protein. Restriction enzyme sites are: B, BamH I; Bg, Bgl II; H, Hind III; R, EcoR I; Xb, Xba I. Other abbreviations are: T7p, T7 promoter; HMW1p, hmw1promoter; ApR, ampicillin resistance gene.

Plasmid pHMW1-15 (ref. 8) contains a Xba I site within the T7 promoter sequence and a unique BamH I site within the coding sequence of the mature HMW1A protein (FIG. 3A). The 1.8 kb Xba I-BamH I fragment of pHMW1-15 was deleted and replaced by an approximately 114 bp Xba I-BamH I fragment generated from oligonucleotides (FIG. 3B). The resultant 11.3 kb plasmid, DS-1046-1-1, thus contains the T7 promoter joined in frame with the hmw1ABC operon that encodes the mature 125 kDa HMW1A protein.

Example 4

This Example illustrates the construction of plasmid DS-1200-3 that expresses the hmw2AB partial C genes encoding the mature 120 kDa HMW2A protein.

Figure 4A:
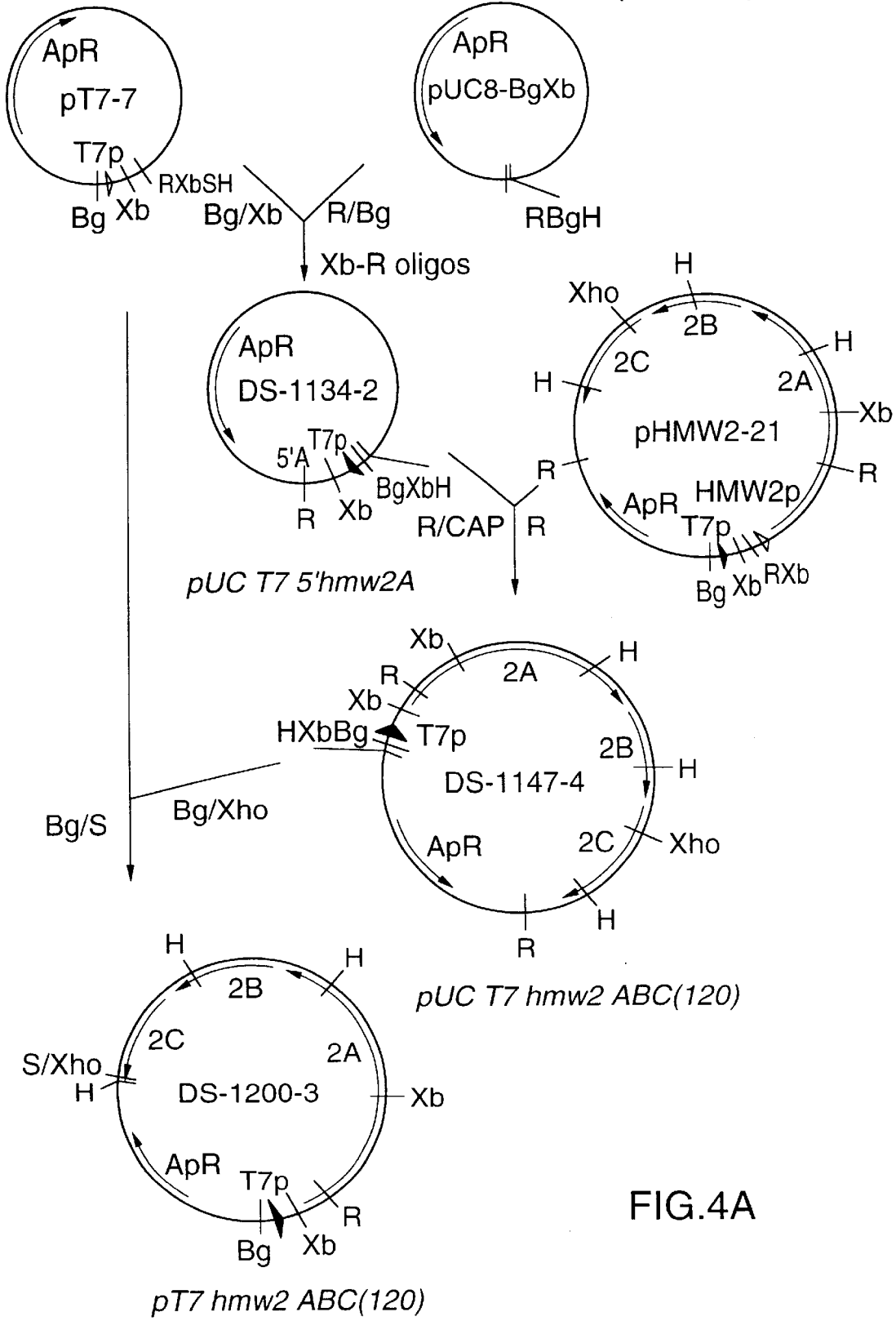
FIG. 4A shows the construction scheme to generate plasmid DS-1200-3 that expresses the hmw2AB genes encoding the mature 120 kDa HMW2A protein. Restriction enzyme sites are: Bg, Bgl II; H, Hind III; R, EcoR I; S, Sal I; Xb, Xba I; Xho, Xho I. Other abbreviations are: T7p, T7 promoter; HMW2p, hmw2 promoter; ApR, ampicillin resistance gene; CAP, calf alkaline phosphatase.

Plasmid pHMW2-21 (ref. 10) contains an EcoR I site within the coding sequence of the mature HMW2A protein. However, it is not unique (FIG. 4A). A multi-step construction process involved first re-creating part of the T7 promoter and the start of the hmw2A gene encoding the mature HMW2A protein, from 105 bp oligonucleotides (FIG. 4B). Plasmid DS-1134-2 contains the complete T7 promoter and the 5'-sequence encoding the mature HMW2A protein. Plasmid DS-1134-2 was linearized with EcoR I, dephosphorylated, and the 8 kb EcoR I fragment from pHMW2-21, containing most of the hmw2A gene and all of the hmw2B and hmw2C genes was inserted. Plasmid DS-1147-4 is a pUC-based plasmid containing the T7 hmw2ABC gene cassette. The entire cassette was removed on a 6.5 kb Bgl II-Xho I fragment and inserted into pT7-7 that had been digested with Bgl II and Sal I, to create plasmid DS-1200-3. Part of the hmw2C gene was deleted in this construct.

Example 5

This Example illustrates the construction of plasmid DS-1122-2 that contains the hmw1A gene encoding the mature 125 kDa HMW1A protein, and part of the hmw1B gene.

Figure 5:
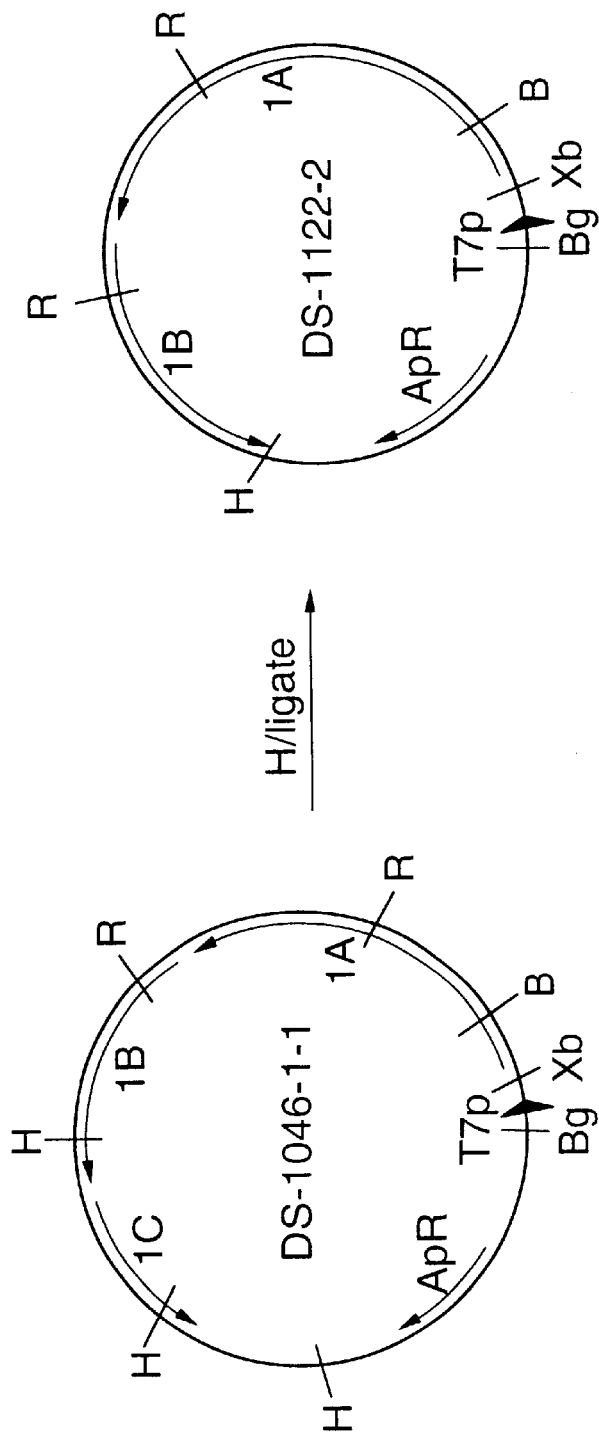
FIG. 5 shows the construction scheme to generate plasmid DS-1122-2 that contains the hmw1A gene encoding the mature 125 kDa HMW1A protein, and part of the hmw1B gene. Restriction enzyme sites are: B, BamH I; Bg, Bgl II; H, Hind III; R, EcoR I; Xb, Xba I. Other abbreviations are: T7p, T7 promoter; ApR, ampicillin resistance gene.

Plasmid DS-1046-1-1 (FIG. 3A; Example 3) contains three Hind III sites, one within the hmw1B gene, one within the hmw1C gene and one in the 3'-region of the multiple cloning site (FIG. 5). When DS-1046-1-1 was digested with Hind III, then re-ligated, plasmid DS-1122-2 was generated that contains a complete hmw1A gene encoding the mature 125 kDa HMW1A protein, part of the hmw1B gene, and no hmw1C gene.

Example 6

This Example illustrates the construction of plasmid JB-2330-7 that contains the hmw1A gene encoding the mature 125 kDa HMW1A protein, with no other hmw genes.

PCR amplification was performed on plasmid DS-1122-2 (FIG. 5; Example 5) DNA to generate a 500 bp fragment from the Kpn I site near the 3'-end of hmw1A, through the terminator, and introducing restriction enzyme sites for Xho I and Hind III at the 3'-end. The fragment was cloned into pCR II, generating plasmid DS-2056-1-1 (FIG. 6A) and the oligonucleotides used are shown in FIG. 6B. Plasmid DS-1122-2 was digested with Kpn I and Hind III which deletes most of the hmw1A gene and all of the hmw1B gene fragment. The 2.6 kb Kpn I-Hind III vector fragment from DS-1122-2 was ligated with the 0.5 kb Kpn I-Hind III fragment from DS-2056-1-1 to generate plasmid JB-2321-1, that contains approximately 0.2 kb of 5'-hmw1A sequence and approximately 0.5 kb of 3'-hmw1A sequence, joined at the Kpn I site. Plasmid JB-2321-1 was linearized with Kpn I, dephosphorylated, and the internal 2.7 kb Kpn I fragment from DS-1122-2 was inserted to create plasmid JB-2330-7. This plasmid contains a T7 hmw1A gene cassette with no additional hmw1 gene sequences.

Example 7

This Example illustrates the construction of plasmid JB-2369-6 that contains tandem copies of the T7 hmw1A gene cassette encoding the mature 125 kDa HMW1A protein.

Figure 6A:
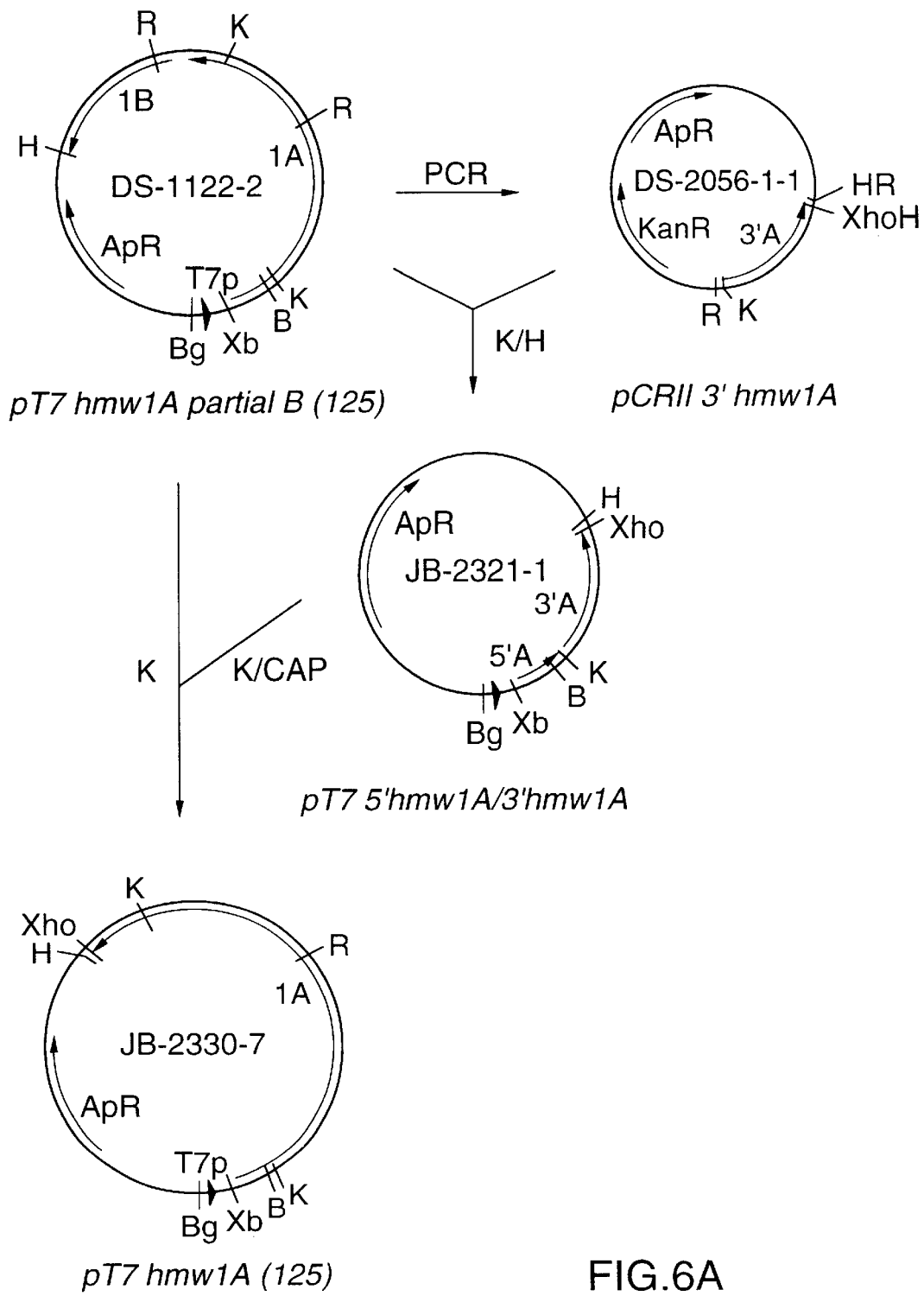
FIG. 6A shows the construction scheme to generate plasmid JB-2330-7 that expresses the hmw1A gene encoding the mature 125 kDa HMW1A protein. Restriction enzyme sites are: B, BamH I; Bg, Bgl II; H, Hind III; K, Kpn I; R, EcoR I; Xho, Xho I. Other abbreviations are: T7p, T7 promoter; ApR, ampicillin resistance gene; KanR, kanamycin resistance gene, CAP, calf alkaline phosphatase.
Figure 6B:
FIG. 6B shows the oligonucleotides used to PCR amplify the 3'-end of hmw1A in the construction scheme of FIG. 6A (SEQ ID NOS: 10, 11, 12, 13 and 14).
Figure 7:
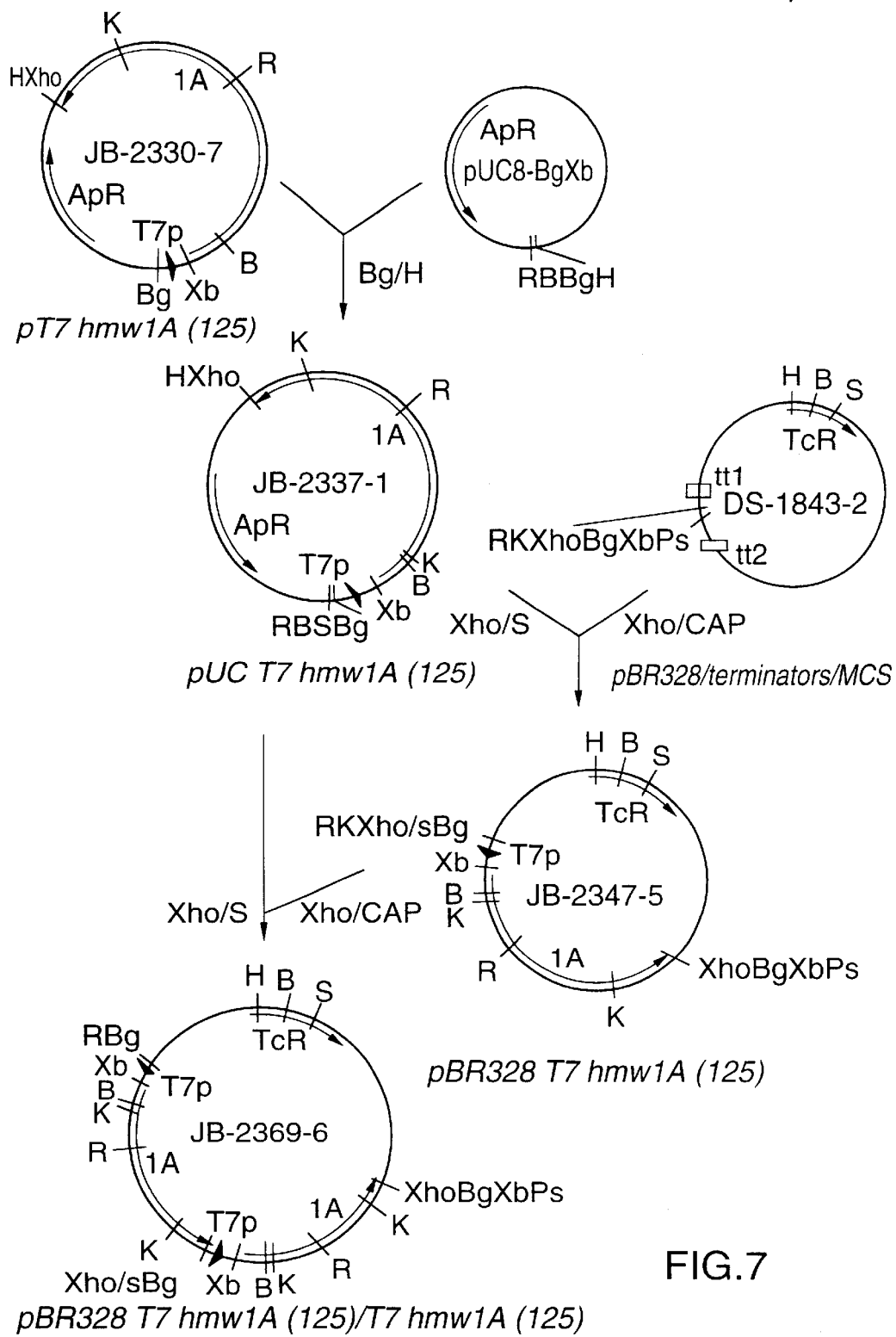
FIG. 7 shows the construction scheme to generate plasmid JB-2369-6 that expresses tandem copies of the T7 hmw1A gene cassette encoding the mature 125 kDa HMW1A protein. Restriction enzyme sites are: B, BamH I; Bg, Bgl II; H, Hind III; K, Kpn I; R, EcoR I; S, Sal I; Xb, Xba I; Xho, Xho I. Other abbreviations are: T7p, T7 promoter; ApR, ampicillin resistance gene; TcR, tetracycline resistance gene; CAP, calf alkaline phosphatase; tt1, transcription terminator 1; tt2 transcription terminator 2; MCS, multiple cloning site.

Plasmid JB-2330-7 (FIG. 6A; Example 6) was digested with Bgl II and Hind III and the T7 hmw1A gene cassette was subcloned into pUC-BgXb that had been digested with Bgl II and Hind III, creating plasmid JB-2337-1 (FIG. 7). Plasmid JB-2337-1 was digested with Sal I and Xho I which released the T7 hmw1A cassette, on a fragment with compatible ends. Vector DS-1843-2 is a pBR328-based plasmid containing transcription terminators and a multiple cloning site with a unique Xho I site. Vector DS-1843-2 was digested with Xho I, dephosphorylated, and then ligated with the 3.5 kb Sal I-Xho I T7 hmw1A gene cassette to generate plasmid JB-2347-5. Because the Sal I and Xho I sites seal, this plasmid contains a unique Xho I site at the 3'-end of the T7 hmw1A gene cassette that can be used to insert additional Sal I-Xho I T7 hmw1A gene cassettes derived from JB-2337-1. Plasmid JB-2369-6 contains two tandem T7 hmw1A genes introduced in this way.

Example 8

This Example illustrates the construction of plasmids DS-2084-3 and DS-2084-1 that contain one or two tandem copies of the T7 hmw2A gene cassette encoding the mature HMW2A protein.

Figure 8A:
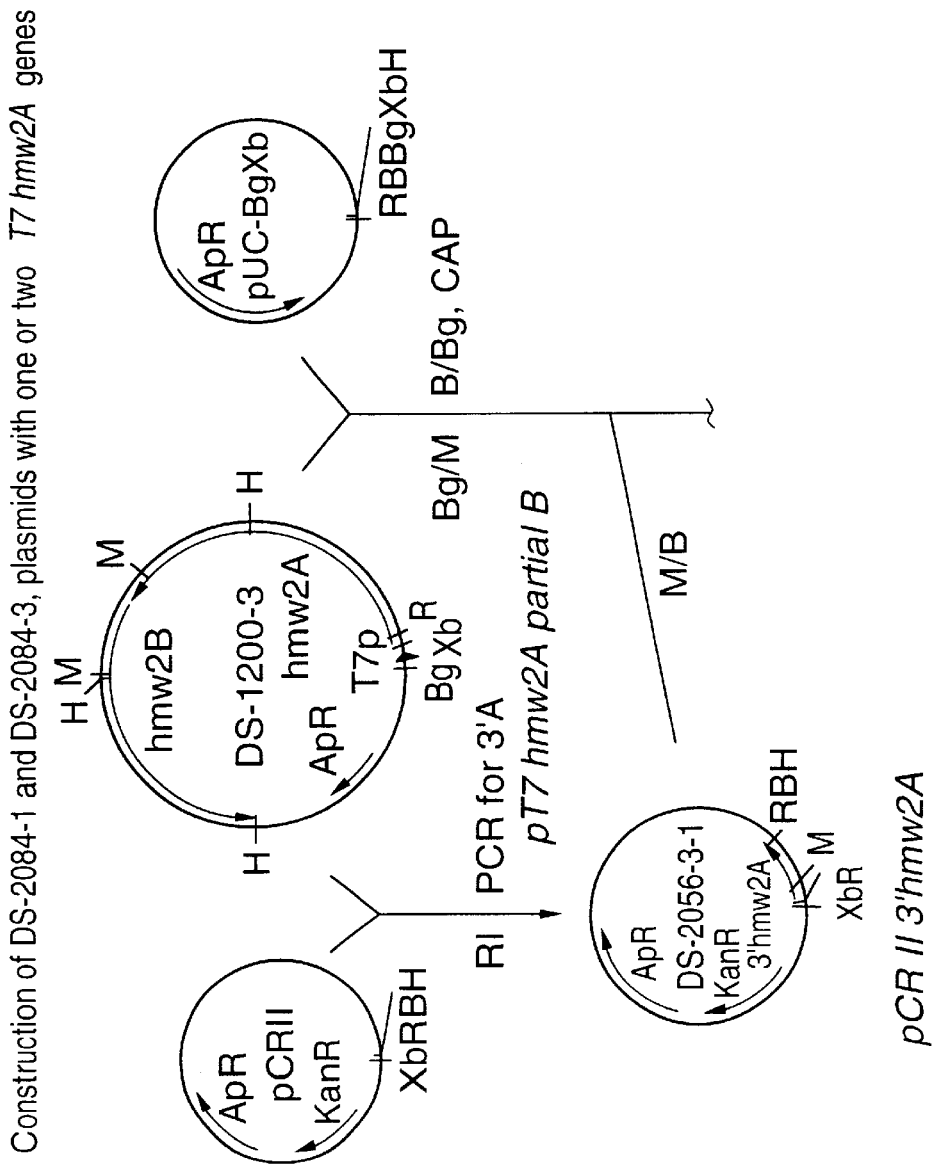
Figure 8A:
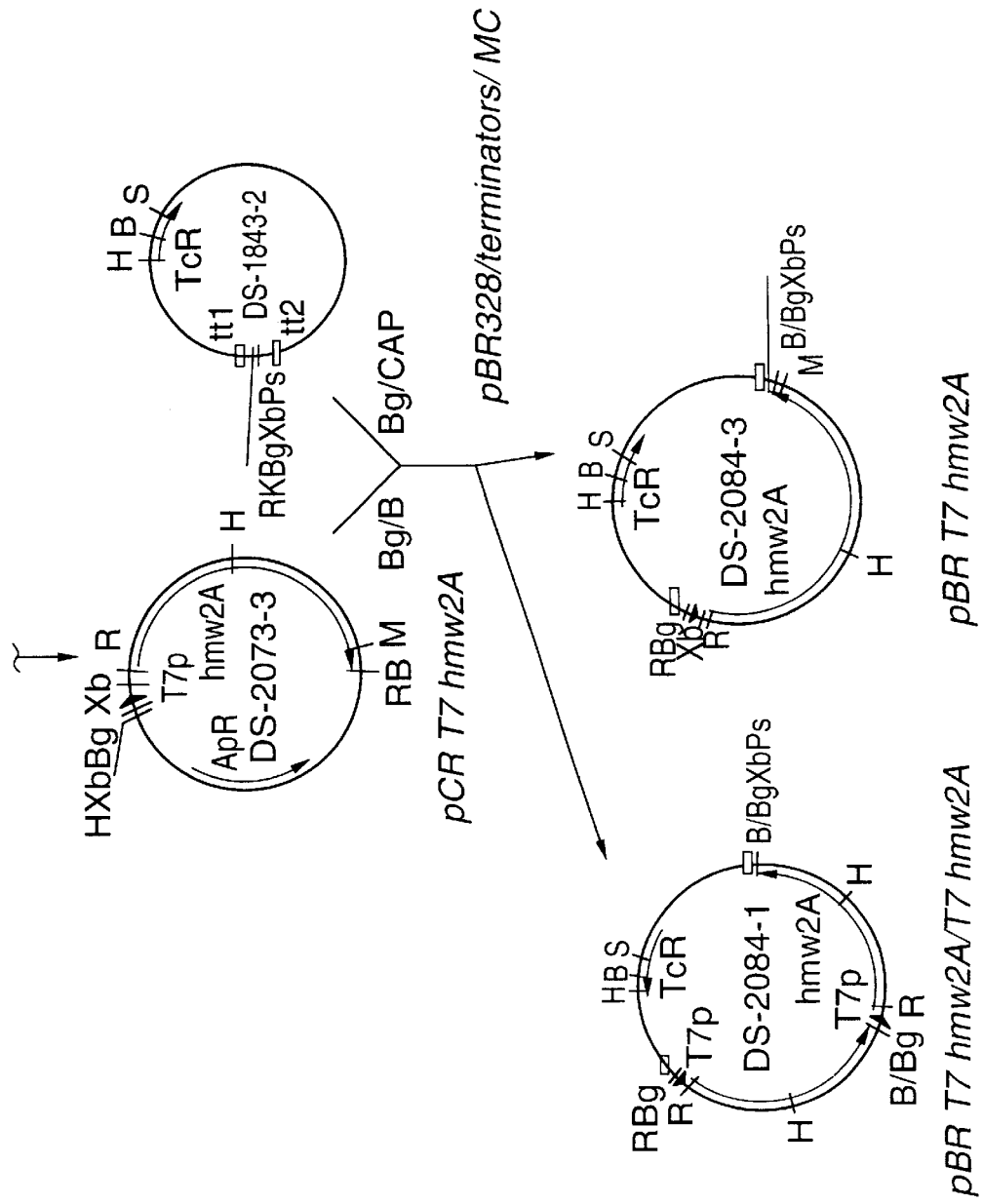

Plasmid DS-1200-3 (FIG. 4A, Example 4) contains the T7 hmw2AB partial C gene cassette. There are two Mlu I sites in DS-1200-3, one located near the 3'-end of hmw2A and the other located near the 5'-end of hmw2B (FIG. 8A). Oligonucleotide primers were used to PCR amplify a 247 bp fragment of the 3'-end of the hmw2A gene from the Mlu I site, and to introduce a unique BamH I site following the termination codon of hmw2A (FIG. 8B). The 247 bp PCR fragment was subcloned into pCRII generating plasmid DS-2056-3-1. Plasmid DS-1200-3 was digested with Bgl II and Mlu I and the 3.2 kb fragment containing the T7 promoter and most of the hmw2A gene was purified. Plasmid pUC-BgXb was digested with Bgl II and BamH I and dephosphorylated. The Bgl II-Mlu I hmw2A gene fragment and the Mlu I-BamH I PCR fragment from DS-2056-3-1 were ligated into the pUC vector to generate plasmid DS-2073-3 which thus contains a 3.4 kb T7 hmw2A gene cassette on a Bgl II-BamH I fragment, with no additional hmw2 genes. Plasmid DS-1843-2 was linearized with Bgl II and the 3.4 kb Bgl II-BamH I cassette was inserted, generating plasmid DS-2084-3 that contains a single T7 hmw2A gene cassette and plasmid DS-2084-1 that contains two tandem T7 hmw2A gene cassettes.

Example 9

This Example illustrates the construction of plasmids JB-2507-7 and BK-86-1-1 that contain tandem T7 hmw1A/ T7 hmw1ABC genes encoding the mature 125 kDa HMW1A protein and are resistant to ampicillin or kanamycin, respectively.

Figure 9:
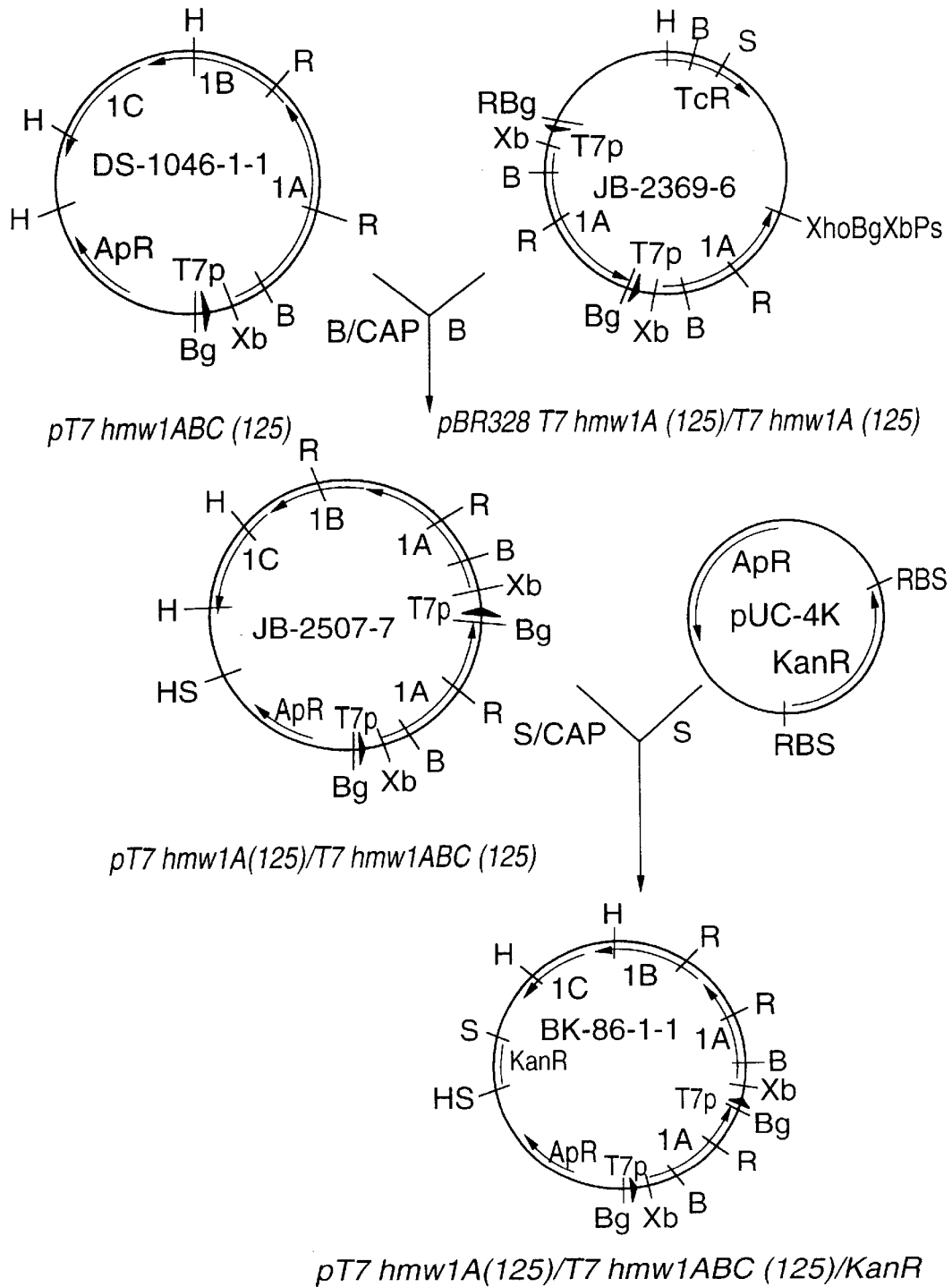
FIG. 9 shows the construction scheme to generate plasmids JB-2507-7 and BK-86-1-1 that contain tandem T7 hmw1A/T7 hmw1ABC genes encoding the mature 125 kDa HMW1A protein, with ampicillin or kanamycin selection, respectively. Restriction enzyme sites are: B, BamH I; Bg, Bgl II; H, Hind III; K, Kpn I; R, EcoR I; S, Sal I; Xb, Xba I; Xho, Xho I. Other abbreviations are: T7p, T7 promoter; ApR, ampicillin resistance gene; KanR, kanamycin resistance gene; TcR, tetracycline resistance gene; CAP, calf alkaline phosphatase.

Plasmid DS-1046-1-1 (FIG. 3A; Example 3) contains the T7 hmw1ABC gene cassette and has a unique BamH I site within the coding region of the mature HMW1A protein. Plasmid JB-2369-6 (FIG. 7; Example 7) contains tandem T7 hmw1A gene cassettes, each of which contains an internal BamH I site within the coding sequence for HMW1A. When plasmid JB-2369-6 was digested with BamH I, a 3.5 kb fragment was generated that contains the 3'-end of the first hmw1A gene and the T7 promoter and 5'-end of the second hmw1A gene. This fragment was ligated into the BamH I site of DS-1046-1-1 to create plasmid JB-2507-7 that contains tandem T7 hmw1A/T7 hmw1ABC gene cassettes (FIG. 9). The unique Sal I site found in the multiple cloning site of the pT7-7 vector backbone, was used to linearize JB-2507-7. The kanamycin resistance cassette was excised from pUC-4K by Sal I digestion, and ligated with the JB-2507-7 vector to generate plasmid BK-86-1-1.

Example 10

This Example illustrates the construction of plasmids BK-35-4 and BK-76-1-1 that contain the T7 hmw1ABC gene cassette and an *E. coli* cer gene and are ampicillin or kanamycin resistant, respectively.

Plasmid DS-2224-1-4 (FIG. 10) contains an *E. coli* cer gene (ref. 13) that was created from approximately 290 bp oligonucleotides cloned into the BamH I site of pUC-BgXb. Plasmid DS-1046-1-1 (FIG. 3; Example 3) contains a unique Bgl II site upstream of the T7 promoter. Plasmid DS-1046-1-1 was linearized with Bgl II, dephosphorylated, and ligated with the 290 bp BamH I fragment containing the cer gene from DS-2224-1-4, to create plasmid BK-35-4. The kanamycin resistance cassette was excised from pUC-4K by Sal I digestion and was inserted at the unique Sal I site of BK-35-4 to create plasmid BK-76-1-1.

Example 11

This Example illustrates the analysis of the production of rHMW1 and rHMW2 proteins from the different constructs produced in the preceding Examples.

Figure 11:
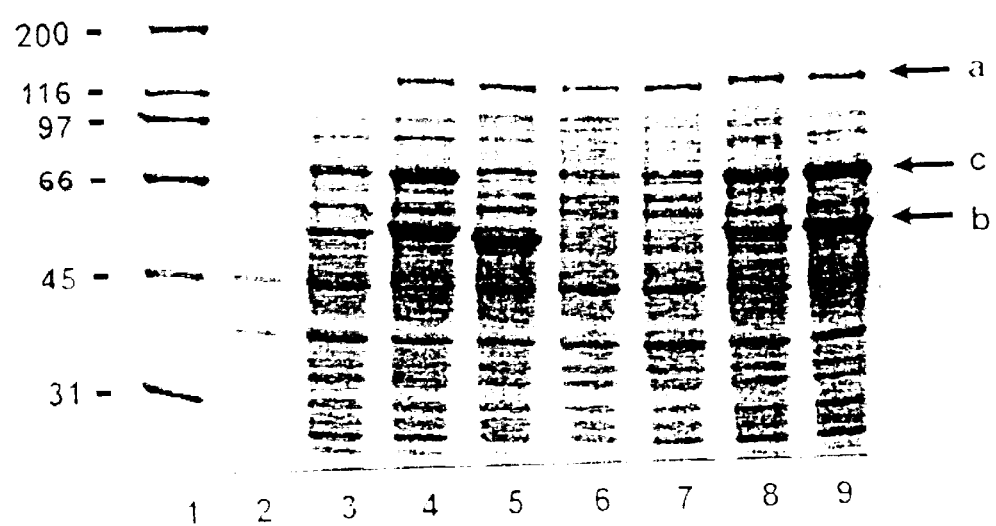
FIG. 11 shows SDS-PAGE analysis of the expression of recombinant HMW1 proteins from various constructs. Lane 1, broad range molecular weight markers; lane 2, DS-1046-1-1 [pT7 hmw1ABC (125)], no induction; lane 3, DS-1091-2 [pT7 hmw1ABC (160)]; lane 4, DS-1046-1-1 [pT7 hmw1ABC (125)]; lane 5, DS-1122-2 [pT7 hmw1A partial B (125)]; lane 6, JB-2330-7 [pT7 hmw1A (125)]; lane 7, JB-2369-6 [pBr328 T7 hmw1A (125)/T7 hmw1A (125)]; lane 8, BK-86-1-1 [pT7 hmw1A (125)/T7 hmw1ABC (125)/kanR]; lane 9, BK-76-1-1 [pT7 hmw1ABC (125)/cer/kanR]; lane 10, broad range molecular weight markers.

Plasmids were introduced into *E. coli* BL21(DE3) cells by electroporation using a BioRad apparatus. Strains were grown at 37° C. in NZCYM medium to an optical density of $A_{578}=0.3$, then induced by the addition of lactose to 1.0% for 4 hours. Samples were adjusted to 0.2 OD/µl with SDS-PAGE lysis+loading buffer and the same amount of protein sample was loaded onto SDS-PAGE gels. FIG. 11 illustrates the relative production of rHMW proteins from various constructs as analysed by SDS PAGE gels. The identification of the lanes in relation to the specific constructs is given in the description of the Figure above. "a" indicates the band for HMWA proteins, "b" indicates the band for HMWB proteins and "c" indicates the band for HMWC proteins.

As may be seen therein, the production of the HMW1A, B, and C proteins from the T7 hmw1ABC(160 construct (lane 3) is negligible. The production of all three proteins is improved in the T7 hmw1ABC(125) construct (lane 4). In lane 5, there is no production of the HMW1C protein and the HMW1B protein is slightly reduced in size due to the truncation of its gene in the T7 hmw1A partial B construct. In lane 6, there is no production of HMW1B or HMW1C protein from the T7 hmw1A(125) construct. Lane 7 shows that there was marginal, if any, improvement in the production of HMW1A from the T7 hmw1A/T7 hmw1A construct. In lane 8, the production of HMW1A, HMW1B and HMW1C proteins is evident when expressed from the T7 hmw1A/T7 hmw1ABC construct. In lane 9, the HMW1A, HMW1B and HMW1C proteins are all produced from the T7 hmw1ABC/cer construct.

Example 12

This Example illustrates the purification of recombinant HMW1 and HMW2 proteins.

Figure 12:
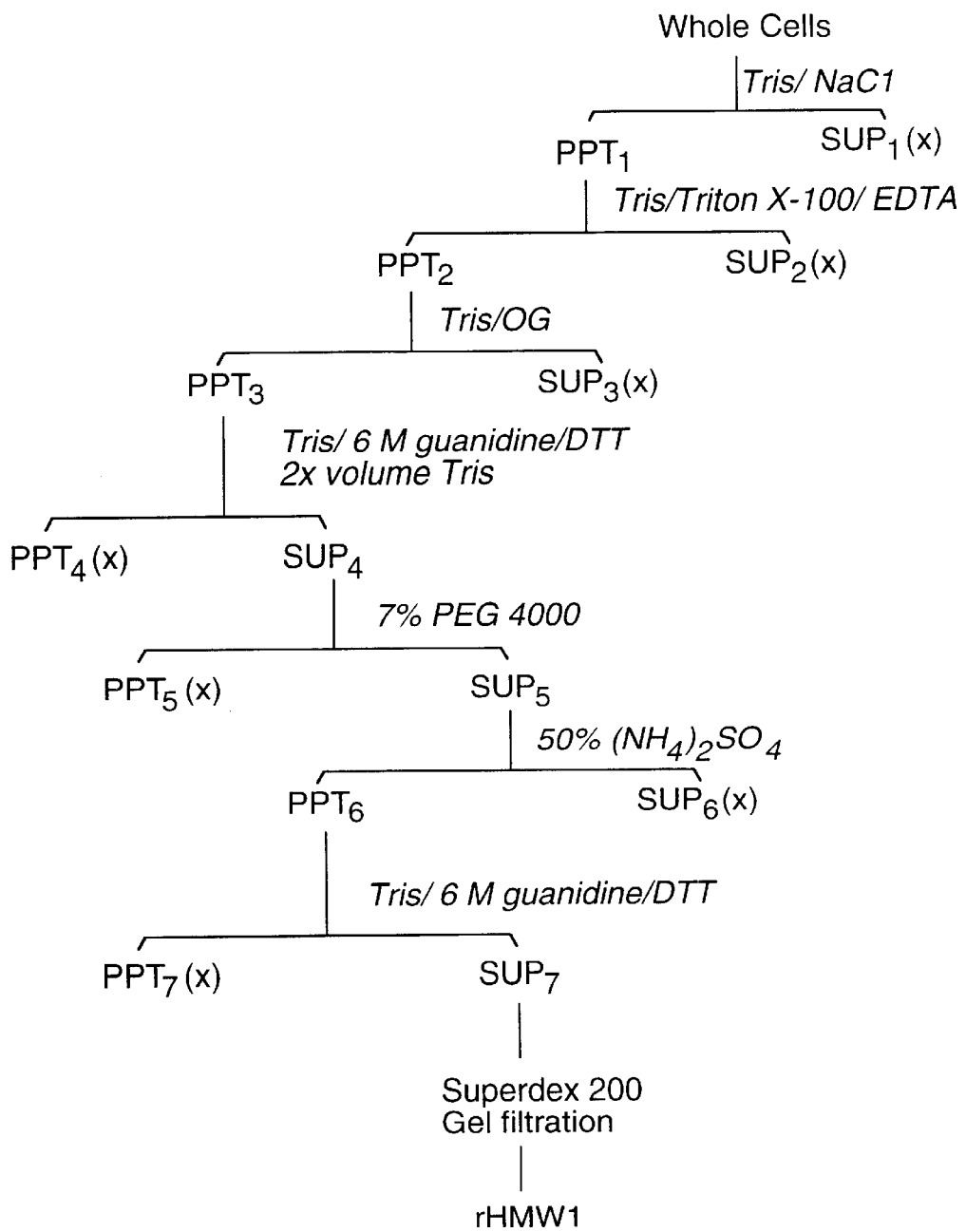
FIG. 12 shows a purification scheme for recombinant HMW1 and HMW2 proteins. Abbreviations are: PPT, pellet; SUP, supernatant; OG, octylglucoside; PEG, polyethylene glycol.

All the recombinant HMW proteins were expressed as inclusion bodies in *E. coli*, regardless of whether there were complete or partial deletion of the B and C genes in the various constructs, and were purified by the same procedure (FIG. 12) *E. coli* cell pellets from 500 ml culture were resuspended in 50 ml of 50 mM Tris-HCl, pH 8.0, containing 0.1 M NaCl, and disrupted by sonication. The extract was centrifuged at 20,000 g for 30 min and the resultant supernatant was discarded. The pellet ($PPT_1$) was further extracted, in 50 ml of 50 mM Tris-HCl, pH 8.0 containing 0.5% Triton X-100 and 10 mM EDTA, then centrifuged at 20,000 g for 30 min, and the supernatant was discarded. The pellet ($PPT_2$) was further extracted in 50 ml of 50 mM Tris-HCl, pH 8.0, containing 1% octylglucoside, then centrifuged at 20,000 g for 30 min, and the supernatant was discarded.

The resultant pellet ($PPT_3$), obtained after the above extractions, contains the inclusion bodies. The pellet was solubilized in 6 ml of 50 mM Tris-HCl, pH 8.0, containing 6 M guanidine and 5 mM DTT. Twelve ml of 50 mM Tris-HCl, pH 8.0 was added to this solution and the mixture was centrifuged at 20,000 g for 30 min. The supernatant ($SUP_4$) was precipitated with polyethylene glycol (PEG) 4000 at a final concentration of 7%. The resultant pellet ($PPT_5$) was removed by centrifugation at 20,000 g for 30 min and the supernatant was precipitated by $(NH_4)_2SO_4$ at 50% saturation. After the addition of $(NH_4)_2SO_4$, the solution underwent phase separation with protein going to the upper phase, which was then subjected to centrifugation at 20,000 g for 30 min. The resultant pellet ($PPT_6$) was dissolved in 2 ml of 50 mM Tris-HCl, pH 8.0, containing 6 M guanidine HCl and 5 mM DTT and the clear solution was purified on a Superdex 200 gel filtration column equilibrated in 50 mM Tris-HCl, pH 8.0, containing 2 M guanidine HCl. The fractions were analysed by SDS-PAGE and those containing the purified rHMW1 were pooled and dialysed overnight at 4° C. against PBS, then centrifuged at 20,000 g for 30 min. The protein remained soluble under these conditions and glycerol was added to the rHMW1 preparation at a final concentration of 20% for storage at −20° C.

Figure 13:
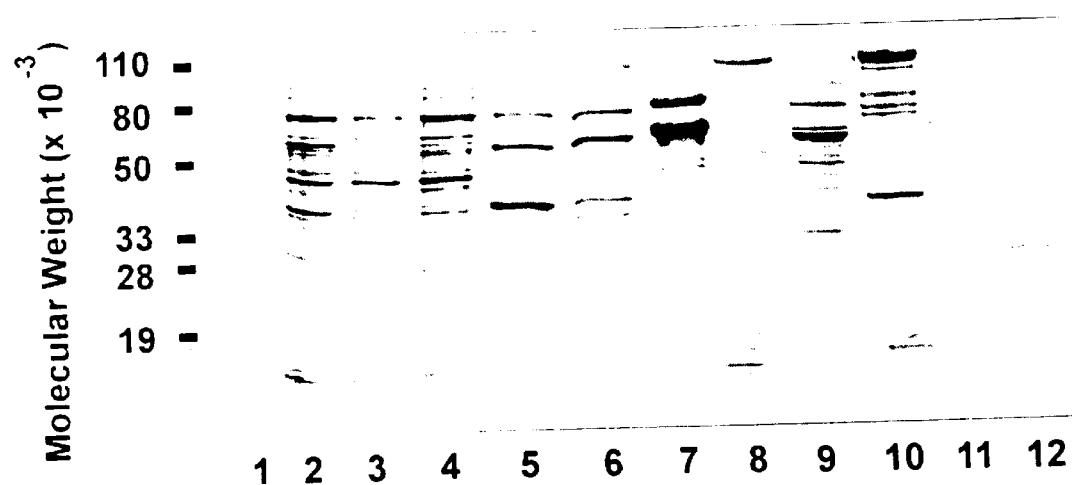
FIG. 13 shows the SDS-PAGE analysis of rHMW1 extractions. Lane 1, prestained protein molecular weight markers; lane 2, *E. coli* whole cell lysates; lane 3, soluble proteins in the Tris-HCl/NaCl extraction; lane 4, soluble proteins in the Tris-HCl/Triton X-100/EDTA extraction; lane 5, soluble proteins in the Tris-HCl/octylglucoside extraction; lane 6, pellet after Tris-HCl/octylglucoside extraction; lane 7, insoluble proteins in 2M guanidine HCl; lane 8, supernatant of 7% PEG precipitation; lane 9, pellet of 7% PEG precipitation; lane 10, interphase pellet of 50% ammonium sulfate precipitation; lane 11, proteins recovered in the lower phase; lane 12, proteins recovered in the upper phase.
Figure 14:
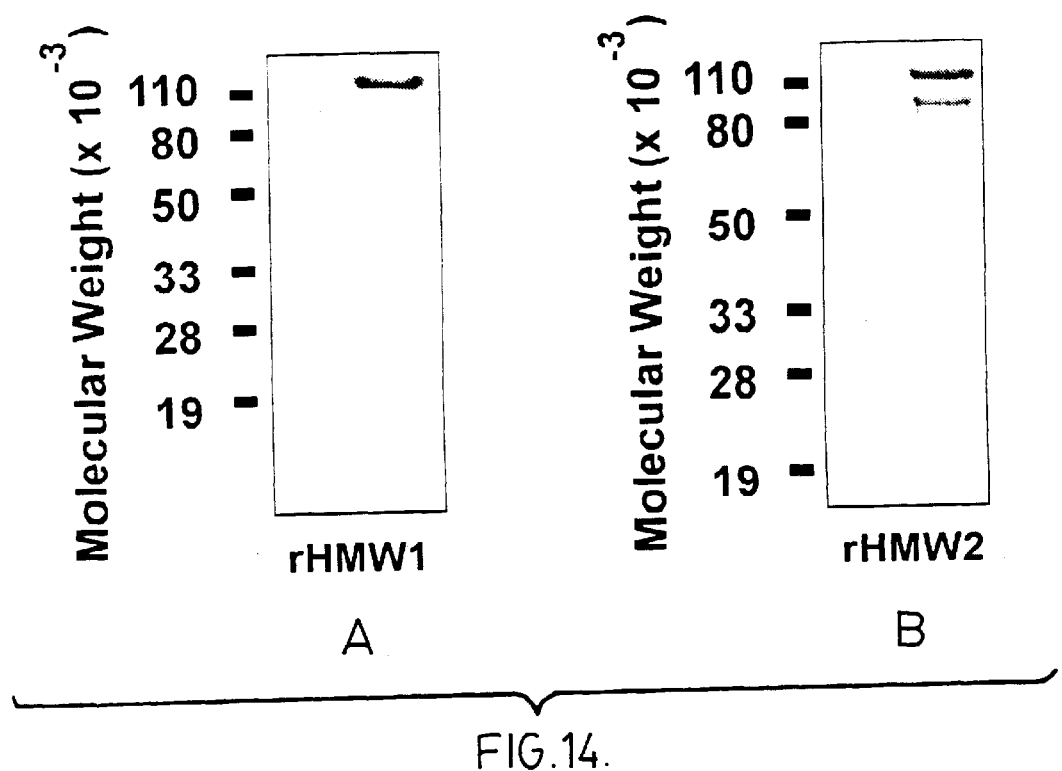
FIG. 14, comprising panels A and B, shows an SDS-PAGE analysis of the purified rHMW1 and rHMW2.

SDS-PAGE analysis of a representative rHMW1 protein (abc/cer) at various stages of purification is shown in FIG. 13. The identification of the lanes is given above in the description of the Figures. Three major protein bands at approximately 110, 80, and 60 kDa, (lane 6) were evident after the initial three extractions with 50 mM Tris-HCl/0.1 M NaCl, pH 8.0 (lane 3); 50 mM Tris-HCl/0.5% Triton X-100, pH 8.0 (lane 4); and 50 mM Tris-HCl/1% octylglucoside, pH 8.0 (lane 5). These three proteins represent the products of hmw1A, C and B genes, respectively, as confirmed by N-terminal amino acid sequencing. The products of the B and C genes were less soluble in the guanidine hydrochloride solution (lane 7), and were easily separated from the gene A product (HMW1, lane 8) by diluting the guanidine HCl concentration from 6 M to 2 M. Precipitation with 7% polyethylene glycol (PEG) 4000 removed other contaminating proteins (lane 9) from the rHMW1 preparation. A final ammonium sulfate precipitation not only concentrated rHMW1 from the PEG soluble fraction (lane 10), but also effectively removed the residual PEG (lane 11) and $(NH_4)_2SO_4$ salt (lane 12) through a phase separation that resulted from the mixing of the PEG solution with a high concentration of $(NH_4)_2SO_4$. The-rHMW1 pellet was then dissolved in 50 mM Tris-HCl, pH 8.0, containing 6 M guanidine HCl and 5 mM DTT, and purified on a Superdex 200 gel filtration column pre-equilibrated in 50 mM Tris-HCl, pH 8.0, containing 2 M guandine HCl (FIG. 14, panel A). The average yield of the purified rHMW1 is about 10 mg $L^{-1}$ culture. SDS-PAGE analysis of the purification of rHMW2A from construct T7 hmw2A/T7 hmw2A is shown in FIG. 14, panel B.

Example 13

This Example illustrates the stability of the purified rHMW1A protein.

Figure 15:
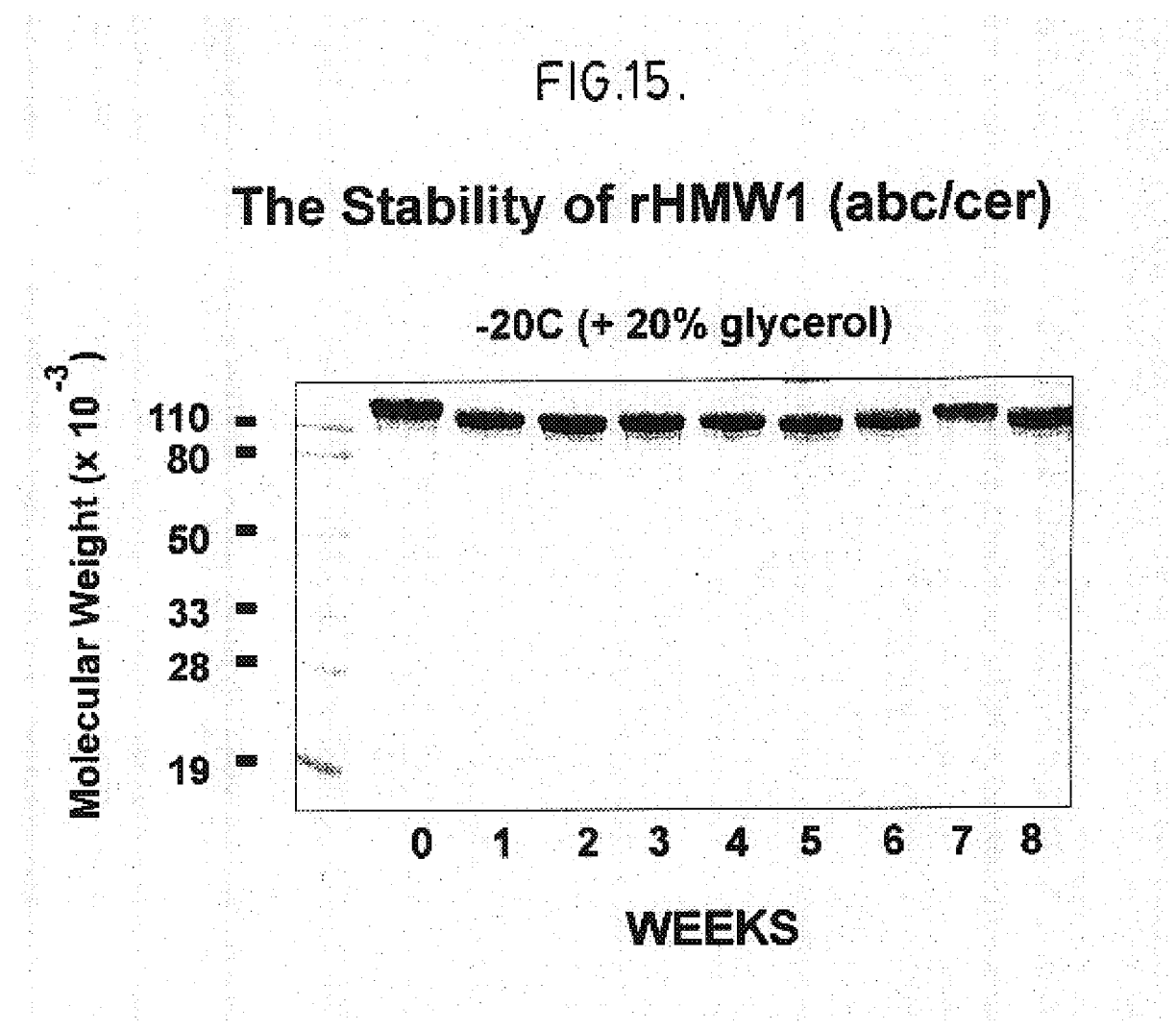

To study the stability of rHMW1A, the purified rHMW1A protein produced in accordance with Example 12 was stored at 4° C. or −20° C. with or without glycerol. In the absence of glycerol, the protein was found to be degraded when stored at 4° C. and tended to precipitate when stored at −20° C. The addition of glycerol to a final concentration of 20% not only significantly enhanced the solubility of rHMW1A, but also increased the stability of the protein when stored at −20° C. The protein remained intact for at least eight weeks even after repeated freezing and thawing (FIG. 15).

Example 14

This Example illustrates the immunogenicity of rHMW1A and rHMW2A proteins produced from different constructs.

Figure 10:
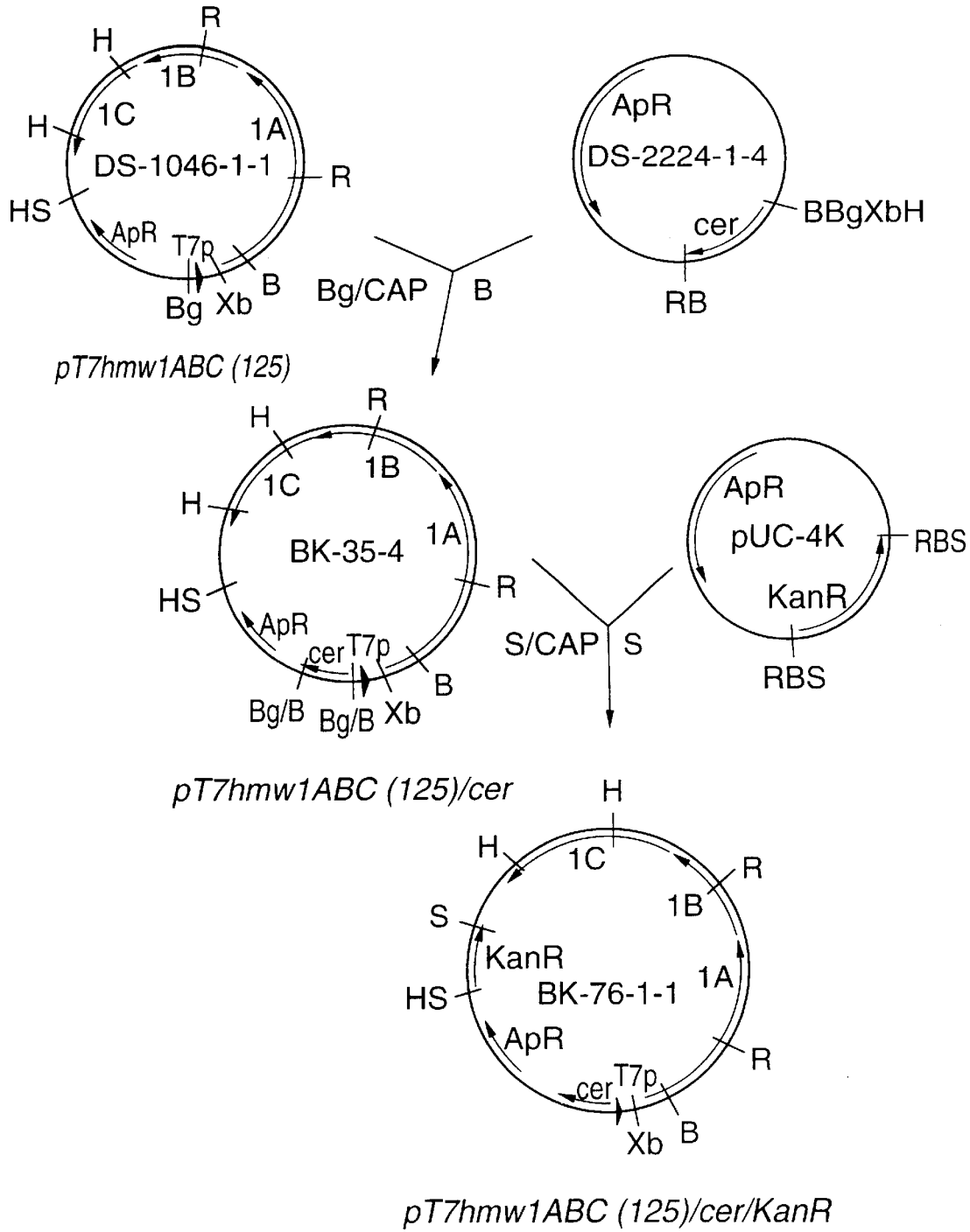
FIG. 10 shows the construction scheme to generate plasmids BK-35-4 and BK-76-1-1 that contain T7 hmw1ABC/cer genes encoding the mature 125 kDa HMW1A protein, utilizing ampicillin or kanamycin selection, respectively. Restriction enzyme sites are: B, BamH I; Bg, Bgl II; H, Hind III; K, Kpn I; R, EcoR I; S, Sal I; Xb, Xba I. Other abbreviations are: T7p, T7 promoter; ApR, ampicillin resistance gene; KanR, kanamycin resistance gene; CAP, calf alkaline phosphatase.

To study the immunogenicity of the rHMW1 protein produced from T7 hmw1ABC (pDS-1046-1-1; FIG. 3A, Example 3) or T7 hmw1ABC/cer (pBK-76-1-1; FIG. 10, Example 10) constructs and purified by the procedure of Example 12, groups of five BALB/c mice (Charles River, Quebec) were immunized s.c. on days 1, 29, and 43 with 0.3, 1, and 3 µg of antigen, in the presence $AlPO_4$ (1.5 mg per dose). Blood samples were collected on days 0, 14, 28, 42 and 56.

Figure 16A:
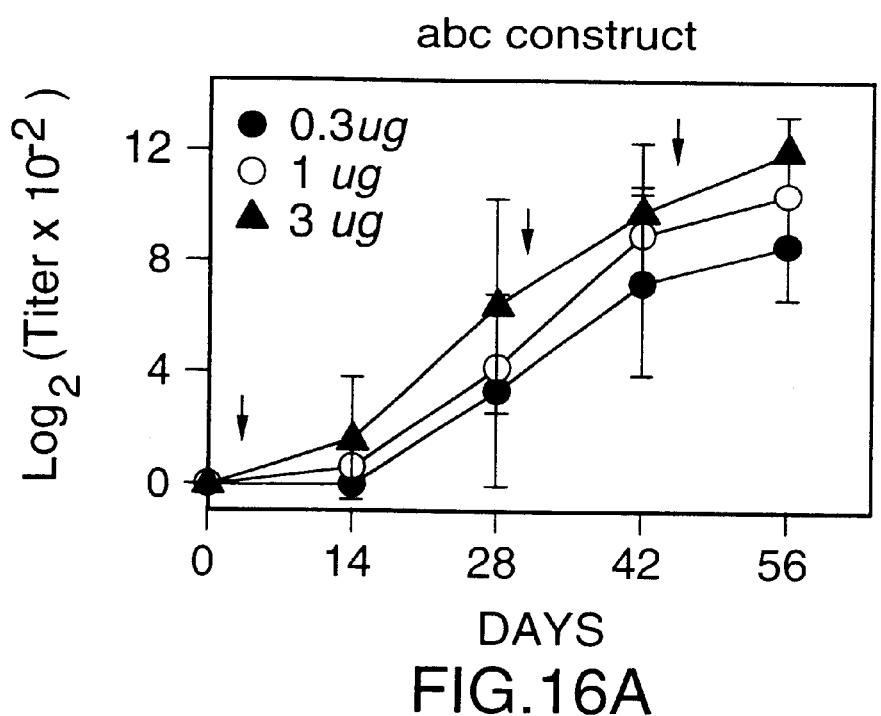
FIG. 16, comprising panels A and B, shows the immunogenicity of rHMW1A protein produced from various constructs.
Figure 16B:
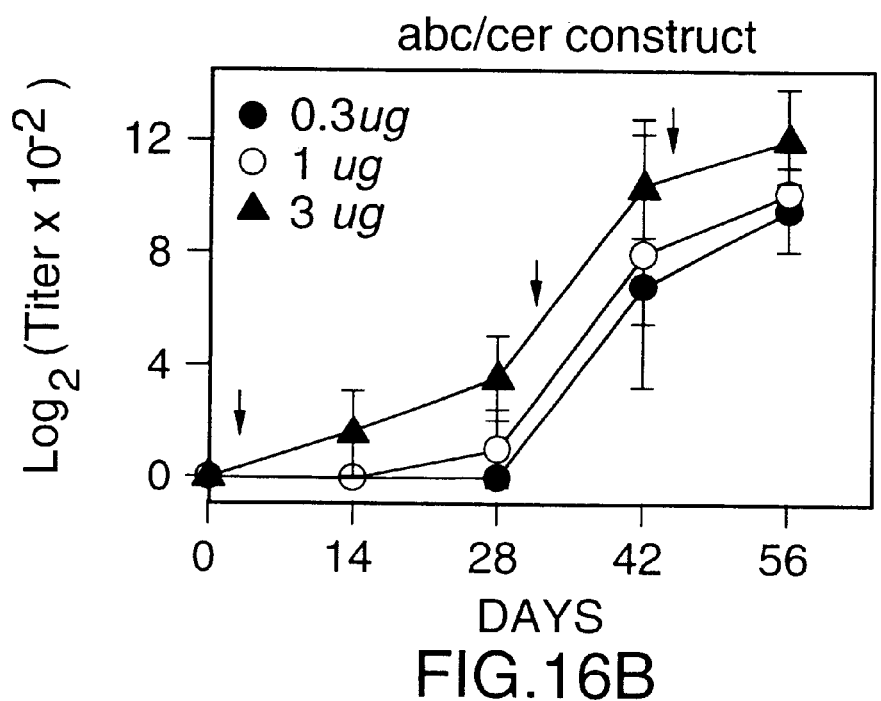

Mice immunized with purified rHMW1 derived from the T7 hmw1ABC or T7 hmw1ABC/cer constructs (0.3 to 3 µg per dose), generated dose-dependent anti-rHMW1 antibody responses (FIG. 16), suggesting that both proteins had remained immunogenic after inclusion body extraction and solubilization. No statistically significant difference was found in the antibody titers induced by the protein from these two constructs in mice.

To compare the immunogenicity of rHMW1 and rHMW2 proteins produced from several different constructs and purified according to Example 12, groups of 9 chinchillas (Moulton Chinchilla Ranch) were immunized i.m. on days 1, 14, and 28 with 30 µg of rHMW protein in the presence AlPO$_4$ (1.5 mg per dose). Blood samples were collected on day 42. Chinchilla anti-HMW antibody responses induced by various forms of rHMW are summarized in Table 1.

It was found that the rHMW1 prepared from the T7 hmw1ABC (abc) (pDS-1046-1-1; FIG. 3A, Example 3), T7 hmw1A/T7 hmw1ABC (a/abc) (pBK-86-1-1; FIG. 9, Example 9), T7 hmw1ABC/cer (abc/cer) (pBK76-1-1; FIG. 10, Example 10), and T7 hmw1A/T7 hmw1A (2xa) (pJB-2369-6; FIG. 7, Example 7) constructs, but not the T7 hmw1AB(125) (abΔ) (pDS-1122-2; FIG. 5, Example 5) construct, induced significant antibody titers in chinchillas after three immunizations. Similarly, the rHMW2 prepared from T7 hmw2ABC (abc) (pDS-1147-4; FIG. 4A, Example 4) or T7 hmw2A/T7 hmw2A (2xa) (pDS-2084-1; FIG. 8A, Example 8) constructs and purified following the procedure of Example 12 elicited significant antibody titers in chinchillas after three immunizations.

Anti-rHMW IgG titers were determined by antigen-specific enzyme-linked immunosorbent assays (EIAs). Microtiter wells (Nunc-MAXISORP, Nunc, Denmark) were coated with 50 µl of protein antigen (0.5 µg ml$^{-1}$). The reagents used in the assays are as follows: affinity-purified F(ab')$_2$ fragments of goat anti-mouse IgG (Fc-specific) conjugated to horseradish peroxidase (Jackson ImmunoResearch Labs, Mississauga, Ontario); affinity-purified guinea pig anti-IgG antibody (1 µg ml$^{-1}$) (prepared by this laboratory); and affinity-purified F(ab')$_2$ fragment of goat anti-guinea pig IgG (H+L) antibodies conjugated to horseradish peroxidase (HRP) (Jackson ImmunoResearch Laboratories) used as a reporter. Chinchilla IgG was purified from chinchilla serum according to Barenkamp (ref. 14). Generation and purification of guinea pig anti-chinchilla IgG antibodies were described earlier (ref. 15). The reactions were developed using tetramethylbenzidine (TMB/H$_2$O$_2$, ADI, Mississauga, Ontario) and absorbancies were measured at 450 nm (using 540 nm as a reference wavelength) in a Flow Multiskan MCC microplate reader (ICN Biomedicals, Mississauga, Ontario). The reactive titer of an antiserum was defined as the reciprocal of the dilution consistently showing a two-fold increase in absorbance over that obtained with the pre-bleed serum sample.

Example 15

This Example illustrates the protective ability of rHMW1A and rHMW2A proteins produced from different constructs.

The immunization and intranasal challenge with freshly grown streptomycin resistant NTHi strain 12 in chinchillas has been described (ref. 15). Briefly, groups of 8 to 9 animals were immunized three times i.m. with one of: 30 µg of purified rHMW1 or rHMW2, 2×10$^9$ cfu of heat inactivated (56° C., 10 min) NTHi whole cells in alum, or alum alone on days 0, 14 and 28. Serum samples and nasal wash samples were taken on day 42 for measurement of anti-HMW1 or anti-rHMW2 antibody titers by EIAs.

On day 44, animals were lightly anesthetized using xylazine/ketamine HCl by intramuscular injection (0.06 mg xylazine and 0.3 mg ketamine HCl per kg body weight). Intranasal inoculations were performed via passive inhalation (50 µl per nares, total 0.1 ml per animal) of freshly cultured streptomycin-resistant NTHi strain 12 in BHI medium supplemented with hemin and NAD both at 2 µg ml$^{-1}$. The dose of bacterial challenge was 1×10$^8$ cfu per animal. Nasopharyngeal lavages were performed 4 days post inoculation on anesthetized chinchillas (xylazine/ketamine HCl, same route and dose as on day 44). Secretions were obtained by irrigating the nasopharynx with 1 ml sterile saline and collecting fluid out of the contralateral nares. Normally, about 500 µl of fluid was collected from each animal and 25 µl of sample was plated on a chocolate agar plate in the presence of 50 µl of streptomycin (20 mg ml$^{-1}$).

The protective effect of parenteral immunization with various rHMW1 and rHMW2 preparations on NP colonization of chinchilla nasopharynx with NTHi strain 12 is summarized in Table 2. 67 to 88% of the control animals immunized with alum only, had culture-positive nasal lavage fluids. In contrast, 67 to 80% of animals immunized with the rHMW1 protein purified from the constructs abc (pDS-1046-1-1), a/abc (pBK86-1-1), or abc/cer (pBK-76-1-1) were largely protected. In animals immunized with the rHMW1 protein derived from either construct abA (pDS-1122-2) or construct 2xa (pJB-2369-6), 70 to 90% were infected. These results clearly indicated that, in order to achieve a significant protection against NTHi strain 12 colonization in the chinchilla model, the rHMW1 protein must be derived from a construct with intact ABC genes.

Similar results were also observed with rHMW2 protein. As shown in Table 2, animals immunized with the rHMW2 protein purified from the construct abc (pDS-1147-4), but not from the construct 2xa (pDS-2084-1), were protected against NTHi strain 12 colonization in the chinchilla model. In all cases, significant protection was observed in chinchillas immunized with the heat-inactivated NTHi 12 whole cell preparations, prepared in accordance with Example of U.S. Pat. No. 5,603,938.

Example 16

This Example illustrates the cloning and sequence analysis of hmwA genes from additional NTHi strains.

Chromosomal DNA was prepared from several NTHi strains and PCR was performed using the oligonucleotide primers shown in FIG. 17. The sense primer (5522.SL, SEQ ID NO: 21) corresponds to the conserved region in the hmwA genes encoding the residues immediately upstream of the processing site for the mature HMW proteins. The antisense primer (5523.SL, SEQ ID NO: 24) corresponds to the start of the hmwB gene that is also conserved.

PCR amplification was performed as follows: each reaction mixture contained 5–100 ng of DNA, 1 µg of each primer, 5 units of taq+ or tsg+ (Sangon) or taq plus long (Stratagene), 2 mM dNTPs, 20 mM Tris-HCl (pH 8.8), 10 mM KCl, 10 mM (NH$_4$)$_2$SO$_4$, 2 mM MgSO$_4$, 0.1% Triton X-100, BSA. Cycling conditions were: 95° C. for 1 min, followed by 25 cycles of 95° C. for 30 sec, 45° C. for 1 min, 72° C. for 2 min; then 72° C. for 10 min.

The nucleotide (SEQ ID NO: 25) and deduced amino acid (SEQ ID NO: 26) sequences of the hmw1A gene from strain Joyc are shown in FIG. 18. The predicted mature HMW1A protein from strain Joyc (encoding sequence SEQ ID NO: 27, amino acid sequence SEQ ID NO: 28) has a molecular weight of 125.9 kDa and a pI of 8.21. There are no RGD motifs found in Joyc HMW1A. The nucleotide (SEQ ID NO: 29) and deduced amino acid (SEQ ID NO: 30) sequences of the hmw2A gene from strain Joyc are shown in FIG. 19. The predicted mature HMW2A, protein from strain Joyc (encoding sequence SEQ ID NO: 31, amino acid sequence SEQ ID NO: 32) has a molecular weight of 100.9 kDa and a pI of 6.91. There are no RGD motifs found in Joyc HMW2A.

The nucleotide (SEQ ID NO: 33) and deduced amino acid (SEQ ID NOS: 34, 35) sequences of the defective hmw1A gene from strain K1 are shown in FIG. 20. Although there is a complete hmw1A gene in strain K1, there is a frame-shift immediately following a poly G tract, that results in early termination of the HMW1A protein after 326 amino acids.

The nucleotide (SEQ ID NO: 38) and deduced amino acid (SEQ ID NO: 39) sequences of the hmw1A gene from strain K21 are shown in FIG. 21. The predicted mature HMW1A protein from strain K21 (encoding sequence SEQ ID NO: 40, amino acid sequence SEQ ID NO: 41) has a molecular weight of 104.4 kDa and a pI of 8.71. There is a single RGD motif located at residues 20 to 22 in K21 HMW1A.

The nucleotide (SEQ ID NO: 42) and deduced amino acid (SEQ ID NO: 43) sequences of the hmw2A gene from strain LCDC2 are shown in FIG. 22. The predicted mature HMW2A protein from strain LCDC2 (encoding sequence SEQ ID NO: 44, amino acid sequence SEQ ID NO: 45) has a molecular weight of 111.7 kDa and a pI of 8.22. There are no RGD motifs found in LCDC2 HMW2A.

The nucleotide (SEQ ID NO: 46) and deduced amino acid (SEQ ID NO: 47) sequences of the hmw1A gene from strain PMHi are shown in FIG. 23. The predicted mature HMW1A protein from strain PMH1 (encoding sequence SEQ ID NO: 48, amino acid sequence ID NO: 49) has a molecular weight of 102.4 kDa and a pI of 6.73. There are two RGD motifs found in PMH1 HMW1A, the first at residues 19 to 21 and the second at residues 505 to 507. The nucleotide (SEQ ID NO: 50) and deduced amino acid (SEQ ID NO: 51) sequences of the hmw2A gene from strain PMH1 are shown in FIG. 24. The predicted mature HMW2A protein from strain PMH1 (encoding sequence SEQ ID NO: 52, amino acid sequence SEQ ID NO: 53) has a molecular weight of 103.9 kDa and a pI of 9.07. There are two RGD motifs found in PMH1 HMW2A, the first at residues 26 to 28 and the second at residues 532 to 534.

The nucleotide (SEQ ID NO: 54) and deduced amino acid (SEQ ID NO: 55) sequences of the hmw1A gene from strain 15 are shown in FIG. 25. The predicted mature HMW1A protein from strain 15 (encoding seqeunce SEQ ID NO: 56, amino acid sequence SEQ ID NO: 57) has a molecular weight of 103.5 kDa and a pI of 8.06. There are no RGD motifs found in strain 15 HMW1A. The nucleotide (SEQ ID NO: 58) and deduced amino acid (SEQ ID NO: 59) sequences of the hmw2A gene from strain 15 are shown in FIG. 26. The predicted mature HMW2A protein from strain 15 (encoding sequence SEQ ID NO: 60, amino acid sequence SEQ ID NO: 61) has a molecular weight of 121.9 kDa and a pI of 8.22. There are no RGD motifs in strain 15 HMW2A.

The nucleotide (SEQ ID NOS: 62, 66) and deduced amino acid sequence (SEQ ID NOS: 63, 67) for the hmw1A and hmw2A genes, from strain 12, as contained in U.S. Pat. No. 5,603,938, are shown in FIGS. 27 and 28 respectively.

An alignment of the deduced HMW1A and HMW2A protein sequences with the published HMW1A and HMW2A protein sequences from strain 12 (SEQ ID NOS: 63, 67) is shown in FIG. 29. The cleavage site for the mature proteins is shown by the arrow. Regions of similarity can be identified especially between residues about 980 to 1168 and, at the carboxyl terminal, from about residue 1360 to the end. There appear to be repeats in some proteins inserted around residue 1219, most notably in Joyc HMW1A and K1 HMW1A, that appear to have two tandem inserted repeats, while K21 HMW1A and LCDC2 HMW2A contain single copies of the repeat. Strain 15 HMW2A contains a different repeat segment located in the same area. There is a short segment of semi-conserved sequence inserted at residue 583 that is found in all of the HMW2A proteins, except strain 15 HMW2A. However, it is found in the strain 15 HMW1A protein.

Example 17

This Example illustrates the PCR amplification used to determine whether hmw1A or hmw2A genes had been amplified.

The hmwA genes were PCR amplified using primers based upon sequences conserved between hmw1 and hmw2 operons and thus amplified genes could be either hmw1 or hmw2. Although the hmw genes do not occur in encapsulated strains, the 5'- and 3'-flanking sequences can be found in the genome sequence of *H. influenzae* strain Rd (ref. 16). Oligonucleotide sense primers were generated based upon the 5'-hmw1 flanking sequence from strain Rd gene HI1679 (primer 5672.SL, SEQ ID NO: 70)) and the 5'-hmw2 flanking region from strain Rd gene HI1598 (primer 5676.SL (SEQ ID NO: 71)). Antisense primers were generated based upon internal sequences of the amplified hmwA genes. The oligonucleotide primers are shown in FIG. 20. Primer 5742.SL (SEQ ID NO: 74) was used to amplify hmwA genes from strains K1, K21, PMH1 and 15, while primer 5743.SL (SEQ ID NO: 77) was used to PCR hmwA genes from strains Joyc and LCDC2. Amplified fragments were directly sequenced using the hmwA-specific primers (5742.SL and 5743.SL) and the sequence compared to the sequence of the genes cloned in Example 16. After the PCR amplified hmwA genes were identified as hmw1A or hmw2A, specific PCR primers were used to PCR amplify a second copy of the gene with a start codon engineered at the start of the mature protein. A representative pair of PCR primers, used to amplify the LCDC2 hmw2A gene for expression, are illustrated in FIG. 32B (5972.SL, SEQ ID NO: 88; 5973. SL, SEQ ID NO:91).

Example 18

This Example illustrates the construction of a generic plasmid for expression of hmwABC genes in *E. coli*.

As shown in Example 16, the hmw1A and hmw2A genes can be PCR amplified from any hmw-containing strain of non-typeable *H. influenzae*, but to produce protective recombinant antigen, they must be expressed in the presence of hmwBC genes. A generic expression plasmid was constructed that contains the T7 promoter, strain 12 hmw1BC genes, the *E. coli* cer gene, a kanamycin resistance gene, and a cloning site to insert any hmwA gene.

Figure 31A:
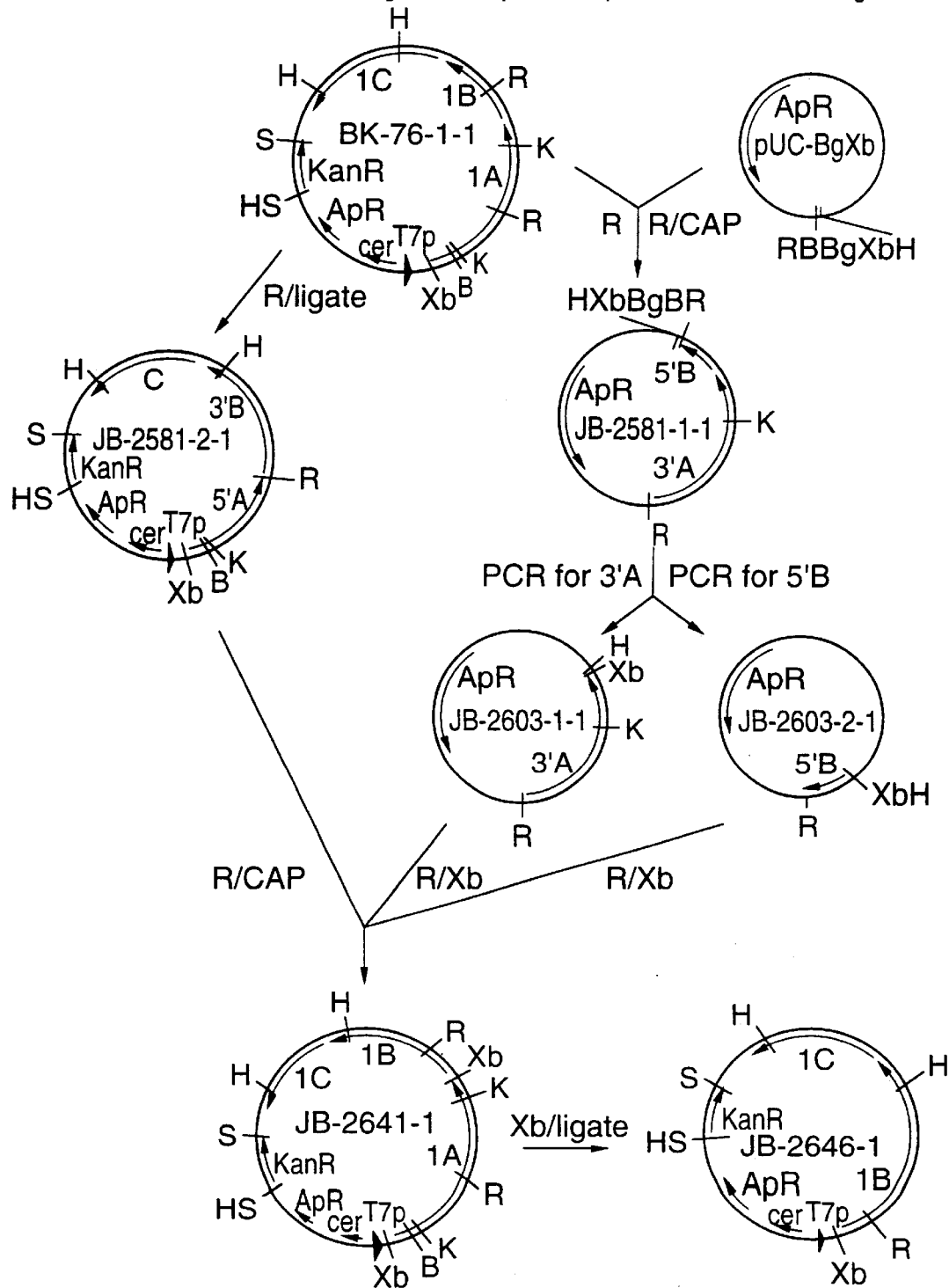
FIG. 31A shows the construction scheme to generate the generic T7 hmwABC expression plasmid JB-2646-1 into which can be inserted any hmwA gene. Restriction enzyme sites are: B, BamH I; Bg, Bgl II; H, Hind III; K, Kpn I; R, EcoR I; S, Sal I; Xb, Xba I. Other abbreviations are: T7p, T7 promoter; ApR, ampicillin resistance gene; KanR, kanamycin resistance gene; CAP, calf alkaline phosphatase.

Plasmid BK-76-1-1 (FIG. 10, Example 10) was digested with EcoR I and re-ligated to generate plasmid JB-2581-2-1, which has the 2 kb EcoR I fragment containing the 3'-end of hmw1A and the 5'-end of hmw1B deleted (FIG. 31A). The 2 kb EcoR I fragment from BK-76-1-1 was subcloned into pUC-BgXb for further manipulation, creating plasmid JB-2581-1-1. FIG. 29B shows the oligonucleotide primers used to amplify the 3'-end of hmw1A (5947.SL, SEQ ID NO: 79; 5948.SL, SEQ ID NO: 82) and the 5'-end of hmw1B (5949.SL, SEQ ID NO: 83; 5950.SL, SEQ ID NO: 86), introducing a Xba I site at the junction of the two genes. Plasmid JB-2603-1-1 contains a 1.5 kb EcoR I-Xba I 3'-fragment of the hmw1A gene and plasmid JB-2603-2-1 contains the approximately 550 bp Xba I-EcoR I fragment of the hmw A-B intergenic sequence and 5'-end of hmw1B. Plasmid JB-2581-2-1 was linearized with EcoR I, dephosphorylated, and ligated with the EcoR I-Xba I inserts from JB-2603-1-1 and JB-2603-2-1, generating plasmid JB-2641-1. This plasmid is identical to BK-76-1-1, except that it contains an extra Xba I site between the hmw1A and hmw1B genes. Plasmid JB-2641-1 was digested with Xba I which deleted the complete hmw1A gene, but left the hmw1BC genes intact. Re-ligation of the vector fragment generated plasmid JB-2646-1 that is the generic expression vector into which hmwA genes can be cloned at the Xba I site (FIG. 31A).

To demonstrate the utility of the generic expression vector, a chimeric T7 hmwABC gene cassette was generated containing the LCDC2 hmw2A gene combined with the strain 12 hmw1BC genes. The LCDC2 hmw2A gene was PCR amplified using the primers illustrated in FIG. 32B and cloned into pCR II, generating plasmid BK-137-3-10, that contains the hmw2A gene in an anti-clockwise orientation. In order to change the orientation of the hmw2A gene for cloning purposes, the plasmid was digested with BamH I to release the hmw2A insert, then both fragments re-ligated. Plasmid BK-177-3-2 contains the LCDC2 hmw2A gene in a clockwise orientation. Plasmid BK-177-3-2 was digested with Nde I and Xho I and the hmw2A fragment was ligated into pT7-7 that had been digested with Nde I and Sal I, to generate plasmid BK-189-2-5. The generic expression plasmid JB-2646-1 (FIG. 29A) was linearized with Xba I and dephosphorylated. Plasmid BK-189-2-5 was digested with Xba I that released the hmw2A gene ready to be inserted into the expression vector. Plasmid DS2334-5 thus contains a T7 hmwABC gene cassette comprised of the hmw2A gene from LCDC2 and the hmw1BC genes from strain 12.

Example 19

This Example illustrates the construction of plasmid DS-2400-13, that contains a T7 hmwA/T7 hmwABC cassette, the E. coli cer gene, and a kanamycin resistance genes.

Plasmid DS-1843-2 is a tetracycline resistant pBR328-based vector containing a multiple cloning site inserted between the EcoR I and Pst I sites. DS-1843-2 was linearized with Xho I and dephosphorylated and the kanamycin resistance gene from pUC-4K was inserted on a Sal I fragment, generating plasmid DS-2372-31 that is both tetracycline and kanamycin resistant. Plasmid DS-2372-31 was linearized with Bgl II and dephosphorylated, and the synthetic E. coli cer gene from DS-2224-1-4 was inserted on a BamH I fragment, generating plasmid DS-2379-2-6. Plasmid DS-1046-1-1 (FIG. 3A, Example 3) was digested with Bgl II and Sal I and the T7 hmwABC gene fragment was inserted into DS-2379-2-6 that had been digested with BamH I and Sal I. The resulting plasmid is a pBR-based kanamycin resistant and tetracycline sensitive vector containing the T7 hmwABC genes and the E. coli cer gene. JB-2369-6 (FIG. 7, Example 7) was digested with BamH I to release an internal 3' hmwA/T7 5' hmwA fragment that was inserted into the unique BamH I site of the pBR T7 hmwABC/cer/kanR vector. The resulting pBR T7 hmwA/T7 hmwABC/cer/kanR plasmid thus contains multiple hmwA genes.

SUMMARY OF THE DISCLOSURE

In summary of this disclosure, the present invention provides nucleic acid molecules and constructs incorporating the same which permit the recombinant production of high molecular weight proteins of non-typeable *Haemophilus influenzae* which are protective. Modifications are possible within the scope of the invention.

TABLE 1

Immunogenicity of various forms of HMW1 and HMW2 in chinchillas.

| HMW preparations | Anti-HMW antibody titers Log2 (Titers/100) |
|---|---|
| HMW1/HMW2 native | 7.11 ± 0.78 |
|  | 7.75 ± 0.66 |
| HMW1 abc | 9.67 ± 1.12 |
|  | 10.78 ± 0.83 |
| HMW1 a/abc | 8.44 ± 0.88 |
| HMW1 abc/cer | 7.11 ± 0.93 |
|  | 7.44 ± 0.88 |
| HMW1 abΔ | 1.00 ± 0.50 |
|  | 2.17 ± 1.67 |
| HMW1 2xa | 12.29 ± 0.49 |
| HMW2 abc | 9.22 ± 1.48 |
|  | 11.44 ± 0.78 |
| HMW2 2xa | 12.89 ± 0.78 |
| alum | <0.05 |
|  | <0.05 |

Groups of 9 chinchillas were immunized (i.m.) on days 1, 14 and 28 with 30 μg of the indicated antigens adsorbed to alum. Blood samples were collected on day 42. The reactive titer of an antiserum was defined as the reciprocal of the dilution consistently showing a two fold increase in absorbance over that obtained with the prebleed serum sample. Two sets of numbers indicate two sets of experiments.

TABLE 2

Protective abilities of various forms of HMW1 and HMW2 against NP colonization with NTHi strain 12 in chinchillas.

| HMW preparations | # of infected animals/ # of total animals challenged (%) | median cfu/25 μl nasal lavage |
|---|---|---|
| HMW1/HMW2 native + alum | 2/9 (22.2%) | 11* |
| alum | 7/9 (77.8%) | 800 |
| HMW1 abc + alum | 2/9 (22.2%) | 6* |
| alum | 7/9 (77.8%) | 800 |
| HMW1 a/abc + alum | 2/9 (22.2%) | 20* |
| alum | 6/9 (66.7%) | 300 |
| HMW1 abc/cer + alum | 3/9 (33.3%) | 60* |
| alum | 7/9 (77.8%) | 1000 |
| HMW1 abΔ + alum | 8/9 (89.9%) | 500 |
| alum | 7/8 (87.5%) | 1270 |
| HMW1 2xa + alum | 5/7 (71.5%) | 400 |
| alum | 7/9 (77.8%) | 630 |
| HMW2 abc + alum | 2/9 (22.2%) | 7* |
| HMW2 2xa + alum | 7/9 (77.8%) | 800 |
| alum | 7/9 (77.8%) | 1000 |

Groups of 9 chinchillas were immunized (i.m.) on days 1, 14 and 28 with 30 μg of indicated antigens adsorbed to alum. Blood samples were collected on day 42. On day 44, animals were challenged by intranasal inoculations with freshly cultured streptomycin-resistant NTHi strain 12. The dose of bacterial challenge was 1×10$^8$ cfu per animal. Nasopharyngeal lavages were performed 4 days post inoculation and 25 μl of the nasal lavage were plated on chocolate agar plates.

An animal was defined as infected if >50 cfu of bacteria were recovered from 25 μl nasal lavage fluid. * Statistical significance was found when compared to the control animals by Mann-Whitney Rank Sum Test (p<0.05).

TABLE 3

Molecular weights of Mature HMW Protein from Various *H. influenzae* non-typeable Strain

| Molecular Weight (kDa) | Non-typeable *H. influenzae* Strain | | | | |
|---|---|---|---|---|---|
| | 12 | JoyC | K21 | LCDC2 | PMH1 | 15 |
| Mature Protein: | | | | | | |
| HMW1 | 125 | 125.9 | 104.4 | | 102.4 | 103.5 |
| HMW2 | 120 | 100.9 | | 111.7 | 103.9 | 121.9 |

REFERENCES

1. Berkowitz et al. 1987. J. Pediatr. 110:509.
2. Claesson et al. 1989. J. Pediatr. 114:97.
3. Black, S. B., H. R. Shinefield, B. Fireman, R. Hiatt, M. Polen, E. Vittinghoff, The Northern California Kaiser Permanent Vaccine Study Center Pediatrics Group. Efficacy in infancy of oligosaccharide conjugate *Haemophilus influenzae* type b (HbOC) vaccine in a United States population of 61,080 children. 1991. Pediatr. Infect. Dis. J. 10:97–104.
4. Madore, D. V. 1996. Impact of immunization on *Haemophilus influenzae* type b disease. Infectious Agents and Disease 5:8–20.
5. Bluestone, C. D. 1982. Current concepts in otolaryngology. Otitis media in children: to treat or not to treat? N. Engl. J. Med. 306:1399–1404.
6. Barenkamp, S. J., and F. F. Bodor. 1990. Development of serum bactericidal activity following nontypable *Haemophilus influenzae* acute otitis media. Pediatr. Infect. Dis. 9:333–339.
7. Barenkamp, S. J., and E. Leininger. 1992. Cloning, expression, and DNA sequence analysis of genes encoding nontypeable *Haemophilus influenzae* high-molecular-weight surface-exposed proteins related to filamentous hemagglutinin of *Bordetella pertussis*. Infect. Immun. 60:1302–1313.
8. Barenkamp, S. J., and J. W. St. Geme III. 1994. Genes encoding high-molecular-weight adhesion proteins of nontypeable *Haemophilus influenzae* are part of gene clusters. Infect. Immun. 62:3320–3328.
9. St. Geme III, J. W. and S. Grass. 1998. Secretion of the *Haemophilus influenzae* HMW1 and HMW2 adhesins involves a periplasmic intermediate and requires the HMWB and HMWC proteins. Molec. Microbiol. 27:617–630.
10. St. Geme III, J. W., S. Falkow, and S. J. Barenkamp. 1993. High-molecular-weight proteins of nontypeable *Haemophilus influenzae* mediate attachment to human epithelial cells. Proc. Natl. Acad. Sci. USA 90:2875–2879.
11. Barenkamp, S. J. 1996. Immunization with high-molecular-weight adhesion proteins of nontypeable *Haemophilus influenzae* modifies experimental otitis media in chinchillas. Infect. Immun. 64:1246–1251.
12. Tabor, S., and C. C. Richardson. 1985. A bacteriophage T7 RNA polymerase/promoter system for controlled exclusive expression of specific genes. Proc. Natl. Acad. Sci. USA 82:1074–1078.
13. Patient, M. E., and D. K. Summers. 1993. ColE1 multimer formation triggers inhibition of *Escherichia coli* cell division. Molec. Microbiol. 9:1089–1095.
14. Barenkamp, S. 1986. Protection by serum antibodies in experimental nontypeable *Haemophilus influenzae* otitis media. Infect. Immun. 52:572–578.
15. Yang, Y.-P., S. M. Loosmore, B. Underdown, and M. H. Klein. 1998. Nasopharyngeal colonization with non-typeable *H. influenzae* in chinchillas. Infect. Immun. 66:1973–1980.
16. Fleischmann et al. 1995. Whole-genome random sequencing and assembly of *Haemophilus influenzae* Rd. Science 269:496–512.
17. O'Hagan, D T. 1992. Oral delivery of vaccines. Formulation and clinical pharmaco kinetic considerations. Clin. Pharmacokinet 22(t): 1–10.
18. Ulmer et al. 1993. Curr. Opinion Invest. Drugs 2:983–989.
19. Lockhoff, O., 1991. Glycolipids as immunomodulators: Synthesis and properties.
20. Nixon-George A., et al., 1990. The adjuvant effect of stearyl tyrosine on a recombinant subunit hepatitis B surface antigen. J. Immunol 144 (12):4798–4802.

What we claim is:

1. A plasmid vector for expression of a high molecular weight (HMW) protein of a non-typeable strain of *Haemophilus influenzae* comprising the T7 promoter, a cloning site for insertion of a nucleic acid molecule which is an A gene of the hmw operon of a non-typable *Haemophilus influenzae* strain, into the plasmid vector and the B and C genes of the hmw operon of a non-typeable *Haemophilus influenzae* strain.

2. The plasmid of claim 1 further comprising the *E. coli* cer gene.

3. The plasmid vector of claim 1 which is plasmid JB-2646-1 (ATCC NO. 203,256).

* * * * *